US007851679B2

(12) United States Patent
Rottmann et al.

(10) Patent No.: US 7,851,679 B2
(45) Date of Patent: Dec. 14, 2010

(54) REPRODUCTIVE ABLATION CONSTRUCTS

(75) Inventors: William H. Rottmann, Summerville, SC (US); Kim H. Norris-Caneda, North Charleston, SC (US); Chunsheng Zhang, North Charleston, SC (US)

(73) Assignee: Arborgen, LLC, Summerville, SC (US)

( * ) Notice: Subject to any disclaimer, the term of this patent is extended or adjusted under 35 U.S.C. 154(b) by 216 days.

(21) Appl. No.: 12/180,180

(22) Filed: Jul. 25, 2008

(65) Prior Publication Data
US 2009/0075326 A1 Mar. 19, 2009

Related U.S. Application Data

(62) Division of application No. 10/946,622, filed on Sep. 22, 2004, now Pat. No. 7,453,025.

(51) Int. Cl.
C12N 15/82 (2006.01)
C12N 15/31 (2006.01)
C12N 15/55 (2006.01)
A01H 5/00 (2006.01)
A01H 5/10 (2006.01)

(52) U.S. Cl. .................... 800/303; 800/269; 800/287; 800/288; 800/319; 435/199; 536/23.2; 536/23.7

(58) Field of Classification Search ................ None
See application file for complete search history.

(56) References Cited

U.S. PATENT DOCUMENTS

| | | | |
|---|---|---|---|
| 4,458,066 | A | 7/1984 | Caruthers et al. |
| 5,491,090 | A | 2/1996 | Handley, III et al. |
| 5,506,136 | A | 4/1996 | Becwar et al. |
| 5,565,340 | A | 10/1996 | Chenchik et al. |
| 5,681,730 | A | 10/1997 | Ellis |
| 5,759,822 | A | 6/1998 | Chenchik et al. |
| 5,856,191 | A | 1/1999 | Handley, III |
| 6,051,757 | A | 4/2000 | Barton et al. |
| 6,132,970 | A | 10/2000 | Stemmer |
| 6,187,994 | B1 | 2/2001 | Baszcynski et al. |
| 6,596,925 | B1 | 7/2003 | Perera et al. |
| 6,682,931 | B2 | 1/2004 | Becwar et al. |
| 6,791,011 | B1 | 9/2004 | Paul et al. |
| 7,157,620 | B2 | 1/2007 | Connett-Porceddu et al. |
| 2002/0100083 | A1 | 7/2002 | Connett-Porceddu et al. |
| 2003/0101487 | A1 | 5/2003 | Kisaka et al. |

FOREIGN PATENT DOCUMENTS

| | | |
|---|---|---|
| EP | 0223399 B1 | 5/1987 |
| EP | 0344029 B1 | 11/1989 |
| EP | 0120516 B1 | 10/1991 |
| EP | 0154204 B1 | 1/1994 |
| EP | 0271988 B1 | 8/1995 |
| EP | 1020527 A1 | 7/2000 |
| JP | H6-504910 | 9/1994 |
| JP | H7-500970 | 2/1995 |
| JP | 2000-41682 | 2/2000 |
| WO | WO 92/04449 | 3/1992 |
| WO | WO 92/13956 | 8/1992 |
| WO | WO 93/10251 | 5/1993 |
| WO | WO 93/19189 | 9/1993 |
| WO | WO 96/28561 | 9/1996 |
| WO | WO 99/61631 | 12/1999 |
| WO | WO 00/55172 | 9/2000 |

OTHER PUBLICATIONS

U.S. Appl. No. 10/861,909, filed Jun. 7, 2004, Chang.
Akio Hayashimoto et al., "A Polyethylene Glycol=Mediated Protoplast Transformation System for Production of Fertile Transgenic Rice Plants", Plant Physiology, The American Society of Plant Physiologists, Jul. 1990, vol. 93, No. 3, pp. 857-863.
Alan H. Christensen et al., "Ubiquitin Promoter-based Vectors for High Level Expression of Selectable and/or Screenable Marker Genes in Monocotyledonous Plants", Transgenic Research, Chapman & Hall, May 1996, vol. 5, No. 3, pp. 213-218.
Antonio Leyva et al., "cis-Element Combinations Determine Phenylalanine Ammonia-Lyase Gene Tissue-Specific Expression Patterns", The Plant Cell, 1992 American Society of Plant Physiologists, Mar. 1992, vol. 4, pp. 263-271.
B. L. Miki et al., "Procedures for Introducing Foreign DNA into Plants", Methods in Plant Molecular Biology and Biotechnology, CRC Press, 1993, pp. 67-88.
Beals, T. P., et al., "A Novel Cell Ablation Strategy Blocks Tobacco Anther Dehiscence," The Plant Cell, 1997, pp. 1527-1545, vol. 9.
Beat Keller et al., "Vascular expression of the grp1.8 promoter is controlled by three specific regulatory elements and one unspecific activating sequence", Plant Molecular Biology, International Society for Plant Molecular Biology, Kluwer Academic Publishers, Oct. 1994, vol. 26, No. 2, pp. 747-756.
Bergelson, J., et al., "Promiscuity in transgenic plants," Nature, 1998, pp. 25-26, vol. 395.
Busch, M. A., et al., "Activation of a Floral Homeotic Gene in Arabidopsis," Science, 1999, pp. 585-587, vol. 285.
Chen, et al., Sexual Plant Reproduction 13(2): 85-94 (2000).
C.J.S.Smith et al., "Antisense RNA Inhibition of Polygalacturonase Gene Expression in Transgenic Tomatoes", Nature, Aug. 1988, vol. 334, No. 25, pp. 724-726.
Christopher J.S. Smith et al., "Inheritance and Effect on Ripening of Antisense Polygalacturonase Genes in Transgenic Tomatoes", Plant Molecular Biology, International Society for Plant Molecular Biology, Kluwer Academic Publishers, Mar. 1990, vol. 14, No. 3, pp. 369-379.

(Continued)

Primary Examiner—David T Fox
(74) Attorney, Agent, or Firm—Foley & Lardner LLP

(57) ABSTRACT

The present invention relates to the regulation of reproductive development, particularly to the genetic ablation of reproductive tissues in angiosperm and gymnosperm species. Reproductive-preferred promoters, regulatory elements, and cytotoxic nucleotide sequences are disclosed herein, as are constructs and methods for genetic ablation.

12 Claims, 47 Drawing Sheets

OTHER PUBLICATIONS

Datta et al., "Nucleotide sequence of a gene encoding soybean repetitive praline-rich protein 3," *Plant Molecular Biology*, 1990, pp. 285-286, vol. 14, Kluwer Academic Publishers, Belgium.

David A. Neustaedter et al., "A Novel Parsley *4CL1 cis*-element is Required for Developmentally Regulated Expression and Protein DNA Complex Formation", The Plant Journal, 1999, Blackwell Science Ltd., vol. 18, No. 1, pp. 77-88.

David M. Stalker et al., "Purification and Properties of a Nitrilase Specific for the Herbicide Bromoxynil and Corresponding Nucleotide Sequence Analysis of the *bxn* Gene*'", The Journal of Biological Chemistry, The American Society for Biochemistry and Molecular Biology, Inc., May 5, 1988, vol. 263, No. 13, pp. 6310-6314.

David McElroy et al., "Isolation of an Efficient Actin Promoter for Use in Rice Transformation", The Plant Cell, 1990 American Society of Plant Physiologists, Feb. 1990, vol. 2, pp. 163-171.

Deyholos, M. K., et al., "Separable Whorl-Specific Expression and Negative Regulation by Enhancer Elements within the Agamous Second Intron," The Plant Cell, 2000, pp. 1799-1810, vol. 12.

Diane Hatton et al., "Two Classes of CIS Sequences Contribute to Tissue-Specific Expression of a PAL2 Promoter in Transgenic Tobacco", The Plant Journal, 1995, vol. 7, No. 6, pp. 859-876.

Donald et al., The EMBO Journal 9(6): 1717-1726 (1990).

E. T. Bolton et al., "A General Method for the Isolation of RNA Complementary to DNA", Biochemistry: Bolton and McCarthy, Proc. Natl. Acad. Sci., 1962, vol. 48, pp. 1390-1397.

Eric Lacombe et al., Characterization of *cis*-elements Required for Vascular Expression of the *Cinnamoyl CoA Reductase* Gene and for Protein DNA Complex Formation, The Plant Journal, 2000 Blackwell Science Ltd., vol. 23, No. 5, pp. 663-676.

Eugene W. Holowachuk et al., "Efficient Gene Synthesis by Klenow Assembly / Extension—Pfu Polymerase Amplification (KAPPA) of Overlapping Oligonucleotides", PCR Methods and Applications, Cold Spring Harbor Laboratory, vol. 4, pp. 299-302, (1995).

Eun-Gyu No et al., "Sequences Upstream and Downstream of Two Xylem-Specific Pine Genes Influence Their Expression", Plant Science, 2000 Elsevier Science, vol. 160, pp. 77-86.

Golovkin et al., "Production of transgenic maize plants by direct DNA uptake into embryogenic protoplasts," *Plant Science*, 1993, pp. 41-52, vol. 90, Elsevier Scientific Publishers Ireland Ltd.

Halina Kononowicz, Subdomains of the Octopine Synthase Upstream Activating Element Direct Cell-Specific Expression in Transgenic Tobacco Plants, The Plant Cell, 1992 American Society of Plant Physiologists, Jan. 1992, vol. 4, pp. 17-27.

Harry J. Klee et al., "Vectors for Transformation of Higher Plants", Bio/Technology, Jul. 1985, vol. 3, pp. 637-642.

Hartley, R.W., Barnase and Barstar Expression of Its Cloned Inhibitor Permits Expression of a Cloned Ribonuclease, J. Mol. Biol., 1988, pp. 913-915, vol. 202.

Haseloff, J., et al., "Simple RNA enzymes with new and highly specific endoribonuclease activities," Nature, 1988, pp. 585-591, vol. 334.

Henry Daniell et al., "Containment of Herbicide Resistance Through Genetic Engineering of the Chloroplast Genome", Apr. 1998, Nature Biotechnology, vol. 16, pp. 345-348.

Hofig et al., Planta 217 (6):858-867 (Oct. 2003).

Ingo Potrykus et al., "Direct Gene Transfer to Cells of a Graminaceous Monocot", Mol. Gen. Genet, Springer-Verlag, 1985, vol. 199, pp. 183-188.

Jofuku, K. D., et al., "Kunitz Trypsin Inhibitor Genes Are Differentially Expressed during the Soybean Life Cycle and in Transformed Tobacco Plants," The Plant Cell, 1989, pp. 1079-1093, vol. 1.

Joëlle Thillet et al., "Site-Directed Mutagenesis of Mouse Dihydrofolate Reductase", The Journal of Biological Chemistry, The American Society for Biochemistry and Molecular Biology, Inc., Sep. 1968, vol. 263, No. 25, pp. 12500-12508.

Karl D. Hauffe et al., "Combinatorial Interactions Between Positive and Negative CIS-acting Elements Control Spatial Patterns of 4CL-1 Expression in Transgenic Tobacco", The Plant Journal, 1993, vol. 4, No. 2, pp. 235-253.

Kathleen D'Halluin et al., "Transgenic Maize Plants by Tissue Electroporation", The Plant Cell, 1992 Society of Plant Physiologists, Dec. 1992, vol. 4, pp. 1495-1505.

Kaul, M. L. H., "Male Sterility in Higher Plants," 1988, Monographs on Theoretical & Applied Genetics, vol. 10, Springer Verlag: Secaucus, NJ.

Koltunow, A. M., et al., "Different Temporal and Spatial Gene Expression Patterns Occur during Anther Development," The Plant Cell, 1990, pp. 1201-1224, vol. 2.

Kuvshinov, V., et al., "Molecular control of transgene escape from genetically modified plants," Plant Science, 2001, pp. 517-522, vol. 160.

Leple, J. C., et al., "Transgenic poplars: expression of chimeric genes using four different constructs," Plant Cell Reports, 1992, pp. 137-141, vol. 11.

Luis Herrara-Estrella et al., Expression of Chimaeric Genes Transferred into Plant Cells Using a Ti-plasmid-derived Vector, Nature, International Weekly Journal of Science, Macmillan Journals Ltd., May 19-25, 1983, vol. 303, No. 5914, pp. 209-213.

Mariani, C., et al., "Induction of male sterility of plants by a chimaeric ribonuclease gene," Nature, 1990, pp. 737-741, vol. 347.

Mark D. Burow et al., "High Frequency Generation of Transgenic Tobacco Plants after Modified Leaf Disk Cocultivation with *Agrobacterium tumefaciens*", Plant Molecular Biology Reporter, Transaction Periodicals Consortium, Rutgers University, May 1990, vol. 8, No. 2, pp. 124-139.

Maud A. W. Hinchee et al., "Production of Transgenic Soybean Plants Using *Agrobacterium*-Mediated DNA Transfer", Bio/Technology, The International Monthly for Industrial Biology, Aug. 1988, vol. 6, pp. 915-922.

McCarthy et al., "The Rate of Change of DNA in Evolution," In *Evolution of Genetic Systems*, 1972, pp. 1-43, H.H. Smith (ed.), Brookhaven Symposium in Biology No. 23, Gordon and Breach, New York.

Michael A. Wosnick et al., "Rapid Construction of Large Synthetic Genes: Total Chemical Synthesis of Two Different Versions of the Bovine Prochymosin Gene", Gene, Elsevier Science Publishers, vol. 60, No. 1, pp. 115-127, (1987).

Michael Bevan, "Binary *Argrobacterium* Vectors for Plant Transformation", IRL Press Limited, 1984, vol. 12, No. 22, pp. 8711-8721.

Michael J. Adang et al., "The Reconstruction and Expression of a *Bacillus thuringiensis cry IIIA* gene in protoplasts and potato plants", Plant Molecular Biology, Mar. 1993, vol. 21, No. 6, pp. 1131-1145.

Mossakowska, D. E., et al., "Kinetic Characterization of the Recombinant Ribonuclease from *Bacillus amyloliquefaciens* (Barnase) and Investigation of Key Residues in Catalysis by Site-Directed Mutagenesis," American Chemical Society, 1989, pp. 3843-3850, vol. 28.

Mouradov, et al. Acta Horticulturae 461: 417-423, (1998).

Nave, E. B., et al., "Enzymatic changes in Post-meiotic Anther Development in *Petunia hybrida*. I. Anther Ontogeny and Isozyme Analyses," J. Plant Physiol, 1986, pp. 451-465, vol. 125.

Nilsson, O., et al., "Genetic ablation of flowers in transgenic *Arabidopsis*," The Plant Journal, 1998, pp. 799-804, vol. 15(6).

Paddon, C. J., et al., "Translation and Processing of *Bacillus amyloliquefaciens* Extracellular RNase," Journal of Bacteriology, 1989, pp. 1185-1187, vol. 171, No. 2.

Patrick Dillon et al., "Use of Polymerase Chain Reaction for the Rapid Construction of Synthetic Genes", PCR Protocols: Current Methods and Applications, Methods in Molecular Biology, 1993, Humana Press Inc., vol. 15, pp. 263-268.

Patrick Paddison et al., "Short Hairpin RNAs (shRNAs) Induce Sequence-Specific Silencing in Mammalian Cells", Genes & Development, Cold Spring Laboratory Press, 2002, vol. 16, pp. 948-958.

Philip V. Ammirato et al., "Crop Species", Handbook of Plant Cell Culture, vol. 2, 1984 Macmillan Publishing Co., NY, 3 pages.

R. B. Horsch et al., "A Simple and General Method for Transferring Genes into Plants", Science 227, Mar. 1985, pp. 1229-1231.

R. B. Horsch et al., Rapid Assay of Foreign Gene Expression in Leaf Discs Transformed by *Agrobacterium tumefaciens*: Role of T-DNA Borders in the Transfer Process, Proc. Natl. Acad. Sci. USA, Jun. 1986, vol. 83, pp. 4428-4432.

Rezniekova, S. A., "Histochemical Study of Reserve Nutrient Substances in Anther of *Lilum candidum*," Acad. Bulg. Sci., 1978, vol. 31, pp. 1067-1071.

Richard A. Jefferson et al., GUS Fusions: Beta-glucuronidase as a Sensitive and Versatile Gene Fusion Marker in Higher Plants, The Embo Journal, IRL Press Limited, Dec. 20, 1987, vol. 6, No. 13, pp. 3901-3907.

Robert T. Fraley et al., "Expression of Bacterial Genes in Plant Cells", Proc. Natl. Acad. Sci. USA, Monsanto Company, Aug. 1983, vol. 80, pp. 4803-4807.

Rogers et al., "Improved Vectors for Plant Transformation: Expression Cassette Vectors and New Selectable Markers," *Methods in Enzymology*, 1987, pp. 252-277, vol. 153, Academic Press, Inc.

S. L. Beaucage, et al., "Deoxynucleoside Phosphoramidites—A New Class of Key Intermediates for Deoxypolynucleotide Synthesis", Tetrahedron Letters, Pergamon Press Ltd., 1981, vol. 22, No. 20, pp. 1859-1862.

Sawhney, V. K., et al., "Enzymatic changes in Post-meiotic Anther Development in *Petunia hybrida*. II. Histochemical Localization of Esterase, Peroxidase, Malate- and Alcohol dehydrogenase," J. Plant Physiol., 1986, pp. 467-473, vol. 125.

Schmidhauser et al., "Regions of Broad-Host-Range Plasmid RK2 Involved in Replication and Stable Maintenance in Nine Species of Gram-Negative Bacteria," *Journal of Bateriology*, Oct. 1985, pp. 446-455, vol. 164, No. 1, American Society for Microbiology.

Shabbir B. Bambot et al., "Efficient Total Gene Synthesis of 1.35-kb Hybrid Alpha-Lytic Protease Gene Using the Polymerase Chain Reaction", PCR Methods and Applications, Cold Spring Harbor Laboratory, Feb. 1993, vol. 2, No. 3, pp. 266-271.

Sibley et al., "The Phylogeny and Classification of the Passerine Birds, Based on Comparisons of the Genetic Material, DNA," *ACTA XVIII Congressus Internationalis Ornithologici*, Aug. 16-24, 1982, pp. 83-121, vol. 1.

Sieburth, L. E., et al., "Molecular Dissection of the Agamous Control Region Shows That cis Elements for Spatial Regulation Are Located Intragenically," The Plant Cell, 1997, pp. 355-365, vol. 9.

Stephen F. Altschul et al., "Basic Local Alignment Search Tool", J. Mol. Biol., Academic Press Limited, Oct. 5, 1990, vol. 215, No. 3, pp. 403-410.

Strauss et al., TGERC Annual Report: Flowering Control, pp. 17-29, Aug. 1998.

T. M. Klein et al., "Factors Influencing Gene Delivery into *ZEA Mays* Cells by High-Velocity Microprojectiles, Bio/Technology," BioActive Compounds From Algae May 1988, vol. 6, pp. 559-563.

Tom I. Bonner et al., "Reduction in the Rate of DNA Reassociation by Sequence Divergence", Journal of Molecular Biology, Mar. 15, 1973, vol. 81, pp. 123-135.

Vancanneyt, G., et al., "Construction of an intron-containing marker gene: Splicing of the intron in transgenic plants and its use in monitoring early events in *Agrobacterium*-medicated plant transformation," Mol. Gen. Genet., 1990, pp. 245-250, vol. 220.

Verheij, H. M., et al., "Structure and Function of Phospholiphase A$_2$," Rev. Physiol. Biochem. Pharmacol., 1981, pp. 93-203, vol. 91.

Vimla Vasil et al., "Herbicide Resistant Fertile Transgenic Wheat Plants Obtained by Microprojectile Bombardment of Regenerable Embryogenic Callus", Bio/Technology, Jun. 1992, vol. 10, pp. 667-674.

Vimla Vasil et al., "Regeneration of Plants From Embryogenic Suspension Culture Protoplasts of Wheat (*Triticum Aestivum* L.)", Bio/Technology, May 1990, vol. 8, pp. 429-434.

Yakovlev, G. I., et al., "Mutational analysis of the active site of RNase of *Bacillus intermedius* (Binase)," FEBS Letters, 1994, pp. 305-306, vol. 354.

Notice of Reasons for Rejection (Translation) received in the related Japanese Patent Application No. 2007-532664, dispatched Jul. 29, 2010.

Figure 1A

```
LOCUS       pWVR220       8006 bp    DNA     circular
DEFINITION  PrMC2.400::H102E::RNS2TER.
SOURCE
  ORGANISM
COMMENT     This file is created by Vector NTI
            http://www.informaxinc.com/
COMMENT     VNTDATE|263385014|
COMMENT     VNTDBDATE|304421719|
COMMENT     VNTNAME|pWVR220|
COMMENT     VNTAUTHORNAME|Demo User|
FEATURES             Location/Qualifiers
     misc_marker     1246..2037
                     /vntifkey="22"
                     /label=npt\III\(kanR)
     misc_marker     2339..3484
                     /vntifkey="22"
                     /label=trfA
     misc_structure  complement(3940..3963)
                     /vntifkey="88"
                     /label=LEFT\BORDER
     CDS             complement(4588..5379)
                     /vntifkey="4"
                     /label=NPT\II\(kanR)
     terminator      complement(4319..4539)
                     /vntifkey="43"
                     /label=NOSTER
     promoter        complement(5380..6689)
                     /vntifkey="29"
                     /label=UBQ10\promoter
     intron          complement(5380..5683)
                     /vntifkey="15"
                     /label=INTRON
     misc_marker     744..1013
                     /vntifkey="22"
                     /label=barstar
     CDS             complement(7094..7423)
                     /vntifkey="4"
                     /label=barnaseH102E
     promoter        complement(7424..7821)
                     /vntifkey="29"
                     /label=PrMC2.400
     terminator      complement(6732..6992)
                     /vntifkey="43"
                     /label=RNS2TER
     misc_structure  complement(7874..7897)
                     /vntifkey="88"
                     /label=RIGHT\BORDER
BASE COUNT     2181 a      1845 c      2006 g      1974 t
ORIGIN
        1 cgccggcgtt gtggatacct cgcggaaaac ttggccctca ctgacagatg aggggcggac
       61 gttgacactt gaggggccga ctcacccggc gcggcgttga cagatgaggg gcaggctcga
      121 tttcggccgg cgacgtggag ctggccagcc tcgcaaatcg gcgaaaacgc ctgattttac
      181 gcgagtttcc cacagatgat gtggacaagc ctggggataa gtgccctgcg gtattgacac
      241 ttgaggggcg cgactactga cagatgaggg gcgcgatcct tgacacttga ggggcagagt
      301 gctgacagat gaggggcgca cctattgaca tttgaggggc tgtccacagg cagaaaatcc
      361 agcatttgca agggtttccg cccgtttttc ggccaccgct aacctgtctt ttaacctgct
      421 tttaaaccaa tatttataaa ccttgttttt aaccaggct gcgcctgtg cgcgtgaccg
      481 cgcacgccga aggggggtgc cccccttct cgaaccctcc cggcccgcta acgcgggcct
      541 cccatccccc caggggctgc gcccctcggc cgcgaacggc ctcaccccaa aaatggcagc
      601 gctggcagtc cataattgtg gtccaatttg cagccgtccg agacaggagg acatcgtcca
      661 gctgaaaccg gggcagaatc cggccatttc tgaagagaaa atggtaaac tgatagaata
      721 aaatcataag aaaggagccg cacatgaaaa aagcagtcat taacggggaa caaatcagaa
      781 gtatcagcga cctccaccag acattgaaaa aggagcttgc ccttccggaa tactacggtg
      841 aaaacctgga cgctttatgg gattgtctga ccggatgggt ggagtaccg ctcgttttgg
      901 aatggaggca gtttgaacaa agcaagcagc tgactgaaaa tggcgccgag agtgtgcttc
      961 aggttttccg tgaagcgaaa gcggaaggct gcgacatcac catcatactt tcttaatacg
     1021 atcaatggga gaggaacaat atggaaacac aaaccacaat tgtggtttca aaatcggctc
     1081 cgtcgatact atgttatacg ccaactttga aaacaacttt gaaaaagctg ttttctggta
     1141 tttaaggttt tagaatgcaa ggaacagtga attggagttc gtcttgttat aattagcttc
     1201 ttgggtatc tttaaatact gtagaaaaga ggaaggaaat aataaatggc taaaatgaga
     1261 atatcaccgg aattgaaaaa actgatcgaa aaataccgct gcgtaaaaga tacgaagga
     1321 atgtctcctg ctaaggtata taagctggtg ggagaaaatg aaacctata tttaaaaatg
```

Figure 1B

```
1381 acggacagcc ggtataaagg gaccacctat gatgtggaac gggaaaagga catgatgcta
1441 tggctggaag gaaagctgcc tgttccaaag gtcctgcact ttgaacggca tgatggctgg
1501 agcaatctgc tcatgagtga ggccgatggc gtcctttgct cggaagagta tgaagatgaa
1561 caaagccctg aaaagattat cgagctgtat gcggagtgca tcaggctctt tcactccatc
1621 gacatatcgg attgtcccta tacgaatagc ttagacagcc gcttagccga attggattac
1681 ttactgaata acgatctggc cgatgtggat tgcgaaaact gggaagaaga cactccattt
1741 aaagatccgc gcgagctgta tgattttta aagacggaaa agcccgaaga ggaacttgtc
1801 tttcccacg gcgacctggg agacagcaac atctttgtga aagatggcaa agtaagtggc
1861 tttattgatc ttgggagaag cggcagggcg gacaagtggt atgacattgc cttctgcgtc
1921 cggtcgatca gggaggatat cggggaagaa cagtatgtcg agctatttt tgacttactg
1981 gggatcaagc ctgattggga gaaaataaaa tattatattt tactggatga attgttttag
2041 tacctagatg tggcgcaacg atgccggcga caagcaggag cgcaccgact tcttccgcat
2101 caagtgtttt ggctctcagg ccgaggccca cggcaagtat ttgggcaagg ggtcgctggt
2161 attcgtgcag ggcaagattc ggaataccaa gtacgagaag gacggccaga cggtctacgg
2221 gaccgacttc attgccgata aggtggatta tctggacacc aaggcaccag gcgggtcaaa
2281 tcaggaataa gggcacattg cccggcgtg agtcgggca atcccgcag gaggtgaat
2341 gaatcggacg tttgaccgga aggcatacag gcaagaactg atcgacgcgg ggttttccgc
2401 cgaggatgcc gaaaccatcg caagccgcac cgtcatgcgt gcgcccgcg aaaccttcca
2461 gtccgtcggc tcgatggtcc agcaagctac ggccaagatc gagcgcgaca gcgtgcaact
2521 ggctcccct gccctgccg cgccatcggc cgccgtggag cgttcgcgtc gtctcgaaca
2581 ggaggcggca ggtttggcga agtcgatgac catcgaccg cgaggaacta tgacgaccaa
2641 gaagcgaaaa accgccggcg aggacctggc aaaacaggtc agcgaggcca agcaggccgc
2701 gttgctgaaa cacacgaagc agcagatcaa ggaaatgcag ctttccttgt tcgatattgc
2761 gccgtggccg gacacgatgc gagcgatgcc aaacgacacg gcccgctctg ccctgttcac
2821 cacgcgcaac aagaaaatcc cgcgcgaggc gctgcaaaac aaggtcattt tccacgtcaa
2881 caaggacgtg aagatcacct acaccggcgt cgagctgcgg gccgacgatg acgaactggt
2941 gtggcagcag gtgttggagt acgcgaagcg caccctatc ggcgagccga tcaccttcac
3001 gttctacgag ctttgccagg acctgggctg gtcgatcaat ggccggtatt acacgaaggc
3061 cgaggaatgc ctgtcgcgcc tacaggcgac ggcgatgggc ttcacgtcg accgcgttgg
3121 gcacctggaa tcggtgtcgc tgctgccaccg cttccgcgtc ctggaccgtg gcaagaaaac
3181 gtcccgttgc caggtcctga tcgacgagga aatcgtcgtg ctgtttgctg gcgaccacta
3241 cacgaaattc atatgggaga agtaccgcaa gctgtcgccg acggcccgac ggatgttcga
3301 ctatttcagc tcgcaccggg agccgtaccc gctcaagctg gaaaccttcc gcctcatgtg
3361 cggatcggat tccacccgcg tgaagaagtg gcgcgagcag gtcggcgaag cctgcgaaga
3421 gttgcgaggc agcggcctgg tggaacacgc ctgggtcaat gatgacctgg tgcattgcaa
3481 acgctagggc cttgtggggt cagttccggc tggggttca gcagccagcg ctttactggc
3541 atttcaggaa caagcgggca ctgctcgacg cacttgcttc gctcagtatc gctcgggacg
3601 cacggcgcgc tctacgaact gccgatagac aactgtcacg gttaagcgag aaatgaataa
3661 ggaagctgat aattcggatc tctgcagagg agatgatatt tgatcacagg cagcaacgct
3721 ctgtcatcgt tacaatcaac atgctaccct ccgcgagatc atccgtgttt caaacccggc
3781 agcttagttg ccgttcttcc gaatagcatc ggtaacatga gcaaagtctg ccgccttaca
3841 acggctctcc cgctgacgcc gtcccggact gatgggctgc ctgtatcgag tggtgatttt
3901 gtgccgagct gccggtcggg gagctgttgg ctggctggtg gcaggatata ttgtggtgta
3961 aacaaattga cgcttagaca acttaataac acattgcgga cgtttttaat gtactggggt
4021 ggttttctt ttcaccagtg agacgggcaa cagctgattg cccttcaccg cctgtccctg
4081 agagagttgc agcaagcggt ccacgctggt tgccccagc aggcgaaaat cctgtttgat
4141 ggtggttccg aaatcggcaa aatcccttat aaatcaaaag aatagcccga gatagggttg
4201 agtgttgttc cagtttggaa caagactcca ctattaaaga acgtggactc caacgtcaaa
4261 gggcgaaaaa ccgtctatca gggcgatggc ccacggccgc tctagaacta gtggatcccc
4321 cctacgtgcg atctagtaac atagatgaca ccgcgcgcga taatttatcc tagtttgcgc
4381 gctatatttt gttttctatc gcgtattaaa tgtataattg cgggactcta atcataaaaa
4441 cccatctcat aaataacgtc atgcattaca tgttaattat tacatgctta acgtaattca
4501 acagaaatta tatgataatc atcgcaagac cggcaacaga attcaatctt aagaaactt
4561 attgccaaat gtttgaacga tccctcagaa gaactcgtca agaaggcgat agaaggcgat
4621 gcgctgcgaa tcgggagcgg cgataccgta aagcacgagg aagcggtcag cccattcgcc
4681 gccaagctct tcagcaatat cacgggtagc caacgctatg tcctgatagc ggtccgccac
4741 acccagccgg ccacagtcga tgaatccaga aaagcggcca tttccacca tgatattcgg
4801 caagcaggca tcgccatggg tcacgacgag atcctcgccg tcgggcatgc gcgccttgag
4861 cctggcgaac agttcggctg gcgcgagccc ctgatgctct tcgtccagat catcctgatc
4921 gacaagaccg gcttccatcc gagtacgtgc tcgctcgatg cgatgtttcg cttggtggtc
4981 gaatgggcag gtagccggat caagcgtatg cagccgccgc attgcatcag ccatgatgga
5041 tactttctcg gcaggagcaa ggtgagatga caggagatgc tgcccgtca cttcgcccaa
5101 tagcagccag tccttcccg cttcagtgac aacgtcgagc acagctgcgc aaggaacgcc
5161 cgtcgtggcc agccacgata gccgcgctgc ctcgtcctgg agttcattca gggcaccgga
5221 caggtcggtc ttgacaaaaa gaaccgggcg cccctgcgct gacagccgga acacggcggc
5281 atcagagcag ccgattgtct gttgtgccca gtcatagccg aatagcctct ccacccaagc
5341 ggccggagaa cctgcgtgca atccatcttg ttcaatcatc tgttaatcac aaaaactcag
5401 attaatcgac aaattcgatc gcacaaacta gaaactaaca ccagatctag atagaaatca
5461 caaatcgaag agtaattatt cgacaaaact caaattattt gaacaaatcg gatgatattt
5521 atgaaacct aatcgagaat taagatgata tctaacgatc aaacccagaa aatcgtcttc
5581 gatctaagat taacagaatc taaaccaaag aacatatcaa aaattgggat cgaacgaaaa
5641 caaaatcgaa gattttgaga gaataaggaa cacagaaatt tacctgatc acggtagaga
5701 gaattgagag aaagttttta agattttgag aaatttgaat ctgaattgtg aagaagaaga
5761 gctctttggg tattgtttta tagaagaaga agaagaaaag acgaggacga ctaggtcacg
```

Figures 1C

```
5821 agaaagctaa ggcggtgaag caatagctaa taataaaatg acacgtgtat tgagcgttgt
5881 ttacacgcaa agttgttttt ggctaattgc cttattttta ggttgaggaa aagtatttgt
5941 gctttgagtt gataaacacg actcgtgtgt gccggctgca accactttga cgccgtttat
6001 tactgactcg tcgacaacca caatttctaa cggtcgtcat aagatccagc cgttgagatt
6061 taacgatcgt tacgatttat atttttttag cattatcgtt ttattttta aatatacggt
6121 ggagctgaaa attggcaata attgaaccgt gggtcccact gcattgaagc gtatttcgta
6181 ttttctagaa ttcttcgtgc tttatttctt ttccttttg ttttttttg ccatttatct
6241 aatgcaagtg ggcttataaa atcagtgaat ttcttggaaa agtaacttct ttatcgtata
6301 acatattgtg aaattatcca tttcttttaa tttttagtg ttattggata tttttgtatg
6361 attattgatt tgcataggat aatgacttt gtatcaagtt ggtgaacaag tctcgttaaa
6421 aaggcaagt ggtttggtga ctcgatttat tcttgttatt taattcatat atcaatggat
6481 cttatttggg gcctggtcca tatttaacac tcgtgttcag tccaatgacc aataatattt
6541 tttcattaat aacaatgtaa caagaatgat acacaaaaca ttctttgaat aagttcgcta
6601 tgaagaaggg aacttatccg gtcctagatc atcagttcat acaaacctcc atagagttca
6661 acatcttaaa caaggatatc ctgatccgtt gacggcgcgc caagcggccg catttaaatg
6721 ggccctatct aatcgaattt tgtaaactgg tttgataagc catcaatgca tcagtcaaga
6781 atgaatcatt gcaactaagt tgatataatt caatttacca tagaactcaa atgttgatat
6841 cttcttatgg attttctgat cttctacatt attagaaaga aacttgattt accagtaatg
6901 atgatacata tccaatagaa cgaaataagc caatctttat aggttttggt agtaaagtta
6961 caacatcaga gacatgtatg tattgtctct cagaagagct cttgaccgat cagagtttga
7021 agaaaaattt attacacact ttatgtaaag ctgaaaaaaa cggcctcccg cagggaagcc
7081 gttttttcg ttatctgatt tttgtaaagg tctgatactc gtccgttgtt ttgtaaatca
7141 gccagtcgct tgagtaaaga atccggtctg aatttctgaa gcctgatgta tagttaatat
7201 ccgttcacg ccatgttcgt ccgcttttgc ccgggagttt gccttccctg tttgagaaga
7261 tgtctccgcc gatgcttttc cccggagcga cgtctgcaag gttcccttt gatgccaccc
7321 agccgagggc ttgtgcttct gattttgtaa tgtaattatc aggtagctta tgatatgtct
7381 gaagataatc cgcaaccccg tcaaacgtgt tgataacctg tgccatgttc ccgtttgata
7441 cctgaatttt ggccattctc ataaatcttc taaaaacagc agaactgact attcaaagaa
7501 agtagaaccc acagaaagta atcaaagtag tttgattaaa tgcgttgtgt atcatcgcag
7561 cccctgctac ggatatttat aggaaaggtt tgagagcaat gtgtgcagca agttgtgtgt
7621 gaatcacctg cttccatggc ggaggataaa taatttagtc acgcatttag ttgaacgtaa
7681 ctactaactc ctctaccgct aatcattctt cttttgcccg ggcaagttca acaacaaccc
7741 cacaatcacg cttcctgtat tttgttttgt tttcaaaaca atagaattca cttttactg
7801 ccaaaattat gttttactcg agagcccggg ctcctgcagg taccttaatt aaaagtttaa
7861 actatcagtg tttgacagga tatattggcg ggtaaaccta agagaaaaga gcgtttatta
7921 gaataatcgg atatttaaaa gggcgtgaaa aggtttatcc gttcgtccat ttgtatgtgc
7981 atgccaacca cagggttccc cagatc
```

Figure 2A

```
LOCUS       pWVCZ20       13001 bp    DNA    circular
SOURCE
  ORGANISM
COMMENT     This file is created by Vector NTI
            http://www.informaxinc.com/
COMMENT     VNTDATE|350136453|
COMMENT     VNTDBDATE|350142683|
COMMENT     VNTNAME|pWVCZ20|
COMMENT     VNTAUTHORNAME|Demo User|
FEATURES             Location/Qualifiers
     promoter        6650..7957
                     /vntifkey="29"
                     /label=UBQ10\promoter
     promoter        2863..4262
                     /vntifkey="29"
                     /label=PrAG\promoter
     CDS             4263..6324
                     /vntifkey="4"
                     /label=GUS(INT)
     misc_feature    98..2841
                     /vntifkey="21"
                     /label=AtAGenh
     misc_feature    1..25
                     /vntifkey="21"
                     /label=Right\Border
     misc_feature    9374..9398
                     /vntifkey="21"
                     /label=Left\Border
     CDS             7958..9018
                     /vntifkey="4"
                     /label=NPT\II\(kanR)
     terminator      9037..9367
                     /vntifkey="43"
                     /label=Nos-T
     terminator      6331..6593
                     /vntifkey="43"
                     /label=Nos-T
BASE COUNT      3662 a      2918 c      2826 g      3595 t
ORIGIN
        1 gtttacccgc caatatatcc tgtcaaacac tgatagttta aactttaat taaggtacct
       61 gcaggagccc gggctgcagg aattcgatat caagcttgat agggtcaaat cgaccacttg
      121 cacagttaag tgattctaat acgaaacctt aaaagcaaac atcggttctt ttgagtcaga
      181 agaaatgcaa cttaatgtga cacatgatgt gaagaaaaaa caaagtaat ataagaaaag
      241 ggaacaatta aatagttaat aaaatatttc cttaaagttg taacaaataa agaatcattt
      301 tatgaaacaa tatgaaccct aaataaatta aaattcctct gaaaccttaa atttatcgag
      361 ctagtgattg gctgccaact gccatgctgg caaaattaga gtgacatgat tggtctgaac
      421 atgtctaggg tttcagacat gtgacatgtg tcaacaaccc attaacacat tgggtataaa
      481 tccaatagac atttgatagt attaaaattg taaccattgg attaaattta aacgtgatgg
      541 atgtaactaa atgacttgtc cgagtaacat cacaacgttc catactttcc ttatttggaa
      601 tataattaaa tttaccattt attcttttt cttgagtttc ctgtatatgt acttgtacat
      661 agatatatat gcacaaatac gtattacaat gacatattat agactttgat gtctgaactc
      721 tcaaccttct cgatggagag atcatgaccg tagatttttt tggatcgtag aaggcagacc
      781 aaactcttaa actattggat ccgtactaaa aatctcactt tcctctcagt acccataatg
      841 agagagaaaa tgataaaaat ccctaaacatt attctctctc tagaaaaaa aagatacttc
      901 aaaaagaaag agaaattgca taaatctatc tacaccaaag atgttgaagc aattccaatg
      961 ctatacttct atgccaaatc tatttattca gtgatcatta atctttttac ttccaagaaa
     1021 tatgaacaat ttagtatcct tataatttt gtctctatat atgtaatatg aacattgggt
     1081 attgaccaaa tgagaaatct aatattaaat ggtcaaaagt agtaatatga tgacattttt
     1141 gaatttataa ataggttaca aattaattca ttatgacata aaaccttctt gtcagaagtc
     1201 aagaactgaa actaacaaaa ctttataata aattagtaaa aatacaaatg aaaaataaaa
     1261 agaaataata tctgagtgat gacgtgatca aagattcttt aacaaagaca acaaatctta
     1321 cagacccaaa acctaatctt gcgctcaatt ccaacctctg aaaaaacctc aaaaatctta
     1381 taaagaaaa taaataaaga aacgaaactc tgatttcgta gagtacccat cggatatata
     1441 aaaagaaatt agtaggtaaa tgaagactaa tttttgattga ctgatttaat ttgaagtcgt
     1501 tgttagcttt tcttgttttg gacatgagaa ttatatattt caggacatga gagttgacaa
     1561 ctgtaaacga ttaagaaaat tgatcttta attttcaaac accatttaat cttgacatgt
     1621 tttatgtttt ggtggagaag aaagtaatca cgtgggactc tctactaata agtatttgga
     1681 aattgcgtgt cgaattagag attactagtt tgagtaatgt agttcgaaat gagattagtt
     1741 attttttaatt ttaaaaagag taatttttaag gaataacaaa aaagagtccc cataagctaa
     1801 tttgtcttaa ttacctcctt gtttcattga ctatttgaaa tcttgaaaat tcagttgaaa
     1861 tttcaaatct atgtttcttt tgaccacttc taaactaatc ttagctcata tataattttc
     1921 caaaactaca aaaataacac taacatttaa cattctcaag agaaaacaaa aacaaaaact
     1981 tagataacca tctaaattgt cctacatgta cgtataagtt ccattatttt ctatcactca
```

Figures 2B

```
2041 tataagttaa aatttcatga aaactcaaaa atctagctag tttcaccttta ttcactctca
2101 cttaccatca catgtgtttg tatcaaatat atgatatgat ataattcatg agagagaaag
2161 agagctagag ataagaaagg aaagtaagag aagaagaga agaaaaagag agacacagac
2221 attaacaaca atggaggatg gatgatcaca aaacagaaga tatgacctca tagtccttcc
2281 ttactctctc cccaatttgt ttcccaaaac ttacttttat agtcataaaa atcaagtttt
2341 tacctattac aacaccagat ctataaatat atctaaatct tcaagtactt gttagtaagg
2401 aaaatagaaa gatataagat tttattatta ttataataac agaaatgagt gaagaaagaa
2461 cacccaacaa agtgaatctt agttctacaa aactgaatct aaaactccac attagaaaaa
2521 accctgatgg tttcttattt cttttcattt attatctaac tctcactcag atctccttta
2581 actttgtacc atttccctca cttcatatat ctatatataa caaactctct cttttttattt
2641 aagtcttaag ggaaaattaa tatacacatg aagacaagaa attagatcta caaaattgtt
2701 acaaaaaccc ccgaagtaaa taaaataaac atatcaaaca aatattccca ctaatgttag
2761 tgtgtttata tatatatgtg tgtggaatat gaaggaaaaa agtgaaaaat aatcctaccc
2821 ataagagcat tcaagaagaa gctcgagggt atcgataagc ttaaactcga cagcaaatat
2881 gatttagatt atgacctaga aataagcata gcattaaagc atatacataa caagcggtga
2941 tatactctga ctgccactgt acttgaggaa aggtagtgga ctctgctcag gtacattagt
3001 ttggtaaggt tggcttggct tctgggtaat atgagaagta aagaagtaaa aggtatttga
3061 ctctagtcaa gtacattgga ttgcctttgt cggggcttgg atggcttggg ttcgtgtgag
3121 aagccaacaa tttataagaa atatataaaa taaaaattaa gtgttggaag
3181 tgaaaacggt ggggcagaaa tatacacaga agagtacttt aacaatgcgc aaccaaggca
3241 gattcacaac ttgatttctg gacctcgaat acgagataat ggtggtaaga aataaaggaa
3301 gagtggagcg catttgaaaa tgaatggaga gcgcacaaaa tggaggacga ataaatgaaa
3361 tataatgcaa gggtgcattt ccctattatt tccagaaatg tatatgtggg gtcggcattc
3421 tcatggcgt cgcattcagg gggtgtcata gcggtccttt gattgcagtg tgggagttgc
3481 aacatgtacc aacaaatcca ttcatcccaa aacctaaatt tatcctctcc attactatta
3541 cctacaccta tacctagtaa atatgtcctg ccttgtaact cctccactgc ctgcacacgt
3601 cttagtcaat ccatctgcct tcaaataggc attattttgt tctttcccct ccgactgaaa
3661 ggctatcgac cgaccgaccg ctcatcttct tcttctgcgc aatttttttct gctggatcat
3721 catcattacc atcatcgcca tccccaccat catcatcatg atggtatctc tatctctccc
3781 tggcaatcga ttgtagagga aaggaagagg gaaggggcat atgtattgat caacctaccc
3841 gaaaaaacaa tctgatcagc cctgctaatc ttgcttataa atctcttatc cactgttcaa
3901 tcattcaggt ttcttcccac tttcaagcaa aggcgcccgg attggccgtg ttcttagatt
3961 ttcaggtact taaatggaca atattcccca cctgaagccg ttctgaaaaa gatttgtttg
4021 tagaaacaaa cgattgtaat atttgcttaa gttgagctta aggggtttgg tacctaactt
4081 gccttgtggt tatttgtttc tcagaactcg ggctgcgtcc aactgtagga acgaaccagc
4141 acaagggggtt gcagctttg ctgttgctgt tgcgcccatt gcttttggac tggtattagt
4201 agttgcagct ttgtttttgca tacgctgtga ggatctgtgc gcggaaattt tgtgtacaaa
4261 tcatgttacg tcctgtagaa accccaaccc gtgaaatcaa aaaactcgac ggcctgtggg
4321 cattcagtct ggatcgcgaa aactgtggaa ttggtcagcg ttggtgggaa agcgcgttac
4381 aagaaagccg ggcaattgct gtgccaggca gttttaacga tcagttcgcc gatgcagata
4441 ttcgtaatta tgcgggcaac gtctggtatc agcgcgaagt ctttataccg aaaggttggg
4501 caggccagcg tatcgtgctg cgtttcgatg cggtcactca ttacggcaaa gtgtgggtca
4561 ataatcagga agtgatggag catcagggcg gctatacgcc atttgaagcc gatgtcacgc
4621 cgtatgttat tgccgggaaa agtgtacgta agtttctgct tctacctttg atatatatat
4681 aataattatc attaattagt agtaatataa tatttcaaat attttttttca aaataaaaga
4741 atgtagtata tagcaattgc ttttctgtag tttataagtg tgtatatttt aatttataac
4801 cttttctaata tatgaccaaa atttgttgat gtgcaggtat caccgtttgt gtgaacaacg
4861 aactgaactg gcagactatc ccgccgggaa tggtgattac cgacgaaaac ggcaagaaaa
4921 agcggtctta cttccatgat ttcttttaact atgccggaat ccatcgcagc gtaatgctct
4981 acaccacgcc gaacacctgg gtggacgatc tcaccgtggt gacgcatgtc gcgcaagact
5041 gtaaccacgc gtctgttgac tggcaggtgg tggccaatgg tgatgtcagc gttgaactgc
5101 gtgatgcgga tcaacaggtg gttgcaactg gacaaggcac tagcgggact ttgcaagtgg
5161 tgaatccgca cctctggcaa ccgggtgaag gttatctcta tgaactgtgc gtcacagcca
5221 aaagccagac agagtgtgat atctaccgc ttcgcgtcgg catccggtca gtggcagtga
5281 agggcgaaca gttcctgatt aaccacaaac cgttctactt tactggcttt ggtcgtcatg
5341 aagatgcgga cttgcgtggc aaaggattcg ataacgtgct gatggtgcac gaccacgcat
5401 taatggactg gattggggcc aactcctacc gtacctcgca ttacccttac gctgaagaga
5461 tgctcgactg ggcagatgaa catggcatcg tggtgattga tgaaactgct gctgtcggct
5521 ttaacctctc tttaggcatt ggtttcgaag cgggcaacaa gccgaaagaa ctgtacagcg
5581 aagaggcagt caacggggaa actcagcgaa cgcacttcca gcgattaaga gagctgatag
5641 cgcgtgacaa aaaccaccca agcgtggtga tgtggagtat tgccaacgaa ccggataccc
5701 gtccgcaagg tgcacgggaa tatttcgcgc cactggcgga agcaacgcgt aaactcgacc
5761 cgacgcgtcc gatcacctgc gtcaatgtaa tgttctgcga cgctcacacc gataccatca
5821 gcgatctctt tgatgtgctg tgcctgaacc gttattacgg atggtatgtc caaagcggcg
5881 atttgaaac ggcagagaag gtactggcag gcctgctca gagaactgc
5941 atcagccgat tatcatcacc gaatacggcg tggatacgtt agccgggctg cactcaatgt
6001 acaccgacat gtggagtgaa gagtatcagt gtgcatggct ggatatgtat caccgcgtct
6061 ttgatcgcgt cagcgccgtc gtcggtgaac aggtatggaa tttcgccgat tttgcgacct
6121 cgcaaggcat attgcgcgtt ggcggtaaca agaaagggat cttcactcgc gaccgcaaac
6181 cgaagtcggc ggcttttctg ctgcaaaaac gctggactgg catgaacttc ggtgaaaaac
6241 cgcagcaggg aggcaaacaa tgaatcaaca actctcctgg cgcaccatcg tcggctacag
```

Figure 2C

```
6301 cctcgggaat tgctaccgga gagagagctc gaatttcccc gatcgttcaa acatttggca
6361 ataaagtttc ttaagattga atcctgttgc cggtcttgcg atgattatca tataatttct
6421 gttgaattac gttaagcatg taataattaa catgtaatgc atgacgttat ttatgagatg
6481 ggtttttatg attagagtcc cgcaattata catttaatac gcgatagaaa acaaaatata
6541 gcgcgcaaac taggataaat tatcgcgcgc ggtgtcatct atgttactag atcgggaatt
6601 cctgcagccc gggggatcca ctagttctag agcggccgct tggcgcgccg tcaacggatc
6661 aggatatcct tgtttaagat gttgaactct atggaggttt gtatgaactg atgatctagg
6721 accggataag ttcccttctt catagcgaac ttattcaaag aatgttttgt gtatcattct 6781 tgttacattg ttattaatga aaaaatatta ttggtcattg gactgaacac gagtgttaaa
6841 tatggaccag gccccaaata agatccattg atatatgaat taaataacaa gaataaatcg
6901 agtcaccaaa ccacttgcct tttttaacga gacttgttca ccaacttgat acaaaagtca
6961 ttatcctatg caaatcaata atcatacaaa aatatccaat aacactaaaa aattaaaaga
7021 aatggataat ttcacaatat gttatacgat aaagaagtta cttttccaag aaattcactg
7081 attttataag cccacttgca ttagataaat ggcaaaaaaa aacaaaaagg aaaagaaata
7141 aagcacgaag aattctagaa aatacgaaat acgcttcaat gcagtgggaa ccacggttca
7201 attattgcca attttcagct ccaccgtata tttaaaaaat aaaacgataa tgctaaaaaa
7261 atataaatcg taacgatcgt taaatctcaa cggctggatc ttatgacgac cgttagaaat
7321 tgtggttgag tcagtaataa acggcgtcaa agtggttgca gccggcacac acgagtcgtg
7381 tttatcaact caaagcacaa atactttttcc tcaacctaaa aataaggcaa ttagccaaaa
7441 acaactttgc gtgtaaacaa cgctcaatac acgtgtcatt ttattattag ctattgcttc
7501 accgccttag cttctctgtg acctagtcgt cctcgtcttt tcttcttctt cttctataaa
7561 acaatacccc aagagctctt cttcttcaca attcagattt caatttctca aaatcttaaa
7621 aactttctct caattctctc taccgtgatc aaggtaaatt tctgtgttcc ttattctctc
7681 aaaatcttcg attttgtttt cgttcgatcc caatttcgta tatgttcttt ggtttagatt
7741 ctgttaatct tagatcgaag acgattttct gggtttgatc gttagatatc atcttaattc
7801 tcgattaggg tttcataaat atcatccgat ttgttcaaat aatttgagtt ttgtcgaata
7861 attactcttc gatttgtgat ttctatctag atctggtgtt agtttctagt ttgtgcgatc
7921 gaatttgtcg attaatctga gtttttctga ttaacagatg attgaacaag atggattgca
7981 cgcaggttct ccggccgctt gggtggagag gctattcggc tatgactggg cacaacagac
8041 aatcggctgc tctgatgccg ccgtgttccg gctgtcagcg caggggcgcc cggttctttt
8101 tgtcaagacc gacctgtccg gtgccctgaa tgaactccag gacgaggcag cgcggctatc
8161 gtggctggcc acgacgggcg ttccttgcgc agctgtgctc gacgttgtca ctgaagcggg
8221 aagggactgg ctgctattgg gcgaagtgcc ggggcaggat ctcctgtcat ctcaccttgc
8281 tcctgccgag aaagtatcca tcatggctga tgcaatgcgg cggctgcata cgcttgatcc
8341 ggctacctgc ccattcgacc accaagcgaa acatcgcatc gagcgagcac gtactcggat
8401 ggaagccggt cttgtcgatc aggatgatct ggacgaagag catcaggggc tcgcgccagc
8461 cgaactgttc gccaggctca aggcgcgcat gcccgacggc gaggatctcg tcgtgaccca
8521 tggcgatgcc tgcttgccga atatcatggt ggaaaatggc cgcttttctg gattcatcga
8581 ctgtggccgc ctgggtgtgg cggaccgcta tcaggacata gcgttggcta cccgtgatat
8641 tgctgaagag cttggcggcg aatgggctga ccgcttcctc gtgctttacg gtatcgccgc
8701 tcccgattcg cagcgcatcg ccttctatcg ccttcttgac gagttcttct gagggatcgt
8761 tcaaacattt ggcaataaag tttcttaaga ttgaatcctg ttgccggtct tgcgatgatt
8821 atcatataat ttctgttgaa ttacgttaag catgtaataa ttaacatgta atgcatgacg
8881 ttatttatga gatgggtttt tatgattaga gtcccgcaat tatacattta atacgcgata
8941 gaaaacaaaa tatagcgcgc aaactaggat aaattatcgc gcgcggtgtc atctatgtta
9001 ctagatcgca cgtaggggg atccactagt tctagagcgg ccgtgggcca tcgcctgat
9061 agacggtttt tcgccctttg acgttggagt ccacgttctt taatagtgga ctcttgttcc
9121 aaactggaac aacactcaac cctatctcgg gctattcttt tgatttataa gggattttgc
9181 cgatttcgga accaccatca aacaggattt tcgcctgctg gggcaaacca gcgtggaccg
9241 cttgctgcaa ctctctcagg gccaggcggt gaagggcaat cagctgttgc ccgtctcact
9301 ggtgaaaaga aaaaccaccc cagtacatta aaaacgtccg caatgtgtta ttaagttgtc
9361 taagcgtcaa tttgtttaca ccacaatata gccagccaa cagctccccg
9421 accggcagct cggcacaaaa tcaccactcg atacaggcag cccatcagtc cgggacggcg
9481 tcagcgggag agccgttgta aggcggcaga ctttgctcat gttaccgatg ctattcggaa
9541 gaacggcaac taagctgccg ggtttgaaac acggatgatc tcgcggaggg tagcatgttg
9601 attgtaacga tgacagagcg ttgctgcctg tgatcaaata tcatctccct cgcagagatc
9661 cgaattatca gccttcttat tcatttctcg cttaaccgtg acagttgtct atcggcagtt
9721 cgtagagcgc gccgtgcgtc ccgagcgata ctgagcgaag caagtgcgtc gagcagtgcc
9781 cgcttgttcc tgaaatgcca gtaaagcgct ggctgctgaa ccccagccg gaactgaccc
9841 cacaaggccc tagcgtttgc aatgcaccag gtcatcattg acccaggcgt gttccaccag
9901 gccgctgcct cgcaactcct gccgaccctgc tcgcgccact tcttcacgcg
9961 ggtggaatcc gatccgcaca tgaggcggaa ggtttccagc ttgagcgggt acggctcccg
10021 gtgcgagctg aaatagtcga acatccgtcg ggccgtcggc gacagcttgc ggtacttctc
10081 ccatatgaat ttcgtgtagt ggtcgccagc aaacagcacg acgatttcct cgtcgatcag
10141 gacctggcaa cgggacgttt tcttgccacg gtccaggacg cggaagcggt gcagcagcga
10201 cacccgattcc aggtgcccaa cgccgtccga cgtgaagccc atcgccgtg cctgtaggcg
10261 cgacaggcat tcctcggcct tcgtgtaata ccggccattg atcgaccagc ccaggtcctg
10321 gcaaagctcg tagaacgtga aggtgatcgg ctccgcgata ggggtgcgct tcgcgtactc
10381 caacacctgc tgccacacca gttcgtcatc gtcggcccgc agctcgacgc cggtgtaggt
10441 gatcttcacg tccttgttga cgtggaaaat gaccttgtct tgcagcgct cgcgcgggat
10501 tttcttgttg cgcgtggtga acagggcaga gcgggccgtg tcgtttggca tcgctcgcat
10561 cgtgtccggc cacggcgcaa tatcgaacaa ggaaagctgc atttccttga tctgctgctt
10621 cgtgtgtttc agcaacgcgg cctgcttggc ctcgctgacc tgttttgcca ggtcctcgcc
```

Figure 2D

```
10681 ggcggttttt cgcttcttgg tcgtcatagt tcctcgcgtg tcgatggtca tcgacttcgc
10741 caaacctgcc gcctcctgtt cgagacgacg cgaacgctcc acggcggccg atggcgcggg
10801 cagggcaggg ggagccagtt gcacgctgtc gcgctcgatc ttggccgtag cttgctggac
10861 catcgagccg acggactgga aggtttcgcg gggcgcacgc atgacggtgc ggcttgcgat
10921 ggtttcggca tcctcggcgg aaaaccccgc gtcgatcagt tcttgcctgt atgccttccg
10981 gtcaaacgtc cgattcattc accctccttg cgggattgcc ccgactcacg ccggggcaat
11041 gtgcccttat tcctgatttg acccgcctgg tgccttggtg tccagataat ccaccttatc
11101 ggcaatgaag tcggtcccgt agaccgtctg gccgtccttc tcgtacttgg tattccgaat
11161 cttgcctgc acgaatacca gcgaccctt gcccaaatac ttgccgtggg cctcggcctg
11221 agagccaaaa cacttgatgc ggaagaagtc ggtgcgctcc tgcttgtcgc cggcatcgtt
11281 gcgccacatc taggtactaa aacaattcat ccagtaaaat ataatatttt atttctccc
11341 aatcaggctt gatccccagt aagtcaaaaa atagctcgac atactgttct tcccgatat
11401 cctccctgat cgacggacg cagaaggcaa tgtcatacca cttgtccgcc ctgccgcttc
11461 tccaagatc aataaagcca cttactttgc catctttcac aaagatgttg ctgtctccca
11521 ggtcgccgtg ggaaaagaca agttcctctt cgggcttttc cgtctttaaa aaatcatca
11581 gctcgcgcgg atctttaaat ggagtgtctt cttcccagtt ttcgcaatcc acatcggcca
11641 gatcgttatt cagtaagtaa tccaattcgg ctaagcggct gtctaagcta ttcgtatagg
11701 gacaatccga tatgtcgatg gagtgaaaga gcctgatgca ctccgcatac agctcgataa
11761 tcttttcagg gctttgttca tcttcatact cttccgagca aaggacgcca tcggcctcac
11821 tcatgagcag attgctccag ccatcatgcc gttcaaagtg caggacctt ggaacaggca
11881 gctttccttc cagccatagc atcatgtcct tttccccgttc cacatcatag gtggtccctt
11941 tataccggct gtccgtcatt tttaaatata ggttttcatt ttctcccacc agcttatata
12001 ccttagcagg agacattcct tccgtatctt ttacgcagcg gtattttcg atcagttttt
12061 tcaattccgg tgatattctc attttagcca tttattattt ccttcctctt ttctacagta
12121 tttaaagata ccccaagaag ctaattataa caagacgaac tccaattcac tgttccttgc
12181 attctaaaac cttaaatacc agaaacagc tttttcaaag ttgtttcaa agttggcgta
12241 taacatagta tcgacggagc cgattttgaa accacaatta tggactgcca gcgctgccat
12301 tttggggtg aggccgttcg cggccgaggg gcgcagcccc tgggggatg ggaggcccgc
12361 gttagcgggc cgggagggtt cgagaagggg gggcacccc cttcggcgtg cgcggtcacg
12421 cgcacagggc gcagccctgg ttaaaaacaa ggtttataaa tattggttta aaagcaggtt
12481 aaaagacagg ttagcggtgg ccgaaaaacg ggcggaaacc cttgcaaatg ctggattttc
12541 tgcctgtgga cagcccctca aatgtcaata ggtgcgcccc tcatctgtca gcactctgcc
12601 cctcaagtgt caaggatcgc gcccctcatc tgtcagtagt cgcgcccctc aagtgtcaat
12661 accgcagggc acttatcccc aggcttgtcc acatcatctg tgggaaactc gcgtaaaatc
12721 aggcgttttc gccgatttgc gaggctggcc agctccacgt cgccggccga aatcgagcct
12781 gcccctcatc tgtcaacgcc gcgcgggtg agtcggcccc tcaagtgtca acgtccgccc
12841 ctcatctgtc agtgagggcc aagttttccg cgaggtatcc acaacgccgg cggatctggg
12901 gaaccctgtg gttggcatgc acatacaaat ggacgaacgg ataaacctt tcacgccctt
12961 ttaaatatcc gattattcta ataaacgctc ttttctctta g
```

Figure 3A

```
LOCUS        pWVCZ23      8534 bp      DNA      circular
SOURCE
  ORGANISM
COMMENT      This file is created by Vector NTI
             http://www.informaxinc.com/
COMMENT      VNTDATE|350136839|
COMMENT      VNTDBDATE|350143806|
COMMENT      VNTNAME|pWVCZ23|
COMMENT      VNTAUTHORNAME|Demo User|
FEATURES             Location/Qualifiers
     misc_feature    1..25
                     /vntifkey="21"
                     /label=Right\Border
     misc_feature    4423..4447
                     /vntifkey="21"
                     /label=Left\Border
     promoter        103..1502
                     /vntifkey="29"
                     /label=PrAG\promoter
     CDS             1503..1936
                     /vntifkey="4"
                     /label=barnaseE73G
     terminator      1943..2210
                     /vntifkey="43"
                     /label=Nos-T
     promoter        2227..2565
                     /vntifkey="30"
                     /label=Nos\Promoter CDS             2586..3479
                     /vntifkey="4"
                     /label=NPT\II\(kanR)
     terminator      3764..4066
                     /vntifkey="43"
                     /label=Nos-T
BASE COUNT     2075 a      2191 c      2113 g      2155 t
ORIGIN
        1 gtttacccgc caatatatcc tgtcaaacac tgatagttta aacttttaat taaggtacct
       61 gcaggagccc gggctctcga ggtcgacggt atcgataagc ttaaactcga cagcaaatat
      121 gatttagatt atgacctaga aataagcata gcattaaagc atatacataa caagcggtga
      181 tatactctga ctgccactgt acttgaggaa aggtagtgga ctctgctcag gtacattagt
      241 ttggtaaggt tggcttggct tctgggtaat atgagaagta aagaagtaaa aggtatttga
      301 ctctagtcaa gtacattgga ttgcctttgt cggggcttgg atggcttggg ttcgtgtgag
      361 aagccaacaa tttataagaa atatatataaa taaaaaataa aaaaatttaa gtgttggaag
      421 tgaaaacggt ggggcagaaa tatacacaga agagtacttt aacaatgcgc aaccaaggca
      481 gattcacaac ttgatttctg gacctcgaat acgagataat ggtggtaaga aataaaggaa
      541 gagtggagcg catttgaaaa tgaatggaga gcgcacaaaa tggaggacga ataaatgaaa
      601 tataatgcaa gggtgcattt ccctattatt tccagaaatg tatatgtggg gtcggcattc
      661 tcatgggcgt cgcattcagg gggtgtcata gcggtccttt gattgcagtg tgggagttgc
      721 aacatgtacc aacaaatcca ttcatcccaa aacctaaatt tatcctctcc attactatta
      781 cctacaccta tacctagtaa atatgtcctg ccttgtaact cctccactgc ctgcacacgt
      841 cttagtcaat ccatctgcct tcaaataggc attattttgt tctttcccct ccgactgaaa
      901 ggctatcgac cgaccgaccg ctcatctcct tcttctgcgc aattttttct gctggatcat
      961 catcattacc atcatcgcca tccccaccat catcatcatg atggtatctc tatctctccc
     1021 tggcaatcga ttgtagagga aaggaagagg gaagggcat atgtattgat caacctaccc
     1081 gaaaaaacaa tctgatcagc cctgctaatc ttgcttataa atctcttatc cactgttcaa
     1141 tcattcaggt ttcttcccac tttcaagcaa aggcgcccgg attggccgtg ttcttagatt
     1201 ttcaggtact taaatggaca atattcccca cctgaagccg ttctgaaaaa gatttgtttg
     1261 tagaaacaaa cgattgtaat atttgcttaa gttgagctta aggggttttgg tacctaactt
     1321 gccttgtggt tatttgtttc tcagaactcg ggctgcgtcc aactgtagga acgaaccagc
     1381 acaaggggtt gcagcttttg ctgttgctgt tcgcccatt gctttgtggc tggtattagt
     1441 agttgcagct ttgttttgca tacgctgtga ggatctgtgc gcggaaattt tgtgtacaaa
     1501 tcatggcaca ggttatcaac acgtttgacg gggttgcgga ttatcttcag acatatcata
     1561 agctacctga taattacatt acaaaatcag aagcacaagc cctcggctgg gtggcatcaa
     1621 aaggaacct tgcagacgtc gctccgggga aaagcggag cggagacatc ttctcaaaca
     1681 gggaaggcaa actccgggc aaaagcggac gaacatggcg tgaagcggat attaactata
     1741 catcaggctt cagaaattca gaccggattc tttactcaag cgactggctg atttacaaaa
     1801 caacggacca ttatcagacc tctacaaaaa tcgataacg aaaaaaacgg cttccctgcg
     1861 ggaggccgtt tttttcagct ttacataaag tgtgtaataa attttcttc aaactctgat
     1921 cggtcaattg cactttgagc tcgaatttcc ccgatcgttc aaacatttgg caataaagtt
     1981 tcttaagatt gaatcctgtt gccggtcttg cgatgattat catataattt ctgttgaatt
     2041 acgttaagca tgtaataatt aacatgtaat gcatgacgtt atttatgaga tgggttttta
     2101 tgattagagt cccgcaatta tacatttaat acgcgataga aaacaaaata tagcgcgcaa
```

Figure 3B

```
2161 actaggataa attatcgcgc gcggtgtcat ctatgttact agatcgggaa ggcgcgccgc
2221 ggccgcaaca ctgatagttt aaactgaagg cgggaaacga caatctgatc atgagcggag
2281 aattaaggga gtcacgttat gacccccgcc gatgacgcgg gacaagccgt tttacgtttg
2341 gaactgacag aaccgcaacg ttgaaggagc cactcagccg cgggtttctg gagtttaatg
2401 agctaagcac atacgtcaga aaccattatt gcgcgttcaa aagtcgccta aggtcactat
2461 cagctagcaa atatttcttg tcaaaaatgc tccactgacg ttccataaat tcccctcggt
2521 atccaattag agtctcatat tcactctcaa tccaaataat ctgcaccgga tctggatcgt
2581 ttcgcatgat tgaacaagat ggattgcacg caggttctcc ggccgcttgg gtggagaggc
2641 tattcggcta tgactgggca caacagacaa tcggctgctc tgatgccgcc gtgttccggc
2701 tgtcagcgca ggggcgcccg gttcttttg tcaagaccga cctgtccggt gccctgaatg
2761 aactgcagga cgaggcagcg cggctatcgt ggctggccaa gacgggcgtt ccttgcgcag
2821 ctgtgctcga cgttgtcact gaagcgggaa gggactggct gctattgggc gaagtgccgg
2881 ggcaggatct cctgtcatct caccttgctc ctgccgagaa agtatccatc atggctgatg
2941 caatgcggcg gctgcatacg cttgatccgg ctacctgccc attcgaccac caagcgaaac
3001 atcgcatcga gcgagcacgt actcgatgg aagccggtct tgtcgatcag gatgatctgg
3061 acgaagagca tcagggctc gcgccagccg aactgttcgc caggctcaag gcgcgcatgc
3121 ccgacggcga tgatctcgtc gtgacccatg gcgatgcctg cttgccgaat atcatggtgg
3181 aaaatggccg ctttctgga ttcatcgact gtggccgct gggtgtggcg gaccgctatc
3241 aggacatagc gttggctacc cgtgatattg ctgaagagct tggcggcgaa tgggctgacc
3301 gcttcctcgt gctttacggt atcgccgctc ccgattcgca gcgcatcgcc ttctatcgcc
3361 ttcttgacga gttcttctga gcgggactct ggggttcgaa atgaccgacc aagcgacgcc
3421 caacctgcca tcacgagatt tcgattccac cgccgccttc tatgaaaggt tgggcttcgg
3481 aatcgttttc cgggacgccg gctggatgat cctccagcgc ggggatctca tgctggagtt
3541 cttcgcccac gggatctctg cggaacaggc ggtcgaaggt gccgatatca ttacgacagc
3601 aacggccgac aagcacaat ccacgatcct gagcgacaat atgatcgggc ccggcgtcca
3661 catcaacggg gtcggcggcg actgccagg caagaccgag atgcaccgcg atatcttgct
3721 gcgttcggat attttcgtgg agttccccgc acagacccgg atgatcccg atcgttcaaa
3781 catttggcaa taaagttttct taagattgaa tcctgttgcc ggtcttgcga tgattatcat
3841 ataatttctg ttgaattaac ttaagcatgt aataattaac atgtaatgca tgacgttatt
3901 tatgagatgg gtttttatga ttagagtccc gcaattatac atttaatacg cgatagaaaa
3961 caaaatatag cgcgcaaact aggataaatt atcgcgcgcg gtgtcatcta tgttactaga
4021 tcgggcctcc tgtcaatgct ggcggcggct ctggtggtgg ttctggtgga tccactagtt
4081 ctagagcggc cgtgggccat cgccctgata gacggttttt cgcccttgga cgttggagtc
4141 cacgttcttt aatagtggac tcttgttcca aactgaaca acactcaacc ctatctcggg
4201 ctattctttt gatttataag ggattttgcc gatttcggaa ccaccatcaa acaggatttt
4261 cgcctgctgg ggcaaaccag cgtggaccgc ttgctgcaac tctctcaggg ccaggcggtg
4321 aagggcaatc agctgttgcc cgtctcactg gtgaaaagaa aaaccacccc agtacattaa
4381 aaacgtccgc aagtgttat taagttgtct aagcgtcaat ttgtttacac cacaatatat
4441 cctgccacca gccagccaac agctccccga ccggcagctc ggcacaaaat caccactcga
4501 tacaggcagc ccatcagtcc gggacggcgt cagcgggaga gccgttgtaa ggcggcagac
4561 tttgctcatg ttaccgatgc tattcggaag aacggcaact aagctgccgg gtttgaaaca
4621 cggatgatct cgcggagggt agcatgttga ttgtaacgat gacagagcgt tgctgcctgt
4681 gatcaaatat catctccctc gcagagatt gaattatcga ccttcttatt catttctcgc
4741 ttaaccgtga cagttgtcta tcggcagttc gtagagcgcg ccgtgcgtcc cgagcgatac
4801 tgagcgaagc aagtgcgtcg agcagtgccc gcttgttcct gaaatgccag taaagcgctg
4861 gctgctgaac cccagccgg aactgacccc acaaggccct agcgtttgca atgcaccagg
4921 tcatcattga cccaggcgtg ttccaccagg ccgctgcctc gcaactcttc gcaggcttcg
4981 ccgacctgct cgcgccactt cttcacgcgg gtggaatccg atccgcacat gaggcggaag
5041 gtttccagct tgagcgggta cggctcccgg tgcgagctga aatagtcgaa catccgtcgg
5101 gccgtcggcg acagcttgcg gtacttctcc catatgaatt tcgtgtagtg gtcgccagca
5161 aacagcacga cgatttcctc gtcgatcagg acctggcaac gggacgtttt cttgccacgg
5221 tccaggacgc ggaagcggtg cagcagcgac accgattcca ggtgcccaac ggtcggac
5281 gtgaagccca tcgccgtcgc ctgtaggcgc gacaggcatt cctcggcctt cgtgtaatac
5341 cggccattga tgaccagcc caggtcctgg caaagctcgt agaacgtgaa ggtgatcggc
5401 tcgccgatag gggtgcgctt cgcgtactcc aacacctgct gccacaccag ttcgtcatcg
5461 tcggccgca gctcgacgcc ggtgtaggtg atcttcacgt ccttgttgac gtggaaatg
5521 accttgtttt gcagcgcctc gcgcggatt ttcttgttcg gcgtggtgaa cagggcagag
5581 cgggccgtgt cgtttggcat cgctcgcatc gtgtccggcc acggcgcaat atcgaacaag
5641 gaaagctgca tttccttgat ctgctgcttc gtgtgtttca gcaacgcggc ctgcttggcc
5701 tcgctgacct gttttgccag gtcctcgccg gcggttttc gcttcttggt cgtcatagtt
5761 cctcgcgtgt cgatggtcat cgacttcgtc aaacctgccg cctcctgttc gagacgacgc
5821 gaacgctcca cggcggccga tggcgcgggc agggcagggg gagccagttg cacgctgtcg
5881 cgctcgatct tggccgtagc ttgctggacc atcgagccga cggactggaa ggtttcgcgg
5941 ggcgcacgca tgacggtgcg gcttgcgatg gtttcggcat cctcggcgga aaacccgcgc
6001 tcgatcagtt cttgcctgta tgccttccgg tcaaacgtcc gattcattca ccctccttgc
6061 gggattgccc cgactcacgc cggggcaatg tgcccttatt cctgatttga cccgcctggt
6121 gccttggtgt ccagataatc cacccttatcg gcaatgaagt cggtcccgta gaccgtctgg
6181 ccgtccttct cgtacttggt attccgaatc ttgccctgca cgaataccag cgacccctg
6241 cccaaatact tgccgtgggc ctcggcctga gagccaaaac acttgatgcg gaagaagtcg
6301 gtgcgctcct gcttgtcgcc ggcctcgttg cgcacatcct aggtactaaa acaattcatc
6361 cagtaaaata taatatttta ttttctccca atcaggcttg atccccagta agtcaaaaaa
6421 tagctcgaca tactgttctt cccgatatc ctccctgatc gaccgacgc agaaggcaat
6481 gtcataccac ttgtccgccc tgccgcttct cccaagatca taaagccac ttactttgcc
6541 atctttcaca aagatgttgc tgtctcccag gtcgccgtgg gaaaagacaa gttcctcttc
```

Figure 3C

```
6601 gggctttttcc gtctttaaaa aatcatacag ctcgcgcgga tctttaaatg gagtgtcttc
6661 ttcccagttt tcgcaatcca catcggccag atcgttattc agtaagtaat ccaattcggc
6721 taagcggctg tctaagctat tcgtataggg acaatccgat atgtcgatgg agtgaaagag
6781 cctgatgcac tccgcataca gctcgataat cttttcaggg ctttgttcat cttcatactc
6841 ttccgagcaa aggacgccat cggcctcact catgagcaga ttgctccagc catcatgccg
6901 ttcaaagtgc aggacctttg gaacaggcag ctttccttcc agccatagca tcatgtcctt
6961 ttcccgttcc acatcatagg tggtcccttt ataccggctg tccgtcattt ttaaatatag
7021 gttttcattt tctcccacca gcttatatac cttagcagga gacattcctt ccgtatcttt
7081 tacgcagcgg tattttttcga tcagttttttt caattccggt gatattctca ttttagccat
7141 ttattatttc cttcctcttt tctacagtat ttaaagatac cccaagaagc taattataac
7201 aagacgaact ccaattcact gttccttgca ttctaaaacc ttaaatacca gaaaacagct
7261 ttttcaaagt tgtttttcaaa gttggcgtat aacatagtat cgacggagcc gattttgaaa
7321 ccacaattat gggagagacc ataatgtggt ccaatttgca gcagccgtcc gagacaggag
7381 gacatcgtcc agctgaaacc ggggcagaat ccggccattt ctgaagagaa aaatggtaaa
7441 ctgatagaat aaaatcataa gaaaggagcc gcacatgaaa aaagcagtca ttaacgggga
7501 acaaatcaga agtatcagcg acctccacca gacattgaaa aaggagcttg cccttccgga
7561 atactacggt gaaaacctgg acgctttatg ggattgtctg accggatggg tggagtaccc
7621 gctcgttttg gaatggaggc agtttgaaca aagcaagcag ctgactgaaa atggcgccga
7681 gagtgtgctt caggttttcc gtgaagcgaa agcggaaggc tgcgacatca ccatcatact
7741 ttcttaatac gatcaatggg agatgaacaa tatggaaaca caaccacaa ttatgtctct
7801 cagcccacaa ttatggactg ccagcgctgc cattttttggg gtgaggccgt tcgcggccga
7861 ggggcgcagc ccctggggggg atgggaggcc cgcgttagcg ggccgggagg gttcgagaag
7921 gggggcgcacc cccccttcggc gtgcgcggtc acgcgcacag ggcgcagccc tggttaaaaa
7981 caaggtttat aaatattggt ttaaaagcag gttaaaagac aggttagcgg tggccgaaaa
8041 acgggcggaa acccttgcaa atgctggatt ttctgcctgt ggacagcccc tcaaatgtca
8101 ataggtgcgc ccctcatctg tcagcactct gcccctcaag tgtcaaggat cgcgcccctc
8161 atctgtcagt agtcgcgccc ctcaagtgtc aataccgcag ggcacttatc cccaggcttg
8221 tccacatcat ctgtgggaaa ctcgcgtaaa atcaggcgtt ttcgccgatt tgcgaggctg
8281 gccagctcca cgtcgccggc cgaaatcgag cctgcccctc atctgtcaac gccgcgccgg
8341 gtgagtcggc ccctcaagtg tcaacgtccg cccctcatct gtcagtgagg gccaagtttt
8401 ccgcgaggta tccacaacgc cggcggatct ggggaaccct gtggttggca tgcacataca
8461 aatggacgaa cggataaacc ttttcacgcc cttttaaata tccgattatt ctaataaacg
8521 ctctttttctc ttag
```

Figure 4A

```
LOCUS       pWVCZ24      11300 bp    DNA     circular
SOURCE
  ORGANISM
COMMENT     This file is created by Vector NTI
            http://www.informaxinc.com/
COMMENT     VNTDATE|350136867|
COMMENT     VNTDBDATE|350144320|
COMMENT     VNTNAME|pWVCZ24|
COMMENT     VNTAUTHORNAME|Demo User|
FEATURES             Location/Qualifiers
     misc_feature    98..2841
                     /vntifkey="21"
                     /label=AtAGenh
     misc_feature    1..25
                     /vntifkey="21"
                     /label=Right\Border
     promoter        2869..4268
                     /vntifkey="29"
                     /label=PrAG\promoter
     CDS             4269..4702
                     /vntifkey="4"
                     /label=barnaseE73G
     terminator      4709..4976
                     /vntifkey="43"
                     /label=Nos-T
     promoter        4993..5331
                     /vntifkey="30"
                     /label=Nos\Promoter
     CDS             5352..6316
                     /vntifkey="4"
                     /label=NPT\II\(kanR)
     terminator      6531..6833
                     /vntifkey="43"
                     /label=Nos-T
     misc_feature    7189..7213
                     /vntifkey="21"
                     /label=Left\Border
BASE COUNT     3164 a    2619 c    2490 g    3027 t
ORIGIN
        1 gtttacccgc caatatatcc tgtcaaacac tgatagttta aactttaat taaggtacct
       61 gcaggagccc gggctgcagg aattcgatat caagcttgat agggtcaaat cgaccacttg
      121 cacagttaag tgattctaat acgaaacctt aaaagcaaac atcggttctt ttgagtcaga
      181 agaaatgcaa cttaatgtga cacatgatgt gaagaaaaaa caaagtaat ataagaaaag
      241 ggaacaatta aatagttaat aaaatattc cttaaagttg taacaaataa agaatcattt
      301 tatgaaacaa tatgaaccct aaataaatta aaattcctct gaaaccttaa atttatcgag
      361 ctagtgattg gctgccaact gccatgctgg caaaattaga gtgacatgat tggtctgaac
      421 atgtctaggg tttcagacat gtgacatgtg tcaacaaccc attaacacat tgggtataaa
      481 tccaatagac atttgatagt attaaaattg taaccattgg attaaattta aacgtgatgg
      541 atgtaactaa atgacttgtc cgagtaacat cacaacgttc catactttcc ttatttggaa
      601 tataattaaa tttaccattt attctttttt cttgagtttc ctgtatatgt acttgtacat
      661 agatatatat gcacaaatac gtattacaat gacatattat agactttgat gtctgaactc
      721 tcaacctct cgatggagag atcatgaccg tagattttt tggatcgtag aaggcagacc
      781 aaactcttaa actattggat ccgtactaaa aatctcactt tcctctcagt acccataatg
      841 agagagaaaa tgataaaaat ccctaaacaa attctctctc tagaaaaaaa aagatacttc
      901 aaaagaaag agaaattgca taaatctatc tacaccaaag atgttgaagc aattccaatg
      961 ctatacttct atgccaaatc tatttattca gtgatcatta atctttttac ttccaagaaa
     1021 tatgaacaat ttagtatcct tataattttt gtctctatat atgtaatatg aacattgggt
     1081 attgaccaaa tgagaaatct aatattaaat ggtcaaaagt agtaatatga tgacatttt
     1141 gaatttataa ataggttaca aattaattca ttatgacata aaaccttctt gtcagaagtc
     1201 aagaactgaa actaacaaaa ctttataata aattagtaaa aatacaaatg aaaaataaaa
     1261 agaaataata tctgagtgat gacgtgatca aagattcttt aacaaagaca acaaatctta
     1321 cagacccaaa acctaatctt gcgctcaatt ccaacctctg aaaaacctc aaaaatctta
     1381 taaaagaaaa taaataaaga aacgaaactc tgatttcgta gagtacccat cggatatata
     1441 aaaagaaatt agtaggtaaa tgaagactaa tttttgattga ctgattaat ttgaagtcgt
     1501 tgttagcttt tcttgttttg gacatgagaa ttatatattt caggacatga gagttgacaa
     1561 ctgtaaacga ttaagaaaat tgatctttta attcaaac accatttaat cttgacatgt
     1621 tttatgtttt ggtgggagaag aaagtaatca cgtgggactc tctactaata agtatttgga
     1681 aattgcgtgt cgaattagag attactagtt tgagtaatgt agttcgaaat gagattagtt
     1741 attttaaatt ttaaaaagag taattttaag gaataacaaa aaagagtccc cataagctaa
     1801 tttgtcttaa ttacctcctt gtttcattga ctatttgaaa tcttgaaat tcagttgaaa
     1861 tttcaaatct atgtttcttt tgaccacttc taaactaatc ttagctcata tataattttc
     1921 caaaactaca aaaataaacc taacatttaa cattctcaag agaaaacaaa aacaaaaact
     1981 tagataacca tctaaattgt cctacatgta cgtataagtt ccattatttt ctatcactca
```

Figure 4B

```
2041 tataagttaa aatttcatga aaactcaaaa atctagctag tttcaccttt ttcactctca
2101 cttaccatca catgtgtttg tatcaaatat atgatatgat ataattcatg agagagaaag
2161 agagctagag ataagaaagg aaagtaagag aaagaagaga agaaaaagag agacacagac
2221 attaacaaca atggaggatg gatgatcaca aaacagaaga tatgacctca tagtccttcc
2281 ttactctctc cccaatttgt ttcccaaaac ttactttat agtcataaaa atcaagtttt
2341 tacctattac aacaccagat ctataaatat atctaaatct tcaagtactt gttagtaagg
2401 aaaatagaaa gatataagat tttattatta ttataataac agaaatgagt gaagaaagaa
2461 cacccaacaa agtgaatctt agttctacaa aactgaatct aaaactccac attagaaaaa
2521 accctgatgg tttcttattt cttttcattt attatctaac tctcactcag atctccttta
2581 actttgtacc atttccctca cttcatatat ctatatataa caaactctct cttttattt
2641 aagtcttaag ggaaaattaa tatacacatg aagacaagaa attagatcta caaaattgtt
2701 acaaaaaccc ccgaagtaaa taaaataaac atatcaaaca aatattccca ctaatgttag
2761 tgtgtttata tatatatgtg tgtgaatat gaaggaaaaa agtgaaaat aatcctaccc
2821 ataagagcat tcaagaagaa gctcgaggtc gacggtatcg ataagcttaa actcgacagc
2881 aaatatgatt tagattatga cctagaaata agcatagcat taaagcatat acataacaag
2941 cggtgatata ctctgactgc cactgtactt gaggaaaggt agtggactct gctcaggtac
3001 attagtttgg taaggttggc ttggcttctg ggtaatatga gaagtaaaga agtaaaaggt
3061 atttgactct agtcaagtac attggattgc ctttgtcggg gcttggatgg cttgggttcg
3121 tgtgagaagc caacaattta taagaaatat ataaaataaa aaataaaaaa atttaagtgt
3181 tggaagtgaa aacggtgggg cagaaatata cacagaagag tactttaaca atgcgcaacc
3241 aaggcagatt cacaacttga tttctggacc tcgaatacga gataatggtg gtaagaaata
3301 aaggaagagt ggagcgcatt tgaaaatgaa tggagagcgc acaaaatgag ggacgaataa
3361 atgaaatata atgcaagggt gcatttccct attatttcca gaaatgtata tgtggggtcg
3421 gcattctcat gggcgtcgca ttcaggggt gtcatagcgg tcctttgatt gcagtgtggg
3481 agttgcaaca tgtaccaaca aatccattca tcccaaaacc taaatttatc ctctccatta
3541 ctattaccta cacctatacc tagtaaatat gtcctgcctt gtaactcctc cactgcctgc
3601 acacgtctta gtcaatccat ctgccttcaa ataggcatta ttttgttctt tccccctccga
3661 ctgaaaggct atcgaccgac cgaccgctca tcttcttctt ctgcgcaatt ttttctgctg
3721 gatcatcatc attaccatca tcgccatccc caccatcatc atcatgatgt tatctctatc
3781 tctccctggc aatcgattgt agaggaaagg aagagggaag gggcatatgt attgatcaac
3841 ctaccccgaaa aaacaatctg ttacagccctg ctaatcttgc ttataaatct cttatccact
3901 gttcaatcat tcaggtttct tcccacttc aagcaaaggc gcccggattg gccgtgttct
3961 tagattttca ggtacttaaa tggacaatat tccccacctg aagcacgttct gaaaaagatt
4021 tgtttgtaga aacaaacgat tgtaatattt gcttaagttg agcttaaggg gtttggtacc
4081 taacttgcct tgtggttatt tgtttctcag aactcgggct gcgtccaact gtaggaacga
4141 accagcacaa ggggttgcag cttttgctgt tgctgttgcg cccattgctt ttggactggt
4201 attagtagtt gcagctttgt tttgcatacg ctgtgaggat ctgtgcgcgg aaattttgtg
4261 tacaaatcat ggcacaggtt atcaacacgt ttgacggggt tgcggattat cttcagacat
4321 atcataagct acctgataat tacattacaa attcagaagc acaagccctc ggctgggtgg
4381 catcaaaagg gaaccttgca gacgtcgctc cggggaaaag catcggcgga gacatcttct
4441 caaacaggga aggcaaactc ccgggcaaaa gcggacgaac atggcgtgaa gcggatatta
4501 actatacatc aggcttcaga aattcagacc ggattcttta ctcaagcgac tggctgattt
4561 acaaaacaac ggaccattat cagacctcta caaaaatcag ataacgaaaa aaacggcttc
4621 cctgcgggag gccgtttttt tcagctttac ataaagtgtg taataaattt ttcttcaaac
4681 tctgatcggt caattgcact ttgagctcga atttcccga tcgttcaaac atttggcaat
4741 aaagtttctt aagattgaat cctgttgccg gtcttgcgat gattatcata taatttctgt
4801 tgaattacgt taagcatgta ataattaaca tgtaatgcat gacgttattt atgagatggg
4861 tttttatgat tagagtcccg caattataca tttaatacgc gatagaaaac aaaatatagc
4921 gcgcaaacta ggataaatta tcgcgcgcgg tgtcatctat gttactagat cgggaaggcg
4981 cgccgcggcc gcaacactga tagtttaaac tgaaggcggg aaacgacaat ctgatcatga
5041 gcggagaatt aagggagtca cgttatgacc cccgccgatg acgccgggaca agccgtttta
5101 cgtttggaac tgacagaacc gcaacgttga aggagccact cagccgcggg tttctggagt
5161 ttaatgagct aagcacatac gtcagaaacc attattcgcg gttcaaaagt cgcctaaggt
5221 cactatcagc tagcaaatat ttcttgtcaa aaatgctcca ctgacgttcc ataaattccc
5281 ctcggtatcc aattagagtc tcatattcac tctcaatcca aataatctgc accggatctg
5341 gatcgtttcg catgattgaa caagatggat tgcacgcagg ttctccgcc gcttgggtgg
5401 agaggctatt cggctatgac tgggcacaac agacaatcgg ctgctctgat gccgccgtgt
5461 tccggctgtc agcgcagggg cgcccggttc ttttttgtcaa gaccgacctg tccggtgccc
5521 tgaatgaact gcaggacgag gcagcgcggc tatcgtggct ggccacgacg ggcgttcctt
5581 gcgcagctgt gctcgacgtt gtcactgaag cgggaaggga ctggctgcta ttgggcgaag
5641 tgccggggca ggatctcctg tcatctcacc ttgctcctgc cgagaaagta tccatcatgg
5701 ctgatgcaat gcggcggctg catacgcttg atccggctac ctgcccattc gaccaccaag
5761 cgaaacatcg catcgagcga gcacgtactc ggatggaagc cggtcttgtc gatcaggatg
5821 atctggacga agagcatcag gggctcgcgc cagccgaact gttcgccagg ctcaaggcgc
5881 gcatgcccga cggcgatgat ctcgtcgtga cccatggcga tgcctgcttg ccgaatatca
5941 tggtggaaaa tggccgcttt tctggattca tcgactgtgg ccggctgggt gtggcggacc
6001 gctatcagga catagcgttg gctacccgtg atattgctga agagcttggc ggcgaatggg
6061 ctgaccgctt cctcgtgctt tacggtatcg ccgctcccga ttcgcagcga atcgccttct
6121 atcgccttct tgacgagttc ttctgagcgg gactctgggg ttcgaaatga ccgaccaagc
6181 gacgcccaac ctgccatcac gagatttcga ttccaccgcc gccttctatg aaaggttggg
6241 cttcggaatc gttttccggg acgccggctg atgatcctc cagcgcgggg atctcatgct
6301 ggagttcttc gcccacggga tctctgcgga caggcggctc gaagtgcgcg atatcattac
6361 gacagcaacg gccgacaagc acaacgccac gatcctgagc gacaatatga tgggcccgg
6421 cgtccacatc aacggcgtcg gcggcgactg cccaggcaag accgagatgc accgcgatat
```

Figure 4C

```
 6481 cttgctgcgt tcggatattt tcgtggagtt cccgccacag acccggatga tccccgatcg
 6541 ttcaaacatt tggcaataaa gtttcttaag attgaatcct gttgccggtc ttgcgatgat
 6601 tatcatataa tttctgttga attacgttaa gcatgtaata attaacatgt aatgcatgac
 6661 gttatttatg agatgggttt ttatgattag agtcccgcaa ttatacattt aatacgcgat
 6721 agaaaacaaa atatagcgcg caaactagga taaattatcg cgcgcggtgt catctatgtt
 6781 actagatcgg gcctcctgtc aatgctggcg gcggctctgg tggtggttct ggtggatcca
 6841 ctagttctag agcggccgtg ggccatcgcc ctgatagacg gtttttcgcc ctttgacgtt
 6901 ggagtccacg ttctttaata gtggactctt gttccaaact ggaacaacac tcaaccctat
 6961 ctcgggctat tcttttgatt tataagggat tttgccgatt tcggaaccac catcaaacag
 7021 gattttcgcc tgctggggca aaccagcgtg gaccgcttgc tgcaactctc tcagggccag
 7081 gcggtgaagg gcaatcagct gttgccgtc tcactggtga aagaaaaac caccccagta
 7141 cattaaaaac gtccgcaatg tgttattaag ttgtctaagc gtcaatttgt ttacaccaca
 7201 atatatcctg ccaccagcca gccaacagct ccccgaccgg cagctcggca caaaatcacc
 7261 actcgataca ggcagcccat cagtccggga cggcgtcagc gggagagccg ttgtaaggcg
 7321 gcagactttg ctcatgttac cgatgctatt cggaagaacg gcaactaagc tgccgggttt
 7381 gaaacacgga tgatctcgcg gagggtagca tgttgattgt aacgatgaca gagcgttgct
 7441 gcctgtgatc aaatatcatc tccctcgcag agatccgaat tatcagcctt cttattcatt
 7501 tctcgcttaa ccgtgacagt tgtctatcgg cagttcgtag agcgcgccgt gcgtcccgag
 7561 cgatactgag cgaagcaagt gcgtcgagca gtgcccgctt gttcctgaaa tgccagtaaa
 7621 gcgctggctg ctgaaccccc agccggaact gaccccacaa ggccctagcg tttgcaatgc
 7681 accaggtcat cattgaccca ggcgtgttcc accaggccgc tgcctgcaa ctcttcgcag
 7741 gcttcgccga cctgctcgcg ccacttcttc acgcgggtgg aatccgatcc gcacatgagg
 7801 cggaaggttt ccagcttgag cgggtacggc tcccggtgcg agctgaaata gtcgaacatc
 7861 cgtcgggccg tcggcgacag cttgcggtac ttctcccata tgaatttcgt gtagtggtcg
 7921 ccagcaaaca gcacgacgat ttcctcgtcg atcaggacct ggcaacggga cgttttcttg
 7981 ccacggtcca ggacgcggaa gcggtgcagc agcgacacg attccaggtg cccaacgcgg
 8041 tcggacgtga agcccatcgc cgtcgcctgt aggcgcgaca ggcattcctc ggccttcgtg
 8101 taataccggc cattgatcga ccagcccagg tcctggcaaa gctcgtagaa cgtgaaggtg
 8161 atcggctcgc cgatagggt gcgcttcgcg tactccaaca cctgctgcca caccagttcg
 8221 tcatcgtcgg cccgcagctc gacgccggtg taggtgatct tcacgtcctt gttgacgtgg
 8281 aaaatgacct tgttttgcag cgcctcgcgc gggatttttct tgttgcgcgt ggtgaacagg
 8341 gcagagcggg ccgtgtcgtt tggcatcgct cgcatcgtgt ccggccacgg cgcaatatcg
 8401 aacaaggaaa gctgcatttc cttgatctgc tgcttcgtgt gtttcagcaa cgcggcctgc
 8461 ttggcctcgc tgacctgttt tgccaggtcc tcgccggcgg ttttcgctt cttggtcgtc
 8521 atagttcctc gcgtgtcgat ggtcatcgac ttcgccaaac ctgccgcctc ctgttcgaga
 8581 cgacgcgaac gctccacggc ggccgatggc gcgggcaggg caggggagc cagttgcacg
 8641 ctgtcgcgct cgatcttggc cgtagcttgc tggaccatcg agccgacgga ctggaaggtt
 8701 tcgcggggcg cacgcatgac ggtgcggctt gcgatggttt cggcatcctc ggcggaaaac
 8761 cccgcgtcga tcagttcttg cctgtatgcc ttccggtcaa acgtccgatt cattcaccct
 8821 ccttgcggga ttgccccgac tcacgccggg gcaatgtgcc cttattcctg atttgacccg
 8881 cctggtgcct tggtgtccag ataatccacc ttatcggcaa tgaagtcggt cccgtagacc
 8941 gtctggccgt cctctctgta cttggtattc cgaatcttgc cctgcacgaa taccagcgac
 9001 cccttgccca aatacttgcc gtgggcactt gcctgagagc caaaacactt gatgcggaag
 9061 aagtcggtgc gctcctgctt gtcgccggca tcgttgcgcc acatctaggt actaaaacaa
 9121 ttcatccagt aaaatataat attttatttt ctcccaatca ggcttgatcc ccagtaagtc
 9181 aaaaaatagc tcgacatact gttcttcccc gatatcctcc ctgatcgacc ggacgcagaa
 9241 ggcaatgtca taccacttgt ccgccctgcc gcttcatcca agatcaataa agccacttac
 9301 tttgccatct ttcacaaaga tgttgctgtc tcccaggtcg ccgtgggaaa agacaagttc
 9361 ctcttcgggc ttttccgtct ttaaaaaatc atacagctcg cgcggatctt taatggagt
 9421 gtcttcttcc cagtttttcgc aatccacatc ggccagatcg ttattcagta agtaatccaa
 9481 ttcggctaag cggctgtcta agctattcgt atagggacaa tccgatatgt cgatggagtg
 9541 aaagagcctg atgcactccg catacagctt gataatcttt tcagggcttt gttcatcttc
 9601 atactcttcc gagcaaagga cgccatcggc ctcactcatg agcagattgc tccagccatc
 9661 atgccgttca aagtgcagga cctttggaac aggcagcttt ccttccagcc atagcatcat
 9721 gtccttttcc cgttccacat cataggtggt cccttttatac cggctgtccg tcattttaa
 9781 ataggttt tcatttctc ccaccagctt atataccta gcaggagaca ttccttccgt
 9841 atcttttacg cagcggtatt tttcgatcag tttttcaat tccggtgata ttctcatttt
 9901 agccatttat tatttccttc ctcttttcta cagtatttaa agataccca agaagctaat
 9961 tataacaaga cgaactccaa ttcactgttc cttgcattct aaaaccttaa ataccagaaa
10021 acagcttttt caaagttgtt ttcaaagttg gcgtataaca tagtatcgac ggagccgatt
10081 ttgaaaccac aattatggga gagaccataa tgtggtccaa tttgcagcag ccgtccgaga
10141 caggaggaca tcgtccagct gaaaccggg cagaatccgg ccatttctga agagaaaaat
10201 ggtaaactga tagaataaaa tcataagaaa ggagccgcac atgaaaaaag cagtcattaa
10261 cggggaacaa atcagaagta tcagcgacct ccaccagaca ttgaaaaagg agcttgccct
10321 tccggaatac tacggtgaaa acctgaccg tttatgggat tgtctgaccg gatgggtgga
10381 gtaccgctc gtttgaat ggaggcagtt tgaacaaagc aagcagctga ctgaaaatgg
10441 cgccgagagt gtgcttcagg ttttccgtga agcgaaagcg gaaggctgcg acatcaccat
10501 catactttct taatacgatc aatgggagat gaacaatatg gaaacacaaa ccacaattat
10561 gtctctcagc ccacaattat ggactgccag cgctgccatt tttggggtga ggcgttcgc
10621 ggccgagggg cgcagcccct ggggggatgg gaggcccgcg ttagcgcgac gggagggttc
10681 gagaaggggg ggcaccccc tcggcgtgc gcggtccacgc gcacagggcg cagcctggt
10741 taaaaacaag gtttataaat attggtttaa aagcaggtta aagacaggt tagcggtggc
10801 cgaaaacgg gcggaaaccc ttgcaaatgc tggattttct gcctgtggac agcccctcaa
10861 atgtcaatag gtgcgcccct catctgtcag cactctgccc ctcaagtgtc aaggatcgcg
```

Figure 4D

```
10921 ccoctcatct gtcagtagtc gcgcccctca agtgtcaata ccgcagggca cttatcccca
10981 ggcttgtcca catcatctgt gggaaactcg cgtaaaatca ggcgttttcg ccgatttgcg
11041 aggctggcca gctccacgtc gccggccgaa atcgagcctg cccctcatct gtcaacgccg
11101 cgccgggtga gtcggcccct caagtgtcaa cgtccgcccc tcatctgtca gtgagggcca
11161 agttttccgc gaggtatcca caacgccggc ggatctgggg aaccctgtgg ttggcatgca
11221 catacaaatg gacgaacgga taaaccttt cacgcccttt taaatatccg attattctaa
11281 taaacgctct ttctcttag
```

Figure 5A

```
LOCUS       pARB599B     12631 bp    DNA    circular
SOURCE
  ORGANISM
COMMENT     C inserted at position 10437 to match sequence analysis (multiple reads)
            ->TTTCCACCCTGG T inserted at position 10268 to match sequence analysis (multiple reads)
            ->GAAGGTTTGAG At position 9892, C substituted (inserted) for T, to match sequence
analysis (multiple reads)
            ->TTTATATCGTAT Extra A deleted from position 9575 to match sequence analysis (multiple
reads)
            ->TATTTAGTTAAAA COMMENT     This file is created by Vector NTI
            http://www.informaxinc.com/
COMMENT     ORIGDB|GenBank
COMMENT     VNTDATE|303987976|
COMMENT     VNTDBDATE|350144422|
COMMENT     VNTNAME|pARB599B|
COMMENT     VNTAUTHORNAME|D006|
FEATURES           Location/Qualifiers
     misc_marker   933..1202
                   /vntifkey="22"
                   /label=barstar
     misc_marker   1435..2226
                   /ORF
                   /vntifkey="22"
                   /label=npt\III\\\(kanR)
     misc_marker   2528..3673
                   /ORF
                   /vntifkey="22"
                   /label=trfA
     misc_feature  3897..4910
                   /vntifkey="21"
                   /label=ColE1\region
     rep_origin    4617..4617
                   /vntifkey="33"
                   /label=ColE1\origin
     misc_signal   complement(5150..5173)
                   /feature
                   /vntifkey="87"
                   /label=LEFT\BORDER
     terminator    complement(5234..5483)
                   /vntifkey="43"
                   /label=NOSTER
     CDS           complement(5497..6288)
                   /vntifkey="4"
                   /label=NPT2
     promoter      complement(6289..7602)
                   /vntifkey="29"
                   /label=UBQ10\promoter
     intron        complement(6289..6592)
                   /vntifkey="15"
                   /label=INTRON
     promoter      complement(8339..8727)
                   /vntifkey="29"
                   /label=PrMC2.400
     terminator    complement(7643..7903)
                   /vntifkey="43"
                   /label=RNS2TER
     CDS           complement(8005..8337)
                   /vntifkey="4"
                   /label=barnaseH102E
     misc_signal   complement(57..80)
                   /feature
```

Figure 5B

```
                    /vntifkey="87"
                    /label=RIGHT\BORDER
     CDS            11037..11225
                    /gene="Euc 200bp frag"
                    /product="Euc4CL RNAi 200bp fragment"
                    /vntifkey="4"
                    /label=Euc\200bp\frag
     CDS            complement(11948..12136)
                    /gene="Euc 200bp frag"
                    /product="Euc4CL RNAi 200bp fragment"
                    /vntifkey="4"
                    /label=Euc\200bp\frag
     promoter       8751..10998
                    /vntifkey="29"
                    /label=MTU4CL\promoter
     intron         11254..11876
                    /vntifkey="15"
                    /label=Y\intron
     3'UTR          12144..12360
                    /vntifkey="50"
                    /label=SUB\3'UTR
     terminator     12367..12631
                    /vntifkey="43"
                    /label=Nos
                    /note="5'"
BASE COUNT      3692 a      2640 c      2786 g      3513 t
ORIGIN
        1 ggccgcattt gggctcctgc aggtacctta attaaaagtt taaactatca gtgtttgaca
       61 ggatatattg gcgggtaaac ctaagagaaa agagcgttta ttagaataat cggatattta
      121 aaagggcgtg aaaaggttta tccgttcgtc catttgtatg tgcatgccaa ccacagggtt
      181 cccagatcc gccggcgttg tggatacctc gcggaaaact tggccctcac tgacagatga
      241 ggggcggacg ttgacacttg aggggccgac tcaccggcg cggcgttgac agatgagggg
      301 caggctcgat ttcggccggc gacgtggagc tggccagcct cgcaaatcgg cgaaaacgcc
      361 tgattttacg cgagtttccc acagatgatg tggacaagcc tggggataag tgccctgcgg
      421 tattgacact tgaggggcgc gactactgac agatgagggg cgcgatcctt gacacttgag
      481 gggcagagtg ctgacagatg aggggcgcac ctattgacat ttgaggggct gtccacaggc
      541 agaaaatcca gcatttgcaa gggtttccgc ccgttttcg gccaccgcta acctgtcttt
      601 taacctgctt ttaaaccaat atttataaac cttgttttta accagggctg cgccctgtgc
      661 gcgtgaccgc gcacgccgaa gggggtgcc ccccttctc gaacctccc ggcccgctaa
      721 cgcgggcctc ccatccccc agggcgtgcg ccctcggcc gcgaacggcc tcaccccaaa
      781 aatggcagcg ctggcagtcc ataattgtgg tccaatttgc agccgtccga gacaggagga
      841 catcgtccag ctgaaaccgg ggcagaatcc ggccatttct gaagagaaaa atggtaaact
      901 gatagaataa aatcataaga aaggagccgc acatgaaaaa agcagtcatt aacgggaac
      961 aaatcagaag tatcagcgac ctccaccaga cattgaaaaa ggagcttgcc cttccggaat
     1021 actacggtga aaacctggac gctttatggg attgtctgac cggatgggtg gagtaccgc
     1081 tcgttttgga atggaggcag tttgaacaaa gcaagcagct gactgaaaat ggcgcgaga
     1141 gtgtgcttca ggttttccgt gaagcgaaag cggaaggctg cgacatcacc atcatacttt
     1201 cttaatacga tcaatgggag atgaacaata tggaaacaca aaccacaatt gtggtttcaa
     1261 aatcggctcc gtcgatacta tgttatacgc caactttgaa aacaactttg aaaaagctgt
     1321 tttctggtat ttaaggtttt agaatgcaag gaacagtgaa ttggagttcg tcttgttata
     1381 attagcttct tggggtatct ttaaatactg tagaaaagag gaaggaaata ataaatggct
     1441 aaaatgagaa tatcaccgga attgaaaaaa ctgatcgaaa aataccgctg cgtaaaagat
     1501 acggaaggaa tgtctcctgc taaggtatat aagctggtgg gagaaaatga aaacctatat
     1561 ttaaaaatga cggacagccg gtataaaggg accacctatg atgtggaacg ggaaaaggac
     1621 atgatgctat ggctggaagg aaagctgcct gttccaaagg tcctgcactt tgaacggcat
     1681 gatggctgga gcaatctgct catgagtgag gccgatggcg tcctttgctc ggaagagtat
     1741 gaagatgaac aaagccctga aaagattatc gagctgtatg cggagtgcat caggctcttt
     1801 cactccatcg acatatcgga ttgtccctat acgaatagct tagacagccg cttagccgaa
     1861 ttggattact tactgaataa cgatctggcc gatgtggatt gcgaaaactg ggaagaagac
     1921 actccattta aagatccgcg cgagctgtat gattttttaa agacgaaaa gcccgaagag
     1981 gaacttgtct tttcccacgg cgacctggga gacagcaaca tctttgtgaa agatggcaaa
     2041 gtaagtggct ttattgatct tgggagaagc ggcagggcgg acaagtggta tgacattgcc
     2101 ttctgcgtcc ggtcgatcag ggaggatatc ggggaagaac agtatgtcga gctatttttt
     2161 gacttactgg ggatcaagcc tgattgggag aaaataaaat attatatttt actggatgaa
     2221 ttgttttagt acctagatgt ggcgcaacga tgccggcgac aagcaggagc gcaccgactt
     2281 cttccgcatc aagtgttttg gctctcaggc cgaggcccac ggcaagtatt tgggcaaggg
     2341 gtcgctggta ttcgtgcagg gcaagattcg gaataccaag tacgagaagg acggccagac
     2401 ggtctacggg accgacttca ttgccgataa ggtggattat ctggacacca aggcaccagg
     2461 cgggtcaaat caggaataag ggcacattgc cccggcgtga gtcggggcaa tcccgcaagg
     2521 agggtgaatg aatcggacgt ttgaccggaa ggcatacagg caagaactga tcgacgcggg
     2581 gttttccgcc gaggatgccg aaaccatcgc aagccgcacc gtcatgcgtg cgccccgcga
     2641 aaccttccag tccgtcggct cgatggtcca gcaagctacg gccaagatcg agcgcgacag
     2701 cgtgcaactg gctcccctg ccctgccgc gccatcggcc gcgtggagc gttcgcgtcg
     2761 tctcgaacag gaggcggcag gtttggcgaa gtcgatgacc atcgacacgc gaggaactat
```

Figure 5C

```
2821 gacgaccaag aagcgaaaaa ccgccggcga ggacctggca aaacaggtca gcgaggccaa
2881 gcaggccgcg ttgctgaaac acacgaagca gcagatcaag gaaatgcgc tttccttgtt
2941 cgatattgcg ccgtggccgg acacgatgcg agcgatgcca aacgacacgg cccgctctgc
3001 cctgttcacc acgcgcaaca agaaaatccc gcgcgaggcg ctgcaaaaca aggtcatttt
3061 ccacgtcaac aaggacgtga agatcaccta caccggcgtc gagctgcggg ccgacgatga
3121 cgaactggtg tggcagcagg tgttggagta cgcgaagcgc accccctatcg gcgagccgat
3181 caccttcacg ttctacgagc tttgccagga cctgggctgg tcgatcaatg gccggtatta
3241 cacgaaggcc gaggaatgcc tgtcgcgcct acaggcgacg gcgatgggct tcacgtccga
3301 ccgcgttggg cacctggaat cggtgtcgct gctgcaccgc ttccgcgtcc tggaccgtgg
3361 caagaaaacg tcccgttgcc aggtcctgat cgacgaggaa atcgtcgtgc tgtttgctgg
3421 cgaccactac acgaaattca tatgggagaa gtaccgcaag ctgtcgccga cggcccgacg
3481 gatgttcgac tatttcagct cgcaccggga gccgtacccg ctcaagctgg aaaccttccg
3541 cctcatgtgc ggatcggatt ccacccgcgt gaagaagtgg cgcgagcagg tcggcgaagc
3601 ctgcgaagag ttgcgaggca gcggcctggt ggaacacgcc tgggtcaatg atgacctggt
3661 gcattgcaaa cgctagggcc ttgtggggtc agttccggct ggggggttcag cagccagcgc
3721 tttactggca tttcaggaac aagcgggcac tgctcgacgc acttgcttcg ctcagtatcg
3781 ctcgggacgc acggcgcgct ctacgaactg ccgatagaca actgtcacgg ttaagcgaga
3841 aatgaataag aaggctgata attcggatct ctgcgaggga gatgatattt gatccggtgt
3901 gaaataccgc acagatcgt aaggagaaaa taccgcatca ggcgctcttc cgcttcctcg
3961 ctcactgact cgctgcgctc ggtcgttcgg ctgcggcgag cggtatcagc tcactcaaag
4021 gcggtaatac ggttatccac agaatcaggg gataacgcag gaaagaacat gtgagcaaaa
4081 ggccagcaaa aggccaggaa ccgtaaaaag gccgcgttgc tggcgttttt ccataggctc
4141 cgcccccctg acgagcatca caaaaatcga cgctcaagtc agaggtggcg aaacccgaca
4201 ggactataaa gataccaggc gtttccccct ggaagctccc tcgtgcgctc tcctgttccg
4261 accctgccgc ttaccggata cctgtccgcc tttctccctt cgggaagcgt ggcgctttct
4321 catagctcac gctgtaggta tctcagttcg gtgtaggtcg ttcgctccaa gctgggctgt
4381 gtgcacgaac ccccgttca gcccgaacta cgtcgcttat ccggtaacta tcgtcttgag
4441 tccaaccccgg taagacacga cttatcgcca ctggcagcag ccactggtaa caggattagc
4501 agagcgaggt atgtaggcgg tgctacagag ttcttgaagt ggtggcctaa ctacggctac
4561 actaagga cagtatttgg tatctgcgct ctgctgaagc cagttacctt cggaaaaaga
4621 gttggtagct cttgatccgg caaacaaacc accgctggta gcggtggttt ttttgttgc
4681 aagcagcaga ttacgcgcag aaaaaaagga tatcaagaag atcctttgat ctttctacg
4741 gggtctgacg ctcagtggaa cgaaaactca cgttaaggga ttttggtcat gagattatca
4801 aaaaggatct tcacctagat ccttttaaat taaaaatgaa gttttaaatc aatctaaagt
4861 atatatgagt aaacttggtc tgacagttac caatgcttca tcagtgaggc tgatcacagg
4921 cagcaacgct ctgtcatcgt tacaatcaac atgctaccct ccgcgagatc atccgtgttt
4981 caaacccggc agcttagttg ccgttcttcc gaatagcatc ggtaacatga gcaaagtctg
5041 ccgccttaca acggctctcc cgctgacgcc gtccggact gatgggctgc ctgtatcgag
5101 tggtgatttt gtgccgagct gccggtcggg gagctgttg ctggctggtg gcaggatata
5161 ttgtggtgta aacaaattga cgcttagaca acttaataac acaccgcggt ctagaactag
5221 tggatccccc ctacgtgcga tctagtaaca tagatgacac cgcgcgcgat aatttatcct
5281 agtttgcgcg ctatattttg ttttctatcg cgtattaaat gtataattgc gggactctaa
5341 tcataaaaac ccatctcata aataacgtca tgcattacat gttaattatt acatgcttaa
5401 cgtaattcaa cagaaattat atgataatca tcgcaagacc ggcaacagga ttcaatctta
5461 agaaacttta ttgccaaatg tttgaacgat ccctcagaag aactcgtcaa gaaggcgata
5521 gaaggcgatg cgctgcgaat cgggagcggc gataccgtaa agcacgagga agcggtcagc
5581 ccattcgccg ccaagctctt cagcaatatc acgggtagcc aacgctatgt cctgatagcg
5641 gtccgccaca cccagccggc cacagtcgat gaatccagaa aagcggccat tttccaccat
5701 gatattcggc aagcaggcat cgccatggt cacgacgaga tcctcgccgt cgggcatgcg
5761 cgccttgagc ctggcgaaca gttcggctgg cgcgagcccc tgatgctctt cgtccagatc
5821 atcctgatcg acaagaccgg cttccatccg agtacgtgct cgctcgatgc gatgtttcgc
5881 ttggtggtcg aatgggcagg tagccggatc aagcgtatgc agccgccgca ttgcatcagc
5941 catgatggat actttctcgg caggagcaag gtgagatgac aggagatcct gccccggcac
6001 ttcgcccaat agcagccagt cccttcccgc ttcagtgaca acgtcgagca cagctgcgca
6061 aggaacgccc gtcgtggcca gccacgatag ccgcgctgcc tcgtcctgga gttcattcag
6121 ggcaccggac aggtcggtct tgacaaaaag aaccgggcgc ccctgcgctg acagccggaa
6181 cacggcggca tcagagcagc cgattgtctg ttgtgcccag tcatagccga atagcctctc
6241 cacccaagcg gccggagaac ctgcgtgcaa tccatcttgt tcaatcatct gttaatcaga
6301 aaaactcaga ttaatcgaca aattcgatc cacaaactag aaactaacac cagatctaga
6361 tagaaatcac aaatcgaaga gtaattattc gacaaaactc aaattatttg aacaaatcgg
6421 atgatattta tgaaacccta atcgagaatt aagatgatat ctaacgatca aacccagaaa
6481 atcgtcttcg atctaagatt aacagaatct aaaccaaaga acatatacga aattgggatc
6541 gaacgaaaac aaaatcgaag attttgagag aataaggaac acagaaattt accttgatca
6601 cggtagagag aattgagaga aagttttaa gattttgaga aattgaaatc tgaattgtga
6661 agaagaagag ctctttgggt attgtttat agaagaagaa gaagaaaaga cgaggacgac
6721 taggtcacga gaaagctaag gcggtgaagc aatagctaat aataaaatga cacgtgtatt 6781 gagcgttgtt tacacgcaaa gttgtttttg gctaattgcc ttattttag gttgaggaaa
6841 agtatttgtg cttttgagttg ataaacacga ctcgtgtgtg ccggctgcaa ccactttgac
6901 gccgtttatt actgactcgt cgacaaccac aatttctaac ggtcgtcata agatccagcc
6961 gttgagattt aacgatcgtt acgatttata tttttttagc attatcgttt tattttttaa
7021 atatacggtg gagctgaaaa ttggcaataa ttgaaccgtg gtcccactg cattgaagcg
7081 tatttcgtat tttctagaat tcttcgtgct ttatttcttt tccttttgt ttttttttgc
7141 catttatcta atgcaagtgg gcttataaaa tcagtgaatt tcttggaaaa gtaacttctt
```

Figure 5D

```
 7201 tatcgtataa catattgtga aattatccat ttctttta at ttttagtgt tattggatat
 7261 ttttgtatga ttattgattt gcataggata atgactttt g tatcaagttg gtgaacaagt
 7321 ctcgttaaaa aaggcaagtg gtttggtgac tcgatttatt cttgttattt aattcatata
 7381 tcaatggatc ttatttgggg cctggtccat atttaacact cgtgttcagt ccaatgacca
 7441 ataatatttt ttcattaata acaatgtaac aagaatgata cacaaaacat tctttgaata
 7501 agttcgctat gaagaaggga acttatccgg tcctagatca tcagttcata caaacctcca
 7561 tagagttcaa catcttaaac aaggatatcc tgatccgttg acggcgcgcc aagcggggcc
 7621 gcatttaaat gggccctatc taatcgaatt ttgtaaactg gtttgataag ccatcaatgc
 7681 atcagtcaag aatgaatcat tgcaactaag ttgatataat tcaatttacc atagaactca
 7741 aatgttgata tcttcttatg gattttctga tcttctacat tattagaaag aaacttgatt
 7801 taccagtaat gatgatacat atcaaataga acgaaataag ccaatcttta taggttttgg
 7861 tagtaaagtt acaacatcag agacatgtat gtattgtctc tcagaagagc tcttgaccga
 7921 tcagagtttg aagaaaaatt tattacacac tttatgtaaa gctgaaaaaa acggcctccc
 7981 gcagggaagc cgttttttt c gttatctgat ttttgtaaag gtctgatact cgtccgttgt
 8041 tttgtaaatc agccagtcgc ttgagtaaag aatccggtct gaatttctga agcctgatgt
 8101 atagttaata tccgcttcac gccatgttcg tccgcttttg cccgggagtt tgccttccct
 8161 gtttgagaag atgtctccgc cgatgctttt ccccggagcg acgtctgcaa ggttcccttt
 8221 tgatgccacc cagccgaggg cttgtgcttc tgatttgta atgtaattat caggtagctt
 8281 atgatatgtc tgaagataat ccgcaacccc gtcaaacgtg ttgataacct gtgccatgtt
 8341 cccgtttgat acctgaattt tggccattct cataaatctt ctaaaaacag cagaactgac
 8401 tattcaaaga aagtagaacc cacagaaagt aatcaaagta gtttgattaa atgcgttgtg
 8461 tatcatcgca gcccctgcta cggatattta taggaaaggt ttgagagcaa tgtcgtgcagc
 8521 aagttgtgtg tgaatcacct gcttccatgg cggaggataa ataatttagt cacgcattta
 8581 gttgaacgta actactaact cctctaccgc taatcattct tcttttgccc gggcaagttc
 8641 aacaacaacc ccacaatcac gcttcctgta ttttgttttg tttt caaaac aatagaattc
 8701 acttttt act gccaaaatta tgtttactc gagagcccaa atgcggccgc ggccgggtgg
 8761 tgacatttat tcataaattc atctcaaaac aagaaggatt tacaaaaata aagaaaaca
 8821 aaattttcat ctttaacata attataattg tgttcacaaa atlcaaactt aaacccttaa
 8881 tataaagaat ttctttcaac aatacacttt aatcacaact tcttcaatca caacctcctc
 8941 caacaaaatt aaaatagatt aataaataaa taaacttaac tatttaaaaa aaatattat
 9001 acaaaattta ttaaaacttc aaaataaaca aactttttat acaaaattca tcaaaactt
 9061 aaaataaagc taaacactga aaatgtgagt acatttaaaa ggacgctgat cacaaaaatt
 9121 ttgaaaacat aaacaaactt gaaactctac cttttaagaa tgagtttgtc gtctcattaa
 9181 ctcattagtt ttatagttcg aatccaatta acgtatcttt tatttt atgg aataagggtg
 9241 ttttaataag tgattttggg atttttttag taattt attt gtgatatgtt atggagtttt
 9301 taaaaatata tatatatata tatattttg ggttgagttt acttaaaatt tggaaaggt
 9361 tggtaagaac tataaattga gttgtgaatg agtgtttt at ggattttt ta agatgttaaa
 9421 tttatatatg taattaaaat tttatttt ga ataacaaaaa ttataattgg ataaaaaatt
 9481 gttttgttaa atttagagta aaaatttcaa aatctaaaat aattaaacac tattattttt
 9541 aaaaaatttg ttggtaaatt ttatcttata tttagttaaa atttagaaaa aattaatttt
 9601 aaattaataa actttt gaag tcaaatattc caaatatttt ccaaaatatt aaatctattt
 9661 tgcattcaaa atacaattta aataataaaa cttcatggaa tagattaacc aatttgtata
 9721 aaaaccaaaa atctcaaata aaatttaaat tacaaaacat tatcaacatt atgatttcaa
 9781 gaaagacaat aaccagtttc caataaaata aaaaacctca tggcccgtaa ttaagatctc
 9841 attaattaat tcttattttt taatttttt t acatagaaaa tatctttata tcgtatccaa
 9901 gaaatataga atgttctcgt ccagggacta ttaatctcca aacaagttc aaaatcatta
 9961 cattaaagct catcatgtca tttgtggatt ggaaattata ttgtataaga gaaatataga
10021 atgttctcgt ctagggacta ttaatttcca aacaaatttc aaaatcatta cattaaagct
10081 catcatgtca tttgtggatt ggaaattaga caaaaaaat cccaaatatt tctctcaatc
10141 tcccaaaata tagttcgaac tccatatttt tggaaattga gaattttctt acccaataat
10201 atatttt ttt atacatttta gagattttcc agacatattt gctctgggat ttattggaat
10261 gaaggtttga gttataaact ttcagtaatc caagtatctt cggtttttga agatactaaa
10321 tccattatat aataaaaaca catttt aaac accaatttaa tgggatttca gatttgtatc
10381 ccatgctatt ggctaaggca tttt tcttat tgtaatctaa ccaattctaa tttccaccct
10441 ggtgtgaact gactgacaaa tgcggtccga aaacagcgaa tgaaatgtct gggtgatcgg
10501 tcaaacaagc ggtgggcgag agagcgcggg tgttggccta gccgggatgg gggtaggtag
10561 acggcgtatt accggcgagt tgtccgaatg gagttttcgg ggtaggtagt aacgtagacg
10621 tcaatggaaa aagtcataat ctccgtcaaa aatccaaccg ctccttcaca tcgcagagtt
10681 ggtggccacg ggaccctcca cccactcact cgatccgctg ccgtggttgc ccattattca
10741 accatacgcc acttgactct tcaccaacaa ttccaggccg gctttctata caatgtactg
10801 cacaggaaaa tccaatataa aaagccggcc tctgcttcct tctcagtagc ccccagctca
10861 ttcaattctt cccactgcag gctacatttg tcagacacgt tttccgccat ttttcgcctg
10921 tttctgcgga gaatttgatc aggttcggat tgggattgaa tcaattgaaa ggttttt att
10981 ttcagtattt cgatcgccgg atccccgggg ctgcaggaat tgggctgcag atcgatattt
11041 gatttcacat gctattgtaa tgtatttatt gtttcaattc cgaattagac aaagtgctta
11101 aagctctctt ttcggatttt tttttt catt aatgtataat aattgcggac attacaatat
11161 actgtacaac gtgatttgag cttgatgaat tacaagattg gaagaacttc gaagacaaaa
11221 aaaaaatcga tctgcaggaa ttcgtccagc agtaattcgg taccoctgat cagcactgct
11281 gccaagaatg taagtttt ta ttttctttat atgttcaaac agttttataa agtactataa
11341 gcttttttt a gccaaaagaa atatcttaag tttt agtaac caataaagaa ttattgcggc
11401 ctccttattt aattatagta catatgtcat agtagatttg ttttttatta ttattatttt
11461 ttattttt tt atagttttt t acaaattcga cttggataccc ttatgatttg gaagatactc
11521 catttaattt tatgagttgt gtttgaaaac atattttaag actaaacacg tagagaacat
11581 tcttaacaaa tttgtaaata aataaattta actctattct ctaggattta aatattatag
```

Figure 5E

```
11641 gtatatatat aattttctaa taagtttata tcgagtcact catacgagtt gtgtagaaag
11701 ttaatcacgg gtaccaattt taaattaaaa ataagaataa ttatatgatc ttaaatttat
11761 acaactctga taaaagattg ggctttgaca tctttgaaga aaactagatt tagtaatatt
11821 ctgattaaat tgggttcaca ctttgtagtg ggcacacttt ccggggttcga aatcgaaatc
11881 tggaagctta tcgatctcga ggggcccact agtatcgatc tcgaggggcc cactagtatc
11941 gatcgatttt tttttttgtct tcgaagttct tccaatcttg taattcatca agctcaaatc
12001 acgttgtaca gtatattgta atgtccgcaa ttattataca ttaatgaaaa aaaaaatccg
12061 aaaagagagc tttaagcact ttgtctaatt cggaattgaa acaataaata cattacaata
12121 gcatgtgaaa tcaaatatcg atccgatggg tgttatttgt ggataataaa ttcgggtgat
12181 gttcagtgtt tgtcgtattt ctcacgaata aattgtgttt atgtatgtgt tagtgttgtt
12241 tgtctgtttc agaccctctt atgttatatt tttctttttcg tcggtcagtt gaagccaata
12301 ctggtgtcct ggccggcact gcaataccat ttcgtttaat ataaagactc tgttatccgt
12361 gagctcgaat ttccccgatc gttcaaacat ttggcaataa agtttcttaa gattgaatcc
12421 tgttgccggt cttgcgatga ttatcatata atttctgttg aattacgtta agcatgtaat
12481 aattaacatg taatgcatga cgttatttat gagatgggtt tttatgatta gagtcccgca
12541 attatacatt taatacgcga tagaaaacaa aatatagcgc gcaaactagg ataaattatc
12601 gcgcgcggtg tcatctatgt tactagatcg c
```

Figure 6A

```
LOCUS       pARB639B       16396 bp    DNA     circular          20-SEP-2004
SOURCE
  ORGANISM
COMMENT     T inserted at position 9913 to match sequence analysis (multiple reads)
            ->TTTCTTGTTCTTC Extra A deleted from position 13340 to match sequence analysis (multiple
reads)
            ->TATTTAGTTAAAA At position 13657, C substituted (inserted) for T, to match sequence
analysis (multiple reads)
            ->TTTATATCGTAT T inserted at position 14033 to match sequence analysis (multiple reads)
            ->GAAGGTTTGAG C inserted at position 14202 to match sequence analysis (multiple reads)
            ->TTTCCACCCTGG COMMENT     This file is created by Vector NTI
            http://www.informaxinc.com/
COMMENT     ORIGDB|GenBank
COMMENT     VNTDATE|307364054|
COMMENT     VNTDBDATE|350144386|
COMMENT     VNTNAME|pARB639B|
COMMENT     VNTAUTHORNAME|D006|
FEATURES            Location/Qualifiers
     primer_bind    3439..3460
                    /vntifkey="28"
                    /label=BKBT1>
     primer_bind    complement(5094..5116)
                    /vntifkey="28"
                    /label=BKBT2<
     primer_bind    5032..5052
                    /vntifkey="28"
                    /label=LFBORD1>
     primer_bind    complement(841..859)
                    /vntifkey="28"
                    /label=BARPROR1<
     primer_bind    complement(197..217)
                    /vntifkey="28"
                    /label=RTBORD1<
     primer_bind    7273..7295
                    /vntifkey="28"
                    /label=UQNPR1>
     primer_bind    6332..6354
                    /vntifkey="28"
                    /label=UQNPR3>
     primer_bind    5959..5976
                    /vntifkey="28"
                    /label=UQNPR4>
     primer_bind    5553..5572
                    /vntifkey="28"
                    /label=UQNPR5>
     primer_bind    1171..1188
                    /vntifkey="28"
                    /label=NPT3F1>
     primer_bind    6735..6753
                    /vntifkey="28"
                    /label=UQNPR7>
     primer_bind    1727..1750
                    /vntifkey="28"
                    /label=NPT3F2>
     primer_bind    2668..2687
```

Figure 6B

```
                        /vntifkey="28"
                        /label=TRFAF1>
        primer_bind     2965..2983
                        /vntifkey="28"
                        /label=TRFAF2>
        primer_bind     582..597
                        /vntifkey="28"
                        /label=ORIVF1>
        primer_bind     4749..4770
                        /vntifkey="28"
                        /label=LFBORD2>
        misc_marker     933..1202
                        /vntifkey="22"
                        /label=barstar
        misc_marker     1435..2226
                        /ORF
                        /vntifkey="22"
                        /label=npt\III\\\(kanR)
        misc_marker     2528..3673
                        /ORF
                        /vntifkey="22"
                        /label=trfA
        misc_feature    3897..4910
                        /vntifkey="21"
                        /label=ColE1\region
        rep_origin      4617..4617
                        /vntifkey="33"
                        /label=ColE1\origin
        misc_signal     complement(5150..5173)
                        /feature
                        /vntifkey="87"
                        /label=LEFT\BORDER
        terminator      complement(5234..5483)
                        /vntifkey="43"
                        /label=NOSTER
        CDS             complement(5497..6288)
                        /vntifkey="4"
                        /label=NPT2
        promoter        complement(6289..7602)
                        /vntifkey="29"
                        /label=UBQ10\promoter
        intron          complement(6289..6592)
                        /vntifkey="15"
                        /label=INTRON
        promoter        complement(8319..9718)
                        /vntifkey="29"
                        /label=PrAG
        enhancer        9719..12490
                        /vntifkey="9"
                        /label=AtAGenh
        CDS             complement(7986..8318)
                        /vntifkey="4"
                        /label=BarnaseE73G
        terminator      complement(7608..7878)
                        /vntifkey="43"
                        /label=NOSTER
        misc_signal     complement(57..80)
                        /feature
                        /vntifkey="87"
                        /label=RIGHT\BORDER
        primer_bind     9746..9773
                        /vntifkey="28"
                        /label=AtAGTN5>
        primer_bind     10047..10066
                        /vntifkey="28"
                        /label=AGenhseq-1>
        primer_bind     10579..10600
                        /vntifkey="28"
                        /label=AGenhseq-2>
        primer_bind     11154..11171
                        /vntifkey="28"
                        /label=AGenhseq-3>
        primer_bind     11770..11791
                        /vntifkey="28"
```

Figure 6C

```
                        /label=AGenhseq-4>
        primer_bind     complement(8095..8112)
                        /vntifkey="28"
                        /label=Barnseq2<
        primer_bind     complement(8913..8930)
                        /vntifkey="28"
                        /label=PRPseq3<
        primer_bind     8498..8517
                        /vntifkey="28"
                        /label=PrAGKpn<
        primer_bind     9388..9405
                        /vntifkey="28"
                        /label=PRPseq1>
        primer_bind     9342..9359
                        /vntifkey="28"
                        /label=PRPseq2<
        CDS             14802..14990
                        /gene="Euc 200bp frag"
                        /product="Euc4CL RNAi 200bp fragment"
                        /vntifkey="4"
                        /label=Euc\200bp\frag
        CDS             complement(15713..15901)

/gene="Euc 200bp frag"
                        /product="Euc4CL RNAi 200bp fragment"
                        /vntifkey="4"
                        /label=Euc\200bp\frag
        promoter        12516..14763
                        /vntifkey="29"
                        /label=MTU4CL\promoter
        intron          15019..15641
                        /vntifkey="15"
                        /label=Y\intron
        3'UTR           15909..16125
                        /vntifkey="50"
                        /label=SUB\3'UTR
        terminator      16132..16396
                        /vntifkey="43"
                        /label=Nos
                        /note="5'"
BASE COUNT     4852 a      3244 c      3426 g      4874 t
ORIGIN
        1 ggccgcattt gggctcctgc aggtacctta attaaaagtt taaactatca gtgtttgaca
       61 ggatatattg gcgggtaaac ctaagagaaa agagcgttta ttagaataat cggatattta
      121 aaagggcgtg aaaaggttta tccgttcgtc catttgtatg tgcatgccaa ccacagggtt
      181 ccccagatcc gccggcgttg tggatacctc gcgaaaaact tggccctcac tgacagatga
      241 gggcggacg ttgacacttg aggggccgac tcacccgcg cggcgttgac agatgagggg
      301 caggctcgat ttcggccggc gacgtggagc tggccagcct cgcaaatcgg cgaaaacgcc
      361 tgattttacg cgagtttccc acagatgatg tggacaagcc tggggataag tgccctgcgg
      421 tattgacact tgaggggcgc gactactgac agatgagggg cgcgatcctt gacacttgag
      481 gggcagagtg ctgacagatg aggggcgcac ctattgacat ttgaggggct gtccacaggc
      541 agaaaatcca gcatttgcaa gggtttccgc ccgttttcg gccaccgcta acctgtcttt
      601 taacctgctt ttaaaccaat atttataaac cttgttttta accagggctg cgccctgtgc
      661 gcgtgaccgc gcacgccgaa gggggtgcc ccccttctc gaaccctccc ggcccgctaa
      721 cgcgggcctc ccatcccccc aggggctgcc ccctcggcc gcgaacggcc tcaccccaaa
      781 aatggcagcg ctggcagtcc ataattgtgg tccaatttgc agccgtccga gacaggagga
      841 catcgtccag ctgaaaccgg ggcagaatcc ggccatttct gaagagaaaa atggtaaact
      901 gatagaataa aatcataaga aaggagccgc acatgaaaaa agcagtcatt aacggggaac
      961 aaatcagaag tatcagcgac ctccaccaga cattgaaaaa ggagcttgcc cttccggaat
     1021 actacggtga aaacctggac gctttatggg attgtctgac cggatgggtg gagtacccgc
     1081 tcgttttgga atggaggcag tttgaacaaa gcaagcagct gactgaaaat ggcgccgaga
     1141 gtgtgcttca ggttttccgt gaagcgaaag cggaaggctg cgacatcacc atcatacttt
     1201 cttaatacga tcaatgggag atgaacaata tggaaacaca aaccacaatt gtggtttcaa
     1261 aatcggctcc gtcgatacta tgttatacgc caactttgaa aacaactttg aaaaagctgt
     1321 tttctggtat ttaaggtttt agaatgcaag gaacagtgaa ttggagttcg tcttgttata
     1381 attagcttct tggggtatct ttaaatactg tagaaaagag gaaggaaata ataaatggct
     1441 aaaatgagaa tatcaccgga attgaaaaaa ctgatcgaaa aataccgctg cgtaaaagat
     1501 acgaaggaa tgtctcctgc taaggtatat aagctggtgg gagaaaatga aaacctatat
     1561 ttaaaaatga cggacagccg gtataaaggg accacctatg atgtggaacg ggaaaaggac
     1621 atgatgctat ggctggaagg aaagctgcct gttccaaagg tcctgcactt tgaacggcat
     1681 gatgctgga gcaatctgct catgagtgag gccgatggcg tcctttgctc ggaagagtat
     1741 gaagatgaac aaagccctga aagattatc gagctgtatg cggagtgcat caggctcttt
     1801 cactccatcg acatatcgga ttgtccctat acgaatagct tagacagccg cttagccgaa
     1861 ttggattact tactgaataa cgatctggcc gatgtggatt gcgaaaactg ggaagaagac
```

Figure 6D

```
1921 actccattta aagatccgcg cgagctgtat gatttttaa agacggaaaa gcccgaagag
1981 gaacttgtct tttcccacgg cgacctggga gacagcaaca tctttgtgaa agatggcaaa
2041 gtaagtggct ttattgatct tgggagaagc ggcagggcgg acaagtggta tgacattgcc
2101 ttctgcgtcc ggtcgatcag ggaggatatc ggggaagaac agtatgtcga gctattttt
2161 gacttactgg ggatcaagcc tgattgggag aaaataaaat attatatttt actggatgaa
2221 ttgttttagt acctagatgt ggcgcaacga tgccggcgac aagcaggagc gcaccgactt
2281 cttccgcatc aagtgttttg gctctcaggc cgaggcccac ggcaagtatt tgggcaaggg
2341 gtcgctggta ttcgtgcagg gcaagattcg gaataccaag tacgagaagg acggccagac
2401 ggtctacggg accgacttca ttgccgataa ggtggattat ctggacacca aggaccaggg
2461 cgggtcaaat caggaataag ggcacattgc cccggcgtga gtcgggcaa tcccgcaagg
2521 agggtgaatg aatcggacgt ttgaccggaa ggcatacagg caagaactga tcgacgcggg
2581 gttttccgcc gaggatgccg aaaccatcgc aagccgcacc gtcatgcgtg cgccccgcga
2641 aaccttccag tccgtcggct cgatggtcca gcaagctacg gccaagatcg agcgcgacag
2701 cgtgcaactg gctcccctg ccctgcccgc gccatcggcc gccgtggagc gttcgcgtcg
2761 tctcgaacag gaggcggcag gtttggcgaa gtcgatgacc atcgacacgc gaggaactat
2821 gacgaccaag aagcgaaaaa ccgccggcga ggacctggca aaacaggtca gcgaggccaa
2881 gcaggccgcg ttgctgaaac acacgaagca gcagatcaag gaaatgcagc tttccttgtt
2941 cgatattgcg ccgtggccgg acacgatgcg agcgatgcca aacgacacgg cccgctctgc
3001 cctgttcacc acgcgcaaca agaaaatccc gcgcgaggcg ctgcaaaaca aggtcatttt
3061 ccacgtcaac aaggacgtga agatcaccta caccggcgtc gagctgcggg ccgacgatga
3121 cgaactggtg tggcagcagg tgttggagta cgcgaagcgc accctatcg gcgagccgat
3181 caccttcacg ttctacgagc tttgccagga cctgggctgg tcgatcaatg gccggtatta
3241 cacgaaggcc gaggaatgcc tgtcgcgcct acaggcgacg gcgatgggct tcacgtccga
3301 ccgcgttggg cacctggaat cggtgtcgct gctgcaccgc ttccgcgtcc tggaccgtgg
3361 caagaaaacg tcccgttgcc aggtcctgat cgacgaggaa atcgtcgtgc tgtttgctgg
3421 cgaccactac acgaaattca tatgggagaa gtaccgcaag ctgtcgccga cggcccgacg
3481 gatgttcgac tattcagct cgcaccggga gccgtacccg ctcaagctgg aaaccttccg
3541 cctcatgtgc ggatcggatt ccacccgcgt gaagaagtgg cgcgagcagg tcggcgaagc
3601 ctgcgaagag ttgcgaggca gcggcctggt ggaacacgcc tgggtcaatg atgacctggt
3661 gcattgcaaa cgctagggcc ttgtggggtc agttccggct ggggttcag cagccagcgc
3721 tttactggca tttcaggaac aagcgggcac tgctcgacgc acttgcttcg ctcagtatcg
3781 ctcgggacgc acggcgcgct ctacgaactg ccgatagaca actgtcacgg ttaagcgaga
3841 aatgaataag aaggctgata attcggatct ctgcgaggga gatgatattt gatccggtgt
3901 gaaataccgc acagatgcgt aaggagaaaa taccgcatca ggcgctcttc cgcttcctcg
3961 ctcactgact cgctgcgctc ggtcgttcgg ctgcggcgag cggtatcagc tcactcaaag
4021 gcggtaatac ggttatccac agaatcaggg gataacgcag gaaagaacat gtgagcaaaa
4081 ggccagcaaa aggccaggaa ccgtaaaaag gccgcgttgc tggcgttttt ccataggctc
4141 cgccccctg acgagcatca caaaaatcga cgctcaagtc agaggtggcg aaacccgaca
4201 ggactataaa gataccaggc gtttccccct ggaagctccc tcgtgcgctc tcctgttccg
4261 accctgccgc ttaccggata cctgtccgcc tttctccctt cgggaagcgt ggcgctttct
4321 catagctcac gctgtaggta tctcagttcg gtgtaggtcg ttcgctccaa gctgggctgt
4381 gtgcacgaac cccccgttca gcccgaccgc tgcgccttat ccggtaacta tcgtcttgag
4441 tccaacccgg taagacacga cttatcgcca ctggcagcag ccactggtaa caggattagc
4501 agagcgaggt atgtaggcgg tgctacagag ttcttgaagt ggtggcctaa ctacggctac
4561 actagaagga cagtatttgg tatctgcgct ctgctgaagc cagttacctt cggaaaaaga
4621 gttggtagct cttgatcggc aaacaaacc accgctggta gcggtggttt ttttgtttgc
4681 aagcagcaga ttacgcgcag aaaaaaagga tatcaagaag atcctttgat cttttctacg
4741 gggtctgacg ctcagtggaa cgaaaactca cgttaaggga ttttggtcat gagattatca
4801 aaaaggatct tcacctagat ccttttaaat taaaaatgaa gttttaaatc aatctaaagt
4861 atatatgagt aaacttggtc tgacagttac caatgcttca tcagtgaggc tgatcacagg
4921 cagcaacgct ctgtcatcgt tacaatcaac atgctaccct ccgcgagatc atccgtgttt
4981 caaaccggc agcttagttg ccgttcttcc gaatagcatc ggtaacatga gcaaagtctg
5041 ccgccttaca acggctctcc cgctgacgcc gtcccggact gatgggctgc ctgtatcgag
5101 tggtgatttt gtgccgagct gccggtcggg gagctgttgg ctggctggtg cgaggatata
5161 ttgtggtgta aacaaattga cgcttagaca acttaataac acaccgcggt ctagaactag
5221 tggatccccc ctacgtgcga tctagtaaca tagatgacac cgcgcgcgat aatttatcct
5281 agtttgcgcg ctatattttg tttctatcg cgtattaaat gtataattgc gggactctaa
5341 tcataaaaac ccatctcata aataacgtca tgcattacat gttaattatt acatgcttaa
5401 cgtaattcaa cagaaattat atgataatca tcgcaagacc ggcaacagga ttcaatctta
5461 agaaactta ttgccaaatg tttgaacgat ccctcagaag aactcgtcaa gaaggcgata
5521 gaaggcgatg cgctgcgaat cgggagcggc gataccgtaa agcacgagga gcggtcagc
5581 ccattcgccg ccaagctctt cagcaatatc acgggtagcc aacgctatgt cctgatagcg
5641 gtccgccaca cccagccggc cacagtcgat gaatccagaa aagcggccat tttccaccat
5701 gatattcggc aagcaggcat cgccatggt cacgacgaga tcctcgccgt cgggcatgcg
5761 cgccttgagc ctggcgaaca gttcggctgg cgcgagcccc tgatgctctt cgtccagatc
5821 atcctgatcg acaagaccgg cttccatccg agtacgtgct cgctcgatgc gatgtttcgc
5881 ttggtggtcg aatgggcagg tagccggatc agccgcgca ttgcatcagc
5941 catgatggat actttctcgg caggagcaag gtgagatgac aggagatcct gccccggcac
6001 ttcgcccaat agcagccagt cccttcccgc ttcagtgaca acgtcgagca cagctgcgca
6061 aggaacgccc gtcgtggcca gccacgatag ccgcgctgcc tcgtcctgga gttcattcag
6121 ggcaccggac aggtcggtct tgacaaaaag aaccgggcgc ccctgcgctg acagccggaa
6181 cacggcggca tcagagcagc cgattgtctg ttgtgcccag tcatagccga atagcctctc
6241 cacccaagcg gccggagaac ctgcgtgcaa tccatcttgt tcaatcatct gttaatcaga
6301 aaaactcaga ttaatcgaca aattcgatcg cacaaactag aaactaacac cagatctaga
```

Figure 6E

```
6361 tagaaatcac aaatcgaaga gtaattattc gacaaaactc aaattatttg aacaaatcgg
6421 atgatattta tgaaaccota atcgagaatt aagatgatat ctaacgatca aacccagaaa
6481 atcgtcttcg atctaagatt aacagaatct aaaccaaaga acatatacga aattgggatc
6541 gaacgaaaac aaaatcgaag attttgagag aataaggaac acagaaattt accttgatca
6601 cggtagagag aattgagaga aagttttaa gattttgaga aattgaaatc tgaattgtga
6661 agaagaagag ctctttgggt attgttttat agaagaagaa gaagaaaaga cgaggacgac
6721 taggtcacga gaaagctaag gcggtgaagc aatagctaat aataaaatga cacgtgtatt
6781 gagcgttgtt tacacgcaaa gttgtttttg gctaattgcc ttatttttag gttgaggaaa
6841 agtatttgtg ctttgagttg ataaacacga ctcgtgtgtg ccggctgcaa ccactttgac
6901 gccgtttatt actgactcgt cgacaaccac aatttctaac ggtcgtcata agatccagcc
6961 gttgagattt aacgatcgtt acgatttata ttttttagc attatcgttt tatttttaa
7021 atatacggtg gagctgaaaa ttggcaataa ttgaaccgtg ggtcccactg cattgaagcg
7081 tatttcgtat tttctagaat tcttcgtgct ttatttcttt tcctttttgt ttttttttgc
7141 catttatcta atgcaagtgg gcttataaaa tcagtgaatt tcttggaaaa gtaacttctt
7201 tatcgtataa catattgtga aattatccat ttctttaat ttttagtgt tattggatat
7261 ttttgtatga ttattgattt gcataggata atgactttg tatcaagttg gtgaacaagt
7321 ctcgttaaaa aaggcaagtg gtttggtgac tcgatttatt cttgttattt aattcatata
7381 tcaatggatc ttatttgggg cctggtccat atttaacact cgtgttcagt ccaatgacca
7441 ataatatttt ttcattaata acaatgtaac aagaatgata cacaaaacat tctttgaata
7501 agttcgctat gaagaaggga acttatccgg tcctagatca tcagttcata caaacctcca
7561 tagagttcaa catcttaaac aaggatatcc tgatccgttg acggcgcgcc ttcccgatct
7621 agtaacatag atgacaccgc cgcgataat ttatcctagt ttgcgcgcta tattttgttt
7681 tctatcgcgt attaaatgta taattgcggg actctaatca taaaaccca tctcataaat
7741 aacgtcatgc attacatgtt aattattaca tgcttaacgt aattcaacag aaattatatg
7801 ataatcatcg caagaccggc aacaggattc aatcttaaga aactttattg ccaaatgttt
7861 gaacgatcgg ggaaattcga gctcaaagtg caattgaccg atcagagttt gaagaaaaat
7921 ttattacaca ctttatgtaa agctgaaaaa aacggcctcc cgcagggaag ccgttttttt
7981 cgttatctga tttttgtaaa ggtctgataa tggtccgttg ttttgtaaat cagccagtcg
8041 cttgagtaaa gaatccggtc tgaatttctg aagcctgatg tatagttaat atccgctcca
8101 cgccatgttc gtccgctttt gcccgggagt ttgccttccc tgtttgagaa gatgtctccg
8161 ccgatgcttt tcccggagc gacgtctgca aggttcectt ttgatgccac ccagccgagg
8221 gcttgtgctt ctgatttgt aatgtaatta tcaggtagct tatgatatgt ctgaagataa
8281 tccgcaaccc cgtcaaacgt gttgataacc tgtgccatga tttgtacaca aaatttccgc
8341 gcacagatcc tcacagcgta tgcaaaacaa agctgcaact actaatacca gtccaaaagc
8401 aatgggcgca acagcaacag caaaagctgc aacccottgt gctggttcgt tcctacagtt
8461 ggacgcagcc cgagttctga gaaacaaata accacaaggc aagttaggta ccaaacccct
8521 taagctcaac ttaagcaaat attacaaatc tttgtttcta caaacaaatc tttttcagaa
8581 cggcttcagg tggggaatat tgtccattta agtacctgaa aatctaagaa cacggccaat
8641 ccgggcgcct ttgcttgaaa gtgggaagaa acctgaatga ttgaacagtg gataagagat
8701 ttataagcaa gattagcagg gctgatcaga ttgttttttc gggtaggttg atcaatacat
8761 atgccccttc cctcttcctt tcctctacaa tcgattgcca gggagagata gagataccat
8821 catgatgatg atggtgggga tggcgatgat ggtaatgatg atgatccagc agaaaaaatt
8881 gcgcagaaga agaagatgag cggtcggtcg gtcgatagcc tttcagtcgg aggggaaaga
8941 acaaaataat gcctatttga aggcagatgg attgactaag acgtgtgcag gcagtggagg
9001 agttacaagg caggacatat ttactaggta taggtgtagg taatagtaat ggagaggata
9061 aatttaggtt ttgggatgaa tggatttgtt ggtacatgtt gcaactccca cactgcaatc
9121 aaaggaccgc tatgacaccc cctgaatgcg acgcccatga gaatgccgac cccacatata
9181 catttctgga aataataggg aaatgcaccc ttgcattata tttcattat tcgtcctcca
9241 ttttgtgcgc tctccattca ttttcaaatg cgctccactc ttcctttatt tcttaccacc
9301 attatctcgt attcgaggtc cagaaatcaa gttgtgaatc tgccttggtt gcgcattgtt
9361 aaagtactct tctgtgtata tttctgcccc accgttttca cttccaacac ttaaattttt
9421 ttatttttta ttttatatat ttcttataaa ttgttggctt ctcacacgaa cccaagccat
9481 ccaagcccg acaaaggcaa tccaatgtac ttgactagag tcaaatacct tttacttctt
9541 tacttctcat attaccagaa agccaagcca accttaccaa actaatgtac ctgagcagag
9601 tccactacct ttcctcaagt acagtggcag tcagagtata tcaccgcttg ttatgtatat
9661 gctttaatgc tatgcttatt tctaggtcat aatctaaatc atatttgctg tcgagtttaa
9721 gcttatcgat accgtcgacc tcgagcttct tcttgaatgc tcttatgggt aggattattt
9781 ttcactttt tccttcatat tccacacaca tatatatata aacacactaa cattagtggg
9841 aatatttgtt tgatatgttt attttattta cttcgggggt ttttgtaaca attttgtaga
9901 tctaatttct tgttcttcat gtgtatatta attttcccctt aagacttaaa taaaaagaga
9961 gagtttgtta tatatagata tatgaagtga gggaaatggt acaaagttaa aggagatctg
10021 agtgagagtt agataataaa tgaaaagaaa taagaaacca tcaggggtttt ttctaatgtg
10081 gagttttaga ttcagttttg tagaactaag attcactttg ttgggtgttc tttcttcact
10141 catttctgtt attataataa taataaaatc ttatatcttt ctattttcct tactaacaag
10201 tacttgaaga tttagatata tttatagatc tggtgttgta ataggtaaaa acttgattt
10261 tgtgactata aaagtaagtt ttgggaaaca aattggggag agagtaagga aggactatga
10321 ggtcatatct tctgttttgt gatcatccat cctccattgt tgttaatgtc tgtgtctctc
10381 ttttcttct cttcttctc ttactttcct ttcttatctc tagctctctt tctctctcat
10441 gaattatatc atatcatata tttgatacaa acacatgtga tggtaagtga gagtgaataa
10501 ggtgaaacta gctagatttt tgagttttca tgaaatttta acttatatga gtgatagaaa
10561 ataatggaac ttatacgtac atgtaggaca atttagatgg ttatctaagt ttttgttttt
10621 gttttctctt gagaatgtta aatgttagtg ttattttgt agttttgaa aattatatat
10681 gagctaagat tagtttagaa gtggtcaaaa gaaacataga tttgaaattt caactgaatt
10741 ttcaagattt caaatagtca atgaaacaag gaggtaatta agacaaatta gcttatgggg
```

Figure 6F

```
10801 actcttttt gttattcctt aaaattactc tttttaaaat taaaaataac taatctcatt
10861 tcgaactaca ttactcaaac tagtaatctc taattcgaca cgcaatttcc aaatacttat
10921 tagtagagag tcccacgtga ttactttctt ctccaccaaa acataaaaca tgtcaagatt
10981 aaatggtgtt tgaaaattaa aagatcaatt ttcttaatcg tttacagttg tcaactctca
11041 tgtcctgaaa tatataattc tcatgtccaa aacaagaaaa gctaacaacg acttcaaatt
11101 aaatcagtca atcaaaatta gtcttcattt acctactaat ttcttttat atatccgatg
11161 ggtactctac gaaatcagag tttcgtttct ttatttattt tcttttataa gatttttgag
11221 gtttttcag aggttggaat tgagcgcaag attaggtttt gggtctgtaa gatttgttgt
11281 ctttgttaaa gaatctttga tcacgtcatc actcagatat tatttcttt tattttttcat
11341 ttgtatttt actaatttat tataaagttt tgttagtttc agttcttgac ttctgacaag
11401 aaggttttat gtcataatga attaatttgt aacctattta taaattcaaa aatgtcatca
11461 tattactact tttgaccatt taatattaga tttctcattt ggtcaatacc caatgttcat
11521 attacatata tagagacaaa aattataagg atactaaatt gttcatattt cttggaagta
11581 aaaagattaa tgatcactga ataaatagat ttggcataga agtatagcat tggaattgct
11641 tcaacatctt tggtgtagat agatttatgc aatttctctt tctttttgaa gtatcttttt
11701 ttttctagag agagaataat gttagggatt tttatcattt tctctctcat tatgggtact
11761 gagaggaaag tgagatttt agtacggatc caatagttta agagtttggt ctgccttcta
11821 cgatccaaaa aaatctacgg tcatgatctc tccatcgaga aggttgagag ttcagacatc
11881 aaagtctata atatgtcatt gtaatacgta tttgtgcata tatatctatg tacaagtaca
11941 tatacaggaa actcaagaaa aaagaataaa tggtaaattt aattatattc caaataagga
12001 aagtatggaa cgttgtgatg ttactcggac aagtcattta gttacatcca tcacgtttaa
12061 atttaatcca atggttacaa ttttaatact atcaaatgtc tattggattt atacccaatg
12121 tgttaatggg ttgttgacac atgtcacatg tctgaaaccc tagacatgtt cagaccaatc
12181 atgtcactct aattttgcca gcatggcagt tggcagccaa tcactagctc gataaattta
12241 aggtttcaga ggaattttaa tttatttagg gttcatattg tttcataaaa tgattcttta
12301 tttgttacaa ctttaaggaa atattttatt aactatttaa ttgttcccttt ttcttatatt
12361 actttttgttt ttcttcaca tcatgtgtca cattaagttg catttcttct gactcaaaag
12421 aaccgatgtt tgcttttaag gtttcgtatt agaatcactt aactgtgcaa gtggtcgatt
12481 tgaccctatc aagcttgata tcgaattgcg gccgcggccg ggtggtgaca tttattcata
12541 aattcatctc aaaacaagaa ggatttacaa aaataaaaga aaacaaaatt ttcatctta
12601 acataattat aattgtgttc acaaaattca aacttaaacc cttaatataa agaatttctt
12661 tcaacaatac actttaatca caacttctt aatcacaacc tcctccaaca aaattaaaat
12721 agattaataa ataaatacaa ttaactattt aaaaaaaaat attatacaaa atttattaaa
12781 acttcaaaat aaacaaactt tttatacaaa attcatcaaa actttaaaat aaagctaaac
12841 actgaaaatg tgagtacatt taaaaggacg ctgatcacaa aaatttgaa aacataaaca
12901 aacttgaaac tctacctttt aagaatgagt ttgtcgtctc attaactcat tagttttata
12961 gttcgaatcc aattaacgta tctttttattt tatggaataa gggtgtttta ataagtgatt
13021 ttgggatttt tttagtaatt tatttgtgat atgttatgga gttttttaaaa atatatatat
13081 atatatatat ttttgggttg agtttactta aaatttggaa aaggttggta agaactataa
13141 attgagttgt gaatgagtgt tttatggatt ttttaagatg ttaaatttat atatgtaatt
13201 aaaatttat tttgaataac aaaaattata attggataaa aaattgtttt gttaaattta
13261 gagtaaaaat ttcaaaatct aaaataatta aacactatta tttttaaaaa atttgttggt
13321 aaatttatc ttatatttag ttaaaattta gaaaaaatta attttaaatt aataaactt
13381 tgaagtcaaa tattccaaat attttccaaa atattaaatc tattttgcat tcaaaataca
13441 atttaaataa taaaacttca tggaatagat tgataaaaac caaaaatctc
13501 aaataaaatt taaattacaa aacattatca acattatgat ttcaagaaag acaataacca
13561 gtttccaata aaataaaaaa cctcatggcc cgtaattaag atctcattaa ttaattctta
13621 tttttaatt ttttacata gaaaatatct ttatatcgta tccaagaaat atagaatgtt
13681 ctcgtccagg gactattaat ctccaaacaa gtttcaaaat cattacatta aagctcatca
13741 tgtcatttgt ggattggaaa ttatattgta taagagaaat atagaatgtt ctcgtctagg
13801 gactattaat ttccaaacaa atttcaaaat cattacatta aagctcatca tgtcatttgt
13861 ggattggaaa ttagacaaaa aaaatcccaa atatttctct caatctccca aaatatagtt
13921 cgaactccat atttttggaa attgagaatt ttttaccca ataatatatt tttttataca
13981 ttttagagat tttccagaca tatttgctct gggatttatt ggaatgaagg tttgagttat
14041 aaactttcag taatccaagt atcttcggtt tttgaagata ctaaatccat tatataataa
14101 aaacacattt taaacaccaa tttaatggga tttcagattt gtatcccatg ctattggcta
14161 aggcattttt cttattgtaa tctaaccaat tctaatttcc accctggtgt gaactgactg
14221 acaaatgcgg tccgaaaaca gcgaatgaaa tgtctgggtg atcggtcaaa caagcggtgg
14281 gcgagagagc gcggtgttg gcctagccgg gatggggta ggtagacggc gtattaccgg
14341 cgagttgtcc gaatggagtt ttcggggtag gtagtaacgt agacgtcaat ggaaaaagtc
14401 ataatctccg tcaaaaatcc aaccgctcct tcacatcgca gagttggtgg ccacgggacc
14461 ctccaccac tcactcgatc gcctgccgtg gttgcccatt attcaaccat acgccacttg
14521 actcttcacc aacaattcca ggccggcttt ctatacaatg tactgcacag gaaaatccaa
14581 tataaaaagc cggcctctgc ttccttctca gtagccccca gctcattcaa ttcttccccac
14641 tgcaggctac atttgtcaga cacgttttcc gccattttc gcctgtttct gcggagaatt
14701 tgatcaggtt cggattggga ttgaatcaat tgaaaggttt ttatttcag tatttcgatc
14761 gccggatccc cgggctgca ggaattgggc tgcagatcga tatttgattt cacatgctat
14821 tgtaatgtat ttattgtttc aattccgaat tagacaaagt gcttaaagct ctcttttcgg
14881 atttttttt tcattaatgt ataataattg cggacattac aatatactgt acaacgtgat
14941 ttgagcttga tgaattacaa gattggaaga acttcgaaga caaaaaaaaa atcgatctgc
15001 aggaattcgt ccagcagtaa ttcggtaccc ctgatcagca ctgctgccaa gaatgtaagt
15061 ttttatttct ttatatgtt caaacagttt tataaagtac tataagcttt ttttagccaa
15121 aagaaatatc ttaagtttta gtaaccaata aagaattatt gcggcctcct tatttaatta
15181 tagtacatat gtcatagtag atgttttttt tattattatt atttttttatt ttttttatagt
```

Figure 6G

```
15241 tttttacaaa ttcgacttgg agaccttatg atttggaaga tactccattt aattttatga
15301 gttgtgtttg aaaacatatt ttaagactaa acacgtagag aacattctta acaaatttgt
15361 aaataaataa atttaactct attctctagg atttaaatat tataggtata tatataattt
15421 tctaataagt ttatatcgag tcactcatac gagttgtgta gaaagttaat cacgggtacc
15481 aattttaaat taaaaataag aataattata tgatcttaaa tttatacaac tctgataaaa
15541 gattgggctt tgacatcttt gaagaaaact agatttagta atattctgat taaattgggt
15601 tcacactttg tagtgggcac actttccggg ttcgaaatcg aaatctggaa gcttatcgat
15661 ctcgaggggc ccactagtat cgatctcgag gggcccacta gtatcgatcg attttttttt
15721 tgtcttcgaa gttcttccaa tcttgtaatt catcaagctc aaatcacgtt gtacagtata
15781 ttgtaatgtc cgcaattatt atacattaat gaaaaaaaaa atccgaaaag agagctttaa
15841 gcactttgtc taattcggaa ttgaaacaat aaatacatta caatagcatg tgaaatcaaa
15901 tatcgatccg atgggtgtta tttgtggata ataaattcgg gtgatgttca gtgtttgtcg
15961 tatttctcac gaataaattg tgtttatgta tgtgttagtg ttgtttgtct gtttcagacc
16021 ctcttatgtt atattttct tttcgtcggt cagttgaagc caatactggt gtcctggccg
16081 gcactgcaat accatttcgt ttaatataaa gactctgtta tccgtgagct cgaatttccc
16141 cgatcgttca aacatttggc aataaagttt cttaagattg aatcctgttg ccggtcttgc
16201 gatgattatc atataatttc tgttgaatta cgttaagcat gtaataatta acatgtaatg
16261 catgacgtta tttatgagat gggttttat gattagagtc ccgcaattat acatttaata
16321 cgcgatagaa aacaaaatat agcgcgcaaa ctaggataaa ttatcgcgcg cggtgtcatc
16381 tatgttacta gatcgc
```

Figure 7A

```
LOCUS       pAGF243      7970 bp    DNA    circular
DEFINITION  PrMC2.400-3::H102E::RNS2TER in pWVR13.
SOURCE
  ORGANISM
COMMENT     This file is created by Vector NTI
            http://www.informaxinc.com/
COMMENT     VNTDATE|307549965|
COMMENT     VNTDBDATE|307550293|
COMMENT     VNTNAME|pAGF243|
COMMENT     VNTAUTHORNAME|khnorri|
FEATURES             Location/Qualifiers
     misc_marker     1246..2037
                     /vntifkey="22"
                     /label=npt\III\(kanR)
     misc_marker     2339..3484
                     /vntifkey="22"
                     /label=trfA
     misc_structure  complement(3940..3963)
                     /vntifkey="88"
                     /label=LEFT\BORDER
     CDS             complement(4588..5379)
                     /vntifkey="4"
                     /label=NPT\II\(kanR)
     terminator      complement(4319..4539)
                     /vntifkey="43"
                     /label=NOSTER
     promoter        complement(5380..6689)
                     /vntifkey="29"
                     /label=UBQ10\promoter
     intron          complement(5380..5683)
                     /vntifkey="15"
                     /label=INTRON
     misc_marker     744..1013
                     /vntifkey="22"
                     /label=barstar
     promoter        complement(7424..7785)
                     /vntifkey="29"
                     /label=PrMC2.400-3
     CDS             complement(7094..7423)
                     /vntifkey="4"
                     /label=H102Ebarnase
     terminator      complement(6732..6992)
                     /vntifkey="43"
                     /label=RNS2TER
     misc_structure  complement(7838..7861)
                     /vntifkey="88"
                     /label=RIGHT\BORDER
BASE COUNT     2175 a    1836 c    2000 g    1959 t
ORIGIN
        1 cgccggcgtt gtggatacct cgcggaaaac ttggccctca ctgacagatg aggggcggac
       61 gttgacactt gaggggccga ctcacccggc gcggcgttga cagatgaggg gcaggctcga
      121 tttcggccgg cgacgtggag ctggccagcc tgcaaatcg gcgaaaacgc ctgatttac
      181 gcgagtttcc cacagatgat gtggacaagc ctgggataa gtgccctgcg gtattgacac
      241 tgaggggcg cgactactga cagatgaggg gcgcgatcct tgacacttga ggggcagagt
      301 gctgacagat gaggggcgca cctattgaca tttgaggggc tgtccacagg cagaaaatcc
      361 agcatttgca agggtttccg ccgtttttc ggccaccgct aacctgtctt ttaacctgct
      421 tttaaaccaa tatttataaa ccttgttttt aaccaggget gcgccctgtg cgcgtgaccg
      481 cgcacgccga aggggggtgc ccccccttct cgaaccctcc cggcccgcta acgcgggcct
      541 cccatccccc cagggggctgc gccctcggc cgcgaacggc ctcacccaa aaatggcagc
      601 gctggcagtc cataattgtg gtccaattg cagccgtccg agacaggagg acatcgtcca
      661 gctgaaaccg gggcagaatc cggccatttc tgaagagaaa aatggtaaac tgatagaata
      721 aaatcataag aaaggagccg cacatgaaaa aagcagtcat taacggggaa caaatcagaa
      781 gtatcagcga cctccaccag acattgaaaa aggagcttgc ccttccggaa tactacggtg
      841 aaaactggaa cgctttatgg gattgtctga ccggatgggt ggagtacccg ctcgttttgg
      901 aatggaggca gtttgaacaa agcaagcagc tgactgaaaa tggcgccgag agtgtgcttc
      961 aggttttccg tgaagcgaaa gcggaaggct gcgacatcac catcatactt tcttaatacg
     1021 atcaatggga gaggaacaat atgaaacac aaaccacaat tgtggtttca aaatcggctc
     1081 cgtcgatact atgttatacg ccaaccttga aaacaacttt gaaaaagctg tttctctggta
     1141 tttaaggttt tagaatgcaa ggaacagtga attggagttc gtcttgttat aattagcttc
     1201 ttgggtatc tttaaatact gtagaaaaga ggaaggaaat aataaatggc taaaatgaga
     1261 atatcaccgg aattgaaaaa actgatcgaa aaataccgct gcgtaaaaga tacggaagga
     1321 atgtctcctg ctaaggtata taagctggtg ggagaaaatg aaaacctata tttaaaaatg
     1381 acggacagcc ggtataaagg gaccacctat gatgtggaac gggaaaagga catgatgcta
```

Figure 7B

```
1441 tggctggaag gaaagctgcc tgttccaaag gtcctgcact ttgaacggca tgatggctgg
1501 agcaatctgc tcatgagtga ggccgatggc gtcctttgct cggaagagta tgaagatgaa
1561 caaagccctg aaaagattat cgagctgtat gcggagtgca tcaggctctt tcactccatc
1621 gacatatcgg attgtccata tacgaatagc ttagacagcc gcttagccga attggattac
1681 ttactgaata acgatctggc cgatgtggat tgcgaaaact gggaagaaga cactccattt
1741 aaagatccgc gcgagctgta tgattttta aagacggaaa agcccgaaga ggaacttgtc
1801 ttttcccacg gcgacctggg agacagcaac atctttgtga aagatggcaa agtaagtggc
1861 tttattgatc ttgggagaag cggcagggcg gacaagtggt atgacattgc cttctgcgtc
1921 cggtcgatca gggaggatat cggggaagaa cagtatgtcg agctattttt tgacttactg
1981 gggatcaagc ctgattggga gaaaataaaa tattatatt tactggatga attgttttag
2041 tacctagatg tggcgcaacg atgccggcga caagcaggag cgcaccgact tcttccgcat
2101 caagtgtttt ggctctcagg ccgaggccca cggcaagtat ttgggcaagg ggtcgctggt
2161 attcgtgcag ggcaagattc ggaataccaa gtacgagaag gacggccaga cggtctacgg
2221 gaccgacttc attgccgata aggtggatta tctggacacc aaggcaccag gcgggtcaaa
2281 tcaggaataa gggcacattg ccccggcgtg agtcgggggca atcccgcaag gagggtgaat
2341 gaatcggacg tttgaccgga aggcatacag gcaagaactg atcgacgcgg ggttttccgc
2401 cgaggatgcc gaaaccatcg caagccgcac cgtcatgcgt gcgcccgcg aaaccttcca
2461 gtccgtcggc tcgatggtcc agcaagctac ggccaagatc gagcgcgaca gcgtgcaact
2521 ggctcccct gccctgcccg cgccatcggc cgccgtggag cgttcgcgtc gtctcgaaca
2581 ggaggcggca ggtttggcga agtcgatgac catcgacacg cgaggaacta tgacgaccaa
2641 gaagcgaaaa accgccgcg aggacctggc aaaacaggtc agcgaggcca agcaggccgc
2701 gttgctgaaa cacacgaagc agcagatcaa ggaaatgcag cttccttgt tcgatattgc
2761 gccgtggccg gacacgatgc gagcgatgcc aaacgacacg gcccgctctg ccctgttcac
2821 cacgcgcaac aagaaaatcc cgcgcgaggc gctgcaaaac aaggtcattt tccacgtcaa
2881 caaggacgtg aagatcacct acaccggcgt cgagctgcgg gccgacgatg acgaactggt
2941 gtggcagcag gtgttggagt acgcgaagcg caccccctatc ggcgagccga tcaccttcac
3001 gttctacgag ctttgccagg acctgggctg gtcgatcaat ggccggtatt acacgaaggc
3061 cgaggaatgc ctgtcgcgcc tacaggcgac ggcgatgggc ttcacgtccg accgcgttgg
3121 gcacctggaa tcggtgtcgc tgctgcaccg cttccgcgtc ctggaccgtg gcaagaaaac
3181 gtcccgttgc caggtcctga tcgacgagga aatcgtcgtg ctgtttgctg gcgaccacta
3241 cacgaaattc atatgggaga agtaccgcaa gctgtcgccg acggcccgac ggatgttcga
3301 ctatttcagc tcgcaccggg agccgtccc gctcaagctg gaaaccttcc gcctcatgtg
3361 cggatcggat tccacccgcg tgaagaagtg gcgcgagcag gtcggcgaag cctcgaaga
3421 gttgcgaggc agcggcctgg tggaacacgc ctgggtcaat gatgacctgg tgcattgcaa
3481 acgctagggc cttgtggggt cagttccggc tggggggttca gcagccagcg ctttactggc
3541 atttcaggaa caagcgggca ctgctcgacg cacttgcttc gctcagtatc gctcgggacg
3601 cacggcgcgc tctacgaact gccgatagac aactgtcacg gttaagcgag aaatgaataa
3661 gaaggctgat aattcggatc tctgcgaggg agatgatatt tgatcacagg cagcaacgct
3721 ctgtcatcgt tacaatcaac atgctaccct ccgcgagatc atccgtgttt caaacccggc
3781 agcttagttg ccgttcttcc gaatagcatc ggtaacatga gcaaagtctg ccgccttaca
3841 acggctctcc cgctgacgcc gtcccggact gatgggctgc ctgtatcgag tggtgatttt
3901 gtgccgagct gccggtcggg gagctgttgg ctggctggtg gcaggatata ttgtggtgta
3961 aacaaattga cgcttagaca acttaataac acattgcgga cgttttaat gtactgggggt
4021 ggttttctt ttcaccagtg agacgggcaa cagctgattg ccccttcaccg cctggcctg
4081 agagagttgc agcaagcggt ccacgctggt ttgccccagc aggcgaaaat cctgtttgat
4141 ggtggttccg aaatcggcaa aatcccttat aaatcaaaag aatagcccga gatagggttg
4201 agtgttgttc cagtttggaa caagagtcca ctattaaaga acgtggactc caacgtcaaa
4261 gggcgaaaaa ccgtctatca gggcgatggc ccacggccgc tctagaacta gtggatcccc
4321 cctacgtgcg atctagtaac atagatgaca ccgcgcgcga taatttatcc tagtttgcgc
4381 gctatattt gttttctatc gcgtattaaa tgtataattg cgggactcta atcataaaaa
4441 cccatctcat aaataacgtc atgcattaca tgttaattat tacatgctta acgtaattca
4501 acagaaatta tatgataatc atcgcaagac cggcaacagg attcaatctt aagaaacttt
4561 attgccaaat gtttgaacga tccctcagaa gaactcgtca agaaggcgat agaaggcgat
4621 gcgctgcgaa tcgggagcgg cgataccgta agcacgagg aagcggtcag cccattcgcc
4681 gccaagctct tcagcaatat cacgggtagc caacgctatg tcctgatagc ggtccgccac
4741 acccagccgg ccacagtcga tgaatccaga aaagcggcca ttttccacca tgatattcgg
4801 caagcaggca tcgccatggg tcacgatcg atcctcgacg tcgggcatgc gcgccttgag
4861 cctggcgaac agttcggctg gcgcgagccc ctgatgctct tcgtccagat catcctgatc
4921 gacaagaccg gcttccatcc gagtacgtgc tcgctcgatg cgatgtttcg cttggtggtc
4981 gaatgggcag gtagccggat caagcgtatg cagccgccgc attgcatcag ccatgatgga
5041 tactttctcg gcaggagcaa ggtgagatga caggagatcc tgccccgcca cttcgcccaa
5101 tagcagccag tcccttcccg cttcagtgac aacgtcgagc acagctgcgc aaggaacgcc
5161 cgtcgtggcc agccacgata gccgcgctgc ctcgtcctgg agttcattca gggcaccgga
5221 caggtcggtc ttgacaaaaa gaaccgggcg cccctgcgct gacagccgga acacggcggc
5281 atcagagcag ccgattgtct gttgtgccca gtcatagccg aatagcctct ccacccaagc
5341 ggccgagaa cctgcgtgca atccatcttg ttcaatcatc tgttaatcag aaaaactcag
5401 attaatcgac aaattcgatc gcacaaacta gaaactaaca ccagatctag atagaaatca
5461 caaatcgaag agtaattatt cgacaaaact caaattattt gaacaaatcg gatgatattt
5521 atgaaaccct aatcgagaat taagatgata tctaacgatc aaaccccagaa aatcgtcttc
5581 gatctaagat taacagaatc taaaccaaag aacatatacg aaattgggat cgaacgaaaa
5641 caaaatcgaa gattttgaga gaataaggaa cacagaaatt taccttgatc acggtagaga
5701 gaattgagag aaagttttta agatttgag aaattgaaat ctgaattgtg aagaagaaga
5761 gctctttggg tattgtttta tagaagaaga agaagaaaag acgaggacga ctaggtcacg
5821 agaaagctaa ggcggtgaag caatagctaa taataaaatg acacgtgtat tgagcgttgt
```

Figure 7C

```
5881 ttacacgcaa agttgttttt ggctaattgc cttattttta ggttgaggaa aagtatttgt
5941 gctttgagtt gataaacacg actcgtgtgt gccggctgca accactttga cgccgtttat
6001 tactgactcg tcgacaacca caatttctaa cggtcgtcat aagatccagc cgttgagatt
6061 taacgatcgt tacgatttat atttttttag cattatcgtt ttatttttta aatatacggt
6121 ggagctgaaa attggcaata attgaaccgt gggtcccact gcattgaagc gtatttcgta
6181 ttttctagaa ttcttcgtgc tttatttctt ttcctttctg ttttttttg ccatttatct
6241 aatgcaagtg ggcttataaa atcagtgaat ttcttggaaa agtaacttct ttatcgtata
6301 acatattgtg aaattatcca tttcttttaa tttttttagtg ttattggata tttttgtatg
6361 attattgatt tgcataggat aatgacttct gtatcaagtt ggtgaacaag tctcgttaaa
6421 aaaggcaagt ggtttggtga ctcgatttat tcttgttatt taattcatat atcaatggat
6481 cttatttggg gcctggtcca tatttaacac tcgtgttcag tccaatgacc aataatattt
6541 tttcattaat aacaatgtaa caagaatgat acacaaaaca ttctttgaat aagttcgcta
6601 tgaagaaggg aacttatccg gtcctagatc atcagttcat acaaacctcc atagagttca
6661 acatcttaaa caaggatatc ctgatccgtt gacggcgcgc caagcggccg catttaaatg
6721 ggccctatct aatcgaattt tgtaaactgg tttgataagc catcaatgca tcagtcaaga
6781 atgaatcatt gcaactaagt tgatataatt caatttacca tagaactcaa atgttgatat
6841 cttcttatgg attttctgat cttctacatt attagaaaga aacttgattt accagtaatg
6901 atgatacata tccaatagaa cgaaataagc caatctttat aggttttggt agtaaagtta
6961 caacatcaga gacatgtatg tattgtctct cagaagagct cttgaccgat cagagtttga
7021 agaaaaattt attacacact ttatgtaaag ctgaaaaaaa cggcctcccg cagggaagcc
7081 gttttttcg ttatctgatt tttgtaaagg tctgatactc gtccgttgtt ttgtaaatca
7141 gccagtcgct tgagtaaaga atccggtctg aatttctgaa gcctgatgta tagttaatat
7201 ccgcttcacg ccatgttcgt ccgcttttgc ccgggagttt gccttccctg tttgagaaga
7261 tgtctccgcc gatgcttttc ccggagcga cgtctgcaag gttcccttct gatgccaccc
7321 agccgagggc ttgtgcttct gattttgtaa tgtaattatc aggtagctta tgatatgtct
7381 gaagataatc cgcaaccccg tcaaacgtgt tgataacctg tgccataaat cttctaaaaa
7441 cagcagaact gactattcaa agaaagtaga acccacagaa agtaatcaaa gtagtttgat
7501 taaatgcgtt gtgtatcatc gcagcccctg ctacggatat ttataggaaa ggtttgagag
7561 caatgtgtgc agcaagttgt gtgtgaatca cctgcttcca tgcggagga taaataattt
7621 agtcacgcat ttagttgaac gtaactacta actcctctac cgctaatcat tcttcttttg
7681 cccgggcaag ttcaacaaca accccacaat cacgcttcct gtattttgtt ttgttttcaa
7741 aacaatagaa ttcactttt actgccaaaa ttatgtttta ctcgagagcc cgggctcctg
7801 caggtacctt aattaaaagt ttaaactatc agtgtttgac aggatatatt ggcgggtaaa
7861 cctaagagaa aagagcgttt attagaataa tcggatattt aaaagggcgt gaaaaggttt
7921 atccgttcgt ccatttgtat gtgcatgcca accacagggt tccccagatc
```

Figure 8A

```
LOCUS       pABDP010     10312 bp    DNA    circular           20-SEP-2004
DEFINITION  Complementary copy of CZ28-bstar + UBQ10::NPTII::E9/LPAG1d4::bstar::NOST.
SOURCE
  ORGANISM
COMMENT     This file is created by Vector NTI
            http://www.informaxinc.com/
COMMENT     VNTDATE|350147921|
COMMENT     VNTDBDATE|350147921|
COMMENT     VNTNAME|pABDP010|
COMMENT     VNTAUTHORNAME|dlpetri|
COMMENT     Vector_NTI_Display_Data_(Do_Not_Edit!)
COMMENT     (SXF FEATURES             Location/Qualifiers
     misc_marker     complement(8611..9402)
                     /vntifkey="22"
                     /label=NPTIII
     misc_marker     complement(7164..8309)
                     /vntifkey="22"
                     /label=trfA
     misc_signal     6685..6709
                     /vntifkey="87"
                     /label=LB
     terminator      4318..4963
                     /vntifkey="43"
                     /label=E9
     CDS             5730..6059
                     /vntifkey="4"
                     /label=barstar
     terminator      6065..6332
                     /vntifkey="43"
                     /label=NOS-T
                     /note="Added BamHI and XhoI sites to 3' end"
     promoter        4964..5729
                     /vntifkey="29"
                     /label=LPAG1d4
     CDS             3522..4317
                     /vntifkey="4"
                     /label=NPTII
     misc_signal     4314..4316
                     /vntifkey="87"
                     /label=TGA
     promoter        2212..3521
                     /vntifkey="29"
                     /label=UBQ10\promoter
     intron          3218..3521
                     /vntifkey="15"
                     /label=INTRON
     misc_signal     1..25
                     /vntifkey="87"
                     /label=RB
                     /note="Right Border of T-DNA"
     misc_signal     1474..1476
                     /vntifkey="87"
                     /label=ATG
                     /note="ATG of Barnase E73G"
     CDS             1474..1912
                     /vntifkey="4"
                     /label=Barnase\E73G
     terminator      1920..2178
                     /vntifkey="43"
                     /label=NOS-T
     promoter        82..1473
                     /vntifkey="29"
                     /label=LPAG1-P
                     /note="LPAG1 promoter- still determining exact location of 5'
end"
BASE COUNT     2628 a     2467 c     2322 g     2895 t
ORIGIN
        1 gtttacccgc caatatatcc tgtcaaacac tgatagttta aacttttaat taaggtacct
       61 gcaggagccc gggctctcga gcagcaaata tgatttagat tatgacctag aaataagcat
      121 agcattaaag catatacaaa acaagcggtg atatactctg actgccactg tacttgagga
```

Figure 8B

```
 181 aaggtagtgg actctgctca ggtacattag tttggtaagg ttggcttggc ttctgggtaa
 241 tatgagaagt aaagaagtaa aaggtatttg actctagtca agtacattgg attgccttcg
 301 tcggggcttg gatggcttgg gttcgtgtga gaagccaaca atttataaaa aaatatattg
 361 aaaaaaaaaa aaatcgtcta agtgttggaa gtgaaaacgg tgggacataa atatacacag
 421 aagagtactt taacaatgcg caaccaaggc agattcacaa cttgatttct ggacctcgaa
 481 tacgagataa tggtggtaag aaataaagga agagtggagt gcatttgaaa atgaatggag
 541 agcgcacaaa atggaggacg aataaatgaa atataatgca agagtgcatt tccctattat
 601 ttccagaaat gtatatgtgg ggtcggcatt cacatgggcg tcgcattcag ggggtgtcat
 661 agcggtcctt tgattgcagt gtgggagttg caacatgtac caacaaattc attcatccca
 721 aaacctaaat ttatcctctc cattactatt acctacacct atacctagta aatatgtcct
 781 gccttgtaac tcctccactg cctgcacacg tcttagtcaa tccatctgcc ttcaaatagg
 841 cattattttg ttctttcccc tccgactgaa aggctatcga ccgaccgacc gctcatcttc
 901 ttcttctgcg caatttttc tgctggatca tcatcattac catcatcgcc atcccacca
 961 tcatcatcat gatggtatct ctatctctcc ctggcaatcg attgtagagg aaaggaagag
1021 ggaaggggca tatgtattga tcaacctacc cgaaaaaaca atctgatcag ccctgctaat
1081 cttgcttata aatctcttat ccactgttca atcattcagg ttttcttccca cttccaagca
1141 aaggcgcccg gattggccgt gttcttagat tttcaggtac ttaaatggac aatattcccc
1201 acctgaagcc gttctgaaaa agatttgttt gtagaaacaa acgattgtaa tatttgctta
1261 agttgagctt aaggggtttg gtacctaact tgccttgtgg ttatttgttt ctcagaactc
1321 gggctgcgtc caactgtagg aacgaaccag cacaaggggt tgcagctttt gctgttgctg
1381 ttgcgcccat tgcttttgga ctggtattag tagttgcagc tttgtttttgc atacgctgtg
1441 aggatctgtg cgcggaaatt ttgtgtacaa atcatggcac aggttatcaa cacgtttgac
1501 ggggttgcgg attatcttca gacatatcat aagctacctg ataattacat tacaaaatca
1561 gaagcacaag ccctcggctg ggtggcatca aaagggaacc ttgcagacgt cgctccgggg
1621 aaaagcatcg gcggagacat cttctcaaac agggaaggca aactcccggg caaaagcgga
1681 cgaacatggc gtggagcgga tattaactat acatcaggct tcagaaattc agaccggatt
1741 ctttactcaa gcgactggct gatttacaaa acaacggacc attatcagac ctttacaaaa
1801 atcgataaac gaaaaaaacg gcttccctgc gggaggccgt tttttcagc tttacataaa
1861 gtgtgtaata aattttttctt caaactctga tcggtcaatt gcactttgag ctcgaatttc
1921 cccgatcgtt caaacatttg gcaataaagt ttcttaagat tgaatcctgt tgccggtctt
1981 gcgatgatta tcatataatt tctgttgaat tacgttaagc atgtaataat taacatgtaa
2041 tgcatgacgt tatttatgag atgggttttt atgattagag tcccgcaatt atacatttaa
2101 tacgcgatag aaaacaaaat atagcgcgca aactaggata aattatcgcg cgcgtgtca
2161 tctatgttac tagatcggga aggcgcgccg cggccgcttg gcgcgccgtc aacggatcag
2221 gatatccttg tttaagatgt tgaactctat ggaggtttgt atgaactgat gatctaggac
2281 cggataagtt cccttcttca tagcgaactt attcaaagaa tgttttgtgt atcattcttg
2341 ttacattgtt attaatgaaa aaatattatt ggtcattgga ctgaacacga gtgttaaata
2401 tggaccaggc cccaaataag atccattgat atatgaatta aataacaaga ataaatcgag
2461 tcaccaaacc acttgccttt tttaacgaga cttgttcacc aacttgatca aaaagtcatt
2521 atcctatgca aatcaataat catacaaaaa cactaaaaaa ttaaaagaaa
2581 tggataattt cacaatatgt tatacgataa agaagttact tttccaagaa attcactgat
2641 tttataagcc cacttgcatt agataaatgg caaaaaaaaa caaaaggaa aagaaataaa
2701 gcacgaagaa ttctagaaaa tacgaaatac gcttcaatgc agtgggaccc acggttcaat
2761 tattgccaat tttcagctcc accgtatatt taaaaaataa aacgataatg ctaaaaaaat
2821 ataaatcgta acgatcgtta aatctcaacg gctggatctt atgacgaccg ttagaaattg
2881 tggttgtcga cgagtcagta ataaacggcg tcaaagtggt tgcagccggc acacacgagt
2941 cgtgtttatc aactcaaagc acaaatactt ttcctcaacc taaaaataag gcaattagcc
3001 aaaacaact ttgcgtgtaa acaacgctca atacacgtgt catttttatta ttagctattg
3061 cttcaccgcc ttagctttct cgtgacctag tcgtcctcgt cttttcttct tcttcttcta
3121 taaaacaata cccaaagagc tcttcttctt cacaattcag atttcaattt ctcaaaatct
3181 taaaaactt ctctcaattc tctctaccgt gatcaaggta aatttctgtg ttccttattc
3241 tctcaaaatc ttcgattttg ttttcgttcg atcccaattt cgtatatgtt cttttggttta
3301 gattctgtta atcttagatc gaagacgatt ttctgggttt gatcgttaga tatcatctta
3361 attctcgatt agggtttcat aaatatcatc cgatttgttc aaataatttg agttttgtcg
3421 aataattact cttcgatttg tgatttctat ctagatctgg tgttagtttc tagtttgtgc
3481 gatcgaattt gtcgattaat ctgagttttt ctgattaaca gatgattgaa caagatggat
3541 tgcacgcagg ttctccggcc gcttgggtgg agaggctatt cggctatgac tgggcacaac
3601 agacaatcgc ctgctctgat gccgccgtgt tccggctgtc agcgcagggg cgcccggttc
3661 tttttgtcaa gaccgacctg tccggtgccc tgaatgaact ccaggacgag gcagcgcggc
3721 tatcgtggct ggccacgacg ggcgttcctt gcgcagctgt gctcgacgtt gtcactgaag
3781 cgggaaggga ctgctgcta ttgggcgaag tgccgggca ggatctcctg tcatctcacc
3841 ttgctcctgc cgagaaagta tccatcatgg ctgatgcaat gcggcggctg catacgcttg
3901 atccggctac ctgcccattc gaccaccaag cgaaacatcg catcgagcga gcacgtactc
3961 ggatggaagc cggtcttgtc gatcaggatg atctggacga agagcatcag gggctcgcgc
4021 cagccgaact gttcgccagg ctcaaggcgc gcatgcccga cggcgaggat ctcgtcgtga
4081 cccatggcgg tgcctgcttg ccgaatatca tggtggaaaa tggccgcttt tctggattca
4141 tcgactgtgg ccggctggt gtgcggacc gctatcagga catagcgttg gctaccgtg
4201 atattgctga agagcttggc ggcgaatggg ctgaccgctt cctcgtgctt tacggtatcg
4261 ccgctcccga ttcgcagcgc atcgccttct atcgccttct tgacgagttc ttctgagaat
4321 tcagctttcg ttcgtatcat cggtttcgac aacgttcgtc aagttcaatg catcagtttc
4381 attgcgcaca caccagaatc ctactgagtt cgagtattat ggcattggga aaactgtttt
4441 tcttgtacca tttgttgtgc ttgtaattta ctgtgttttt tattcggttt tcgctatcga
4501 actgtgaaat ggaaatggat ggagaagagt taatgaatga tatggtcctt ttgttcattc
```

Figure 8C

```
4561 tcaaattaat attatttgtt ttttctctta tttgttgtgt gttgaatttg aaattataag
4621 agatatgcaa acatttttgtt ttgagtaaaa atgtgtcaaa tcgtggcctc taatgaccga
4681 agttaatatg aggagtaaaa cacttgtagt tgtaccatta tgcttattca ctaggcaaca
4741 aatatatttt cagacctaga aaagctgcaa atgttactga atacaagtat gtcctcttgt
4801 gttttagaca tttatgaact ttcctttatg taattttcca gaatccttgt cagattctaa
4861 tcattgcttt ataattatag ttatactcat ggatttgtag ttgagtatga aaatattttt
4921 taatgcattt tatgacttgc caattgattg acaacgcaag cttttcattc atcccaaaac
4981 ctaaatttat cctctccatt actattacct acacctatac ctagtaaata tgtcctgcct
5041 tgtaactcct ccactgcctg cacacgtctt agtcaatcca tctgccttca aataggcatt
5101 attttgttct ttcccctccg actgaaaggc tatcgaccga ccgaccgctc atcttcttct
5161 tctgcgcaat tttttctgct ggatcatcat cattaccatc atcgccatcc ccaccatcat
5221 catcatgatg gtatctctat ctctccctgg caatcgattg tagaggaaag gaagagggaa
5281 ggggcatatg tattgatcaa cctacccgaa aaacaatct gatcagccct gctaatcttg
5341 cttataaatc tcttatccac tgttcaatca ttcaggtttc ttcccacttc caagcaaagg
5401 cgcccggatt ggccgtgttc ttagattttc aggtacttaa atggacaata ttccccacct
5461 gaagccgttc tgaaaaagat ttgtttgtag aaacaaacga ttgtaatatt tgcttaagtt
5521 gagcttaagg ggtttggtac ctaacttgcc ttgtggttat ttgtttctca gaactcgggc
5581 tgcgtccaac tgtaggaacg aaccagcaca aggggttgca gcttttgctg ttgctgttgc
5641 gcccattgct tttggactgg tattagtagt tgcagctttg ttttgcatac gctgtgagga
5701 tctgtgcgcg gaaatttttgt gtacaaatca tgaaaaaagc agtcattaac ggggaacaaa
5761 tcagaagtat cagcgacctc caccagacat tgaaaaggga gcttgcccct cggaaatact
5821 acggtgaaaa cctggacgct ttatgggatt gtctgaccgg atgggtggag taccgctcg
5881 ttttggaatg gaggcagttt gaacaaagca agcagctgac tgaaaatggc gccgagagtg 5941 tgcttcaggt tttccgtgaa gcgaaagcgg aaggctgcga catcaccatc atactttctt
6001 aatacgatca atgggagatg aacaatatgg aaacacaaac cacaattatg tctctcagcg
6061 agctcgaatt tccccgatcg ttcaaacatt tggcaataaa gtttcttaag attgaatcct
6121 gttgccggtc ttgcgatgat tatcatataa tttctgttga attacgttaa gcatgtaata
6181 attaacatgt aatgcatgac gttatttatg agatgggttt ttatgattag agtcccgcaa
6241 ttatacattt aatacgcgat agaaaacaaa atatagcgcg caaactagga taaattatcg
6301 cgcgcggtgt catctatgtt actagatcgg ggatccacta gttctagagc ggcgtgggcc
6361 atcgccctga tagacggttt ttcgcccttt gacgttggag tccacgttct ttaatagtgg
6421 actcttgttc caaactggaa caacactcaa ccctatctcg ggctattctt ttgatttata
6481 agggattttg ccgatttcgg aaccaccatc aaacaggatt ttcgcctgct ggggcaaacc
6541 agcgtggacc gcttgctgca actctctcag ggccaggcgg tgaagggcaa tcagctgttg
6601 cccgtctcac tggtgaaaag aaaaaccacc ccagtacatt aaaaacgtcc gcaatgtgtt
6661 attaagttgt ctaagcgtca atttgtttac accacaatat atcctgccac cagccagcca
6721 acagctcccc gaccggcagc tcggcacaaa atcaccactc gatacaggca gccatcagt
6781 ccgggacggc gtcagcggga gagccgttgt aaggcggcag actttgctca tgttaccgat
6841 gctattcgga agaacggcaa ctaagctgcc gggtttgaaa cacggatgat ctcgcggagg
6901 gtagcatgtt gattgtaacg atgacagagc gttgctgcct gtgatcaaat atcatctccc
6961 tcgcagagat ccgaattatc agccttctta ttcattttctc gcttaaccgt gacagttgtc
7021 tatcggcagt tcgtagagcg cgccgtgcgt cccgagcgat actgagcgaa gcaagtgcgt
7081 cgagcagtgc ccgcttgttc ctgaaatgcc agtaaagcgc tggctgctga accccagcc
7141 ggaactgacc ccacaaggcc ctagcgtttg caatgcacca ggtcatcatt gacccaggcg
7201 tgttccacca ggccgctgcc tcgcaactct cgccgaccgt cgcgcgcac
7261 ttcttcacgc gggtggaatc cgatccgcac atgaggcgga aggtttccag cttgagcggg
7321 tacggctccc ggtgcgagct gaaatagtcg aacatccgtc gggccgtcgg cgacagcttg
7381 cggtacttct cccatatgaa tttcgtgtag tggtcgccag caaacagcac gacgatttcc
7441 tcgtcgatca ggacctggca acgggacgtt ttcttgccac ggtccaggac gcggaagcgg
7501 tgcagcagcg acaccgattc caggtgccca acgcggtcgg acgtgaagcc catcgccgtc
7561 gcctgtaggc gcgacaggca ttcctcgcc ttcgtgtaat accggccatt gatcgaccag
7621 cccaggtcct ggcaaagctc gtagaacgtg aaggtgatcg gctcgccgat aggggtgcgc
7681 ttcgcgtact ccaacacctg ctgccacacc agttcgtcat cgtcggcccg cagctcgacg
7741 ccggtgtagg tgatcttcac gtccttgttg acgtggaaaa tgaccttgtt ttgcagcgcc
7801 tcgcgcggga ttttcttgtt gcgcgtggtg aacagggcag agcgggccgt gtcgtttggc
7861 atcgctcgca tcgtgtccgg ccacggcgca atatcgaaca aggaaagctg catttccttg
7921 atctgctgct tcgtgtgttt cagcaacgcg gcctgcttgg cctcgctgac ctgttttgcc
7981 aggtcctcgc cggcggtttt tgcttcttg gtcgtcatag ttcctcgcgt gtcgatgtc
8041 atcgacttcg ccaaacctgc cgcctcctgt tcgagacgac gcgaacgctc cacggcggcc
8101 gatgcgcgg gcagggcagg gggagccagt tgcacgctgt cgcgctcgat cttggccgta
8161 gcttgctgga ccatcgagcc gacggactgg aaggtttcgc ggggcgcacg catgacggtg
8221 cggcttgcga tggtttcggc atcctcggcg gaaaaccccg cgtcgatcag ttcttgcctg
8281 tatgccttcc ggtcaaacgt ccgattcatt caccctcctt gcgggattgc ccgactcac
8341 gccggggcaa tgtgccctta ttcctgattt gaccgcctg tgtgcttggt gtccagataa
8401 tccaccttat cggcaatgaa gtcggtcccg tagacgtct ggccgtcctt ctcgtacttg
8461 gtattccgaa tcttgccctg cacgcaatac agcgaccct tgcccaaata cttgccgtgg
8521 gcctcggcct gagagccaaa acactgatgc cggaagaagt cggtcgcgtc ctgcttgtcg
8581 ccggcatcgt tgcgccacat ctaggtacta aaacaattca tccagtaaaa tataatattt
8641 tatttctcc caatcaggct tgatcccccag taagtcaaaa aatagctcga catactgttc
8701 ttccccgata tcctccctga tcgaccggac gcagaaggca atgtcatacc acttgtccgc
8761 cctgcgcgct ctcccaagat caataaagcc acttactttg ccatctttca caaagatgtt
8821 gctgtctccc aggtcgccgt gggaaaagac aagttcctct tcgggctttt ccgtctttaa
```

Figure 8D

```
 8881 aaaatcatac agctcgcgcg gatctttaaa tggagtgtct tcttcccagt tttcgcaatc
 8941 cacatcggcc agatcgttat tcagtaagta atccaattcg gctaagcggc tgtctaagct
 9001 attcgtatag ggacaatccg atatgtcgat ggagtgaaag agcctgatgc actccgcata
 9061 cagctcgata atcttttcag ggctttgttc atcttcatac tcttccgagc aaaggacgcc
 9121 atcggcctca ctcatgagca gattgctcca gccatcatgc cgttcaaagt gcaggacctt
 9181 tggaacaggc agctttcctt ccagccatag catcatgtcc ttttcccgtt ccacatcata
 9241 ggtggtccct ttataccggc tgtccgtcat ttttaaatat aggttttcat tttctcccac
 9301 cagcttatat accttagcag gagacattcc ttccgtatct tttacgcagc ggtatttttc
 9361 gatcagtttt ttcaattccg gtgatattct cattttagcc atttattatt tccttcctct
 9421 tttctacagt atttaaagat acccaagaa gctaattata acaagacgaa ctccaattca
 9481 ctgttccttg cattctaaaa ccttaaatac cagaaaacag cttttcaaa gttgttttca
 9541 aagttggcgt ataacatagt atcgacggag ccgattttga aaccacaatt atggactgcc
 9601 agcgctgcca tttttggggt gaggccgttc gcggccgagg ggcgcagccc ctgggggat
 9661 gggaggcccg cgttagcggg ccgggagggt tcgagaaggg ggggcacccc ccttcggcgt
 9721 gcgcggtcac gcgcacaggg cgcagccctg gttaaaaaca aggtttataa atattggttt
 9781 aaaagcaggt taaagacag gttagcggtg gccgaaaaac gggcggaaac ccttgcaaat
 9841 gctggatttt ctgcctgtgg acagccctc aaatgtcaat aggtgcgcc ctcatctgtc
 9901 agcactctgc ccctcaagtg tcaaggatcg cgcccctcat ctgtcagtag tcgcgccct
 9961 caagtgtcaa taccgcaggg cacttatccc caggcttgtc cacatcatct gtgggaaact
10021 cgcgtaaaat caggcgtttt cgccgatttg cgaggctggc cagctccacg tgccggccg
10081 aaatcgagcc tgccctcat ctgtcaacgc cgcgccgggt gagtcggccc ctcaagtgtc
10141 aacgtccgcc cctcatctgt cagtgagggc caagtttttcc gcgaggtatc cacaacgccg
10201 gcggatctgg ggaaccctgt ggttggcatg cacatacaaa tggacgaacg gataaacctt
10261 ttcacgccct tttaaatatc cgattattct aataaacgct cttttctctt ag
```

Figure 9A

```
LOCUS       pABDP04      10312 bp    DNA     circular
DEFINITION  Complementary copy of CZ28-bstar + UBQ10::NPTII::E9/LPAG1d4::bstar::NOST.
SOURCE
  ORGANISM
COMMENT     This file is created by Vector NTI
            http://www.informaxinc.com/
COMMENT     VNTDATE|350150026|
COMMENT     VNTDBDATE|350150026|
COMMENT     VNTNAME|pABDP04|
COMMENT     VNTAUTHORNAME|dlpetri|
COMMENT     Vector_NTI_Display_Data_(Do_Not_Edit!)
COMMENT     (SXF FEATURES             Location/Qualifiers
     misc_marker     complement(8611..9402)

/vntifkey="22"
                     /label=NPTIII
     misc_marker     complement(7164..8309)
                     /vntifkey="22"
                     /label=trfA
     misc_signal     6685..6709
                     /vntifkey="87"
                     /label=LB
     terminator      4318..4963
                     /vntifkey="43"
                     /label=E9
     CDS             5730..6059
                     /vntifkey="4"
                     /label=barstar
     terminator      6065..6332
                     /vntifkey="43"
                     /label=NOS-T
                     /note="Added BamHI and XhoI sites to 3' end"
     promoter        4964..5729
                     /vntifkey="29"
                     /label=LPAG1d4
     CDS             3522..4317
                     /vntifkey="4"
                     /label=NPTII
     misc_signal     4314..4316
                     /vntifkey="87"
                     /label=TGA
     promoter        2212..3521
                     /vntifkey="29"
                     /label=UBQ10\promoter
     intron          3218..3521
                     /vntifkey="15"
                     /label=INTRON
     misc_signal     1..25
                     /vntifkey="87"
                     /label=RB
                     /note="Right Border of T-DNA"
     misc_signal     1474..1476
                     /vntifkey="87"
                     /label=ATG
                     /note="ATG of Barnase E73G"
     CDS             1474..1912
                     /vntifkey="4"
                     /label=Barnase\F106S
     terminator      1920..2178
                     /vntifkey="43"
                     /label=NOS-T
     promoter        82..1473
                     /vntifkey="29"

/label=LPAG1-P
                     /note="LPAG1 promoter- still determining exact location of 5'
end"
BASE COUNT     2629 a     2468 c     2321 g     2894 t
ORIGIN
        1 gtttacccgc caatatatcc tgtcaaacac tgatagttta aactttaat taaggtacct
       61 gcaggagccc gggctctcga gcagcaaata tgatttagat tatgacctag aaataagcat
```

Figure 9B

```
 121 agcattaaag catatacaaa acaagcggtg atatactctg actgccactg tacttgagga
 181 aaggtagtgg actctgctca ggtacattag tttggtaagg ttggcttggc ttctgggtaa 241 tatgagaagt aaagaagtaa aaggtatttg actctagtca agtacattgg attgccttcg
 301 tcggggcttg gatggcttgg gttcgtgtga gaagccaaca atttataaaa aaatatattg
 361 aaaaaaaaaa aaatcgtcta agtgttggaa gtgaaaacgg tgggacataa atatacacag
 421 aagagtactt taacaatgcg caaccaaggc agattcacaa cttgatttct ggacctcgaa
 481 tacgagataa tggtggtaag aaataaagga agagtggagt gcatttgaaa atgaatggag
 541 agcgcacaaa atggaggacg aataaatgaa atataatgca agagtgcatt tccctattat
 601 ttccagaaat gtatatgtgg ggtcggcatt cacatgggcg tcgcattcag ggggtgtcat
 661 agcggtcctt tgattgcagt gtgggagttg caacatgtac caacaaattc attcatccca
 721 aaacctaaat ttatcctctc cattactatt acctacacct atacctagta aatatgtcct
 781 gccttgtaac tcctccactg cctgcacacg tcttagtcaa tccatctgcc ttcaaatagg
 841 cattattttg ttctttcccc tccgactgaa aggctatcga ccgaccgacc gtcatcttc
 901 ttcttctgcg caattttttc tgctggatca tcatcattac catcatcgcc atccccacca
 961 tcatcatcat gatggtatct ctatctctcc ctggcaatcg attgtagagg aaaggaagag
1021 ggaagggggca tatgtattga tcaacctacc cgaaaaaaca atctgatcg ccctgctaat
1081 cttgcttata aatctcttat ccactgttca atcattcagg tttcttccca cttccaagca
1141 aaggcgcccg gattggccgt gttcttagat tttcaggtac ttaaatggac aatattcccc
1201 acctgaagcc gttctgaaaa agatttgttt gtagaaacaa acgattgtaa tatttgctta
1261 agttgagctt aaggggtttg gtacctaact tgccttgtgg ttatttgttt ctcagaactc
1321 gggctgcgtc caactgtagg aacgaaccag cacaagggt tgcagctttt gctgttgctg
1381 ttgcgcccat tgcttttgga ctggtattag tagttgcagc tttgtttgc atacgctgtg
1441 aggatctgtg cgcggaaatt ttgtgtacaa atcatggcac aggttatcaa cacgtttgac
1501 ggggttgcgg attatcttca gacatatcat aagctacctg ataattacat tacaaaatca
1561 gaagcacaag ccctcggctg ggtggcatca aaagggaacc ttgcagacgt cgctccgggg
1621 aaaagcatcg gcggagacat cttctcaaac agggaaggca aactcccggg caaaagcgga
1681 cgaacatggc gtgaagcgga tattaactat acatcaggct tcagaaattc agaccggatt
1741 ctttactcaa gcgactggct gatttacaaa acaacggacc attatcagac ctctacaaaa
1801 atcagataac gaaaaaaacg gcttccctgc gggaggccgt ttttttcagc tttacataaa
1861 gtgtgtaata aatttttctt caaactctga tcggtcaatt gcactttgag ctcgaatttc
1921 cccgatcgtt caaacatttg gcaataaagt ttcttaagat tgaatcctgt tgccggtctt
1981 gcgatgatta tcatataatt tctgttgaat tacgttaagc atgtaataat taacatgtaa
2041 tgcatgacgt tatttatgag atgggttttt atgattagag tcccgcaatt atacatttaa
2101 tacgcgatag aaaacaaaat atagcgcgca aactaggata aattatcgcg cgcggtgtca
2161 tctatgttac tagatcggga aggcgcgccg cggccgcttg gcgcgccgtc aacggatcag
2221 gatatccttg tttaagatgt tgaactctat ggaggtttgt atgaactgat gatctaggac
2281 cggataagtt cccttcttca tagcgaactt attcaaagaa tgttttgtgt atcattcttg
2341 ttacattgtt attaatgaaa aaatattatt ggtcattgga ctgaacacga gtgttaaata
2401 tggaccaggc cccaaataag atccattgat atatgaatta aataacaaga ataaatcgag
2461 tcaccaaacc acttgccttt tttaacgaga cttgttcacc aacttgatac aaaagtcatt
2521 atcctatgca aatcaataat catacaaaaa tatccaataa cactaaaaaa ttaaaagaaa
2581 tggataattt cacaatatgt tatacgataa agaagttact tttccaagaa attcactgat
2641 tttataagcc cacttgcatt agataaatgg caaaaaaaaa caaaaggaa aagaaataaa
2701 gcacgaagaa ttctgaaaaa tacgaaatac gcttcaatgc agtgggaccc acggttcaat
2761 tattgccaat tttcagctcc accgtatatt taaaaaataa aacgataatg ctaaaaaaat
2821 ataaatcgta acgatcgtta aatctcaacg gctggatctt atgacgaccg ttagaaattg
2881 tggttgtcga cgagtcagta ataaacggcg tcaaagtggt tgcagccggc acacacgagt
2941 cgtgttatc aactcaaagc acaaatactt ttcctcaacc taaaaataag gcaattagcc
3001 aaaaacaact ttgcgtgtaa acaacgctca atacacgtgt cattttatta ttagctattg
3061 cttcaccgcc ttagcttct cgtgacctag tcgtcctcgt cttttcttct tcttcttcta
3121 taaaacaata cccaaagagc tcttcttctt cacaattcag atttcaattt ctcaaaatct
3181 taaaaacttt ctctcaattc tctctaccgt gatcaaggta aatttctgtg ttccttattc
3241 tctcaaaatc ttcgattttg ttttcgttcg atcccaattt cgtatatgtt ctttggttta
3301 gattctgtta atcttagatc gaagacgatt ttctgggttt gatcgttaga tatcatctta
3361 attctcgatt agggtttcat aaatatcatc cgatttgttc aaataatttg agttttgtcg
3421 aataattact cttcgatttg tgatttctat ctagatctgg tgttagtttc tagtttgtgc
3481 gatcgaattt gtcgattaat ctgagttttt ctgattaaca gatgattgaa caagatggat
3541 tgcacgcagg ttctccggcc gcttgggtgg agaggctatt cggctatgac tgggcacaac
3601 agacaatcgg ctgctctgat gccgccgtgt tccggctgtc agcgcagggg cgcccggttc
3661 tttttgtcaa gaccgacctg tccggtgccc tgaatgaact ccaggacgag gcagcgcggc
3721 tatcgtggct ggccacgacg ggcgttcctt gcgcagctgt gctcgacgtt gtcactgaag
3781 cgggaaggga ctggctgcta ttgggcgaag tgccggggca ggatctcctg tcatctcacc
3841 ttgctcctgc cgagaaagta tccatcatgg ctgatgcaat gcggcggctg catacgcttg
3901 atccggctac ctgcccattc gaccaccaag cgaaacatcg catcgagcga gcacgtactc
3961 ggatggaagc cggtcttgtc gatcaggatg atctggacga gagcatcag gggctcgcgc
4021 cagccgaact gttcgccagg ctcaaggcgc gcatgcccga cggcgaggat ctcgtcgtga
4081 cccatggcga tgcctgcttg ccgaatatca tggtggaaaa tggccgcttt tctggattca
4141 tcgactgtgg ccggctgggt gtggcggacc gctatcagga catagcgttg gctacccgtg
4201 atattgctga agagcttggc ggcgaatggg ctgaccgctt cctcgtgctt tacggtatcg
4261 ccgctcccga ttcgcagcgc atcgccttct atcgccttct tgacgagttc ttctgagaat
4321 tcagctttcg ttcgtatcat cggtttcgac aacgttcgtc aagttcaatg catcagtttc 4381 attgcgcaca caccagaatc ctactgagtt cgagtattat ggcattggga aaactgtttt
```

Figure 9C

```
4441 tcttgtacca tttgttgtgc ttgtaattta ctgtgttttt tattcggttt tcgctatcga
4501 actgtgaaat ggaaatggat ggagaagagt taatgaatga tatggtcctt ttgttcattc
4561 tcaaattaat attatttgtt ttttctctta tttgttgtgt gttgaatttg aaattataag
4621 agatatgcaa acattttgtt ttgagtaaaa atgtgtcaaa tcgtggcctc taatgaccga
4681 agttaatatg aggagtaaaa cacttgtagt tgtaccatta tgcttattca ctaggcaaca
4741 aatatatttt cagacctaga aaagctgcaa atgttactga atacaagtat gtcctcttgt
4801 gttttagaca tttatgaact ttcctttatg taattttcca gaatccttgt cagattctaa
4861 tcattgcttt ataattatag ttatactcat ggatttgtag ttgagtatga aaatattttt
4921 taatgcattt tatgacttgc caattgattg acaacgcaag cttttcattc atcccaaaac
4981 ctaaatttat cctctccatt actattacct acacctatac ctagtaaata tgtcctgcct
5041 tgtaactcct ccactgcctg cacacgtctt agtcaatcca tctgccttca aataggcatt
5101 attttgttct ttcccctccg actgaaaggc tatcgaccga ccgaccgctc atcttcttct
5161 tctgcgcaat ttttctgct ggatcatcat cattaccatc atcgccatcc ccaccatcat
5221 catcatgatg gtatctctat ctctccctgg caatcgattg tagaggaaag gaagagggaa
5281 ggggcatatg tattgatcaa cctacccgaa aaaacaatct gatcagccct gctaatcttg
5341 cttataaatc tcttatccac tgttcaatca ttcaggtttc ttcccacttc caagcaaagg
5401 cgcccggatt ggccgtgttc ttagattttc aggtacttaa atggacaata ttccccacct
5461 gaagccgttc tgaaaaagat ttgtttgtag aaacaaacga ttgtaatatt tgcttaagtt
5521 gagcttaagg ggtttggtac ctaacttgcc ttgtggttat ttgtttctca gaactcgggc
5581 tgcgtccaac tgtaggaacg aaccagcaca aggggttgca gcttttgctg ttgctgttgc
5641 gcccattgct tttggactgg tattagtagt tgcagctttg ttttgcatac gctgtgagga
5701 tctgtgcgcg gaaattttgt gtacaaatca tgaaaaaagc agtcattaac ggggaacaaa
5761 tcagaagtat cagcgaccctc caccagacat tgaaaaagga gcttgccctt ccggaatact
5821 acggtgaaaa cctggacgct ttatgggatt gtctgaccgg atgggtggag tacccgctcg
5881 ttttgaatg gaggcagttt gaacaaagca agcagctgac tgaaaatggc gccgagagtg
5941 tgcttcaggt tttccgtgaa gcgaaagcgg aaggctgcga catcaccatc atactttctt
6001 aatacgatca atgggagatg aacaatatgg aaacacaaac cacaattatg tctctcagcg
6061 agctcgaatt tccccgatcg ttcaaacatt tggcaataaa gtttcttaag attgaatcct
6121 gttgccggtc ttgcgatgat tatcatataa tttctgttga attacgttaa gcatgtaata
6181 attaacatgt aatgcatgac gttatttatg agatgggttt ttatgattag agtcccgcaa
6241 ttatacattt aatacgcgat agaaaacaaa atatagcgcg caaactagga taaattatcg
6301 cgcgcggtgt catctatgtt actagatcgg ggatccacta gttctagagc ggcgtgggcc
6361 atcgccctga tagacggttt ttcgcccttt gacgttggag tccacgttct ttaatagtgg
6421 actcttgttc caaactggaa caacactcaa ccctatctcg ggctattctt ttgattata
6481 agggatttg ccgatttcgg aaccaccatc aaacaggatt ttcgcctgct ggggcaaacc 6541 agcgtggacc gcttgctgca actctctcag ggccaggcgg tgaagggcaa tcagctgttg
6601 cccgtctcac tggtgaaaag aaaaaccacc ccagtacatt aaaaacgtcc gcaatgtgtt
6661 attaagttgt ctaagcgtca atttgtttac accacaatat atcctgccac cagccagcca
6721 acagctcccc gaccggcagc tcggcacaaa atcaccactc gatacaggca gcccatcagt
6781 ccgggacggc gtcagcggga gagccgttgt aaggcggcag actttgctca tgttaccgat
6841 gctattcgga agaacggcaa ctaagctgcc gggtttgaaa cacggatgat ctcgcggagg
6901 gtagcatgtt gattgtaacg atgacagagc gttgctgcct gtgatcaaat atcatctccc
6961 tcgcagagat ccgaattatc agccttctta ttcatttctc gcttaaccgt gacagttgtc
7021 tatcggcagt tctgtagagcg cgccgtgcgt cccgagcgat actgagcgaa gcaagtgcgt
7081 cgagcagtgc ccgcttgttc ctgaaatgcc agtaaagcgc tggctgctga accccagcc
7141 ggaactgacc ccacaaggcc ctagcgtttg caatgcacca ggtcatcatt gacccaggcg
7201 tgttccacca ggccgctgcc tcgcaactct tcgcaggctt cgccgacctg ctcgcgccac
7261 ttcttcacgc gggtggaatc cgatccgcac atgaggcgga aggtttccag cttgagcggg
7321 tacggctccc ggtgcgagct gaaatagtcg aacatccgtc gggccgtcgg cgacagcttg
7381 cggtacttct cccatatgaa tttcgtgtag tggtcgccag caaacagcac gacgatttcc
7441 tcgtcgatca ggacctggca acgggacgtt ttcttgccac ggtccaggac gcggaagcgg
7501 tgcagcagcg acaccgattc caggtgccca acgcggtcgg acgtgaagcc catcgccgtc
7561 gcctgtaggc gcgacaggca ttcctcggcc ttcgtgtaat accggccatt gatcgaccag
7621 cccaggtcct ggcaaagctc gtagaacgtg aaggtgatcg gctcgcgcgat aggggtgcgc
7681 ttcgcgtact ccaacacctg ctgccacacc agttcgtcat cgtcggcccg cagctcgacg
7741 ccggtgtagg tgatcttcac gtccttgtt acgtggaaaa tgaccttgtt ttgcagcgcc
7801 tcgcgcggga ttttcttgtt gcgcgtggtg aacagggcag agcgggccgt gtcgtttggc
7861 atcgctcgca tcgtgtccgg ccacgcgca atatcgaaca aggaaagctg catttccttg
7921 atctgctgct tcgtgtgttt cagcaacgcg gcctgcttgg cctcgctgac ctgttttgcc
7981 aggtcctcgc cggcggtttt tcgcttcttg gtcgtcatag ttcctcgcgt gtcgatggtc
8041 atcgacttcg ccaaacctgc cgctcctgtt tcgagacgac gcgaacgctc cacggcggcc
8101 gatggcgcgg gcagggcagg gggagccagt tgcacgctgt cgcgctcgat cttggcgta
8161 gcttgctgga ccatcgagcc gacggactgg aaggttcgc ggggcgcacg catgacggtg
8221 cggcttgcga tggtttcggc atcctcggcg gaaaaccccg cgtcgatcag ttcttgcctg
8281 tatgccttcc ggtcaaacgt ccgattcatt caccctcctt gcgggattgc cccgactcac
8341 gccggggcaa tgtgccctta ttcctgattt gacccgcctg gtgccttggt gtccagataa
8401 tccacctat cggcaatgaa gtcggtcccg tagaccgtct ggccgtcctt ctcgtacttg
8461 gtattccgaa tcttgccctg cacgaatacc agcgaccct tgcccaaata cttgccgtgg
8521 cctccggcct gagagccaaa acacttgatg cggaagaagt cggtgcgctc ctgcttgtcg
8581 ccggcatcgt tgcgccacat ctaggtacta aaacaattca tccagtaaaa tataatattt
8641 tattttctcc caatcaggct tgatcccag taagtcaaaa aatagctcga catactgttc
8701 ttccccgata tcctccctga tcgaccggac gcagaaggca atgtcatacc acttgtccgc
8761 cctgccgctt ctcccaagat caataaagcc acttactttg ccatctttca caaagatgtt
```

Figure 9D

```
8821 gctgtctcc aggtcgccgt gggaaaagac aagttcctct tcgggctttt ccgtctttaa
8881 aaaatcatac agctcgcgcg gatctttaaa tggagtgtct tcttcccagt tttcgcaatc
8941 cacatcggcc agatcgttat tcagtaagta atccaattcg gctaagcggc tgtctaagct
9001 attcgtatag ggacaatccg atatgtcgat ggagtgaaag agcctgatgc actccgcata
9061 cagctcgata atcttttcag ggctttgttc atcttcatac tcttccgagc aaaggacgcc
9121 atcggcctca ctcatgagca gattgctcca gccatcatgc cgttcaaagt gcaggacctt
9181 tggaacaggc agctttcctt ccagccatag catcatgtcc ttttccgtt ccacatcata
9241 ggtggtccct ttataccggc tgtccgtcat ttttaaatat aggttttcat tttctcccac
9301 cagcttatat accttagcag gagacattcc ttccgtatct tttacgcagc ggtattttc
9361 gatcagtttt ttcaattccg gtgatattct cattttagcc atttattatt tccttcctct
9421 tttctacagt atttaaagat accccaagaa gctaattata acaagacgaa ctccaattca
9481 ctgttccttg cattctaaaa ccttaaatac cagaaaacag ctttttcaaa gttgttttca
9541 aagttggcgt ataacatagt atcgacggag ccgattttga aaccacaatt atggactgcc
9601 agcgctgcca tttttggggt gaggccgttc gcggccgagg ggcgcagccc ctgggggggat
9661 gggaggcccg cgttagcggg ccgggagggt tcgagaaggg ggggcacccc ccttcggcgt
9721 gcgcggtcac gcgcacaggg cgcagccctg gttaaaaaca aggtttataa atattggttt
9781 aaaagcaggt taaagacag gttagcggtg gccgaaaaac gggcggaaac ccttgcaaat
9841 gctggatttt ctgcctgtgg acagccctc aaatgtcaat aggtgcgccc ctcatctgtc
9901 agcactctgc ccctcaagtg tcaaggatcg cgccctcat ctgtcagtag tgcgccct
9961 caagtgtcaa tacgcaggg cacttatccc caggcttgtc cacatcatct gtgggaaact
10021 cgcgtaaaat caggcgtttt cgccgatttg cgaggctggc cagctccacg tgccggccg
10081 aaatcgagcc tgcccctcat ctgtcaacgc cgcgccgggt gagtcggccc ctcaagtgtc
10141 aacgtccgcc cctcatctgt cagtgagggc caagttttcc gcgaggtatc cacaacgccg
10201 gcggatctgg ggaaccctgt ggttggcatg cacatacaaa tggacgaacg gataaacctt
10261 ttcacgccct tttaaatatc cgattattct aataaacgct cttttctctt ag
```

REPRODUCTIVE ABLATION CONSTRUCTS

This application is a divisional of application Ser. No. 10/946,622 filed 22 Sep. 2004, now U.S. Pat. No. 7,453,025.

FIELD OF INVENTION

The present invention relates to the regulation of reproductive development. In particular, this invention relates to the genetic ablation of reproductive tissues in angiosperm and gymnosperm species. Reproductive-preferred promoters, regulatory elements, and cytotoxic nucleotide sequences are provided. Constructs and methods for genetic ablation are also included in the invention.

BACKGROUND OF THE INVENTION

With the advent of plant genetic engineering technology, the ecological implications of genetically modified crops are of great concern, particularly when there are no inherent barriers to the spread of transgenes through sexual reproduction. Specifically, concerns have arisen in cases when transgenes can spread from a transgenic plant to a weedy species through hybridization, or when the crop species itself exists in weedy forms. Bergelson et al. *Nature* 395: 25 (1998). One way to address such concerns is by genetically engineering sterility in a plant through complete ablation of reproductive structures.

Recently, there has been significant interest in using an ablation system for controlling reproductive development in plants. Reproductive control has been achieved in several plant species by genetic ablation, which entails linking a reproductive-preferred promoter with a cytotoxic gene to ablate reproductive cells. For example, barnase, an extracellular ribonuclease from *Bacillus amyloliquifaciens* has been employed for inducing male sterility. Paddon et al. *J. Bacteriol.* 171:1185-1187 (1989). European Patent No. 344,029 describes a system for producing a male sterile plant by transforming a plant with a DNA encoding barnase under the control of a tapetum-specific promoter. Transformation of tobacco and oilseed rape plants with such a promoter-gene construct prevented the plants from producing fertile pollen. Mariani et al., *Nature* 347: 737-741 (1990). Flowers of transgenic *Arabidopsis thaliana* plants expressing a fusion construct of the APETALA3 (AP3) promoter and the diphtheria toxin A chain (DTA) gene lack petals and stamens, suggesting that transgene expression ablated petal and stamen cells. Transgenic *Arabidopsis* expressing the DTA gene under control of the LEAFY promoter produced no flowers. Tobacco plants transformed with a tobacco stigma-specific promoter driving the barnase gene lacked the stigmatic secretory zone and were female sterile.

Although genetic ablation has been effective, the promoters generally used for ablation are not well-suited for tissue-specific expression. As a consequence, leaky gene expression can significantly reduce and damage plant vegetative growth. Depending on the plant species, ablation can reduce vegetative growth by 80%. Strauss, S. H. and Meilan, R. TGERC Annual Report (1998). For genetic ablation to be commercially useful in the forestry industry, the amount of damage to vegetative tissues must be minimized to nominal levels.

While numerous patents and patent application publications disclose genetic ablation using a variety of promoters and cytotoxic genes, there is little disclosure addressing the effects of ablation on a plant's vegetative growth and development. The LFY promoter from *Arabidopsis*, which is expressed strongly in floral meristems and weakly in developing leaves, has been used for producing plants with ablated flowers. Nilsson et al., *Plant J.* 15:799-804 (1998). However, very few plants transformed with LFY had ablated flowers and uncompromised vegetative development. Therefore, it would be impractical to use a similar approach for reproductive ablation in a tree species, since it would take years to produce, grow, and test many transgenic trees to identify those few trees that have sterility and normal vegetative growth.

The genetic ablation of a reproductive organ requires a delicate balance between promoter activity and ablation gene toxicity. While the barnase gene is widely used for ablation in plants, barnase-induced toxicity frequently causes detrimental effects on plant growth and development. Thus, it may be desirable to reduce the toxicity of barnase, such that reproductive ablation occurs without deleterious and unrecoverable damages to a plant's vegetative growth.

Concurrent with the production of a mutant barnase having reduced toxicity, it may also be desirable to minimize leaky expression of a reproductive ablation construct in a plant's vegetative tissues. By minimizing leaky or ectopic expression of a reproductive ablation construct in a plant, expression of a mutant barnase gene in the vegetative tissues may be better tolerated by the plant due to attenuated ablation, which depends on promoter activity and RNase activity of a barnase mutant.

Accordingly, there exists a need for a reproductive ablation system having reduced barnase-induced toxicity and minimal leaky expression in a plant's vegetative tissues.

SUMMARY OF THE INVENTION

The present invention provides an isolated polynucleotide selected from the group consisting of SEQ ID NOs: 1-8 and 13-17, as well as a plasmid comprising the sequence depicted in any one of SEQ ID NOs. 18-27.

The present invention also provides a plasmid comprising the sequence depicted in any one of FIG. 1 (i.e., SEQ ID NO. 18), FIG. 2 (i.e., SEQ ID NO. 19), FIG. 3 (i.e., SEQ ID NO. 20), FIG. 4 (i.e., SEQ ID NO. 21), FIG. 5 (i.e., SEQ ID NO. 22), FIG. 6 (i.e., SEQ ID NO. 23), FIG. 7 (i.e., SEQ ID NO. 24), FIG. 8 (i.e., SEQ ID NO. 25), FIG. 9 (i.e., SEQ ID NO. 26), or FIG. 19 (i.e., SEQ ID NO. 27).

Also provided is an isolated polynucleotide that confers reproductive-preferred gene expression in a plant cell, wherein the polynucleotide comprises the sequence depicted in any one of SEQ ID NOs. 1, 2, 3, 4, or 16.

In one embodiment, the polynucleotide confers male-preferred gene expression in a plant cell.

Also provided is a promoter comprising the sequence depicted in any one of SEQ ID NOs. 1, 2, 3, 4, or 16.

In one embodiment, the polynucleotide of SEQ ID NOs. 1-8 is expressed or is active in a pre-male or pre-female reproductive structure.

Also provided is an isolated polynucleotide that has a sequence identity that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% in sequence to any one of SEQ ID NOs: 1, 2, 3, 4, or 16.

In another embodiment, a polynucleotide is provided that has a sequence selected from the group consisting of (i) sequences that are complementary to a polynucleotide of any one of SEQ ID NOs. 1-8 and 16-17, (ii) sequences that are reverse sequences of a polynucleotide of any one of SEQ ID NOs. 1-8 and 16-17, and (iii) sequences that are reverse complements of a polynucleotide of any one of SEQ ID NOs. 1-8 and 16-17.

Also provided is an isolated polynucleotide that hybridizes under stringent conditions to a polynucleotide of claim 1, wherein said isolated polynucleotide hybridizes over its full-length sequence to a polynucleotide of any of one of SEQ ID NOs. 1-26.

Also provided is an isolated polynucleotide comprising the sequence depicted in SEQ ID NO. 17.

In one embodiment, a polynucleotide is provided that has the sequence of any one of SEQ ID NOs. 1-4 and 16 which is capable of at least one of (i) binding to a nucleic acid molecule or (ii) regulating expression of an operably-linked gene in a dicotyledonous plant.

In another embodiment, a polynucleotide is provided that has the sequence of any one of SEQ ID NOs. 1-4 and 16 which is capable of at least one of (i) binding to a nucleic acid molecule or (ii) regulating expression of an operably-linked gene in a gymnosperm.

In one embodiment, a polynucleotide is provided that has the sequence of any one of SEQ ID NOs. 1-4 and 16 which is capable of upregulating or downregulating the expression of an operably-linked gene in a plant.

In one aspect of the present invention, a construct is provided that comprises an isolated polynucleotide selected from any one of SEQ ID NO: 1, 2, 3, 4, or 16 and functional variants thereof operably linked to a desired nucleic acid, wherein said promoter regulates the expression of said desired nucleic acid in a plant cell transformed with the construct. In one embodiment, the polynucleotide upregulates or downregulates expression of said desired nucleic acid. In another embodiment, the desired nucleic acid encodes an expression product that is capable of disrupting reproductive development in a plant.

The present invention provides a plant transformed with any of the constructs disclosed herein. In one embodiment, the phenotype of such a transformed plant expresses a difference in reproductive development compared with a plant of the same species that is not transformed with said construct. In one embodiment, the difference in reproductive development occurs in a male reproductive structure. In another embodiment, the difference in reproductive development occurs in any one of anther, filament, tapetum, pollen, microsporophyll, or staminate cone. In an alternative embodiment, the difference in reproductive development occurs in a female reproductive structure. In that case, in one embodiment, the difference in reproductive development occurs in any one of stigma, style, ovary, megaspore, ovuliferous cone. In yet another embodiment, the difference in reproductive development occurs in a pre-male or pre-female reproductive structure.

In one aspect, a desired nucleic acid may produce an RNA transcript, which, in one embodiment, may comprise an antisense sequence of a gene that is endogenous to the plant cell. In one embodiment, the RNA transcript induces RNA interference of a gene that is normally expressed in the plant cell.

Also provided is a plant cell comprising a construct comprising (i) a polynucleotide having the sequence of any one of SEQ ID NOs: 1, 2, 3, 4, or 16 or functional variants thereof and (ii) a desired nucleic acid, wherein said polynucleotide is operably linked to said desired nucleic acid. A transgenic plant comprising such a plant cell is also provided.

In one aspect, the present invention provides a method for producing a transgenic plant, comprising (a) transforming a plant cell with a construct that comprises (i) at least one polynucleotide having the sequence of any one of SEQ ID NOs. 1, 2, 3, 4, or 16 or functional variants thereof and (ii) a desired nucleic acid, wherein said polynucleotide regulates the activity of said desired sequence; (b) culturing said transformed plant cell under conditions that promote growth of a plant, wherein said plant is a transgenic plant that exhibits a phenotype that is different from a plant of the same species that does not contain said construct.

In one embodiment, the phenotype of the transformed plant is characterized by a difference in reproductive development compared with a plant of the same species that does not contain the construct. In another embodiment, the phenotype of the transformed plant is characterized by a difference in male reproductive development compared with a plant of the same species that does not contain the construct. Alternatively, the phenotype of the transformed plant is characterized by a difference in female reproductive development compared with a plant of the same species that does not contain the construct. In yet another embodiment, the phenotype of the transformed plant is characterized by a difference in a pre-male or pre-female reproductive structure compared with a plant of the same species that does not contain the construct.

In another aspect, a method for conferring reproductive sterility in a plant is provided, comprising (a) introducing into a plant cell a construct comprising (i) a promoter having the sequence of any one of SEQ ID NOs: 1, 2, 3, 4, or 16 or functional variants thereof and (ii) a nucleic acid encoding a gene that is capable of ablating reproductive development, wherein said nucleic acid is sense relative to said promoter and wherein said promoter regulates the expression of said gene; (b) culturing said transformed plant cell under conditions that promote growth of a plant, wherein said plant is a transgenic plant that exhibits a phenotype that is different from a plant of the same species that does not contain said construct; and (c) selecting a plant that is reproductive-sterile.

In another aspect is a method for ablating a reproductive structure in a plant, comprising (a) introducing into a plant cell a construct comprising (i) a promoter having the sequence of any one of SEQ ID NOs: 1, 2, 3, 4, or 16 or functional variants thereof and (ii) a nucleic acid encoding a gene that is capable of ablating reproductive development, wherein said promoter regulates the expression of said gene; (b) culturing said transformed plant cell under conditions that promote growth of a plant, wherein said plant is a transgenic plant that exhibits a phenotype that is different from a plant of the same species that does not contain said construct; and (c) selecting a plant having an ablated reproductive structure. In one embodiment, the plant is selected from an angiosperm or gymnosperm species.

Also provided is a method for altering pollen fertility, comprising (a) introducing into a plant cell of a woody plant a construct comprising (i) a promoter having the sequence of any one of SEQ ID NOs: 1, 2, 3, 4, or 16 or functional variants thereof and (ii) and a desired nucleic acid, wherein said promoter regulates the expression of said desired nucleic acid; (b) culturing said transformed plant cell under conditions that promote growth of a plant; and (c) obtaining a plant having altered pollen fertility. In one embodiment, the woody plant is selected from a species of *Eucalyptus* or *Pinus*.

Also provided herein is an isolated polynucleotide selected from any one of SEQ ID NO: 5-8 and variants thereof. In one embodiment, any one of these polynucleotides encods a mutant barnase enzyme. In one embodiment, such a polynucleotide encodes a mutant barnase enzyme having attenuated activity compared with a wild-type barnase enzyme. In one embodiment, the variant has a sequence identity that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% in sequence to any one of SEQ ID NOs: 5-8.

Also provided is an isolated polynucleotide having a sequence selected from (i) sequences that are complementary to a polynucleotide of any one of SEQ ID NOs: 5-8, (ii) sequences that are reverse sequences of a polynucleotide of any one of SEQ ID NOs: 5-8, and (iii) sequences that are reverse complements of a polynucleotide of any one of SEQ ID NOs: 5-8.

In another embodiment, an isolated polynucleotide that hybridizes under stringent conditions to a polynucleotide of any one of SEQ ID NOs: 5-8, wherein the isolated polynucleotide hybridizes over its full-length sequence to a polynucleotide of any one of SEQ ID NO: 5-8.

In another aspect, a method for conferring reproductive sterility in a plant without disturbing vegetative growth is provided, comprising (a) introducing into a plant cell a construct comprising (i) a promoter having reproductive-preferred activity; (ii) a nucleic acid encoding a gene that is capable of ablating reproductive development, wherein said promoter regulates the expression of said gene; (b) culturing said transformed plant cell under conditions that promote growth of a plant, wherein said plant is a transgenic plant that exhibits a phenotype that is different from a plant of the same species that does not contain said construct; and (c) selecting a plant having reproductive-sterility and undisturbed vegetative growth.

Also provided is a method for ablating reproductive development in a plant without disturbing vegetative growth, comprising (a) introducing into a plant cell a construct comprising (i) a promoter having the sequence of any one of SEQ ID NOs: 1, 2, 3, 4, or 16 or functional variants thereof, (ii) a nucleic acid encoding a gene that is capable of ablating reproductive development, wherein said promoter regulates the expression of said gene; (b) culturing said transformed plant cell under conditions that promote growth of a plant, wherein said plant is a transgenic plant that exhibits a phenotype that is different from a plant of the same species that does not contain said construct; and (c) selecting a plant having ablated reproductive development and undisturbed vegetative growth.

Also provided is a method for conferring male-sterility in a plant without disturbing vegetative growth, comprising (a) introducing into a plant cell a construct comprising (i) a promoter having reproductive-preferred expression; (ii) a nucleic acid encoding a mutant barnase, wherein said mutant barnase has attenuated activity compared with wild-type barnase; (b) culturing said transformed plant cell under conditions that promote growth of a plant, wherein said plant is a transgenic plant that exhibits a reproductive phenotype that is different from a plant of the same species that does not contain said construct; and (c) selecting a plant having male-sterility and undisturbed vegetative growth. In one embodiment, the promoter has a sequence selected from the group consisting of SEQ ID NOs: 1, 2, 3, 4, and 16. In another embodiment, the promoter is a functional variant of any one of the sequences selected from the group consisting of SEQ ID NOs: 1, 2, 3, 4, and 16.

In one embodiment, the nucleic acid of (ii) above has the sequence of any of one of SEQ ID NOs: 5-8.

The present invention also provides in one embodiment, a plant having ablated reproductive development and unaffected vegetative growth.

The present invention also provides in another embodiment, a woody plant having ablated reproductive development and normal vegetative growth.

In a further aspect, a method for obtaining wood is provided, comprising (a) introducing into a plant cell of a woody plant a construct comprising (i) a promoter having the sequence of any one of SEQ ID NOs: 1, 2, 3, 4, or 16 or functional variants thereof and (ii) and a desired nucleic acid, wherein said promoter regulates the expression of said desired nucleic acid; (b) culturing said transformed plant cell under conditions that promote growth of a plant; and (c) obtaining wood from said plant.

In another aspect is a method for obtaining wood pulp, comprising (a) introducing into a plant cell of a woody plant a construct comprising (i) a promoter having the sequence of any one of SEQ ID NOs: 1, 2, 3, 4, or 16 or functional variants thereof and (ii) and a desired nucleic acid, wherein said promoter regulates the expression of said desired nucleic acid; (b) culturing said transformed plant cell under conditions that promote growth of a plant; and (c) obtaining wood pulp from said plant.

Also provided is a method for ablating a reproductive structure in a plant, comprising (a) introducing into a plant cell a plasmid selected from the group consisting of SEQ ID NO 13-15; (b) culturing said transformed plant cell under conditions that promote growth of a plant, wherein said plant is a transgenic plant that exhibits a phenotype that is different from a plant of the same species that does not contain said plasmid; and (c) selecting a plant having an ablated reproductive structure. In another embodiment, a plasmid selected from the group consisting of SEQ ID NO 18-26 may be introduced into the plant cell in step (a) above.

Also provided is a method for conferring reproductive sterility in a plant, comprising (a) introducing into a plant cell a plasmid selected from the group consisting of SEQ ID NO 13-15; (b) culturing said transformed plant cell under conditions that promote growth of a plant, wherein said plant is a transgenic plant that exhibits a phenotype that is different from a plant of the same species that does not contain said plasmid; and (c) selecting a plant having an ablated reproductive structure. In another embodiment, a plasmid selected from the group consisting of SEQ ID NO 18-26 may be introduced into the plant cell in step (a) above.

In another embodiment, a plant is provided that is stably transformed with any of the plasmids disclosed herein. In one embodiment the plasmid that is stably introduced into the plant has the sequence of any one of SEQ ID NOs. 13-15 or 18-26.

The present invention also provides a method for conferring reproductive sterility in a transgenic plant, comprising (a) transforming a plant cell with a construct having a reproductive-preferred promoter operably linked to a cytotoxic gene and a non-reproductive-preferred promoter operably linked to a gene encoding a protein that inhibits said cytotoxic gene; wherein said reproductive-preferred promoter is active in an angiosperm or gymnosperm reproductive structure and said non-reproductive-preferred promoter is not active in an angiosperm or gymnosperm reproductive structure; (b) culturing said transformed plant cell under conditions that promote growth of a plant; and (c) selecting a transgenic plant having an ablated reproductive structure. In one embodiment, the reproductive-preferred promoters are selected from the group consisting of SEQ ID NOs: 1, 2, 3, 4, or 16. In another embodiment, the non-reproductive-preferred promoters are selected from the group consisting of SEQ ID NO: 3 and SEQ ID NO. 17.

Also provided is a polypeptide comprising the amino acid sequence depicted in any one of SEQ ID NOs.: 9-12 or variant thereof. In one embodiment, the variant of the polypeptide has a sequence identity that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% in sequence to any one of SEQ ID NOs: 9-12.

The present invention also contemplates a construct, comprising a promoter comprising the sequence of either of SEQ ID NOs. 1 or 2 operably linked to a polynucleotide comprising the sequence of any one of SEQ ID NOs 5-8. In one embodiment, the polynucleotide comprises the sequence depicted in SEQ ID NO. 5. In one embodiment, the polynucleotide comprises the sequence depicted in SEQ ID NO. 6. In another embodiment, the polynucleotide comprises the sequence depicted in SEQ ID NO. 7. In another embodiment, the polynucleotide comprises the sequence depicted in SEQ ID NO. 8. Also provided is a plant transformed with this construct.

Also provided is a construct comprising a promoter comprising the sequence of either of SEQ ID NOs. 1 or 2 operably linked to a polynucleotide that encodes a polypeptide comprising the amino acid sequence depicted in any one of SEQ ID NOs. 9-12. Also provided is a plant transformed with this construct.

In one embodiment, one of these constructs may also comprise a non-reproductive preferred promoter operably linked to a barstar gene.

The non-reproductive preferred promoter disclosed herein may comprise the sequence depicted in SEQ ID NO. 3 or SEQ ID NO. 17.

Also provided is a method of inducing formation of strobili in Pinus comprising (a) obtaining a hybrid progeny plant from the cross of pitch pine P. rigida with a loblolly pine P. taeda, (b) transforming the hybrid plant with a desired polynucleotide that is operably linked to a reproductive tissue preferred promoter, (c) regenerating a transgenic hybrid plant from the transformed hybrid plant, and (d) recovering strobili. In one embodiment, the reproductive tissue preferred promoter comprises the sequence depicted in any one of SEQ ID NOs. 1, 2, 3, 4, or 16. In another embodiment, the hybrid plant is transformed by Agrobacterium or biolistics-mediated transformation. In one embodiment, the strobili are male or female. In another embodiment, the strobili are produced by the transgenic hybrid plant within 1-3 years of transformation.

In another aspect, a method of testing a candidate promoter for activity in a gymnosperm reproductive tissue is provided, comprising (a) obtaining a candidate promoter sequence, (b) operably linking the candidate promoter to a reporter gene, (c) introducing the candidate promoter that is operably linked to the reporter gene into a plant material, and (d) identifying expression of the reporter gene in the plant material. In this method, the reporter gene is GUS. In one embodiment, the plant material is a plant explant or plant cell. In another embodiment, the plant material in which the reporter gene expression is identified is selected from the group consisting of petals, stamens, carpels, shoot tips, anthers, tapetum, callus, and embryo.

The present invention also provides a hybrid progeny plant, comprising a reproductive tissue preferred promoter operably linked to a desired polynucleotide, wherein the hybrid progeny plant is obtained from the cross of pitch pine P. rigida with loblolly pine P. taeda. In one embodiment, the reproductive tissue preferred promoter comprises the sequence depicted in any one of SEQ ID NOs. 1, 2, 3, 4, or 16. In one embodiment, the desired polynucleotide comprises the sequence depicted in any one of SEQ ID NOs. 5-8. In another embodiment, the desired polynucleotide encodes a polypeptide that comprises the amino acid sequence depicted in any one of SEQ ID NOs. 9-12. Also provided is a hybrid progeny plant transformed with a construct comprising the sequence of any of SEQ ID NOs. 13-15, wherein the hybrid progeny plant is obtained from the cross of pitch pine P. rigida with loblolly pine P. taeda.

The present invention also provides a method of testing putative flowering control constructs for activity in delaying reproduction in gymnosperms, comprising (i) transforming a somatic embryogenic culture of a hybrid of P. rigida and P. taeda with a promoter operably linked to a desired polynucleotide, (ii) selecting transgenic cells from the transformed culture, (iii) culturing the transgenic cells to obtain at least one somatic embryo, (iv) germinating the embryo to obtain a transgenic plant, (v) growing the plant, and (vi) examining the plant for formation of strobili. In one embodiment, the promoter is a polynucleotide that is selected for testing promoter activity in a plant reproductive tissue. In another embodiment, the culture is transformed via Agrobacterium-mediated- or biolistic transformation. In a further embodiment, the desired polynucleotide is a reporter gene or an ablation construct. In this respect, in one embodiment, the ablation construct has the nucleic acid sequence depicted in any one of SEQ ID NOs. 13-15. In another embodiment, the construct may comprise the sequence depicted in any one of SEQ ID NOs. 18-26. In one embodiment, the plant of step (v) above is grown for 1 to 3 years.

Generally, a desired nucleic acid or desired polynucleotide of the present invention that is operably linked to a promoter or is incorporated into a plasmid or construct disclosed herein may comprise the sequence of any one of SEQ ID NOs. 5-8. In one embodiment, the desired nucleic acid or desired polynucleotide is a mutated barnase gene sequence. In a preferred embodiment, a reproductive-preferred promoter is operably linked to a polynucleotide that promote the genetic ablation of reproductive tissues in angiosperm and gymnosperm species. In a preferred embodiment, the polynucleotide is a mutant barnase gene. In one embodiment, the promoter comprises the sequence depicted in any one of SEQ ID NOs. 1-4 or 16. In another embodiment, the barnase gene has the sequence depicted in any one of SEQ ID NOs. 5-8 or encodes a polypeptide that comprises the sequence depicted in any one of SEQ ID NOs. 9-12. Any construct may comprise such a promoter-desired polynucleotide expression cassette.

BRIEF DESCRIPTION OF THE DRAWINGS

FIG. 1[A-C]—pWVR220 [PrMC2.400::barnaseH102E] (SEQ ID NO. 18)

FIG. 2[A-D]—pWVCZ20 [(AtAGenh)PrAG::GUS(intron)] (SEQ ID NO. 19)

FIG. 3[A-C]—pWVCZ23 [PrAG::barnaseE73G] (SEQ ID NO. 20)

FIG. 4[A-D]—pWVCZ24 [(AtAGenh)PrAG::barnaseE73G] (SEQ ID NO. 21)

FIG. 5[A-E]—pARB599B [PrMC2::barnaseH102E] (SEQ ID NO. 22). Short nucleotide sequences disclosed are residues 10431-10442, 10261-10271, 9885-9896, and 9569-9581 of SEQ ID NO: 22, respectively in order of appearance.

FIG. 6[A-G]—pARB639B [(AtAGenh)PrAG::barnaseE73G] (SEQ ID NO. 23). Short nucleotide sequences disclosed are residues 9906-9918, 13334-13346, 13650-

13661, 14026-14036, and 14196-14207 of SEQ ID NO: 23, respectively in order of appearance.

FIG. 7[A-C]—pAGF243-[PrMC2.400-3::barnaseH102E] (SEQ ID NO. 24)

FIG. 8[A-D]—pABDP010 [complementary copy of CZ28-bstar+UBQ10::NPTII::E9/LPAG1d4::bstar::NOST] (SEQ ID NO. 25)

FIG. 9[A-D]—pABDP04 [complementary copy of CZ28-bstar+UBQ10::NPTII::E9/LPAG1d4::bstar::NOST] (SEQ ID NO. 26)

Figure 10:
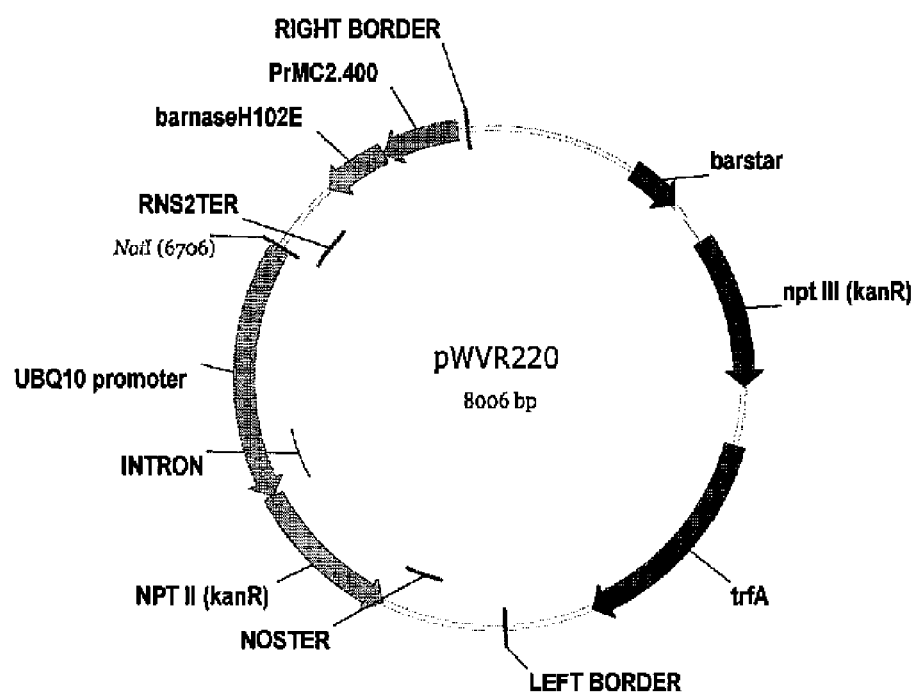
Figure 11:
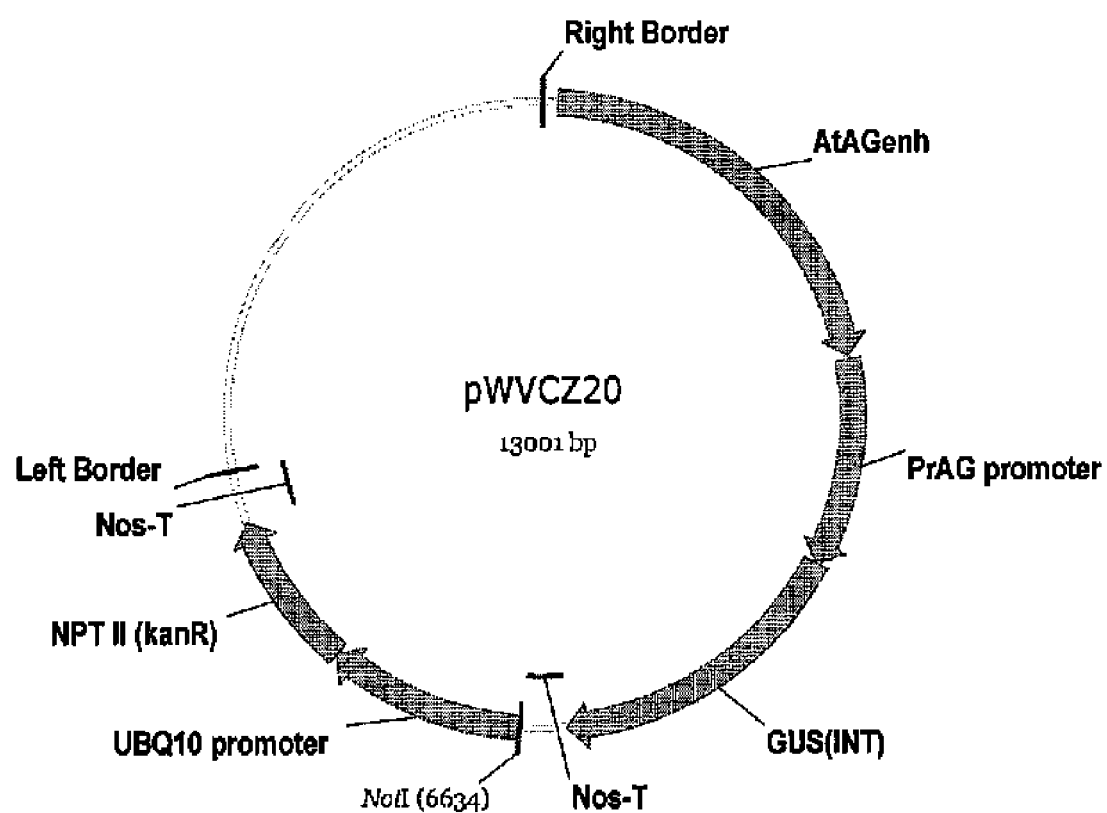
Figure 12:
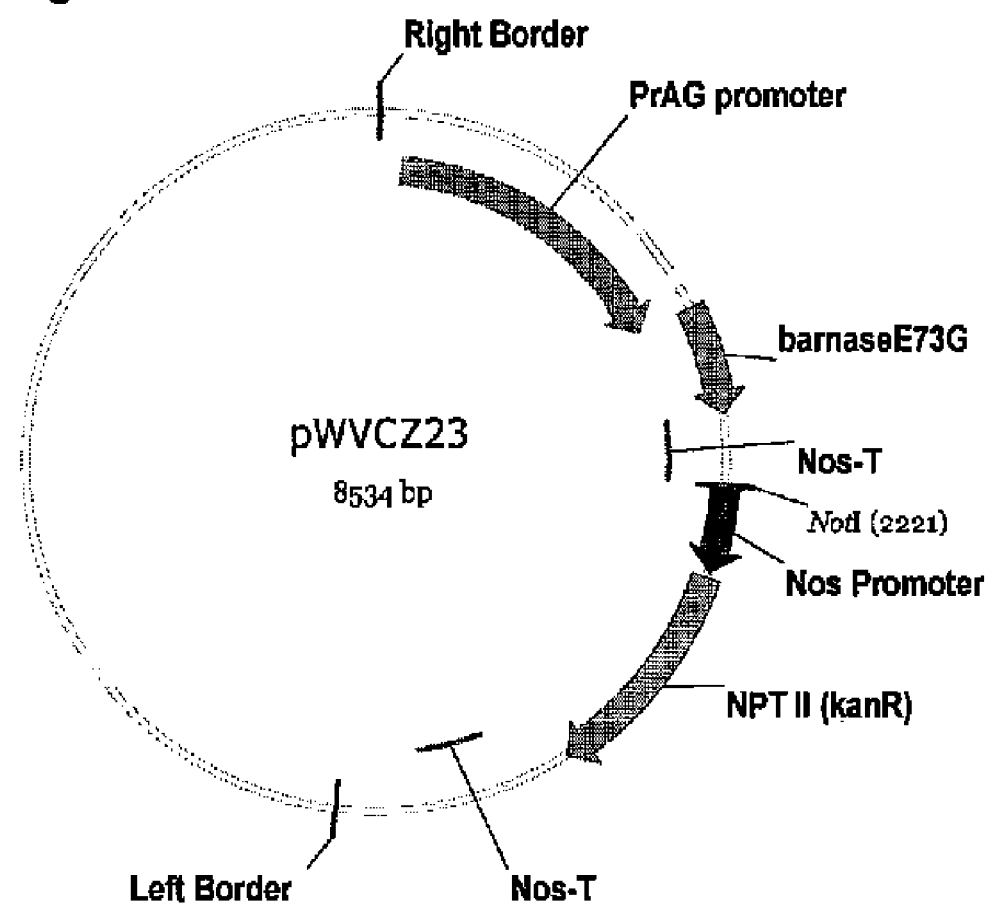
Figure 13:
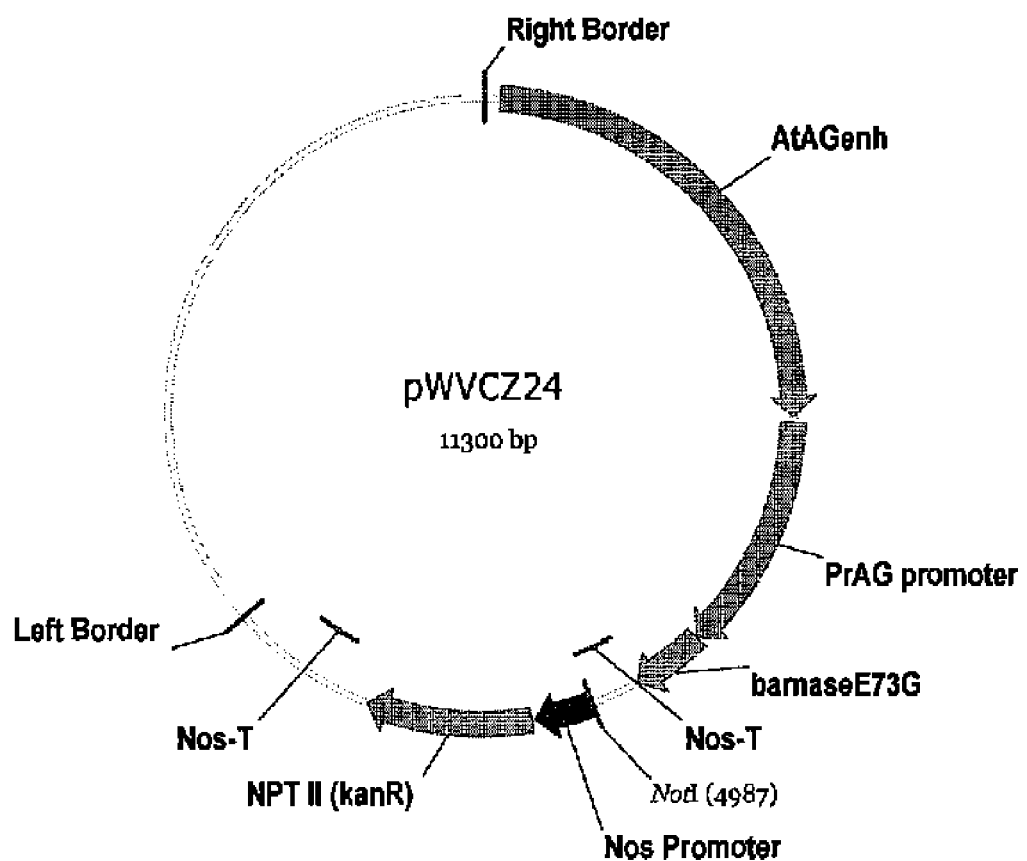
Figure 14:
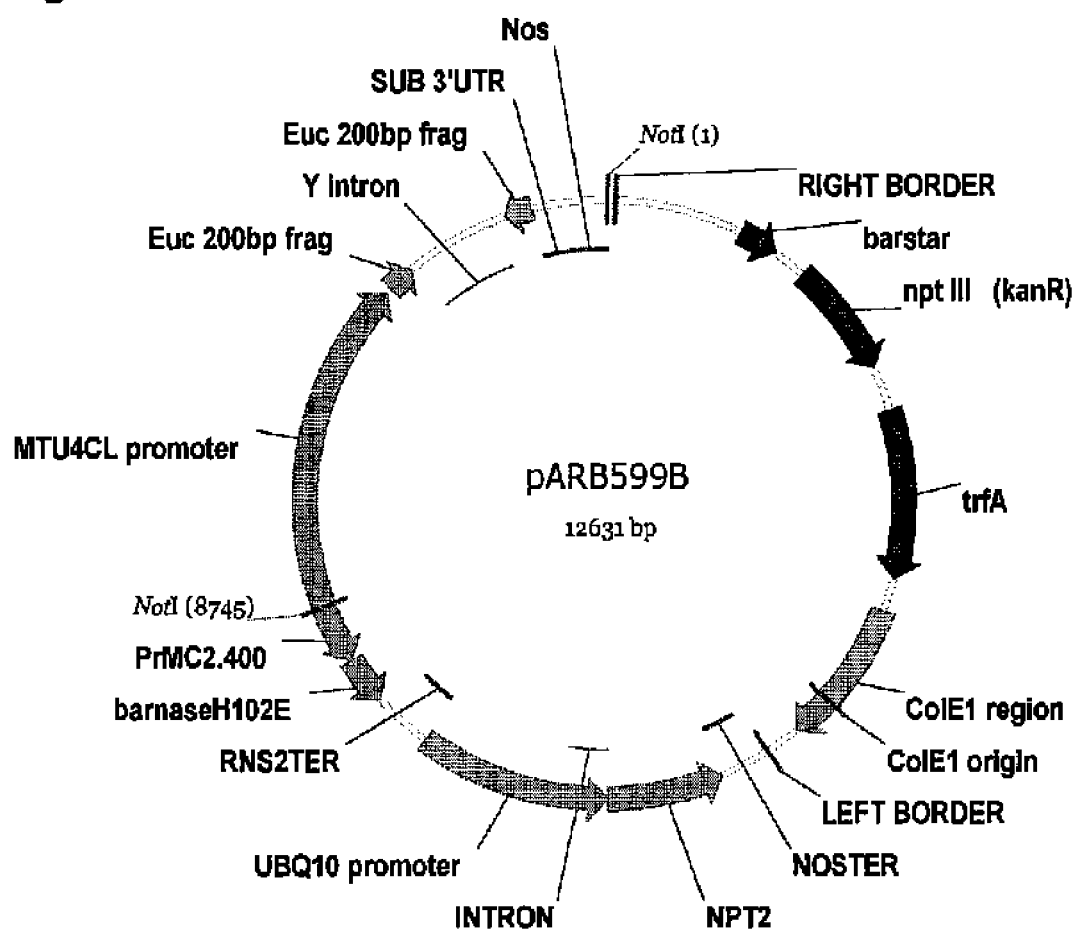
Figure 15:
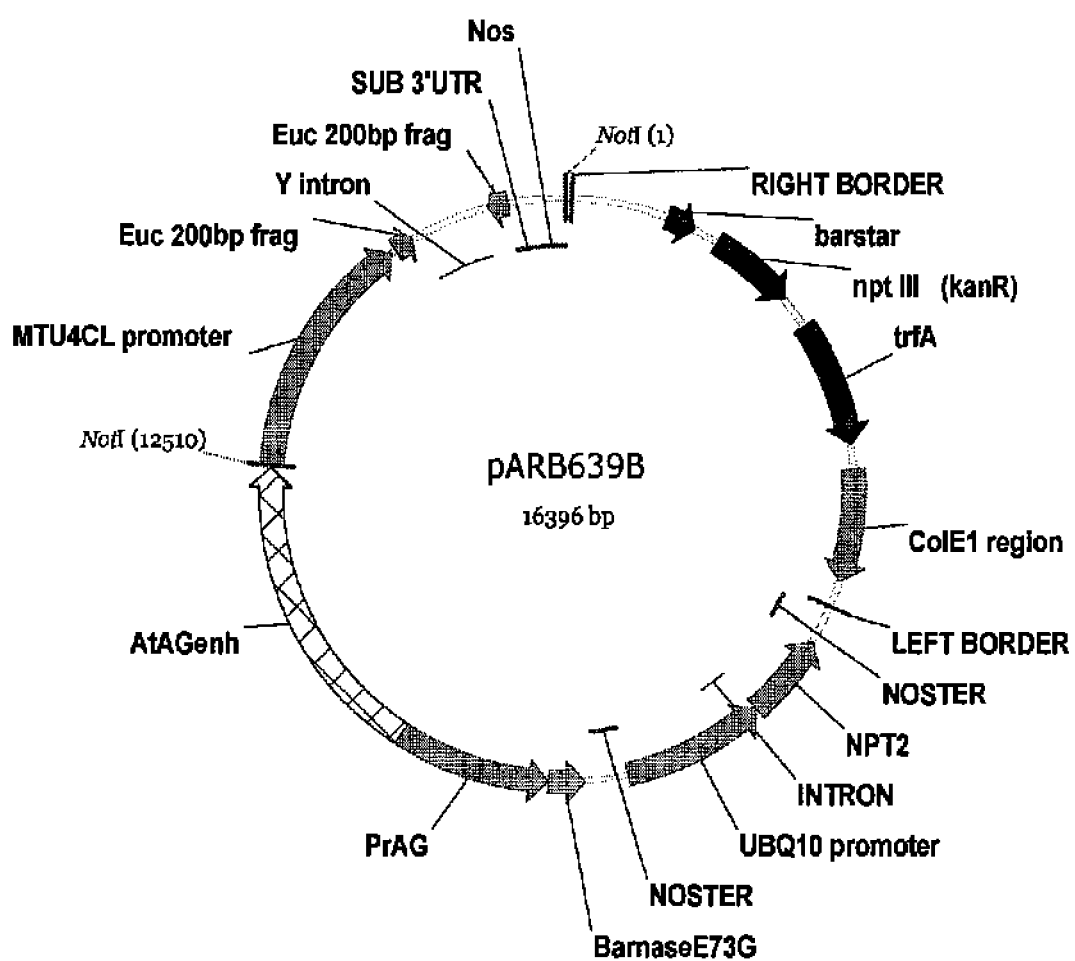
Figure 16:
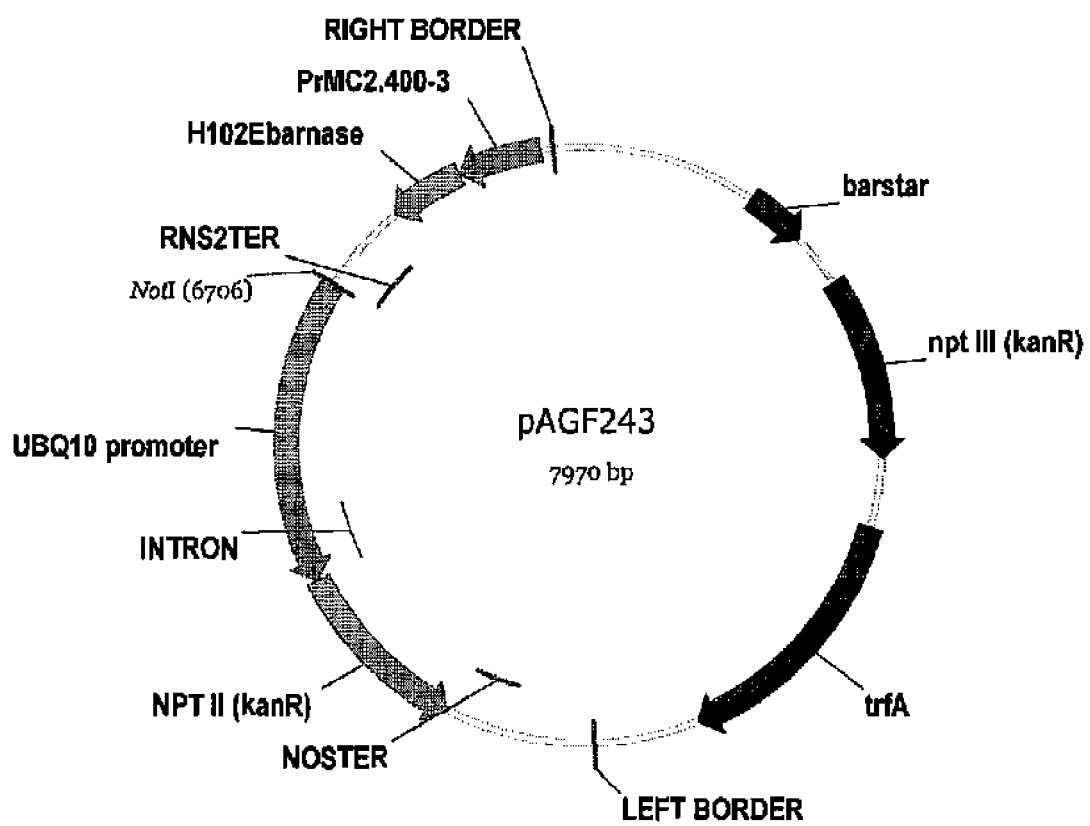
Figure 17:
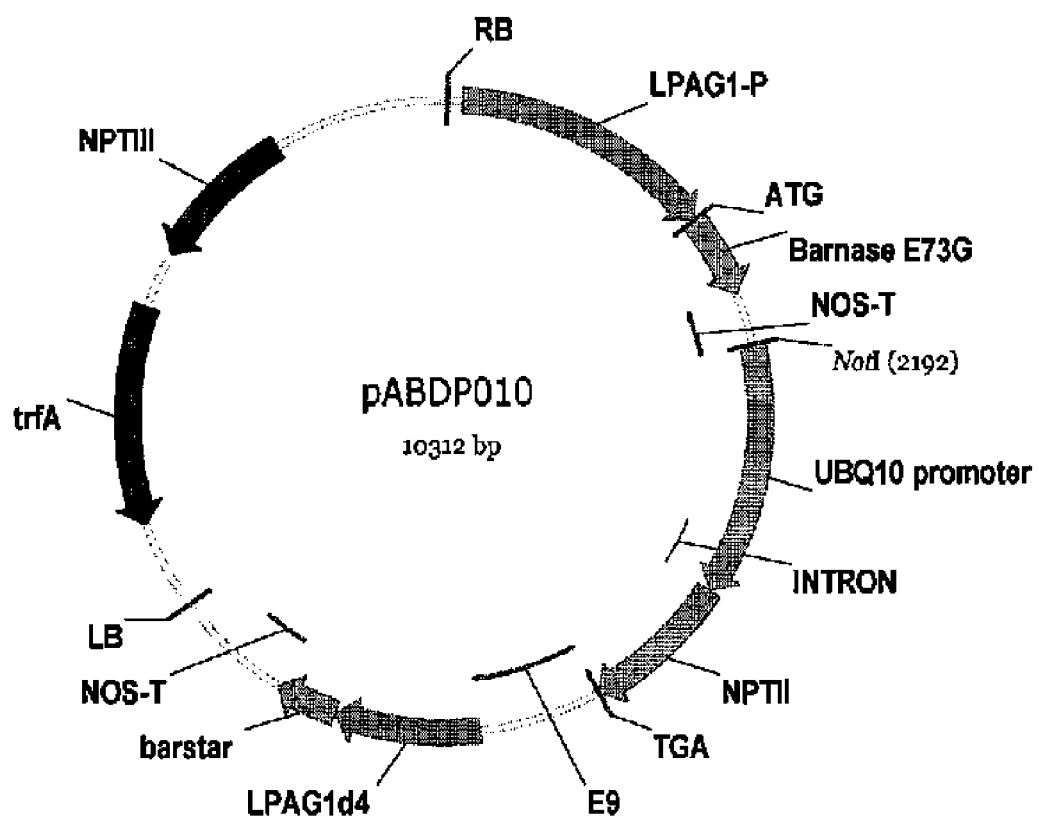
Figure 18:
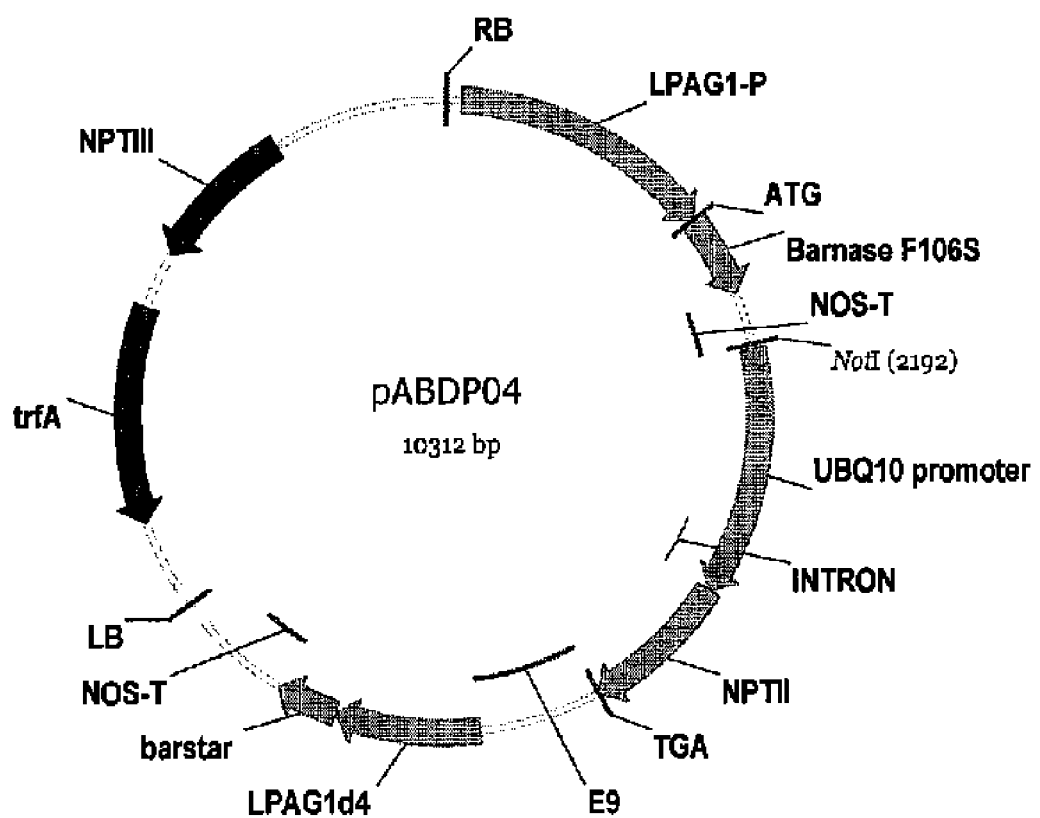
Figure 19:
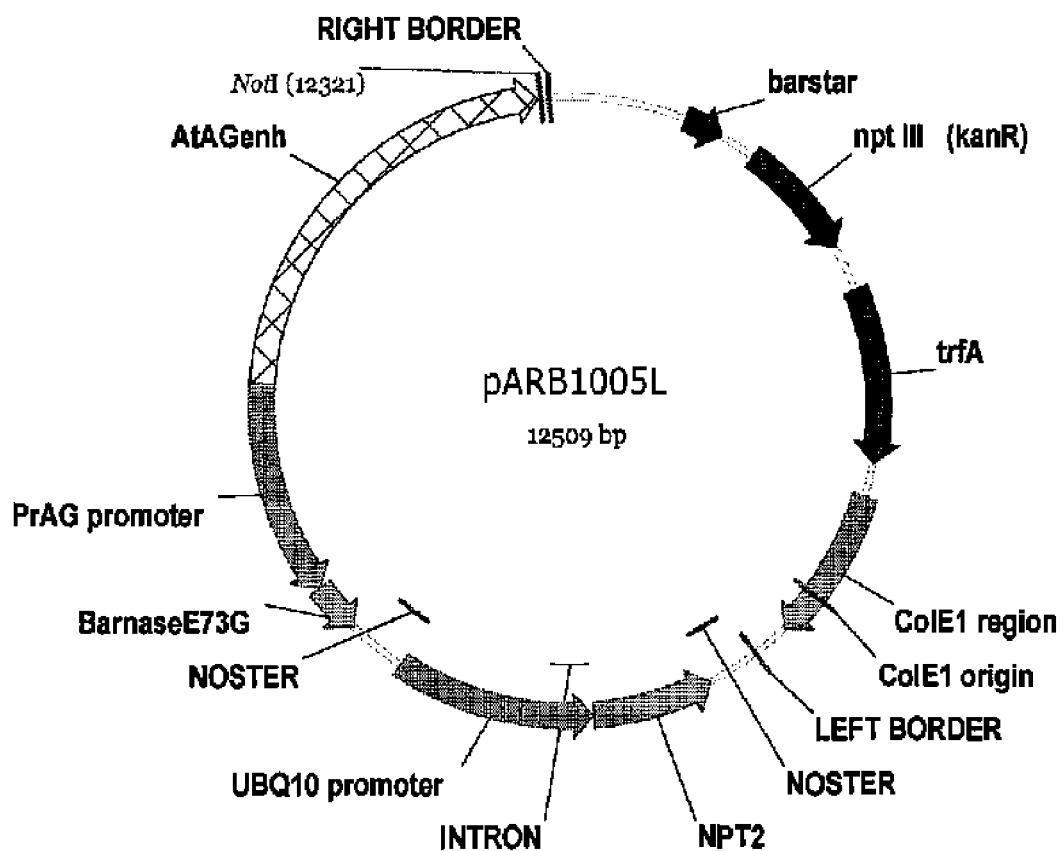

FIG. 10—plasmid map for pWVR220
FIG. 11—plasmid map for pWVCZ20
FIG. 12—plasmid map for pWVCZ23
FIG. 13—plasmid map for pWVCZ24
FIG. 14—plasmid map for pARB599B
FIG. 15—plasmid map for pARB639B
FIG. 16—plasmid map for pAGF243
FIG. 17—plasmid map for pABDP010
FIG. 18—plasmid map for pABDP04
FIG. 19—pARB1005L [(AtAGenh)PrAG::barnaseE73G]

DETAILED DESCRIPTION OF THE EMBODIMENTS

The present invention relates to an isolated nucleic molecule comprising a polynucleotide having at least 95% sequence identity to a sequence selected from the group consisting of any of the polynucleotide sequences set forth below, i.e., SEQ ID NOs. 1-26 as well as those depicted in FIGS. 1-9 and portions thereof. The invention also provides functional fragments of the polynucleotide sequences disclosed herein. The invention further provides complementary nucleic acids, or fragments thereof, to any of the polynucleotide sequences disclosed herein, as well as a nucleic acid, comprising at least 15 contiguous bases, which hybridizes to any of the polynucleotide sequences disclosed herein.

The present invention also relates to an isolated polypeptide sequence comprising a polypeptide having a sequence selected from sequences set forth herein, such as those sequences depicted in SEQ ID NOs 9-12.

The present invention uses terms and phrases that are well known to those practicing the art. Unless defined otherwise, all technical and scientific terms used herein have the same meaning as commonly understood by one of ordinary skill in the art to which this invention belongs. Generally, the nomenclature used herein and the laboratory procedures in cell culture, molecular genetics, and nucleic acid chemistry and hybridization described herein are those well known and commonly employed in the art. Standard techniques are used for recombinant nucleic acid methods, polynucleotide synthesis, microbial culture, cell culture, tissue culture, transformation, transfection, transduction, analytical chemistry, organic synthetic chemistry, chemical syntheses, chemical analysis, and pharmaceutical formulation and delivery. Generally, enzymatic reactions and purification and/or isolation steps are performed according to the manufacturers' specifications. The techniques and procedures are generally performed according to conventional methodology. See, e.g., Sambrook & Russel, MOLECULAR CLONING: A LABORATORY MANUAL, 3$^{rd}$ ed., Cold Spring Harbor Laboratory Press, Cold Spring Harbor, N.Y., 2001.

*Agrobacterium*: as is well known in the field, *Agrobacteria* that are used for transforming plant cells are disarmed and virulent derivatives of, usually, *Agrobacterium tumefaciens* or *Agrobacterium rhizogenes* that contain a vector. The vector typically contains a desired polynucleotide that is located between the borders of a T-DNA.

Angiosperm: vascular plants having seeds enclosed in an ovary. Angiosperms are seed plants that produce flowers that bear fruits. Angiosperms are divided into dicotyledonous and monocotyledonous plants.

Angiosperm Reproductive Structure: includes the male and female tissues that comprise a flower. Typically, angiosperm flowers have four different floral organs: sepals (calyx), petals (corolla), stamens (androcecium), and pistils (gynoecium).

Angiosperm reproductive structure also embraces pre-male and pre-female reproductive structures. Pre-male and pre-female reproductive structures embrace cells and tissues that form before development and differentiation of male and female tissues.

Desired Polynucleotide: a desired polynucleotide of the present invention is a genetic element, such as a promoter, enhancer, or terminator, or gene or polynucleotide that is to be transcribed and/or translated in a transformed cell that comprises the desired polynucleotide in its genome. If the desired polynucleotide comprises a sequence encoding a protein product, the coding region may be operably linked to regulatory elements, such as to a promoter and a terminator, that bring about expression of an associated messenger RNA transcript and/or a protein product encoded by the desired polynucleotide. Thus, a "desired polynucleotide" may comprise a gene that is operably linked in the 5'- to 3'-orientation, a promoter, a gene that encodes a protein, and a terminator. Alternatively, the desired polynucleotide may comprise a gene or fragment thereof in an "antisense" orientation, the transcription of which produces nucleic acids that may form secondary structures that affect expression of an endogenous gene in the plant cell. A desired polynucleotide may also yield a double-stranded RNA product upon transcription that initiates RNA interference of a gene to which the desired polynucleotide is associated. A desired polynucleotide of the present invention may be positioned within a T-DNA, such that the left and right T-DNA border sequences flank or are on either side of the desired polynucleotide. The present invention envisions the stable integration of one or more desired polynucleotides into the genome of at least one plant cell. A desired polynucleotide may be mutated or may be a variant of its wild-type sequence. It is understood that all or part of the desired polynucleotide can be integrated into the genome of a plant. It also is understood that the term "desired polynucleotide" encompasses one or more of such polynucleotides. Thus, a T-DNA of the present invention may comprise one, two, three, four, five, six, seven, eight, nine, ten, or more desired polynucleotides.

Dicotyledonous plant (dicot): a flowering plant whose embryos have two seed halves or cotyledons, branching leaf veins, and flower parts in multiples of four or five. Examples of dicots include but are not limited to, *Eucalyptus, Populus, Liquidambar, Acacia*, teak, mahogany, cotton, tobacco, *Arabidopsis*, tomato, potato sugar beet, broccoli, cassaya, sweet potato, pepper, poinsettia, bean, alfalfa, soybean, carrot, strawberry, lettuce, oak, maple, walnut, rose, mint, squash, daisy, geranium, avocado, cactus, and *Dichondra*.

Endogenous: refers to a gene that is native to a plant genome.

Female reproductive tissues: include, for example, stigma, style, ovary, megaspore, female cones (ovuliferous cones), female gamete, female zygote, megasporocyte, and pre-female reproductive structures.

Female-Sterility Gene: refers to a nucleic acid molecule encoding an RNA, protein, or polypeptide that disrupts growth and development of a female gametophyte, female gamete, female zygote, seed, ovuliferous cone, or pre-female reproductive structure. A plant expressing a female-sterility gene produces no viable seed. There are many different mutations that can lead to female-sterility, involving all stages of development of a specific tissue of the female reproductive organ or pre-female reproductive structure.

Examples of female-sterility genes include, but in no way limiting, encode enzymes which catalyze the synthesis of phytohormones, such as: isopentenyl transferase which is an enzyme that catalyzes the first step in cytokinin biosynthesis and is encoded by gene 4 of *Agrobacterium* T-DNA; or one or both of the enzymes involved in the synthesis of auxin and encoded by gene 1 and gene 2 of *Agrobacterium* T-DNA. Yet other examples of female-sterility genes encode: glucanases; lipases such as phospholipase $A_2$ (Verheij et al. *Rev. Blochem. Pharmacol.* 91:92-203 (1981)); lipid peroxidases; or plant cell wall inhibitors. Still other examples of female-sterility genes encode proteins toxic to plants cells, such as a bacterial toxin (e.g., the A-fragment of diphtheria toxin or botulin).

Still another example of a female-sterility gene is an antisense nucleic acid, or RNA involved in RNA interference (RNAi) such as small interfering RNA (siRNA), which can be useful for inhibiting or completely blocking the expression of a targeted gene. For example, an antisense or RNAi molecule of the invention encodes a nucleic acid strand complementary to a strand that is naturally transcribed in a plant's reproductive cells under the control of an endogenous promoter as described, for example, in European Patent Publication 0,223,399. Such an antisense nucleic acid or RNAi molecule may be capable of binding to the coding and/or non-coding portion of an RNA, naturally produced in the reproductive cell, so as to inhibit the translation of the naturally produced RNA. In one embodiment, an antisense nucleic acid and RNAi molecule of the invention can be expressed in flower, ovuliferous cone, seed, embryo, female gamete, female gametophyte, megasporocyte, and pre-female reproductive structures of the plant under the control of the endogenous promoter of the complementary endogenous DNA strand (or gene) of the plant.

Examples of such an antisense nucleic acid are the antisense DNA sequences of: the STMG-type genes, such as STMG07, STMG08, STMG4B12, and STMG3C9 genes. Jofuku and Goldberg. *The Plant Cell* 1: 1079-1093 (1989). The use of RNAi inhibition of gene expression is described generally in Paddison et al., *Genes & Dev.* 16: 948-958 (2002), and the use of RNAi to inhibit gene expression in plants is specifically described in WO 99/61631, both of which are herein incorporated by reference.

A further example of a female-sterility gene encodes a specific RNA enzyme (i.e., a "ribozyme"), capable of highly specific cleavage against a given target sequence as described by Haseloff and Gerlach et al. *Nature* 334, 585-591 (1998).

Fiber composition: as used herein, fiber composition refers to a trait that can be modified to change the structure, appearance, or use of fiber. Traits that determine fiber composition include but are not limited to fiber length, coarseness, strength, color, cross-sectional, width, and fiber density. For example, it is known that fiber length imparts strength, whereas fiber coarseness determines texture and flexibility.

In angiosperms, Floral Meristems initiate a floral structure having four different types of floral organs: sepals (calyx), petals (corolla), stamens (androecium), and pistils (gynoecium). Each floral organ is initated as a whorl, comprising concentric rings around the flanks of a floral meristem. The floral structure is supported by a pedicel or peduncle.

Flowering plants produce meiospores that are either microspores (male) or megaspores (female).

Foreign: "foreign," with respect to a nucleic acid, means that that nucleic acid is derived from non-plant organisms, or derived from a plant that is not the same species as the plant to be transformed or is not derived from a plant that is not interfertile with the plant to be transformed, or does not belong to the species of the target plant. According to the present invention, foreign DNA or RNA may include nucleic acids that are naturally occurring in the genetic makeup of fungi, bacteria, viruses, mammals, fish or birds, but are not naturally occurring in the plant that is to be transformed. Thus, a foreign nucleic acid is one that encodes, for instance, a polypeptide that is not naturally produced by the transformed plant. A foreign nucleic acid does not have to encode a protein product.

Gene: A gene is a segment of a DNA molecule that contains all the information required for synthesis of a product, polypeptide chain or RNA molecule, and includes both coding and non-coding sequences.

Genetic element: a "genetic element" is any discreet nucleotide sequence including, but not limited to, a promoter, a gene, a terminator, an intron, an enhancer, a spacer, a 5'-untranslated region, a 3'-untranslated region, or a recombinase recognition site.

Genetic modification: stable introduction of DNA into the genome of certain organisms by applying methods in molecular and cell biology.

Gymnosperm: as used herein, refers to a seed plant that bears seed without ovaries. Examples of gymnosperms include conifers, cycads, ginkgos, and ephedras. In gymnosperms, reproductive shoot primordia develop into either male cones (staminate cones) or female cones (ovulate cones).

Gymnosperm Reproductive Structure: includes the male tissues that comprise male pollen cones (staminate cones) and female tissues that comprise female cones (ovulate cones). Gymnosperm reproductive structure also embraces pre-male and pre-female reproductive structures. Pre-male and pre-female reproductive structures embrace cells and tissues that form before development and differentiation of male and female tissues.

Introduction: as used herein, refers to the insertion of a nucleic acid sequence into a cell, by methods including infection, transfection, transformation or transduction.

Lignin: as used herein, refers to a polymeric composition composed of phenylpropanoid units, including polymerized derivatives of monolignols coniferyl, coumaryl, and sinapyl alcohol. Lignin quality refers to the ability of a lignin composition to impart strength to cell wall matrices, assist in the transport of water, and/or impede degradation of cell wall polysaccharides. Lignin composition or lignin structure may be changed by altering the relative amounts of each of monolignols or by altering the type of lignin. For example, guaiacyl lignins (derived from ferulic acid) are prominent in softwood species, whereas guaiacyl-syringyl lignins (derived from ferulic acid and sinapic acid) are characteristic of hardwood species. The degradation of lignin from softwoods, such as pine, requires substantially more alkali and longer incubations, compared with the removal of lignin from hardwoods. Lignin composition may be regulated by either up-regulation or down-regulation of enzymes involved lignin biosynthesis. For example, key lignin biosynthsesis enzymes include, but are not limited to, 4-coumaric acid: coenzyme A ligase (4CL), Cinnamyl Alcohol dehydrogenase (CAD), and Sinapyl Alcohol Dehydrogenase (SAD).

In angiosperms, male gametophytes or pollen grains develop in anthers, and the anthers are borne on stamens. Anther development occurs in two stages that correlate with pollen development. During phase I, sporogenic cells in the anther undergo microsporogenesis; nonsporogenic cells form the epidermis and tapetum. The tapetum is a tissue that surrounds sporogenic cells and provides nutritional materials for developing pollen. Additionally, the tapetum secretes the enzyme callase. During phase II, the anther enlarges and the filament elongates. At this time, pollen grains form, dehiscence occurs, and pollen grains are released.

In gymnosperms, such as conifers, a male pollen cone consists of an axis bearing a series of scales and two pollen sacs on the undersurface of each scale. Male cones consist of numerous microsporophylls that are tightly clustered in a spiral arrangement on a fertile shoot axis. Each microsporophyll bears two microsporangia, also called pollen sacs, on its lower, abaxial side. Within each microsporangium, sporangenous tissue lies. The sporangenous tissue consists of numerous diploid cells, called microsporocytes, which undergo meiosis. Around the periphery of each microsporangium lies the tapetum. Within the microsporangia, the microspores undergo mitosis and following two mitotic divisions, a four-celled male gametophyte is produced. The pollen grain comprises the microspore wall and the contained male gametophyte.

In gymnosperms, a female cone is formed by the fusion of numerous highly modified fertile shoots. In pines, for example, the female cone is comprised of individual units attached to a single, central axis. The individual units are made of an ovuliferous scale (ovule-bearing) and a subtending bract that is almost completely fused to the ovuliferous scale above it. Each ovuliferous scale is formed by the fusion of megasporophylls and other fertile shoot components. On the upper, adaxial surface of each ovuliferous scale are two ovules. The ovules are oriented with their micropyles toward the central cone axis and are partially imbedded in the tissues of the ovuliferous scale. Each ovule has an integument (one multicellular layer) that, except for the micropyles, completely surrounds the megasporangium. The integument or nucellus functions as the nutritive tissue and each nucellus has a single megasporocyte. The megasporocyte is the diploid cell that undergoes meiosis. The micropylar chamber is located within each ovule between the nucellus and the micropyle.

Male reproductive tissues: include, for example, pollen grains, tapetum, anther, filament, pollen mother cells, microspores, microsporocyte, male pollen cones (staminate cones), pollen sacs, and pre-male reproductive structures.

Male-Sterility Gene: refers to a nucleic acid molecule encoding an RNA, protein, or polypeptide that disturbs the proper metabolism, functioning and/or development of any reproductive cell in which the male-sterility gene is expressed, thereby leading to the death and/or destruction of any such reproductive cell. There are many different mutations that can lead to male-sterility, involving all stages of development of a specific tissue of the male reproductive organ or pre-male reproductive structure.

The expression of a male-sterility gene, for example, renders a plant incapable of producing fertile pollen. The expression of a male-sterility gene in a transformed plant may result in a plant producing pollen, though the pollen may be aberrant and non-functional for fertilization. For example, a non-functional pollen may fail to germinate a pollen tube. While by no means limiting, examples of male-sterility genes encode: RNases such as RNase T1 (which degrades RNA molecules by hydrolyzing the bond after any guanine residue) and Barnase; DNases such as an endonuclease (e.g., EcoRI); or proteases such as a papain (e.g., papain zymogen and papain active protein).

Other male-sterility genes encode enzymes which catalyze the synthesis of phytohormones. For example, isopentenyl transferase, an enzyme that catalyzes the first step in cytokinin biosynthesis, and enzymes involved in the synthesis of auxin may be used for inducing male-sterility. Other male-sterility genes encode glucanases; lipases such as phospholipase A.sub.2 (Verheij et al. *Rev. Biochem. Pharmacol.* 91: 92-203 (1981)); lipid peroxidases; or plant cell wall inhibitors. Still other examples of male-sterility genes encode proteins toxic to a plants cell, such as a bacterial toxin (e.g., the B-fragment of diphtheria toxin or botulin).

Still another example of a male-sterility gene is an antisense nucleic acid, or RNA involved in RNA interference (RNAi) such as small interfering RNA (siRNA), which can be useful for inhibiting or completely blocking the expression of a targeted gene. For example, an antisense or RNAi molecule of the invention encodes a nucleic acid strand complementary to a strand that is naturally transcribed in a plant's reproductive cells under the control of an endogenous promoter as described, for example, in European Patent Publication 0,223,399. Such an antisense nucleic acid or RNAi molecule may be capable of binding to the coding and/or non-coding portion of an RNA, naturally produced in the reproductive cell, so as to inhibit the translation of the naturally produced RNA. In one embodiment, an antisense nucleic acid and RNAi molecule of the invention can be expressed in pollen grains, tapetum, anther, filament, pollen mother cells, microspores, microsporocyte, male pollen cones (staminate cones), pollen sacs, and pre-male reproductive structures.

Microsporogenesis is the process by which a diploid cell, the microsporocyte, undergoes meiotic division to produce four, haploid microspores (microspore tetrad). The microspore tetrad is encased in a callose cell wall.

In angiosperms, microsporogenesis occurs in the stamens, the male reproductive tissues of a flower. Each stamen has a filament and an anther. Each anther has one to four chambers, called pollen sacs or anther sacs. Each anther sac produces numerous microsporocytes, also called pollen mother cells.

In gymnosperms, microsporogenesis occurs in the microsporangia or pollen sacs of the microsporophyll. Within the microsporangia, the microspores undergo mitosis and produce a four-celled male gametophyte. A gymnosperm pollen grain comprises the microspore wall and the contained male gametophyte.

Monocotyledonous plant (monocot): a flowering plant having embryos with one cotyledon or seed leaf, parallel leaf veins, and flower parts in multiples of three. Examples of monocots include, but are not limited to, turfgrass, maize, rice, oat, wheat, barley, sorghum, orchid, iris, lily, onion, and palm. Examples of turfgrass include, but are not limited to, *Agrostis* spp. (bentgrass species including colonial bentgrass and creeping bentgrasses), *Poa pratensis* (kentucky bluegrass), *Lolium* spp. (ryegrass species including annual ryegrass and perennial ryegrass), *Festuca arundinacea* (tall fescue) *Festuca rubra commutata* (fine fescue), *Cynodon dactylon* (common bermudagrass varieties including Tifgreen, Tifway II, and Santa Ana, as well as hybrids thereof); *Pennisetum clandestinum* (kikuyugrass), *Stenotaphrum secundatum* (st. augustinegrass), *Zoysia japonica* (zoysiagrass), and *Dichondra micrantha*.

Operably linked: combining two or more molecules in such a fashion that in combination they function properly in a plant cell. For instance, a promoter is operably linked to a structural gene when the promoter controls transcription of the structural gene.

Phenotype: phenotype is a distinguishing feature or characteristic of a plant, which may be altered according to the present invention by integrating one or more "desired polynucleotides" and/or screenable/selectable markers into the genome of at least one plant cell of a transformed plant. The "desired polynucleotide(s)" and/or markers may confer a change in the phenotype of a tranformed plant by modifying any one of a number of genetic, molecular, biochemical, physiological, morphological, or agronomic characteristics or properties of the transformed plant cell or plant as a whole. Thus, expression of one or more, stably integrated desired polynucleotide(s) in a plant genome may yield a phenotype selected from the group consisting of, for example, increased drought tolerance, enhanced cold and frost tolerance, improved vigor, enhanced color, enhanced health and nutritional characteristics, improved storage, enhanced yield, enhanced salt tolerance, enhanced heavy metal tolerance, increased disease tolerance, increased insect tolerance, increased water-stress tolerance, enhanced sweetness, improved vigor, improved taste, improved texture, decreased phosphate content, increased germination, increased micronutrient uptake, improved starch composition, and improved flower longevity.

Plant tissue: a "plant" is any of various photosynthetic, eukaryotic, multicellular organisms of the kingdom Plantae characteristically producing embryos, containing chloroplasts, and having cellulose cell walls. A part of a plant, i.e., a "plant tissue" may be transformed according to the methods of the present invention to produce a transgenic plant. Many suitable plant tissues can be transformed according to the present invention and include, but are not limited to, somatic embryos, pollen, leaves, stems, calli, stolons, microtubers, and shoots. Thus, the present invention envisions the transformation of angiosperm and gymnosperm plants such as turfgrass, wheat, maize, rice, barley, oat, sugar beet, potato, tomato, tobacco, alfalfa, lettuce, carrot, strawberry, cassaya, sweet potato, geranium, soybean, oak, apple, grape, pine, fir, acacia, eucalyptus, walnut, and palm. According to the present invention "plant tissue" also encompasses plant cells. Plant cells include suspension cultures, callus, embryos, meristematic regions, callus tissue, leaves, roots, shoots, gametophytes, sporophytes, pollen, seeds and microspores. Plant tissues may be at various stages of maturity and may be grown in liquid or solid culture, or in soil or suitable media in pots, greenhouses or fields. A plant tissue also refers to any clone of such a plant, seed, progeny, propagule whether generated sexually or asexually, and descendents of any of these, such as cuttings or seed. Of particular interest are conifers such as pine, fir, and spruce, monocots such as Kentucky bluegrass, creeping bentgrass, maize, and wheat, and dicots such as cotton, tomato, lettuce, *Arabidopsis*, tobacco, apple and geranium.

Plant transformation and cell culture: broadly refers to the process by which plant cells are genetically modified and transferred to an appropriate plant culture medium for maintenance, further growth, and/or further development. Such methods are well known to the skilled artisan.

Pollen refers to the microspores of seeds plants and the powdery mass of microspores shed from anthers and staminate pollen cones.

Pre-female reproductive structures: refers to cells and tissues that form before development and differentiation of female tissues in angiosperm and gymnosperm species.

Pre-male reproductive structures: refers to cells and tissues that form before development and differentiation of male tissues in angiosperm and gymnosperm species.

Progeny: a "progeny" of the present invention, such as the progeny of a transgenic plant, is one that is born of, begotten by, or derived from a plant or the transgenic plant. Thus, a "progeny" plant, i.e., an "F1" generation plant is an offspring or a descendant of the transgenic plant produced by the inventive methods. A progeny of a transgenic plant may contain in at least one, some, or all of its cell genomes, the desired polynucleotide that was integrated into a cell of the parent transgenic plant by the methods described herein. Thus, the desired polynucleotide is "transmitted" or "inherited" by the progeny plant. The desired polynucleotide that is so inherited in the progeny plant may reside within a T-DNA construct, which also is inherited by the progeny plant from its parent. The term "progeny" as used herein also may be considered to be the offspring or descendants of a group of plants.

Promoter: is intended to mean a nucleic acid, preferably DNA, that binds RNA polymerase and/or other transcription regulatory elements. As with any promoter, the promoter sequences of the current present invention will facilitate or control the transcription of DNA or RNA to generate an mRNA molecule from a nucleic acid molecule that is operably linked to the promoter. As stated earlier, the RNA generated may code for a protein or polypeptide or may code for an RNA interfering, or antisense molecule.

A promoter, as used herein, may also include regulatory elements. Conversely, a regulatory element may also be separate from a promoter. Regulatory elements confer a number of important characteristics upon a promoter region. Some elements bind transcription factors that enhance the rate of transcription of the operably linked nucleic acid. Other elements bind repressors that inhibit transcription activity. The effect of transcription factors on promoter activity may determine whether the promoter activity is high or low, i.e. whether the promoter is "strong" or "weak."

A plant promoter is a promoter capable of initiating transcription in plant cells, whether or not its origin is a plant cell. Exemplary plant promoters include, but are not limited to, those that are obtained from plants, plant viruses, and bacteria such as *Agrobacterium* or *Rhizobium* which comprise genes expressed in plant cells. Examples of promoters under developmental control include promoters that preferentially initiate transcription in certain tissues, such as tapetum, xylem, leaves, roots, or seeds. Such promoters are referred to as tissue preferred promoters. Promoters which initiate transcription only in certain tissues are referred to as tissue specific promoters. A cell type specific promoter primarily drives expression in certain cell types in one or more organs, for example, vascular cells in roots or leaves. An inducible or repressible promoter is a promoter which is under environmental control. Examples of environmental conditions that may effect transcription by inducible promoters include anaerobic conditions, heat, or the presence of light. Tissue specific, tissue preferred, cell type specific, and inducible promoters constitute the class of non-constitutive promoters. A constitutive promoter is a promoter which is active under most environmental conditions, and in most plant parts.

Polynucleotide is a nucleotide sequence comprising a gene coding sequence or a fragment thereof (comprising at least 15 consecutive nucleotides, at least 30 consecutive nucleotides, or at least 50 consecutive nucleotides), a promoter, an intron, an enhancer region, a polyadenylation site, a translation initiation site, 5' or 3' untranslated regions, a reporter gene, a selectable marker or the like. The polynucleotide may comprise single stranded or double stranded DNA or RNA. The polynucleotide may comprise modified bases or a modified backbone. The polynucleotide may be genomic, an RNA transcript (such as an mRNA) or a processed nucleotide sequence (such as a cDNA). The polynucleotide may comprise a sequence in either sense or antisense orientations.

An isolated polynucleotide is a polynucleotide sequence that is not in its native state, e.g., the polynucleotide is comprised of a nucleotide sequence not found in nature, or the polynucleotide is separated from nucleotide sequences to which it typically is in proximity, or is in proximity to nucleotide sequences with which it typically is not in proximity.

Regenerability: as used herein, refers to the ability of a plant to redifferentiate from a de-differentiated tissue.

Reproductive-preferred promoter refers to a promoter preferentially expressed in a plant's reproductive tissue. Reproductive plant tissue includes both male and female portions of the reproductive structure, as well as pre-male and pre-female reproductive structures. Male reproductive tissues include, for example, pollen grains, tapetum, anther, filament, pollen mother cells, microspores, male pollen cones (staminate cones), and pre-male reproductive structures. Female reproductive tissues include, for example, stigma, style, ovary, megaspores, ovuliferous scale, bract, female pollen cones (ovuliferous cones), and pre-female reproductive structures. Accordingly, a reproductive-preferred promoter may be preferentially expressed in any angiosperm reproductive structure or gymnosperm reproductive structure.

Seed: a "seed" may be regarded as a ripened plant ovule containing an embryo, and a propagative part of a plant, as a tuber or spore. Seed may be incubated prior to *Agrobacterium*-mediated transformation, in the dark, for instance, to facilitate germination. Seed also may be sterilized prior to incubation, such as by brief treatment with bleach. The resultant seedling can then be exposed to a desired strain of *Agrobacterium*.

Selectable/screenable marker: a gene that, if expressed in plants or plant tissues, makes it possible to distinguish them from other plants or plant tissues that do not express that gene. Screening procedures may require assays for expression of proteins encoded by the screenable marker gene. Examples of such markers include the beta glucuronidase (GUS) gene and the luciferase (LUX) gene. Examples of selectable markers include the neomycin phosphotransferase (NPTII) gene encoding kanamycin and geneticin resistance, the hygromycin phosphotransferase (HPT or APHIV) gene encoding resistance to hygromycin, acetolactate synthase (als) genes encoding resistance to sulfonylurea-type herbicides, genes (BAR and/or PAT) coding for resistance to herbicides which act to inhibit the action of glutamine synthase such as phosphinothricin (Liberty or Basta), or other similar genes known in the art.

Sequence identity: as used herein, "sequence identity" or "identity" in the context of two nucleic acid or polypeptide sequences includes reference to the residues in the two sequences which are the same when aligned for maximum correspondence over a specified region.

As used herein, percentage of sequence identity means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

Stamen: refers to the organ of the flower that produces the male gamete and includes an anther and filament.

Tapetum: refers to a layer of cells surrounding microsporogenous cells in the anther of an angiosperm or the microsporangeous cells within a staminate cone of a gymnosperm. Given its close proximity to the developing microspores, the tapetum likely provides nutrients, such as reducing sugars, amino acids and lipids to the developing microspores. Reznickova, C. R., *Acad. Bulg. Sci.* 31:1067 (1978). Nave, et al., *J. Plant Physiol.* 125:451 (1986). Sawhney, et al., *J. Plant Physiol* 125:467 (1986). Tapetal cells also produce beta(1,3) glucanase (callase) which promotes microspore release by digesting the callose cell wall. Therefore, a fragile relationship exists between the tapetum and the microsporogenous cells, and any disruption of tapetal function is likely to result in non-functional pollen grains. It has been shown, for example, lesions in tapetal biogenesis result in male sterility mutants (Kaul, "Male Sterility in Higher Plants" in Monographs on Theoretical and Applied Genetics; Frankel et al. eds.; Springer Verlag; Vol. 10; pp. 15-95; (1988)). Therefore, a gene encoding callase can be used for disrupting male reproductive development. Thus, a failure of the microspores to develop into mature pollen grains can be induced using, for example, a recombinant DNA molecule that comprises a gene capable of disrupting tapetal function under the control of tapetum-specific regulatory sequences.

Transcription factor: Transcription factor refers to a polypeptide sequence that regulates the expression of a gene or genes by either directly binding to one or more nucleotide sequences associated with a gene coding sequence or indirectly affecting the activity of another polypeptide(s) that bind directly to one or more nucleotide sequences associated with a gene coding sequence. A transcription factor may activate (up-regulate) or repress (down-regulate) expression of a gene or genes. A transcription factor may contain a DNA binding domain, an activation domain, or a domain for protein-protein interactions. In the present invention, a transcription factor is capable of at least one of (1) binding to a nucleic acid sequence or (2) regulating expression of a gene in a plant.

Transcription and translation terminators: The expression DNA constructs of the present invention typically have a transcriptional termination region at the opposite end from the transcription initiation regulatory element. The transcriptional termination region may be selected, for stability of the mRNA to enhance expression and/or for the addition of polyadenylation tails added to the gene transcription product.

Transfer DNA (T-DNA): an *Agrobacterium* T-DNA is a genetic element that is well-known as an element capable of integrating a nucleotide sequence contained within its borders into another genome. In this respect, a T-DNA is flanked, typically, by two "border" sequences. A desired polynucleotide of the present invention and a selectable marker may be positioned between the left border-like sequence and the right border-like sequence of a T-DNA. The desired polynucleotide and selectable marker contained within the T-DNA may be operably linked to a variety of different, plant-specific (i.e., native), or foreign nucleic acids, like promoter and terminator regulatory elements that facilitate its expression, i.e., transcription and/or translation of the DNA sequence encoded by the desired polynucleotide or selectable marker.

Transformation of plant cells: A process by which a nucleic acid is stably inserted into the genome of a plant cell. Transformation may occur under natural or artificial conditions using various methods well known in the art. Transformation may rely on any known method for the insertion of nucleic acid sequences into a prokaryotic or eukaryotic host cell, including *Agrobacterium*-mediated transformation protocols, viral infection, whiskers, electroporation, microinjection, polyethylene glycol-treatment, heat shock, lipofection and particle bombardment.

Transgenic plant: a transgenic plant of the present invention is one that comprises at least one cell genome in which an exogenous nucleic acid has been stably integrated. According to the present invention, a transgenic plant is a plant that may comprise only one genetically modified cell and cell genome, or it may comprise several or many genetically modified cells, or all of the cells may be genetically modified. A transgenic plant of the present invention may be one in which expression of the desired polynucleotide, i.e., the exogenous nucleic acid, occurs in only certain parts of the plant. Thus, a transgenic plant may contain only genetically modified cells in certain parts of its structure.

Variant: a "variant," as used herein, is understood to mean a nucleotide sequence that deviates from the reference (i.e., native, standard, or given) nucleotide sequence of a particular gene. The terms, "isoform," "isotype," and "analog" also refer to "variant" forms of a nucleotide sequence.

Variant may also refer to a "shuffled gene" such as those described in Maxygen-assigned patents. For instance, a variant of the present invention may include variants of sequences and desired polynucleotides that are modified according to the methods and rationale disclosed in U.S. Pat. No. 6,132,970, which is incorporated herein by reference.

Vegetative growth: this well-accepted term of art refers to the general, overall development of a plant. To elaborate, after reproduction, meristem cells differentiate into apical-, lateral meristems that ultimately develop into roots and shoots and, later, into leaves and flowers, for instance. Shoot and root architecture, branching patterns, development of stems, axillary buds, and primordial cells into leaves, petals, flowers, and fruit etc. are all considered "vegetative" and part of the "vegetative growth" cycle of a plant. The rate of development of such features depends on a variety of factors, such as the species of the plant, photosynthesis, availability of nutrients, and the general environment in which the plant is growing.

Genetics also plays an important literal and figurative role in shaping a plant's development. For instance, the "simple" or "compound" shape of a leaf, i.e., whether it is characterized by smooth-edges, deep lobes, individual leaflets, or tendrils can be dictated by gene expression. The "LEAFY" gene, for example, plays a role in compound leaf development and is essential for the transition from vegetative to reproductive development. LEAFY was identified in *Arabidopsis* and snapdragon, and has homologues in other angiosperms. The pea homologue, *Unifoliata*, has a mutant phenotype in which compound leaves are reduced to simple leaves, which may indicate a regulatory relationship between shoots and compound leaves.

Similarly, the acacia mutant, "tl," converts tendrils to leaflets, whilst the mutation, afilia, "af," converts leaflet to tendrils. The "af tl" double mutant has a complex architecture, resembling a parsley leaf. Likewise, other genes, which are expressed throughout such "vegetative" plant cells and tissues, coordinate and connote developmental, physiological, and structural characteristics to other discreet parts of the plant. Thus, there are many "vegetative-specific" genes that are expressed, either specifically or predominantly, in all vegetative tissues, such as roots, shoots, stems, and leaves, or which are vegetative-tissue specific. The promoters of such genes are, therefore, useful in directing the expression of a desired gene, endogenous or foreign, to a particular vegetative tissue. Thus, it is possible to preferentially express a gene product in one or more vegetative tissues, whilst avoiding expression of that same product in non-vegetative tissues, such as in reproductive tissue cells.

Wood composition: refers to a trait that can be modified to change the structure, appearance, or use of wood. While not limiting, traits that determine wood composition include cell wall thickness, cell length, cell size, lumen size, cell density, microfibril angle, tensile strength, tear strength, wood color, and length and frequency of cell division.

Wood pulp: refers to fiber generated from wood having varying degrees of purification. Wood pulp can be used for producing paper, paper board, and chemical products.

It is understood that the present invention is not limited to the particular methodology, protocols, vectors, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a gene" is a reference to one or more genes and includes equivalents thereof known to those skilled in the art and so forth. Indeed, one skilled in the art can use the methods described herein to express any native gene (known presently or subsequently) in plant host systems.

Nucleic Acids

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vitro RNA transcripts of the DNA molecules of the present invention. Isolated nucleic acid molecules, according to the present invention, further include such molecules produced synthetically.

Nucleic acid molecules of the present invention may be in the form of RNA, such as mRNA, or in the form of DNA, including, for instance, cDNA and genomic DNA obtained by cloning or produced synthetically. The DNA or RNA may be double-stranded or single-stranded. Single-stranded DNA may be the coding strand, also known as the sense strand, or it may be the non-coding strand, also referred to as the antisense strand.

Unless otherwise indicated, all nucleotide sequences determined by sequencing a DNA molecule herein were determined using an automated DNA sequencer (such as the Model 3700 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 95% identical, more typically at least about 96% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence may be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence in is replaced by the ribonucleotide uridine (U). For instance, reference to an RNA molecule having the sequence of SEQ ID NO: 1 set forth using deoxyribonucleotide abbreviations is intended to indicate an RNA molecule having a sequence in which each deoxynucleotide A, G or C of SEQ ID NO: 1 has been replaced by the corresponding ribonucleotide A, G or C, and each deoxynucleotide T has been replaced by a ribonucleotide U.

The present invention is also directed to fragments of the isolated nucleic acid molecules described herein. By a fragment of an isolated DNA molecule having the nucleotide sequences disclosed herein is intended DNA fragments at least 15 nucleotides, at least 20 nucleotides, at least 30 nucleotides in length, which are useful as diagnostic probes and primers is discussed in more detail below. Of course larger nucleic acid fragments of up to the entire length of the nucleic acid molecules of the present invention are also useful diagnostically as probes, according to conventional hybridization techniques, or as primers for amplification of a target sequence by the polymerase chain reaction (PCR), as described, for instance, in Molecular Cloning, A Laboratory Manual, 3rd. edition, edited by Sambrook, J and Russel, D. W., (2001), Cold Spring Harbor Laboratory Press, Cold Spring Harbor, N.Y., the entire disclosure of which is hereby incorporated herein by reference.

By a fragment at least 20 nucleotides in length, for example, is intended fragments which include 20 or more contiguous bases from the nucleotide sequence of the as disclosed herein, i.e., SEQ ID NOs. 1-26. Nucleic acids comprising the nucleotide sequences disclosed herein can be generated using conventional methods of DNA synthesis which will be routine to the skilled artisan. For example, restriction endonuclease cleavage or shearing by sonication could easily be used to generate fragments of various sizes. Alternatively, the DNA fragments of the present invention could be generated synthetically according to known techniques.

In another aspect, the invention provides an isolated nucleic acid molecule comprising a polynucleotide which hybridizes under stringent hybridization conditions to a portion of the polynucleotide in a nucleic acid molecule of the invention described above. By a polynucleotide which hybridizes to a "portion" of a polynucleotide is intended a polynucleotide (either DNA or RNA) hybridizing to at least about 15 nucleotides, at least about 20 nucleotides, at least about 30 nucleotides, and more than 30 nucleotides of the reference polynucleotide. These fragments that hybridize to the reference fragments are useful as diagnostic probes and primers. A probe, as used herein is defined as at least about 50 contiguous bases of one of the nucleic acids disclosed herein, i.e., SEQ ID NOs. 1-8 and 13-26. For the purpose of the invention, two sequences hybridize when they form a double-stranded complex in a hybridization solution of 6×SSC, 0.5% SDS, 5×Denhardt's solution and 100 µg of non-specific carrier DNA. See Ausubel et al, section 2.9, supplement 27 (1994). Sequences may hybridize at "moderate stringency," which is defined as a temperature of 60° C. in a hybridization solution of 6×SSC, 0.5% SDS, 5×Denhardt's solution and 100 µg of non-specific carrier DNA. For "high stringency" hybridization, the temperature is increased to 68° C. Following the moderate stringency hybridization reaction, the nucleotides are washed in a solution of 2×SSC plus 0.05% SDS for five times at room temperature, with subsequent washes with 0.1×SSC plus 0.1% SDS at 60° C. for 1 h. For high stringency, the wash temperature is increased to 68° C. For the purpose of the invention, hybridized nucleotides are those that are detected using 1 ng of a radiolabeled probe having a specific radioactivity of 10,000 cpm/ng, where the hybridized nucleotides are clearly visible following exposure to X-ray film at −70° C. for no more than 72 hours.

As mentioned previously, the present application is directed to such nucleic acid molecules which are at least 90%, 95%, 96%, 97%, 98%, 99% or 100% identical to a nucleic acid sequence described above. One embodiment encompasses nucleic acid molecules which are at least 95%, 96%, 97%, 98%, 99% or 100% identical to the nucleic acid sequence shown in SEQ ID NOs. 1-8 and 13-26. By a polynucleotide having a nucleotide sequence at least, for example, 95% "identical" to a reference nucleotide sequence, is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to a reference nucleotide sequence refers to a comparison made between two molecules using standard algorithms well known in the art. Although any sequence algorithm can be used to define sequence identity, for clarity, the present invention defines identity with reference to the Basis Local Alignment Search Tool (BLAST) algorithm (Altschul et al., *J. Mol. Biol.* 215:403-410 (1990)), where a promoter sequence set forth in the disclosure is used as the reference sequence to define the percentage identity of polynucleotide homologs over its length. The choice of parameter values for matches, mismatches, and inserts or deletions is arbitrary, although some parameter values have been found to yield more biologically realistic results than others.

When using BLAST or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Relatedness between two polynucleotides also may be described by reference to their ability to hybridize to form double-stranded complexes by the formation of complementary base pairs. Hybridization conditions have been described previously herein. An increase in temperature can be used to break apart these complexes. The more structurally identical two sequences are, the higher the temperature required to break them apart or "melt" them. The temperature required to melt a double-stranded complex is called the "$T_m$." The relationship between the $T_m$ and other hybridization parameters is given by:

$$T_m(°C.)=81.5+16.6(\log_{10}[Na^+])+0.41(\text{fraction }G+C)-0.63(\%\text{ formamide})-(600/l),$$

where $T_m$ is the melting temperature of a DNA duplex consisting of the probe and its target; and l=the length of the hybrid in base pairs, provided l>100 base pairs. Bolton et al., *Proc. Natl. Acad. Sci.* 48:1390 (1962). Generally, a change of 1° C. in the melting point represents from 0.7% to 3.2% difference in DNA sequence similarity. Bonner et al., *Journal of Molecular Biology* 81:123-35 (1973); McCarthy et al., In EVOLUTION OF GENETIC SYSTEMS, H. H. Smith (ed.), Brookhaven Symposium in Biology No. 23, Gordon and Breach, New York, pp. 1-43 (1972). The formation of a stable DNA duplex at 60° C. typically requires at least an 80% sequence identity between sequences. Sibley et al., *ACTA* 1: 83-121 (Proceedings of the 18th International Ornithological Congress, Moscow, Aug. 16-24, 1982, Academy of Sciences of the USSR).

In one embodiment, the nucleic acids of the present invention confer preferential expression of polypeptides or proteins in the reproductive tissues of angiosperm and gymnosperm plants. The nucleic acids of the present invention can also preferentially direct the expression of antisense RNA, or RNA involved in RNA interference (RNAi) such as small interfering RNA (siRNA), in the reproductive tissue of plants, which can be useful for inhibiting or completely blocking the expression of targeted genes.

Reproductive plant tissue includes both male and female portions of reproductive organs. Male tissues include, for example, pollen, tapetum, anther, filament, pollen mother cells, microspores, male pollen cones (staminate cones), and pre-male reproductive structures. Female reproductive tissues include, for example, stigma, style, ovary, megaspores, female cones (ovuliferous cones), and pre-female reproductive structures.

Reproductive-preferred promoter refers to a promoter preferentially expressed in a plant's reproductive tissue. Reproductive plant tissue includes both male and female portions of the reproductive structure, as well promoters expressed in pre-male and pre-female reproductive structures. Male reproductive tissues include, for example, pollen grains, tapetum, anther, filament, pollen mother cells, microspores, and pollen cones. Female reproductive tissues include, for example, stigma, style, ovary, megaspores, and ovuliferous cones. Accordingly, a reproductive-preferred promoter may be preferentially expressed in any reproductive structure of any angiosperm or gymnosperm species, in addition to expression in any pre-male or pre-female tissue of gymnosperm and angiosperm species.

In one embodiment, a reproductive-preferred promoter confers expression of a gene in a male-reproductive tissue. In one embodiment, a reproductive-preferred promoter confers gene expression in the anther, pollen or filament cells of an angiosperm species. In a further embodiment, the reproductive-preferred promoter confers gene expression in the tapetum or anther epidermal cells. In another embodiment, a reproductive-preferred promoter confers gene expression in a male pollen cone, tapetum, microsporophyll, or any other male reproductive tissue present in a gymnosperm. For both angiosperm and gymnosperm species, a reproductive-preferred promoter confers gene expression in a pre-male or pre-female reproductive structure.

A reproductive-preferred promoter can be used for example, to render a plant male-sterile. For example, a reproductive-preferred promoter can be operably linked to a cytotoxic gene, such that expression of the cytotoxic gene in a male reproductive tissue renders the plant incapable of producing fertile male gametes. In another embodiment, a reproductive-preferred promoter may be selected and isolated such that the promoter does not express an operably-linked gene in a non-reproductive tissue, such as a vegetative tissue.

In one embodiment, a reproductive-preferred promoter confers expression of a gene in a female-reproductive tissue. In one embodiment, a reproductive-preferred promoter confers gene expression in the stigma, style, or ovary of an angiosperm species. In another embodiment, a reproductive-preferred promoter confers gene expression in a female cone (ovuliferous cone), megasporophyll, or any other female reproductive tissue present in a gymnosperm species. For both angiosperm and gymnosperm species, a reproductive-preferred promoter confers gene expression in a pre-male or pre-female reproductive structure.

A reproductive-preferred promoter can be used for example, to render a plant female-sterile. In one embodiment, a reproductive-preferred promoter can be operably linked to a cytotoxic gene, such that expression of the cytotoxic gene in a female reproductive tissue renders the plant incapable of producing fertile female gametes, female zygote, and/or seed. In another embodiment, a reproductive-preferred promoter may be selected and isolated such that the promoter does not express an operably-linked gene in a non-reproductive tissue, such as a vegetative tissue.

For example, a reproductive-preferred promoter may be identified by searching for an mRNA which is only present during reproductive development. Additionally, a reproductive-preferred promoter may be present in pre-male and pre-female reproductive tissues. In one embodiment, a reproductive-preferred promoter is identified from mRNA present during development of a plant's male reproductive tissues, including, for example, anthers, pollen, filament, male staminate cones, and pre-male reproductive tissues. In one embodiment, a reproductive-preferred promoter is identified from mRNA present during development of a plant's female reproductive tissues, including, for example, stigma, style, ovary, ovuliferous cones, and pre-female reproductive tissues. Following identification and isolation of a reproductive-preferred mRNA, cDNA is prepared from this reproductive-preferred mRNA. The resultant cDNA may be used as a probe to identify the regions in a plant genome containing DNA coding for a reproductive-preferred mRNA. Once a DNA has been identified, the sequence upstream (i.e., 5') from the DNA coding for a reproductive-preferred promoter may be isolated.

As used herein, promoter is intended to mean a nucleic acid, preferably DNA, that binds RNA polymerase and/or other transcription regulatory elements. As with any promoter, the promoters of the current invention will facilitate or control the transcription of DNA or RNA to generate an mRNA molecule from a nucleic acid molecule that is operably linked to the promoter. As stated earlier, the RNA generated may code for a protein or polypeptide or may code for an RNA interfering, or antisense molecule. As used herein, "operably linked" refers to the chemical fusion, ligation, or synthesis of DNA such that a promoter-nucleic acid sequence combination is formed in a proper orientation for the nucleic acid sequence to be transcribed into an RNA segment. The promoters of the current invention may also contain some or all of the 5' untranslated region (5' UTR) of the resulting mRNA transcript. On the other hand, the promoters of the current invention do not necessarily need to possess any of the 5' UTR.

A promoter, as used herein, may also include regulatory elements. Conversely, a regulatory element may also be separate from a promoter. Regulatory elements confer a number of important characteristics upon a promoter region. Some elements bind transcription factors that enhance the rate of transcription of the operably linked nucleic acid. Other elements bind repressors that inhibit transcription activity. The integrated effect of transcription factors on promoter activity may determine whether the promoter activity is high or low, i.e. whether the promoter is "strong" or "weak." Transcription factors that bind regulatory elements may themselves be regulated by the interaction with other bound proteins or by covalent modification, e.g. phosphorylation, in response to extracellular stimuli. The activity of some transcription factors is modulated by signaling molecules, such as intracellular metabolites or chemicals exogenous to the organism that communicate with the cellular nucleus. Promoters that are unaffected by changes in the cellular environment are referred to as constitutive promoters.

In another embodiment, the nucleic acids of the invention encode expression products that disrupt the metabolism, function, and/or development of the cell in which the nucleic acid is expressed. In one embodiment, the nucleic acids of the invention encode a cytotoxic expression product. In one embodiment, the nucleic acids of the invention embrace barnase. In a further embodiment, the barnase may be mutated by methods known in the art for increasing and/or decreasing barnase activity. In one embodiment, a mutated barnase may have attenuated cytotoxic activity.

The present invention also provides vectors comprising the isolated nucleic acid molecules and polypeptides of the invention. In one embodiment, the vectors of the present invention are Ti-plasmids derived from the *A. tumefaciens*.

In developing the constructs of this invention, the various components of the construct or fragments thereof will normally be inserted into a convenient cloning vector, e.g., a plasmid that is capable of replication in a bacterial host, e.g., *E. coli*. Numerous vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. to tailor the components of the desired sequence. Once the construct has been completed, it may then be transferred to an appropriate vector for further manipulation in accordance with the manner of transformation of the host cell.

A recombinant DNA molecule of the invention typically includes a selectable marker so that transformed cells can be easily identified and selected from non-transformed cells. Examples of such markers include, but are not limited to, a neomycin phosphotransferase (nptII) gene, which confers kanamycin resistance. Potrykus et al., *Mol. Gen. Genet.* 199: 183-188 (1985). Cells expressing the nptII gene can be selected using an appropriate antibiotic such as kanamycin or G418. Other commonly used selectable markers include the bar gene, which confers bialaphos resistance; a mutant EPSP synthase gene (Hinchee et al., Bio/Technology 6:915-922 (1988)), which confers glyphosate resistance; a nitrilase gene, which confers resistance to bromoxynil (Stalker et al. *J. Biol. Chem.* 263:6310-6314 (1988)); a mutant acetolactate synthase gene (ALS), which confers imidazolinone or sulphonylurea resistance (European Patent Application 154,204, 1985); and a methotrexate resistant DHFR gene (Thillet et al. *J. Biol. Chem.* 263:12500-12508 (1988)).

Additionally, vectors may include an origin of replication (replicons) for a particular host cell. Various prokaryotic replicons are known to those skilled in the art, and function to direct autonomous replication and maintenance of a recombinant molecule in a prokaryotic host cell.

The vectors will preferably contain selectable markers. Numerous selectable markers for use in selecting transfected plant cells including, but not limited to, kanamycin, glyphosate resistance genes, and tetracycline or ampicillin resistance for culturing in *E. coli*, *A. tumefaciens* and other bacteria.

A plasmid vector suitable for the introduction of nucleic acid of the current invention into monocots using microprojectile bombardment is composed of the following: the promoter of choice; an intron that provides a splice site to facilitate expression of the gene, such as the Hsp70 intron (PCT Publication WO 93/19189); and a 3' polyadenylation sequence such as the nopaline synthase 3' sequence (NOS 3'). Fraley et al. *Proc Natl Acad Sci USA* 80: 4803-4807 (1983). This expression cassette may be assembled on high copy replicons suitable for the production of large quantities of DNA.

A particularly useful *Agrobacterium*-based plant transformation vector for use in transformation of dicotyledonous plants is plasmid vector pMON530 (Rogers et al. (1987) Improved vectors for plant transformation: expression cassette vectors and new selectable markers. In Methods in Enzymology. Edited by R. Wu and L. Grossman. p 253-277. San Diego: Academic Press). Plasmid pMON530 is a derivative of pMON505 prepared by transferring the 2.3 kb StuI-HindIII fragment of pMON316 (Rogers et al. (1987) Improved vectors for plant transformation: expression cassette vectors and new selectable markers. In Methods in Enzymology. Edited by R. Wu and L. Grossman. p 253-277. San Diego: Academic Press) into pMON526. Plasmid pMON526 is a simple derivative of pMON505 in which the SmaI site is removed by digestion with XmaI, treatment with Klenow polymerase and ligation. Plasmid pMON530 retains all the properties of pMON505 and the CaMV35S-NOS expression cassette and now contains a unique cleavage site for SmaI between the promoter and polyadenylation signal.

Binary vector pMON505 is a derivative of pMON200 (Rogers et al., 1987) in which the Ti plasmid homology region, LIH, has been replaced with a 3.8 kb HindIII to SmaI segment of the mini RK2 plasmid, pTJS75 (Schmidhauser and Helinski. *J. Bacteriol.* 164-155 (1985). This segment contains the RK2 origin of replication, oriV, and the origin of transfer, oriT, for conjugation into *Agrobacterium* using the tri-parental mating procedure (Horsch and Klee *Proc. Natl. Acad. Sci. USA* 83:4428-4432 (1986). Plasmid pMON505 retains all the important features of pMON200 including the synthetic multi-linker for insertion of desired DNA fragments, the chimeric NOS/NPTII'/NOS gene for kanamycin resistance in plant cells, the spectinomycin/streptomycin resistance determinant for selection in *E. coli* and *A. tumefaciens*, an intact nopaline synthase gene for facile scoring of transformants and inheritance in progeny, and a pBR322 origin of replication for ease in making large amounts of the vector in *E. coli*. Plasmid pMON505 contains a single T-DNA border derived from the right end of the pTiT37 nopaline-type T-DNA. Southern blot analyses have shown that plasmid pMON505 and any DNA that it carries are integrated into the plant genome, that is, the entire plasmid is the T-DNA that is inserted into the plant genome. One end of the integrated DNA is located between the right border sequence and the nopaline synthase gene and the other end is between the border sequence and the pBR322 sequences.

Another particularly useful $T_i$ plasmid cassette vector is pMON17227. This vector is described in PCT Publication WO 92/04449 and contains a gene encoding an enzyme conferring glyphosate resistance (denominated CP4), which is an excellent selection marker gene for many plants, including potato and tomato. The gene is fused to the *Arabidopsis* EPSPS chloroplast transit peptide (CTP2), and expression is driven by the promoter of choice.

For secretion of the translated protein into the lumen of the endoplasmic reticulum, the periplasmic space or into the extracellular environment, appropriate secretion signals may be incorporated into the expressed polypeptide. The signals may be endogenous to the polypeptide or they may be heterologous signals.

In one embodiment, the vectors of the current invention are designed in a manner such that the nucleic acids described herein are tissue-specific promoters which are operably linked to DNA encoding a polypeptide of interest. In another embodiment, the polypeptide of interest is a protein involved in an aspect of reproductive development or regulating reproductive development. Polynucleotides encoding many of the proteins involved in reproductive development include, but are not limited to, AGAMOUS (AG), APETALA1 (AP1), APETAL3 (AP3), PISTILLATA (Pt), LEAFY (LFY), and LEUNIG (LUG).

In another embodiment, the coding sequence operably linked to a promoter may code for a gene product that inhibits the expression or activity of proteins involved in reproductive development. For example, a gene encoding the enzyme callase, which digests the callose cell wall surrounding the developing pollen grains, could be operably linked to a tapetum-preferred promoter and expressed before pollen maturation, thereby disrupting pollen development.

In another embodiment, the coding sequence operably linked to a promoter may encode a cytotoxic gene product. For instance, a gene encoding barnase may be operably linked to a reproductive-preferred promoter and expressed in a reproductive tissue. In a further embodiment, standard molecular biology methods may be used for mutating barnase activity. In one embodiment, a mutated barnase has reduced RNase activity compared with a wild type barnase protein. In a further embodiment, a mutated barnase having reduced RNase activity is operably linked to a reproductive-preferred promoter and expressed in a reproductive tissue. In a further embodiment, the expression of a mutated barnase having reduced RNase activity in a reproductive tissue does not compromise vegetative growth and development.

In a further embodiment, the vectors of the current invention are designed such that the nucleic acids of the current invention are operably linked to a nucleic acid encoding an antisense RNA or interfering RNA, which corresponds to a gene that code for a polypeptide of interest, resulting in a decreased expression of a targeted gene product. In one embodiment, the gene products targeted for suppression are proteins involved in reproductive development. The use of RNAi inhibition of gene expression is described generally in Paddison et al., *Genes & Dev.* 16: 948-958 (2002), and the use of RNAi to inhibit gene expression in plants is specifically described in WO 99/61631, both of which are herein incorporated by reference.

The use of antisense technology to reduce or inhibit the expression of specific plant genes has been described, for example in European Patent Publication No. 271,988. Reduction of gene expression led to a change in the phenotype of the plant, either at the level of gross visible phenotypic difference, for example a lack of lycopene synthesis in the fruit of tomato leading to the production of yellow rather than red fruit, or at a more subtle biochemical level, for example, a change in the amount of polygalacturonase and reduction in depolymerisation of pectins during tomato fruit ripening. Smith et. al., *Nature,* 334:724-726 (1988). Smith et. al., *Plant Mol. Biol.,* 14:369-379 (1990). Thus, antisense RNA has been demonstrated to be useful in achieving reduction of gene expression in plants.

In one embodiment of the method of making a plant of the invention, an exogenous DNA capable of being transcribed inside a plant to yield an antisense RNA transcript is introduced into the plant, e.g., into a plant cell. The exogenous DNA can be prepared, for example, by reversing the orientation of a gene sequence with respect to its promoter. Transcription of the exogenous DNA in the plant cell generates an intracellular RNA transcript that is "antisense" with respect to that gene.

The invention also provides host cells which comprise the vectors of the current invention. As used herein, a host cell refers to the cell in which the coding product is ultimately expressed. Accordingly, a host cell can be an individual cell, a cell culture or cells as part of an organism. The host cell can also be a portion of an embryo, endosperm, sperm or egg cell, or a fertilized egg.

The vectors of the current invention are introduced into the host cells by standard procedures known in the art for introducing recombinant vector DNA into the target host cell. Such procedures include, but are not limited to, transfection, infection, transformation, natural uptake, electroporation, biolistics and *Agrobacterium*. Methods for introducing foreign genes into plants are known in the art and can be used to insert a gene construct of the invention into a plant host, including, biological and physical plant transformation protocols. See, for example, Miki et al., 1993, "Procedure for Introducing Foreign DNA Into Plants", In: Methods in Plant Molecular Biology and Biotechnology, Glick and Thompson, eds., CRC Press, Inc., Boca Raton, pages 67-88. The methods chosen vary with the host plant, and include chemical transfection methods such as calcium phosphate, microorganism-mediated gene transfer such as *Agrobacterium* (Horsch et al., *Science* 227:1229-31, (1985)), electroporation, micro-injection, and biolistic bombardment.

Accordingly, the present invention also provides plants or plant cells, comprising the vectors of the current invention. In one embodiment, the plants are angiosperms or gymnosperms. In another embodiment, the plants are selected from Eucalyptus and its hybrids, and *Pinus* species. Alternatively, the plant may be selected from *Pinus banksiana, Pinus brutia, Pinus caribaea, Pinus clasusa, Pinus contorta, Pinus coulteri, Pinus echinata, Pinus eldarica, Pinus ellioti, Pinus jeffreyi, Pinus lambertiana, Pinus massoniana, Pinus monticola, Pinus nigra, Pinus palustrus, pinus pinaster, Pinus ponderosa, Pinus radiata, Pinus resinosa, Pinus rigida, Pinus serotina, Pinus strobus, Pinus sylvestris, Pinus taeda, Pinus virginiana, Abies amabilis, Abies balsamea, Abies concolor, Abies grandis, Abies lasiocarpa, Abies magnifica, Abies procera, Chamaecyparis lawsoniona, Chamaecyparis nootkatensis, Chamaecyparis thyoides, Juniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea pungens, Picea rubens, Picea sitchensis, Pseudotsuga menziesii, Sequoia gigantea, Sequoia sempervirens, Taxodium distichum, Tsuga canadensis, Tsuga heterophylla, Tsuga mertensiana, Thuja occidentalis, Thuja plicata, Eucalyptus alba, Eucalyptus bancroftii, Eucalyptus botryoides, Eucalyptus*

*bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus grandis, Eucalyptus globulus, Eucalyptus gomphocephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus nova-angelica, Eucalyptus obliqua, Eucalyptus occidentalis Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus torelliana, Eucalyptus urnigera, Eucalyptus urophylla, Eucalyptus viminalis, Eucalyptus viridis, Eucalyptus wandoo,* and *Eucalyptus youmanni.* In particular, the transgenic plant may be of the species *Eucalyptus grandis, Pinus radiata, Pinus taeda* L (loblolly pine), *Populus nigra, Populus deltoides, Tectona grandis,* or *Acacia mangium.*

Beyond the ordinary meaning of plant, the term "plants" is also intended to mean the fruit, seeds, flower, strobilus etc. of the plant. The plant of the current invention may be a direct transfectant, meaning that the vector was introduced directly into the plant, such as through *Agrobacterium*, or the plant may be the progeny of a transfected plant. The second or subsequent generation plant may or may not be produced by sexual reproduction, i.e., fertilization. Furthermore, the plant can be a gametophyte (haploid stage) or a sporophyte (diploid stage).

The present invention also provides a method for controlling reproductive development in a plant comprising cultivating a plant or seed comprising the vectors of the current invention. Proper cultivation to induce or sustain the growth or germination of the plants or seeds of the current invention is species-specific, and within the level of ordinary skill in the art. The setting for cultivation may be anywhere which fosters the growth or germination of the plant or seed. Furthermore, cultivation can also include steps such as, but not limited to, providing a stress treatment, (e.g., nitrogen deprivation, heat shock, low temperatures, sucrose deprivation) which can induce embyrogenesis.

The invention further provides isolated regulatory elements that bind transcription factors and are capable of regulating tissue-preferred or tissue-specific expression. The degree of regulation conferred by the regulatory elements may be complete, meaning that transcription is not detectable without the transcription factors, or partial, meaning that transcription is enhanced in the presence of the transcription factors. In one embodiment, at least one regulatory element is operably linked to a heterologous promoter to provide a composite promoter. The composite promoter is expressed preferentially or specifically in reproductive tissue. As used herein, heterologous promoters is a phrase whose meaning term that is relative to the regulatory elements. If a regulatory element and a promoter do not associate with one another in a natural setting, the promoter would be considered heterologous to the regulatory element. Typically, the precise orientation of a regulatory element within a promoter region will not affect its activity. Furthermore, regulatory elements can function normally when inserted into heterologous promoter regions. Thus, for example, reproductive-preferred regulatory elements can be removed from their endogenous promoter and can be inserted into heterologous promoter regions to confer reproductive-specificity or preference. The heterologous promoter may be, for example, a minimal CaMV 35S promoter. Promoters that direct expression in plant cells which are suitable for modification to minimal promoters include the cauliflower virus (CaMV) 35S promoter (Jefferson et al., *EMBO J.*, 6: 3901-07 (1987)), the rice actin promoter (McElroy et al., *Plant Cell,* 2: 163-71 (1990)), the maize ubiquitin-1 promoter (Christensen et al., *Transgenic Research,* 5: 213-18 (1996)), and the nopaline synthase promoter (Kononowics et al., *Plant Cell* 4: 17-27 (1992)).

To prepare the nucleic acids of the invention, genomic libraries were made from *Pinus radiata* and *Pinus taeda,* using a variety of restriction endonucleases to digest the genome into discrete fragments. Genomic libraries can be similarly constructed from any plant species from which it is desirable to obtain tissue-selective promoters. An adaptor was ligated to each of these genomic sequences, according to the procedure provided by Clontech for use of its GenomeWalker™ Systems (Clontech, Palo Alto, Calif.). Promoter sequences then were PCR-amplified using adaptor-specific primers and "gene-specific primers." Alternatively, this PCR amplification step optionally may be conducted by the methodology described in U.S. Pat. No. 5,565,340 and No. 5,759,822, herein incorporated by reference, to yield reaction products of long length and minimal background. Using this general PCR amplification methodology, the identification of the promoter of the invention and its identification as a tissue-selective promoter, is governed by the choice of the "gene-specific primer."

A gene-specific primer is any transcribed sequence that is expressed at high levels in a tissue of interest. In the present invention, the gene-specific primer is a fragment of, or is complementary to, an mRNA that is expressed at high levels in reproductive tissue. In one embodiment, the gene-specific primer is selected by its homology to genes that are known to be expressed specifically in a particular reproductive tissue type. Genes of particular interest are those that are expressed in a particular reproductive tissue at high levels, which typically is an indicator of reproductive-preferred activity of the corresponding promoter.

Expressed sequence tags (ESTs) provide another source of gene-specific primers. An EST is a cDNA fragment of a corresponding mRNA that is present in a given library. Any plant EST database may be searched electronically to find ESTs that share identity to segments of genes that are known to be expressed specifically in a desired tissue type ("in silico screening"). These ESTs thus will provide gene-specific primers for the amplification of the promoter of the corresponding gene in a given genomic library. The amplified gene promoter need not be from the same species from which the EST database was obtained. All that is required is that the EST bears sufficient sequence similarity to the gene promoter of interest to act as a primer for PCR amplification of the target segment of the gene.

An alternative methodology to identify tissue-specific promoters rests on detection of mRNAs that are expressed in one tissue type, but not in another, implying that they are transcribed from a tissue-specific promoter. Populations of mRNAs can be distinguished on this basis by subtractive hybridization, for example. One such suitable subtractive hybridization technique is the PCR-Select™ described by Clontech.

Alternatively, a tissue-specific mRNA distribution can be determined by in situ hybridization of thin slices of plant tissue with radiolabeled probes. Probes that radioactively stain a particular tissue type are then used to detect the promoter associated with the mRNA by Southern analysis of genomic libraries, using the methodologies described below. All of the aforementioned techniques require the preparation of mRNA libraries from the tissue of interest, in this case, reproductive tissue. cDNA libraries may be made from reproductive tissues isolated from woody plant species. For example, male and female buds were isolated from *P. radiata* and *P. taeda*. Briefly, total RNA is isolated using standard techniques, and poly(A) RNA then is isolated and reverse transcribed to construct a reproductive-preferred tissue cDNA library. The cDNA library may be constructed in the λZAP-XR vector, employing Strategene cDNA synthesis and GigapakII Gold™ packaging kits. Reproductive-specific promoters can, in turn, be isolated from such cDNA libraries by PCR using a gene-specific probe and a primer that recognizes a sequence at the 5' end of the promoter. A gene-specific probe can be obtained by the in silico approach described above, or by designing a specific probe based on the sequence of the mRNA, if known. Furthermore, a primer can be synthesized which is complementary to the 5' UTR of the desired target gene. Alternatively, the primer can be designed from a partial amino acid sequence of the encoded protein, as a so-called degenerate primer.

Following isolation of the promoter of interest, various methods can be used to characterize its tissue-specific expression pattern and promoter strength. One commonly employed method is to operably link the promoter to a readily assayed reporter gene. For example, a reproductive-preferred promoter has been operably linked to the gene encoding β-glucuronidase (GUS). Lacombe et al., *Plant J.* 23: 663-76 (2000). Suitable expression constructs can be made using well-known methodologies.

Transformation of plants can be accomplished by any one of many suitable techniques, including *Agrobacterium*-mediated transformation, as described in U.S. Pat. No. 6,051,757. Other methods for transforming trees are known in the art, as exemplified by U.S. Pat. No. 5,681,730, which discloses an accelerated particle transformation method of gymnosperm somatic embryos. Other transformation methods include micro-projectile bombardment (Klein et al., *Biotechnology* 6: 559-63 (1988)), electroporation (Dhalluin et al., *Plant Cell* 4: 1495-1505 (1992)), and polyethylene glycol treatment (Golovkin et al., *Plant Sci.* 90: 41-52 (1993)). Further, U.S. Pat. No. 6,187,994 discloses a recombinase-assisted insertion of the expression construct into a specific, selected site within a plant genome. All of the aforementioned patents and publications are herein incorporated by reference.

A DNA molecule of the present invention can be inserted into the genome of a plant by any suitable method. Suitable plant transformation vectors include those derived from a Ti plasmid of *Agrobacterium tumefaciens*, as well as those disclosed, e.g., by Herrera-Estrella et al. Nature 303:209 (1983), Bevan *Nucleic Acids Res.* 12 (22): 8711-8721 (1984), Klee et al. *Bio/Technology* 3(7): 637-642 (1985) and European Patent publication 120,516. In addition to plant transformation vectors derived from the Ti or root-inducing (Ri) plasmids of *Agrobacterium*, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen. DNA may also be inserted into the chloroplast genome (Daniell et al. *Nature Biotechnology* 16:345-348 (1998)).

When adequate numbers of cells (or protoplasts) containing the nucleic acid of interest are obtained, the cells (or protoplasts) are regenerated into whole plants. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, canola/rapeseed, etc.), Cucurbitaceae (melons and cucumber), Gramineae (wheat, barley, rice, maize, etc.), Solanaceae (potato, tobacco, tomato, peppers), various reproductive crops, such as sunflower, and nut-bearing trees, such as almonds, cashews, walnuts, and pecans. See, e.g., Ammirato et al. (1984) Handbook of Plant Cell Culture-Crop Species. Macmillan Publ. Co.; Fromm, M., (1990) UCLA Symposium on Molecular Strategies for Crop Improvement, Apr. 16-22, 1990. Keystone, Colo.; Vasil et al. *Bio/Technology* 8:429-434 (1990); Vasil et al. *Bio/Technology* 10:667-674 (1992); Hayashimoto et al. *Plant Physiol.* 93:857-863 (1990); and Datta et al. (1990).

The vector comprising the promoter and reporter gene includes a mechanism to select those plant cells successfully transformed with the vector, which may be, for example, kanamycin resistant. The presence of the GUS gene in transformants may be confirmed by a PCR approach, using GUS-specific PCR primers (Clontech, Palo Alto). Segregation of kanamycin resistance in the progeny of the transformed plant cells can be used in conjunction with Southern analysis to determine the number of loci harboring the stably inserted vector. The temporal and spatial pattern of promoter expression is then inferred from a quantification of the reporter gene expression, as described in Jefferson et al., *EMBO J.* 6: 3901-07 (1987). Generally, GUS expression is determined histochemically in thin slices of plant tissues that are fixed first in 90% acetone and then in a buffered solution containing a GUS substrate, 5-bromo-4-chloro-3-indoyl-β-D-glucuronic acid (X-Gluc). The presence of the GUS expression product is indicated by a calorimetric reaction with the X-Gluc.

Reproductive-specific expression, for example, can be conferred by the presence of regulatory elements that specifically bind transcription factors in reproductive tissue. The interaction between reproductive-specific regulatory elements and reproductive-preferred transcription factors depends on the alignment between a subset of base pairs of the regulatory element with amino acid residues of the transcription factor. Likewise, tapetum-specific expression, for example, can be conferred by the presence of regulatory elements that specifically bind transcription factors in tapetal tissue. Base pairs that do not interact with the bound transcription factor may be substituted with other base pairs, while maintaining the overall ability of the regulatory element to bind specifically the tissue-specific transcription factor.

Various methodologies can be used to identify and characterize regulatory elements that affect tissue-preferred or tissue-specific promoter activity, once a promoter is identified as tissue-preferred or specific. In one methodology, the promoter region is sequentially truncated at the 5' end and the series of truncated promoters are each operably linked to a reporter gene. When a regulatory element is deleted, the effect on the promoter activity is inferred by the loss of tissue-specific expression of the reporter gene. Alternatively, a putative regulatory element can be inserted into an expression construct containing a minimal promoter, such as the CaMV 35S minimal promoter (Keller et al., *Plant Mol. Biol.* 26: 747-56) to ascertain if the putative regulatory element confers tissue-specific expression. A minimal promoter contains only those elements absolutely required for promoter activity, such as a RNA polymerase binding site. Additional examples for elucidating putative regulatory elements are provided by studies of tissue-specific regulatory elements that coordinately regulate transcription of the genes encoding L-phenylalanine ammonia-lyase (PAL) and 4-coumarate CoA ligase (4CL). Hatton et al., *Plant J.* 7: 859-76 (1995); Leyva et al., *Plant Cell* 4: 263-71 (1992); Hauffe et al., *Plant J.* 4: 235-53 (1993); Neustaedter et al., *Plant J.* 18: 77-88 (1999), all of which are incorporated herein by reference.

Functional Variants or Fragments of the Promoters of the Invention

Additional variants or fragments of the promoters of the invention are those with modifications interspersed throughout the sequence. Functional variants or fragments, as used herein, are nucleic acids that have a nucleic acid sequence at least about 70% identical to the reference nucleic acid, but still confer tissue-specific expression of coding products. The tissue-specificity or preference of the functional variant must be towards the same tissue as the reference nucleic acid. However, even if the functional variant is not as preferential or as specific as the reference nucleic acid, the variant is still considered a functional variant as used herein. In one embodiment, the sequence of the functional variant or fragment is at least about 75% identical to the reference nucleic acid. In other embodiments, the sequence of the functional variant or fragment is at least about 80%, 85%, 86%, 87%, 88%, 89%, 90%, 91%, 92%, 93%, 94%, 95%, 96%, 97%, 98% or 99%.

Modifications that can produce functional variants may be made by sequential deletion of residues from the 5' end or the deletion of 5' UTR sequences from the 3' end. Alternatively, internal residues may be modified. Modifications that do not affect the function of the promoter regions most likely will be those that do not affect the binding of transcription factors. The modifications encompassed by the invention also include those that occur naturally in the form of allelic variants of the promoters of the invention.

Methods of Making the Nucleic Acids of the Present Invention

The nucleic acids of the invention can be obtained by using well-known synthetic techniques, standard recombinant methods, purification techniques, or combinations thereof. For example, the isolated polynucleotides of the present invention can be prepared by direct chemical synthesis using the solid phase phosphoramidite triester method (Beaucage et al., *Tetra. Letts.* 22: 1859-1862 (1981)), an automated synthesizer (Van Devanter et al., *Nucleic Acids Res.* 12: 6159-6168 (1984)), or the solid support method of U.S. Pat. No. 4,458,066. Chemical synthesis generally produces a single stranded oligonucleotide, which can be converted into double stranded oligonucleotides by hybridization with a complementary sequence, or by polymerization, using the single strand as a template. Also, longer sequences may be obtained by the ligation of shorter sequences.

Alternatively, the nucleic acids of the present invention can be obtained by recombinant methods using mutually priming oligonucleotides. See e.g. Ausubel et al., (eds.), CURRENT PROTOCOLS IN MOLECULAR BIOLOGY (John Wiley & Sons, Inc. 1990). Also, see Wosnick et al., *Gene* 60: 115 (1987); and Ausubel et al. (eds.), SHORT PROTOCOLS IN MOLECULAR BIOLOGY, 3$^{rd}$ ed., (John Wiley & Sons, Inc. 1995). Established techniques using the polymerase chain reaction provide the ability to synthesize polynucleotides at least 2 kilobases in length. Adang et al., *Plant Mol. Biol.* 21: 1131 (1993); Bambot et al., *PCR Methods and Applications* 2: 266 (1993); Dillon et al., "Use of the Polymerase Chain Reaction for the Rapid Construction of Synthetic Genes," in METHODS IN MOLECULAR BIOLOGY, Vol. 15: PCR PROTOCOLS: CURRENT METHODS AND APPLICATIONS, White (ed.), pages 263-268, (Humana Press, Inc. 1993); Holowachuk et al., *PCR Methods Appl.* 4: 299 (1995).

Methods of Using the Nucleic Acids of the Invention

The nucleic acids of the current invention are useful for altering characteristics of a plant. The nucleic acids may be operably linked to a gene of interest to increase the levels of a molecule found in the reproductive tissue. Alternatively, the gene of interest may inhibit reproductive development, thereby conferring sterility to a plant.

One of the primary targets of such manipulated expression is reproductive development. For the reasons set forth above, there is considerable interest in regulating reproductive development, accomplished through genetic ablation. For example, a cytotoxic barnase molecule under the control of a tapetum-preferred promoter has been used for regulating reproductive development. European Patent Publication 344, 029.

For example, a mutant barnase gene having reduced RNase activity may be used for regulating reproductive development. In one embodiment, the mutant barnase gene may be operably linked to a promoter such that expression of the barnase gene could impose little or no damage to vegetative tissues, yet the mutant barnase may provide adequate RNase activity for reproductive ablation.

The present invention, thus generally described, will be understood more readily by reference to the following examples, which are provided by way of illustration and are not intended to be limiting of the present invention.

EXAMPLES

Example 1

Isolation of Reproductive-Preferred Promoters

Reproductive-preferred plant promoters can be isolated from genomic and cDNA libraries. Using the sequence of a reproductive-preferred promoter as a probe, putative reproductive-preferred promoter sequences can be isolated. For example, an AGAMOUS (AG) promoter from *P. radiata* may be used as a probe for identifying other reproductive-preferred promoter sequences.

For example, genomic DNA was isolated from a male-bud from loblolly pine. Following isolation of the male-bud DNA, the *P. radiata* AG1 sequence was used as a probe for screening the male-bud genomic DNA isolated. Using a PCR-based screening approach, two putative loblolly pine AG promoter sequences were isolated, denoted LPAG1 (SEQ ID NO: 1) and LPAG2 (SEQ ID NO: 2). Each cloned LPAG promoter is about 1400 bp, including 600 bp of 5' untranslated region, which contains the first intron of 139 bp of LPAG1 or LPAG2 gene.

The promoters were cloned using a "Genome Walker" kit (Clontech, Palo Alto, Calif.). This is a PCR-based method, which requires four PCR primers to be constructed, two of which must be gene-specific. The gene specific primers are designed generally within the 5' UTR of the gene. The fragment is amplified and then cloned into a T-tailed vector in front of the GUS reporter gene.

Example 2

Methodology to Determine the Tissue Specificity of a Promoter

Following the identification and cloning of a promoter as described in Example 1, the promoter is operably linked with a reporter gene to determine those tissue types in which the promoter is active. To this end, a construct containing an inventive promoter is transformed into *Agrobacterium tume-*

*faciens* by electroporation. Briefly, 40 µl of diluted AgL-1 competent cells are placed on ice and are contacted with about 10 ng of pART27 vector containing the promoter sequence. Electroporation is conducted under the following parameters:

Resistance=129 ohm
Charging voltage=1.44 kV
Field strength=14.4 kV/cm
Pulse duration=5.0 ms Following electroporation, 400 µl of YEP liquid media is added and the cells are allowed to recover for one hour at room temperature. Cells then are centrifuged at 6000 rpm for 3 min and are resuspended in ~50 µl YEP. Cell samples are spread over the surface of a YEP Kan50/Rif50 plate, sealed with parafilm, and incubated at 29° C. for 2 days for colony growth.

Tobacco (*Nicotiana tabacum*) plants are transformed with constructs of interest by *Agrobacterium*-mediated leaf tissue transformation (Burow et al., *Plant Mol. Biol. Rep.* 8:124-139, 1990).

Successfully transformed plants are then assayed for the expression of the operably linked reporter gene. Leaf, stem, root and reproductive regions are immersed in a staining solution (50 mM $NaPO_4$, pH 7.2, 0.5% Triton X-100, 1 mM X-Glucuronide, cycloheximide salt (Ducheffa). A vacuum is applied twice for 5 min to infiltrate the tissue with the staining solution. The tissue is then left shaking overnight at 37° C. for color development. Tissues are checked at three or four time-points to check stain development, and if samples show early development, a piece of tissue is destained in 70% ethanol.

The GUS localization, as shown in Table 1, demonstrate that the disclosed isolated nucleotide sequences confer reporter gene expression preferentially in reproductive tissues, such as the tapetum.

As shown in Example 6, expression of a reproductive-preferred promoter is expected in vegetative tips in the presence of the primary inflorescence when the vegetative growth of axilliary buds is suppressed and the transition from vegetative buds and reproductive buds is fast.

As described in more detail below, the "PRMC2" promoter constructs comprise a reproductive-preferred promoter from *P. radiata* operably linked to a barnase mutant, specifically H102E for PrMC2.400-1 and PrMC2.400-3. GUS expression has not been observed in anthers of tobacco transformed with the PrMC2.400 promoter. Accordingly, an in-frame PrMC2.400 promoter was cloned for use in an ablation construct and used in the experiments described above.

Example 3

Methods of Using a Reproductive-Specific Promoter

Once a promoter having an appropriate tissue-specific and developmental pattern of expression is found, this promoter can be used to regulate a desired characteristic in a transgenic plant. In one embodiment, a tapetum-preferred promoter is used for regulating reproductive development in a plant. In this example, a tapetum-preferred promoter of the invention is operably linked to a gene encoding a cytotoxic protein. For example, a tapetum-preferred promoter may be operably linked to a gene encoding barnase. Expression of barnase in a reproductive-preferred tissue, such as the tapetum, may result in pollen ablation. European Patent Publication 344, 1990.

To construct a transgenic plant having ablated male reproductive development, a fragment of barnase cDNA is operably linked in proper orientation to a reproductive-specific promoter of the invention and a nopaline synthase 3' terminator. The entire construct is inserted as a restriction fragment into the binary vector pBI101.1 (Clontech, Palo Alto, Calif.). Vectors are electroporated into *A. tumefaciens* strain LBA4404 or C58 pMP90, for tobacco or poplar transformations, respectively. See generally, No et al., *Plant Science* 160: 77-86 (2000). A tobacco leaf disc, as described above, or a poplar stem section, is dipped into the *Agrobacterium* culture as described above, according to the procedure of Leple et al., *Plant Cell Rep.* 11: 137-141 (1992). Kanamycin-resistant transformants are tested for activity, transgene copy num-

TABLE 1

In planta GUS reproductive expression

| SEQ ID NO | | No. of Plants GUS + | % GUS Expression | GUS Reproductive Localization in Tobacco | GUS Reproductive Localization in Pine |
|---|---|---|---|---|---|
| 1 | LPAG1 | 15 Tobacco<br>17 Pine | 93 Tobacco<br>70 Pine | Petals, Stamens, Carpels, Vegetative Shoot Tip | Embryogenic calli and regenerated embryo |
| 2 | LPAG2 | 7 Tobacco<br>6 Pine | 64 Tobacco<br>40 Pine | Petals, Stamens, Carpels, Vegetative Shoot Tip | Embryogenic calli and regenerated embryo |
| 3 | PrAG | 1 Tobacco<br>28 Pine | 5.2 Tobacco<br>78 Pine | NO GUS staining | Embryogenic calli and regenerated embryo |
| 4 | PrMC2 400-1 | 24 Tobacco | 100 Tobacco | Anthers, Tapetum | No GUS staining in Embryogenic calli and regenerated embryo |
| 16 | PrMC2 400-3 | 11 (Tobacco)<br>2 (Pine) | 91 (Tobacco)<br>12.5 (Pine) | Anthers, Tapetum | No GUS staining in Embryogenic calli and regenerated embryo | ber is determined by Southern analysis, and suitable transformants are rooted and transferred to a greenhouse.

Example 4

Method for Producing and Selecting an Attenuated Cytotoxic Enzyme

Synthesis of Barnase E73G and Barnase F106S

The barnase mutants F106S and E73G were obtained by random PCR mutagenesis. The PrAG promoter was operably linked to wild-type barnase coding region and three PCR reactions were performed such that the PrAG translation start codon ATG was replaced by barnase translation codon. In the first PCR, the 5' primer, PrAGKpn (5'-GGTTTGGTAC-CTAACTTGCC-3', SEQ ID NO: 27), anneals to the −199 to −179 positions of the PrAG promoter in reference to its translation starting ATG position, while the 3' primer, PrAG-7:

(5'-CGTGTTGATAACCTGTGCCATGATTTGTACACAAAATTTCCG-3,

SEQ ID NO: 28')

anneals to the −21 to +3 positions including the translation starting ATG. The PrAG-7 primer has extra 18 bases which is complementary to the 5' of the barnase coding region. The PCR mixture contains 50 ng of the template DNA (pWVCZ3 DNA), 200 □M of dNTPs, 1.5 mM of MgCl$_2$, and 0.5 □l of Taq DNA polymerase (Perkin Elmer). The DNA is denatured at 95° C. for 20 seconds, reannealed at 55° C. for 30 seconds, and incubated at 72° C. for 60 seconds. This PCR cycle was repeated 25 times. Following PCR, a 220 bp product was gel-purified.

In the second PCR, the 5' primer, PrAG-8:

(5'-CGGAAATTTTGTGTACAAATCATGGCACAGGTTATCAACACG-3',

SEQ ID NO: 29)

anneals to the 5' of the barnase coding region, and this primer has 21 extra bases which are complementary to the 3' of the PrAG promoter. The 3' primer, 3Barn (GGTTCTC-GAGTTTCACGTTAACTGGCTAG), anneals to the 3' of the barnase DNA and carries a Sac I site for cloning. The PCR mixture contains 50 ng of the template DNA (pWVR14), 200 µM of dNTPs, 1.5 m, SEQ ID NO: 30M of MgCl$_2$, and 0.5 µl of Taq DNA polymerase (Perkin Elmer). The DNA is denatured at 95° C. for 20 seconds, reannealed at 55° C. for 30 seconds, and incubated Oat 72° C. for 60 seconds. This PCR cycle was repeated 25 times. Following PCR, a 462 bp product is gel-purified.

In the third PCR, the 5' primer is the PrAGKpn and the 3' primer is 3Barn, and the DNA template is the mixture of the equal amount of the first and the second PCR products (~40 ng each). The amplified product of the third PCR is 640 bp which is the fusion between the 3' of the PrAG promoter and the barnase coding region. After the third PCR, the PCR fragment was digested with Kpn I and Sac I and ligated to the plasmid (pUC19) which already carries the PrAG promoter so that after the ligation the barnase is driven by the full-length of the PrAG promoter.

The ligation mixture was introduced into *E. coli* by electroporation and transformed colonies were grown on LB agar containing 75 ug/ml ampicillin. Plasmids were extracted from two colonies and restriction enzyme digestion confirmed the presence of PrAG::barnase inserts. The plasmid DNAs were sequenced to confirm that they all have a mutation in the barnase coding region.

It was realized that all of the colonies growing on the LB plates contain mutant forms of barnase, and most of the mutations abolished barnase activity. However, some of the mutations decreased barnase activity, as indicated by the smaller sizes of colonies on the LB plates. About 100 colonies were selected and inoculated into 1 ml of LB liquid containing 75 ug/mL ampicillin. Following overnight culture at 37° C., the cell densities of the cultures were compared, and five cultures with significantly lower cell densities were selected. Low cell density indicates that the barnase is active, but much less toxic. The plasmids were purified from the five *E. coli* cultures and reintroduced into *E. coli* to confirm that the introduced plasmids, indeed, cause the smaller size of colonies on the LB agar plates, suggesting attenuated barnase activity carried by the plasmids. The reintroduction of the plasmids into *E. coli* was repeated three times. The confirmed plasmids were sequenced, and the results showed that the plasmid extracted from *E. coli* culture 29-S contained a single nucleotide substitution (A→G) in the codon for glutamate at position 73 of the barnase coding region, leading to the change of the glutamate for glycine. This barnase mutant was named barnase E73G (SEQ ID NO. 9). The plasmid extracted from *E. coli* culture 43-S also contained a single nucleotide substitution (T→C) in the codon for phenylalanine at position 106 of the barnase coding region, leading to the change of phenylalanine for serine. This barnase mutant was named barnase F106S (SEQ ID NO. 10).

Barnase F106S Assay

To assay F106S toxicity, tobacco plants were transformed, as described above in Example 2, with a construct having the PrAG promoter operably linked to a gene encoding mutant barnase F106S. No viable tobacco transformants were produced, as expression of mutant barnase F106S was lethal. These results indicate that there is a need for an attenuated barnase that, for example, can induce male-sterility, without adversely affecting vegetative growth.

Barnase E73G Assay

The barnase mutant E73G was selected for reproductive ablation based on the results of toxicity screening in *E. coli*. Expression of barnase E73G in *E. coli* resulted in a low level of toxicity. Specifically, barnase E73G inhibited *E. coli* growth in LB liquid medium and on LB solid plates. Although the value of reduced RNase activity (toxicity) of the barnase mutants can not be obtained from this biological screen, these results suggest that E73G has attenuated RNase activity.

Further evidence for attenuated barnase activity in barnase E73G may be found in a comparison study between barnase E73G and F106S. In a comparison, barnase F106S caused significantly more *E. coli* toxicity than barnase E73G. These results suggest that barnase F106S has higher RNase activity than barnase E73G.

Barnase H102E

The barnase H102E mutation was selected based upon a report that the corresponding mutation in a related enzyme, binase, had approximately 2% of the activity of the native enzyme. Yakovlev et al. *FEBS Lett.* 354: 305-306 (1994). As described below in Example 5, barnase H102E has attenuated activity. In this mutant, the codon for histidine 102 was substituted by a glutamate codon.

Directed mutagenesis of the barnase segment made use of an existing plasmid, pWVR14, that comprised the wild-type barnase coding region. This prior cloning of barnase used primers BAR5NCO (5'-TGACAACCATGGCACAGGT-TATCAACACGTTTGAC-3, SEQ ID NO: 31') and BAR3MFE (5'-AAAGTGCAATTGACCGATCA- GAGTTTGAAG-3', SEQ ID NO: 32) to amplify the entire coding region from the barnase cassette of plasmid pMT416. Hartley, R. W. *J. Mol. Biol.* 202: 913-915 (1988). The amplified fragment was digested with NcoI and cloned into a prepared vector with one NcoI end and one blunt end. The resulting plasmid, pWVR14, put the barnase segment adjacent to the promoter and 5'-UTR of the SEPALLATA1 gene (SEP1, previously called AGL2) and the mutagenesis procedure made use of the promoter sequence. Primers AGL2PB (5'-TTTCACAACCTCCACACACTT-3', SEQ ID NO: 33) and BARH2E (5'-GTAAAGGTCTGATACTCGTCCGTTG-3', SEQ ID NO: 34) were used to amplify the 5' portion of the coding region plus a segment of the adjoining promoter. Primers BAR5NCO and BAR3MFE were used to amplify the wild-type barnase cassette. After amplification, the fragments were purified away from the primers and PCR reagents using gel electrophoresis and the QIAEX gel purification kit (QIAGEN). Approximately 100 ng of each fragment was combined with 1× Perkin Elmer Taq buffer, 1.6 mM $MgCl_2$, 0.10 mM each dNTP and 0.5 µl Perkin Elmer Taq DNA polymerase in a 50 µl reaction, and the mixture was repeatedly denatured at 95° C., reannealed at 50° C. and incubated at 72° C. (five cycles) in order to allow extension of the 0.75 kb fragment comprising a portion of the SEP1 promoter and the complete barnase coding region. The 0.75 kb fragment was further amplified by adding 10 µl of the extension reaction to a 50 µl mixture containing 20 µmol each of primers AGL2PB and BAR3MFE, 1×PCR buffer, 1.6 mM $MgCl_2$, 0.250 mM each dNTP and 0.5 µl Taq DNA polymerase, and running seven more cycles. The fragment was digested with NcoI, and the barnase segment was gel purified and ligated into a vector with NcoI and blunt ends. The correct mutation was verified by sequence analysis. For subsequent work, such as assembly of pWVR220, the full-length barnase H102E fragment was amplified using primers BAR5NCO and BAR3SAC (5'-GAAGAAGAGCTCTTGACCGATCA-GAGTTTGAAG-3', SEQ ID NO: 35), digested with NcoI and SacI, and purified. Because of the desire to have an NcoI site at the translation initation codon, an extra Alanine codon immediately after the ATG was included in primer BAR5NCO. This resulted in the His to Glu mutation actually being at codon 103 in the final coding region.

Barnase K27A

The barnase K27A mutation was selected based upon a report that the corresponding mutation in a related enzyme, binase, had approximately 20% of the activity of the native enzyme. Yakovlev et al. *FEBS Lett.* 354: 305-306 (1994). Another report suggests that barnase K27A mutant has reduced activity compared with native enzyme. Mossakowska et al. *Biochemistry* 28: 3843-3850 (1989). The barnase coding region was altered so that the codon for lysine 27 was substituted by an alanine codon. Simultaneous amplification and directed mutagenesis of the barnase segment was accomplished using PCR. Primers BAR5NCO (5'-TGA-CAACCATGGCACAGGTTATCAACACGTTTGAC-3', SEQ ID NO: 31) and BARK27AR (5'-TGCTTCTGATGCT-GTAATGTAATTATCAG-3', SEQ ID NO: 36) were used to amplify the 5' portion of the coding region and primers BARK27AF (5'-AATTACATTACAGCATCAGAAGCA-CAAG-3', SEQ ID NO: 37) and BAR3SAC (5'-GAAGAA-GAGCTCTTGACCGATCAGAGTTTGAAG-3', SEQ ID NO: 35) were used to amplify the 3' portion of the coding region from the barnase cassette of plasmid pMT416. After amplification, the fragments were purified away from the primers and PCR reagents, and then were combined. Approximately 100 ng of each fragment was combined with 1× Stratagene High Salt Buffer, 0.175 mM each dNTP and 0.25 µl TaqPlusLong in a 25 µl reaction, and the mixture was repeatedly denatured at 95° C., reannealed at 50° C. and incubated at 72° C. (five cycles) in order to allow extension of the complete coding region. The full barnase K27A fragment was further amplified by adding the extension reaction to a 75 µl mixture containing 20 µmol each of primers BAR5NCO and BAR3SAC, 1× Stratagene High Salt Buffer, 0.175 mM each dNTP and 0.75 µl TaqPlusLong, and running fifteen more cycles. The resulting full-length fragment was digested with NcoI and SacI and purified. The mutated coding sequence is set forth in SEQ ID NO: 8. As noted above, an extra Alanine codon was included immediately after the ATG in primer BAR5NCO. This resulted in the Lys to Ala mutation actually being at codon 28 in the final coding region.

Example 5

Assay for Toxicity of Barnase Mutants in *E. coli*

Barnase DNA was fused at the 3' end of PrAG promoter by PCR, and the resulting PCR fragment was cloned into pUC19 and introduced into *E. coli*. After growing at 37 degrees C. overnight (16 hours) on LB agar supplied with 80 ug/ml ampicillin, single colonies were selected and inoculated into 1 ml of LB liquid containing ampicillin. After overnight incubation, the slow-growing *E. coli* cultures were selected and plasmids were extracted. The purified plasmids were reintroduced into *E. coli*, and single colonies were obtained on LB agar after overnight incubation at 37 degrees C. The diameters of the colonies were measured and compared with the control (pUC19 carrying the insert of barnase H102Y driven by PrAG promoter). The diameter of a single colony carrying a barnase mutant is the average of three independent experiments repeated from the step of introducing the plasmid into *E. coli*.

The toxicity of the barnase mutants was determined by comparing the diameter of the single colonies with control colonies. As shown below in Table 2, a large diameter colony indicates no toxicity, while a small diameter suggests strong toxicity.

TABLE 2

Toxicity of Barnase Mutants in *E. coli*

| Barnase Mutant Construct | Number of Colonies on Plate | Colony Diameter (mm) | Percentage of Colonies having calculated Diameter | Toxicity Level |
|---|---|---|---|---|
| Control (*Barnase H102Y) | 245 | 0.8-1.0 | 85 | None |
| Barnase H102E | <300 | 0.9-1.1 | 85 | None |
| Barnase E73G | 180 | 0.5-0.8 | 85 | Medium |
| Barnase F106S | 320 | 0.2-0.5 | 95 | High |

*Barnase H102Y has no biological RNase activity reported.

Example 6A

Tissue-Preferred Expression of LPAG Promoter

Following the identification and cloning of a promoter by the procedure outlined above in Example 1, a promoter is operably linked with a reporter gene to determine those tissue types in which a promoter is active. To determine the tissue specificity of the LPAG1 and LPAG2 promoters, each promoter was operably linked to the GUS reporter gene and the resulting constructs were introduced into tobacco plants, as described in Example 2.

GUS Analysis of Sepals and Petals

Briefly, to analyze GUS expression of LPAG1 promoter activity in tobacco, sepals and petals were removed from unopened, young flowers that are about 2 to 5 mm in height. The carpels were cut vertically in the middle using a razor blade and the resulting half carpels (attached by 2-3 young stamens) were stained for GUS activity at 37° C. for 16 hours. Three individual flowers from each transgenic line were stained, and the destaining was carried out in 70% and then 95% ethanol.

GUS Analysis of Young Leaves

Young leaves adjacent to flowers were analyzed for GUS expression. For each transgenic line, three young leaves were cut into small squares (9 mm$^2$) and stained for GUS activity at 37° C. for 16 hours, and then destained, as described above for the sepals and petals.

GUS Analysis of Vegetative Shoot Tips

Young shoot tips were collected from individual plants at two different stages of growth. Analysis of the first growth stage encompassed collecting shoot tips from tobacco plants in which 30% of the flowers on the primary terminal inflorescence were already open. This first growth stage analyzed the shoot tips with primary terminal inflorescences. The shoot tips with primary terminal inflorescences represent the axillary shoot tips growing out from the intersection of the primary stems and the primary leaves. Each shoot tip having a primary terminal inflorescence is about 10 to 15 mm long.

Analysis of the second growth stage encompasses collecting shoot tips 6 days post removal of the primary terminal inflorescence. These shoot tips do not have primary terminal inflorescence and represent the axillary shoot tips growing out from the intersection of the primary stems and the primary leaves. Each collected shoot tip without a primary terminal inflorescence is about 25 to 40 mm long.

Most of young leaves surrounding the shoot tips were removed and only one to three leaves were attached to the shoot tips. The dissected shoot tips were cut vertically in the middle and the resulting half tips (still attached by 1-3 leaves) were stained for GUS activity at 37° C. for 16 hours. Three shoot tips were collected and stained from each transgenic line.

As shown below in Table 3, LPAG1 promoter is preferentially active in the stamens and carpels (reproductive tissues) and shows no activity in leaves (vegetative tissues).

TABLE 3

GUS Expression Analysis of LPAG1 Activity in Transgenic Tobacco

| Line No. | Stamens and Carpels | Young Leaves | Analysis of vegetative shoot tips when primary terminal inflorescence is present | Analysis of vegetative shoot tips when primary terminal inflorescence is absent |
| --- | --- | --- | --- | --- |
| 1 | NO | NO | Not tested | Not tested |
| 2 | YES-Medium Expression | NO | YES-Medium Expression | NO |
| 4 | YES-Strong Expression | NO | YES-Strong Expression | YES-Weak Expression |
| 5 | YES-Medium Expression | NO | YES-Medium Expression | NO |

TABLE 3-continued

GUS Expression Analysis of LPAG1 Activity in Transgenic Tobacco

| Line No. | Stamens and Carpels | Young Leaves | Analysis of vegetative shoot tips when primary terminal inflorescence is present | Analysis of vegetative shoot tips when primary terminal inflorescence is absent |
| --- | --- | --- | --- | --- |
| 6 | YES-Medium Expression | NO | YES-Medium Expression | NO |
| 7 | YES-Medium Expression | NO | YES-Medium Expression | NO |
| 8 | YES-Medium Expression | NO | YES-Medium Expression | NO |
| 9 | YES-Strong Expression | NO | YES-Strong Expression | YES-Medium Expression |
| 11 | YES-Weak Expression | NO | NO | NO |
| 12 | YES-Medium Expression | NO | YES-Medium Expression | YES-Weak Expression |
| 13 | YES-Medium Expression | NO | YES-Weak Expression | NO |
| 14 | YES-Strong Expression | NO | YES-Strong Expression | YES-Medium Expression |
| 15 | YES-Weak Expression | NO | YES-Weak Expression | NO |
| 16 | YES-Strong Expression | NO | YES-Medium Expression | NO |
| 17 | YES-Weak Expression | NO | YES-Weak Expression | NO |
| 18 | YES-Weak Expression | NO | YES-Weak Expression | NO |

As shown above in Table 3, LPAG1 promoter activity decreases in shoot tips following removal of the primary terminal inflorescence. In the presence of the primary inflorescence, the vegetative growth of axillary buds is suppressed, and the transition from vegetative buds to reproductive buds is very fast. In some cases, the floral buds emerged when the axillary shoots are only 10 mm in length. During reproductive growth in tobacco, nutrient acquisition and hormone production induce floral gene expression in the axillary shoots. Removal of the primary terminal inflorescence resets the tobacco plants back to vegetative growth, and the growth of axillary buds is no longer subject to the suppression imposed by the terminal flowers.

It was observed that after the removal of the primary terminal inflorescence the axillary buds grow fast and the floral buds are not present when the axillary shoots are 40 mm long. So, in the presence of the terminal flowers, the meristems of axillary shoots are already converted to floral meristems or half way towards floral meristems in which the expression of floral genes, such as LEAFY and AGAMOUS, is turned on, and LPAG1 promoter is also turned on. The removal of the terminal flowers resets the axillary buds back to vegetative growth and the expression of floral genes in the axillary shoot meristems is turned off, and so LPAG1 promoter activity is probably also turned off.

Example 6B

Deletion Analysis of LPAG1 Promoter

Promoter deletion analysis can be used to determine the minimal promoter and regulatory elements within a promoter sequence. Each promoter deletion is operably linked to a reporter gene and the expression profile of the promoter-reporter gene construct is analyzed.

For example, LPAG1 promoter (SEQ ID NO. 1) was serially deleted. Briefly, five serial deletions were made from the 5'-end of the LPAG1 promoter sequence. Each serial deletion deletes approximately 160 bp, for a total of a 800 bp deletion. The following is a summary of preliminary results of LPAG1 promoter deletion. The five serial deletion constructs (dentoted LPAG1d1-LPAG1d5) were introduced into pine and tobacco. Because the deletions are made from the 5'-end of the LPAG1 promoter sequence, it was estimated that the LPAG1d5 deletion construct should cut into the 5' untranslated region of LPAG1 gene and therefore, the LPAG1 promoter sequence should be absent from the LPAG1d5 construct.

Following transformation of pine and tobacco plants with the promoter-deletion constructs, as described in Example 2, transformed calli were analyzed for LPAG1 promoter activity. GUS expression analysis was determined as outlined in Example 5. The results of the LPAG1 promoter deletion experiments are summarized below in Table 4.

TABLE 4

Promoter deletion analysis of LPAG1

| Construct | Promoter Length | Relative Activity in Pine calli | Relative Activity in Tobacco Flowers |
|---|---|---|---|
| LPAG1 | 1400 | Strong | Strong |
| LPAG1 d1 | 1240 | Same as full-length promoter | Same as full-length promoter |
| LPAG1 d2 | 1080 | Same as full-length promoter | Same as full-length promoter |
| LPAG1 d3 | 920 | Same as full-length promoter | Same as full-length promoter |
| LPAG1 d4 | 760 | Same as full-length promoter | Very low GUS activity detected |
| LPAG1 d5 | 600 | NO GUS staining activity detected | NO GUS staining activity detected |

Based on the GUS expression profiles displayed in Table 4, the results clearly suggest that the nucleotide sequences (~150 bp) which are present in LPAG1d3 but absent in LPAG1d4 are essential for the LPAG1 promoter to be active in the stamens and carpels of tobacco flowers, but the same sequences are not essential for the LPAG1 promoter to be active in pine calli since LPAG1d4 still have similar GUS activities in the calli as indicated by GUS staining and MUG assays.

Example 7

Method for Ablating Pine Male and Female Cones Using a Construct having LPAG1 and PrAG Promoters Based on the results shown in Example 6, Table 4, the LPAG1 and PrAG promoters and its promoter deletions can be used for ablating male and female cones in Pine trees.

For example, an ablation construct could have the LPAG1 promoter operably linked to a gene encoding barnase, while the PrAG or LPAG1d4 promoter is operably linked to a gene encoding barstar (barnase inhibitor). As shown above in Example 6, LPAG1 promoter is active in pine cones and embryos while the PrAG or LPAGd4 promoter is active only in pine embryos. By placing the gene encoding barstar under a promoter (PrAG) that shows little activity in a pine cone, barnase toxicity produced by the other promoter (LPAG) can effectively ablate male and female cones. On the other hand, similar levels of activities of the two promoters in pine embryos produce similar amounts of barnase and barstar, and so the barnase toxicity in the embryos is effectively neutralized, leading to transformation and regeneration of pine embryogenic calli and embryos. Following the transformation protocols described in Example 2, pine calli are analyzed for LPAG1 expression.

Example 8

Analysis of AGAMOUS Promoter from *P. radiata*

As described in Example 1, a reproductive-preferred promoter can be identified and cloned from a tree species, such as *P. radiata* or *E. grandis*. The PrAG promoter is an AGAMOUS promoter from *P. radiata*. The PrAG promoter has a length of about 1400 bp, including a 5'-untranslated region. The PrAG promoter is disclosed in WO 00/55172, which is incorporated herein by reference.

To determine whether PrAG confers reproductive-preferred expression, the PrAG promoter was operably linked to a GUS reporter gene having an intron. The resultant PrAG-GUS promoter construct was introduced into tobacco plants, as described in Example 2. Tobacco tissues were analyzed for GUS expression and Table 5 summarizes PrAG promoter activity.

TABLE 5

GUS analysis of PrAG promoter activity

| Tobacco Tissue Sample | GUS Expression Level |
|---|---|
| Leaf | None |
| Petal | Yes |
| Stamen | Yes |
| Carpel | Yes |

Although GUS expression in leaf, petal, stamen, and carpel tissue was not detectable by enzymatic assay, GUS expression in petal, stamen, and carpel tissue was detectable using a more sensitive method, such as RNase Protection Assay with poly(A+) RNA.

Example 9

Floral Specific Enhancer Increases PrAG Promoter Activity

As illustrated in Example 8, the PrAG promoter confers very weak reproductive-preferred promoter expression in tobacco. It has been shown that the *Arabidopsis* AGAMOUS gene contains a floral-specific enhancer (AtAGenh) that resides in the second intron of the A G gene. Sieburth, L. E., and Meyerowitz, E. M. *The Plant Cell* 9, 355-365 (1997). Busch, M. A., Bomblies, K., and Weigel, D. *Science* 285, 585-587 (1999). Deyholos, M. K., and Sieburth, L. E. *The Plant Cell* 12:1799-1810 (2000). It is possible that the AtAGenh enhancer element may upregulate PrAG promoter activity preferentially in the reproductive tissues of angiosperm flowers.

To determine whether AtAGenh enhances PrAG promoter activity in reproductive tissues, the second intron of *Arabidopsis* AG (2750 bp) was isolated and fused to the 5' end of the PrAG promoter operably linked to the GUS reporter gene having an intron ((AtAGenh)PrAG::GUSIN), and the resulting construct (pWVCZ20, See FIG. 2) was introduced into tobacco.

Following tobacco transformation, tobacco tissues were collected and analyzed for GUS expression. As indicated in Table 6 below, GUS staining revealed that, indeed, the AtAGenh enhances PrAG promoter activity primarily in the stamen and carpel, and some increase was also observed in the petal. No GUS staining was observed in sepal, leaf, and the vegetative shoot tip.

TABLE 6

AtAGenh Enhances PrAG promoter Activity

| Tobacco Tissue Sample | GUS Expression PrAG::GUSIN | GUS Expression (AtAGenh)PrAG::GUSIN |
|---|---|---|
| Stamen | Weak Expression | Enhanced GUS Expression |
| Carpel | Weak Expression | Enhanced GUS Expression |
| Petal | Weak Expression | Enhanced GUS Expression |
| Sepal | NO GUS Expression | NO GUS Expression |
| Leaf | NO GUS Expression | NO GUS Expression |
| Vegetative Shoot | NO GUS Expression | NO GUS Expression |

Example 10

Use of a Reproductive-Preferred Promoter::Mutant Barnase Construct for Reproductive Ablation without Disturbing Vegetative Growth As described above in Example 4, various methodologies may be used to produce mutant cytotoxic genes having attenuated cytotoxic effects. By reducing the toxic effect of a barnase enzyme, barnase may be used for reproductive ablation, without compromising a plant's vegetative growth. Moreover, the combination of a reproductive-preferred promoter operably linked to an attenuated barnase provides a means for reproductive ablation, without vegetative destruction. For example, mutant barnase E73G was fused with PrAG to create pWVCZ23 (FIG. 3) and (AtAGenh)PrAG to create pWVCZ24 (FIG. 4), respectively, and the resulting constructs were introduced into tobacco. Following transformation, the tobacco plants were analyzed and the results are shown below in Table 7.

TABLE 7

| Transformation Construct | Flower Phenotype | Percentage of total transgenic plants recovered that do not produce pollen. (%) | Percentage of total transgenic plants recovered that do not produce seed. (%) | Negative Effects on Vegetative Growth |
|---|---|---|---|---|
| (AtAGenh)PrAG::E73G | Degenerated stamen and carpel; retarded petal; normal sepal | 68 | 68 | NO |
| PrAG::E73G | Normal | 10 | 10 | NO |

As shown in Table 7, 68% of tobacco plants transformed with (AtAGenh)PrAG::E73G have a sterile reproductive phenotype, i.e., many transformed plants produced neither viable pollen nor viable seeds. Likewise, 10% of plants transformed with PrAG::E73G produced no viable pollen and seeds. Interestingly, transformation with either construct does not compromise vegetative growth. The above results clearly demonstrate that the ablation cassette, (AtAGenh)PrAG::barnaseE73G, can produce male- and female-sterile tobacco, and this cassette may be able to produce similar ablation effects on other angiosperm plants, including angiosperm and gymnosperm species.

Example 11

Use of a Temperature-Sensitive Barnase for Ablating Reproductive Primordia without Disturbing Vegetative Growth Barnase is a well-characterized enzyme, and numerous mutants have been identified. In particular, barnase mutants having altered stability and/or toxicity have been identified. A temperature-sensitive barnase may be desirable for ablating reproductive primordia without affecting vegetative growth.

For example, a heat-sensitive barnase could be used for reproductive ablation. Expression of a heat-sensitive barnase, for example, may have little toxic effect during the summer (high temperature) when the majority of vegetative growth occurs, but may be toxic during the winter or low temperature production of reproductive buds. A reproductive-preferred promoter, such as PrMC2 (SEQ ID NOs 4 or 16) could be used for minimizing expression of a heat-sensitive barnase in vegetative tissues.

Example 12

Barstar Neutralizes Barnase Toxicity in Transgenic Pine Calli and Regenerated Embryos Barstar is a natural inhibitor of barnase, and it has been used for protecting non-targeted tissues from barnase toxicity and for restoring plant fertility. Beals T. P. and Goldberg R. B. *Plant Cell*. 9:9:1527-45 (1997). Kuvshinov V et al. *Plant Sci*. 160:3:517-522 (2001). Previous experiments demonstrate that three promoters, LPAG1, PrAG, and LPAG1d4, have similar activities in pine calli and regenerated embryos. While LPAG1 promoter has high activity in tobacco flowers, the PrAG and LPAG1d4 promoters showed no or trace activities in the tobacco flowers, suggesting that PrAG and LPAG1d4 promoters may not be active in angiosperm or gymnosperm reproductive tissues. Thus, the PrAG and LPAG1d4 promoters could be operably linked to a gene that neutralizes the cytotoxic effects of barnase, such as barstar, and the promoter::barstar construct would target non-reproductive tissues. Such a promoter::barstar construct, for example PrAG::barstar, would protect vegetative tissues from deleterious barnase expression.

Moreover, it may be beneficial to create an ablation construct having a reproductive-preferred promoter operably linked to barnase and a non-reproductive-preferred promoter operably linked to barstar. For example, a pine cone ablation construct could have the LPAG1 promoter driving barnase while the PrAG or LPAG1d4 promoter drives barstar (such as LPAG1::barnase E73G/PrAG::barstar or LPAG1::barnase E73G/LPAG1d4::barstar), with both cassettes in one backbone. During pine transformation, the toxicity of barnase due to LPAG1 activity in pine calli and regenerated embryos will be effectively neutralized by the barstar produced by the activity of PrAG or LPAG1d4 promoter, and thus the transformation can proceed smoothly. However, in the mature transgenic pine trees, the presence of barnase in the pine-cone buds, due to LPAG1 promoter activity, will effectively kill the cones because of barnase toxicity and the lack of the barstar in the pine-cone buds.

Example 13

Cloning of In-Frame PrMC2.400 Promoter Fragments

The PrMC2.400 promoter sequence was identified and isolated at described in U.S. Patent Application Publication 20030101487, which is incorporated by reference. The PrMC2.400 sequence has an ATG that is not in-frame with the ATG used in pWVR220 and other PrMC2 constructs. Although previous tests in *Arabidopsis* clearly showed that GUS is expressed from the PrMC2.400 promoter, GUS expression has not been observed in anthers of tobacco transformed with the PrMC2.400 promoter. Accordingly, an in-frame PrMC2.400 promoter was cloned for use in an ablation construct.

Using the PCR primers below, two different PrMC2.400 promoter sequences were isolated. As described below, the two PrMC2.400 promoters were cloned into expression vectors to ensure that the sequences are in-frame with an operably linked gene.

There are several in-frame ATGs in the PrMC2.400 promoter sequence, particularly at positions 361, 367, and 397. Using the reverse primers described, two different PrMC2.400 products were produced: PrMC2.400-1 contains all three ATGs; PrMC2.400-3 contains only the first ATG. The reverse primers were phoshorylated at the 5' end so they could be blunt-ligated to the appropriate sites in a cloning vector. The PrMC2-XG primer contains an XhoI site. PCR was performed using a high fidelity Taq polymerase blend (TaqPlus Long, Stratagene). After PCR, the amplification products were gel purified and then digested with XhoI using standard procedures. Each product was cloned into an intermediate vector and sequenced. Sequencing indicated that the PrMC2.400-1 sequence differed by one nucleotide from the original sequence, there is an insertion of a 'T' residue at position 35.

The cloning of the PrMC2.400-1 and PrMC2.400-3 sequences into expression vectors has ensured that all ATG sites remain in-frame with a gene of interest.

PrMC2-XG (for):
(SEQ ID NO: 38)
5'-GAAGAACTCGAGTAAAACATAATTTTGGCAGTAAAAAGTGA-3'

PrMC2-R1 (rev):
(SEQ ID NO: 39)
5'-CATGTTCCCGTTTGATACCTGAATTTTG-3'

PrMC2-R3 (rev):
(SEQ ID NO: 40)
5'-CATAAATCTTCTAAAAACAGCAGAACTGAC-3'

PrMC2-XG+PrMC2—R1: produced a 3966 (KNC) by product designated PrMC2.400-1 (SEQ ID NO: 5)

PrMC2-XG+PrMC2—R3: produced a 3603 (KNC) by product designated PrMC2.400-3 (SEQ ID NO: 16)

Example 14

Cloning In-Frame PrMC2.400-1::Mutant Barnase into Binary Vectors

As described in Example 17, the in-frame promoters PrMC2.400-1 and PrMC2.400-3 may be operably linked to a gene of interest for genetic ablation. For example, the in-frame PrMC2.400-1 promoter may be operably linked to an attenuated barnase sequence for reproductive ablation.

K27A

As described in Example 4, the K27A mutant barnase was previously cloned into a high copy vector, pWVR63. The PCR generated fragment PrMC2.400-1 was cloned into pWVR63 previously digested with NcoI, Mung bean nuclease treated to generate a blunt-end, followed by an XhoI digest and gel purification to isolate the vector fragment. The subsequent intermediate plasmid, pWVR205, now contained the ablation cassette PrMC2.400-1::K27Abarnase::RNS2TER. This cassette was then subcloned into a binary vector using KpnI and ApaI to generate pWVR216.

H102E

As indicated in Example 4, the H102E mutant barnase was previously cloned into a high copy vector, pWVR15. In order to have more convenient restriction enzyme ends for cloning, H102E was generated using PCR primers from pWVR15 template. The mutant barnase H102E was generated using PCR primers:

```
Ag12-PB:
                                         (SEQ ID NO: 33)
5'-TTTCACAACCTCCACACACTT-3'

Bar3Sac:
                                         (SEQ ID NO: 35)
5'-GAAGAAGAGCTCTTGACCGATCAGAGTTTGAAG-3'
```

PCR was performed using a high fidelity Taq polymerase blend (TaqPlus Long, Strategene). Standard three-step PCR methodology was used. The PCR reaction was gel purified and subsequently digested with NcoI and SacI. The restriction digest was gel purified and the fragment isolated and concentrated. This purified PCR fragment was cloned into an intermediate vector previously digested with NcoI and SacI, producing the construct pWVR218. This construct was sequenced to ensure correct mutant barnase sequence. The PCR generated fragment PrMC2.400-1 was then cloned into pWVR218 previously digested with NcoI, Mung bean nuclease treated to generate a blunt-end, followed by an XhoI digest and gel purification to isolate the vector fragment. The subsequent plasmid, pWVR219, now contained the ablation cassette PrMC2.400-1::H102Ebarnase::RNS2TER. This construct was sequenced to ensure correct promoter sequence and promoter:gene junction. This cassette was then subcloned into a binary vector using KpnI and ApaI to generate pWVR220.

E73G

E73G mutant barnase was previously cloned into a high copy vector, as indicated in Example 4. In order to have more convenient restriction enzyme ends for cloning, E73G sequence was generated using PCR primers from a plasmid template. The mutant barnase E73G was generated using PCR primers:

```
Bar5Nco:
                                         (SEQ ID NO: 31)
5'-TGACAACCATGGCACAGGTTATCAACACGTTTGAC-3'

Bar3Sac:
                                         (SEQ ID NO: 35)
5'-GAAGAAGAGCTCTTGACCGATCAGAGTTTGAAG-3'
```

PCR was performed using a high fidelity Taq polymerase blend (TaqPlus Long, Strategene). Standard three-step PCR methodology was used. The PCR reaction was gel purified and subsequently digested with NcoI and SacI. The restriction digest was gel purified and the fragment isolated and concentrated. This purified PCR fragment was cloned into an intermediate vector previously digested with NcoI and SacI producing the construct pWVR230. This construct was sequenced to ensure correct mutant barnase sequence. The PCR generated fragment PrMC2.400-1 was then cloned into pWVR230, previously digested with NcoI, Mung bean nuclease treated to generate a blunt-end, followed by an XhoI digest and gel purification to isolate the vector fragment. The subsequent plasmid, pWVR231, now contained the ablation cassette PrMC2.400-1::E73Gbarnase::RNS2TER. This construct was sequenced to ensure correct promoter sequence and promoter:gene junction. This cassette was then subcloned into a binary vector using KpnI and ApaI to generate pAGF232.

GUS Control

Although previous tests in *Arabidopsis* demonstrated that GUS is expressed from the original PrMC2.400 promoter, no staining has been observed in transformed tobacco anthers. A new reporter cassette (see below) was synthesized so that it matches the frame of the ablation constructs.

The PCR generated fragment PrMC2.400-1 was cloned into pWVR52, previously digested with NcoI, Mung bean nuclease treated to generate a blunt-end, followed by an XhoI digest and gel purification to isolate the vector fragment. The subsequent plasmid, pWVR233, now contained the cassette PrMC2.400-1::GUS::RNS2TER. This construct was sequenced to ensure correct promoter sequence and promoter:gene junction. This cassette was then subcloned into a binary vector using KpnI and ApaI to generate pAGF234.

Example 15

In Planta Expression of PrMC2.400-1: Barnase

*Agrobacterium tumefaciens* strain GV2260 was transformed via electroporation with binary vector pWVR216 or pWVR220 or pAGF232 or pAGF234.

Transgenic plants were produced by *Agrobacterium*-mediated transformation of tobacco (*Nicotiana tabacum*). Transformants were selected on a medium containing kanamycin. Positive transformants were identified by PCR, transferred to soil, and grown under standard greenhouse conditions. Plants were analyzed for overall vegetative growth rate, time of flowering and male-sterility.

Plants expressing the mutant barnase genes driven by the PrMC2.400-1 promoter displayed a male-sterile phenotype. Specifically, the transgenic plants did not produce pollen grains. This was confirmed microscopically, by observing anthers under a compound light microscope. Further, the pollenless plants did not produce fruit capsules and seeds. However, when the plants were cross-pollinated with wt tobacco pollen, normal seed set occurred, indicating that female fertility was unaffected. Additionally, offspring from these cross-pollinations produced a pollenless phenotype, indicating that the transgenes were inherited and the presence of the transgene in the progeny produced male sterile plants.

It was noted that tobacco lines expressing the mutant barnase gene driven by the PrMC2.400-1 promoter had a reduced stamen height, relative to the carpel. Flowering time was also delayed. A reduction in vegetative growth was readily observed for tobacco lines expressing K27A and E73G, relative to the control lines. This reduction in vegetative growth resulted in shorter plants with slower development. Lines expressing H102E showed minimal signs of vegetative effects and were very similar to controls in overall growth. The reduction in vegetative growth could be an indication of 'leakiness' of the expression of the PrMC2.400 promoter in tobacco tissue.

To assay PrMC2.400 promoter activity in vegetative tissues, young leaf tissue, roots, and vegetative shoot tips from lines transformed with PrMC2.400-1::GUS lines were tested for GUS activity. GUS activity was assayed histochemically using the chromogenic substrate X-Gluc. Tissues were vacuum-infiltrated in X-Gluc at room temperature for 1 hour then incubated at 37° C. for 16 hours. Following incubation, the tissues were destained in 100% methanol and then 95% ethanol. These tissues displayed no GUS expression. It is possible that the level of GUS expression is so low that it cannot be detected by this assay.

Additional experiments using PrMC2.400-1 linked to GUS were performed to further understand temporal and spatial expression patterns during anther development in tobacco. Tobacco flower development can be divided into 12 stages to provide reference points for the expression of genes in floral organ systems. Koltunow, et al. *The Plant Cell* 2:1201-1224 (1990). Flower buds were removed at each stage, dissected, stained for GUS activity, and observed microscopically. GUS activity was assayed histochemically using the chromogenic substrate X-Gluc. Floral buds were vacuum-infiltrated in X-Gluc at room temperature for 1 hour then incubated at 37° C. for 16 hours. Tissue was destained in 100% methanol and then 95% ethanol. The results indicate that the PrMC2.400-1 promoter is expressed in only in the anther, and PrMC2.400-1 expression is limited to those developmental stages in which the tapetum is present. The tapetum layer plays a major role in pollen formation. Therefore, expression of a cytotoxic gene in the tapetum layer could prevent pollen production.

Example 16

Cloning PrMC2.400-3::Mutant Barnase into Binary Vectors

H102E

PrMC2.400-3 was generated using primers PrMC2-XG and PrMC2-R3, as described above in Example 13. Template used to amplify this fragment was the binary vector, pWVR220. This purified PCR fragment was cloned into an intermediate vector previously digested with NcoI and SacI, producing the construct pWVR242, which now contained the ablation cassette PrMC2.400-3::H102Ebarnase::RNS2TER. This construct was sequenced to ensure correct promoter sequence and promoter:gene junction. This cassette was then subcloned into a binary vector using KpnI and ApaI to generate pWVR243.

GUS Control

The PCR generated fragment PrMC2.400-3 was cloned into pWVR52 previously digested with NcoI, Mung bean nuclease treated to generate a blunt-end, followed by an XhoI digest and gel purification to isolate the vector fragment. The subsequent plasmid, pWVR244, now contained the cassette PrMC2.400-3::GUS::RNS2TER. This construct was sequenced to ensure correct promoter sequence and promoter:gene junction. This cassette was then subcloned into a binary vector using KpnI and ApaI to generate pWVR245.

Example 17

In Planta Expression of PrMC2.400-3: Barnase

*Agrobacterium tumefaciens* strain GV2260 was transformed via electroporation with binary vector pAGF243 or pAGF245.

Transgenic plants were produced by *Agrobacterium*-mediated transformation of tobacco (*Nicotiana tabacum*). Transformants were selected on a medium containing kanamycin. Positive transformants were identified by PCR, transferred to soil, and grown under standard greenhouse conditions. Plants were observed for overall vegetative growth rate, time of flowering and male-sterility. Transgenic tobacco lines displayed a male-sterile phenotype. Specifically, the plants did not produce pollen grains. Additonally, the PrMC2.400-1::H102E lines had reduced stamen height, relative to carpel height, and flowering time was delayed.

Lines containing PrMC2.400-3 linked to the reporter gene GUS were compared with PrMC2.400-1::GUS lines. The intensity of GUS staining in floral buds, specifically anther tissue, was comparable to the PrMC2.400-1::GUS lines.

Example 18

Construction of Precursor Plasmids with Flowering Control Cassettes

Construction of the plasmids began with a binary vector derived from pBIN19 that was reduced in size through deletion of nonessential DNA segments, pARB310 (SEQ ID NO: Z1). A gene for barstar (Hartley, R. W. *J. Mol. Biol.* 202: 913-915 (1988)) that had been previously cloned with flanking BstXI sites was removed from pWVR200B by BstXI digestion and gel purified. The approximately 470 bp fragment was ligated into pARB310 that had been digested with BstXI, to produce pARB310B.

Next, the ColE1 replication origin and surrounding region were amplified from pART27 (Gleave, 1992) using PCR with the primer pair, ColE1-F4 (5'-GAGAGAGGATCCGGTGT-GAAATACCGCACAG-3', SEQ ID NO: 41) and ColEL1-R4 (5'-GAGAGATGATCAGCCTCACTGATTAAG-CATTGGTAACTG-3', SEQ ID NO: 42). The 1.0 kb ColE1 fragment was digested with BamHI and BclI, then was purified and ligated into the BclI site of pARB310B, between the end of the trfA gene and the left border (LB) of the T-DNA. This generated pAGF50, which acted as a high copy number plasmid in *E. coli*, but still replicated in *Agrobacterium*.

pAGF50 was digested with AscI and NcoI to remove the UBQ3 promoter plus most of the NPTII coding region, and the resulting 5.7 kb fragment was gel purified. The 1.9 kb fragment with UBQ10 promoter linked to the 5'-end of the NPTII coding region was released from pWVR3 by AscI and NcoI digestion, gel purified, and ligated into the pAGF50 fragment to generate pARB1000. This plasmid was further modified by the addition of a SUBIN::GUSIN::NOSTER reporter cassette. SUBIN indicates a ubiquitin promoter from *P. radiata*, which included genomic DNA coding the 5'-UTR and an intron; GUSIN indicates the β-glucuronidase coding region plus an intron from the potato tuberin gene (Vancanneyt et al., 1990). The reporter cassette was removed from pARB494 by DraI digestion and ligated into the SmaI site of pARB1000 to generate pARB1001. In addition to being able to serve as a transformation control, pARB1001 was used as the direct precursor to the flowering control plasmids because it had two NotI sites flanking the reporter gene, which could be used to switch it with other genes of interest.

The male-specific flowering control gene, PrMC2.400:: barnaseH102E::RNS2TER, was present in pWVR219, with an unwanted NotI site near the 3'-end. The plasmid was digested with NotI, and then the site was destroyed by treating with T4 DNA polymerase in the presence of dNTPs and religating the vector. The PrMC2.400::barnaseH102E:: RNS2TER cassette was excised from the altered pWVR219 with AscI and XhoI, and the 1.1 kb fragment was gel purified. pARB1001 was prepared by partial digestion with XhoI to linearize the plasmid, followed by complete digestion with AscI. The PrMC2.400::barnaseH102E::RNS2TER cassette was ligated to the prepared pARB1001 vector to generate pARB1002. The structure of the plasmid was verified with single-pass sequencing.

The (AtAGenh)PrAG::barnaseE73G::NOSTER cassette was removed from pWVCZ24 by EcoRI and AscI digestion. A NotI adapter comprising the oligonucleotides, EcoNot1 (5'-AATGCGGCCGCAGAGA-3', SEQ ID NO: 43) and EcoNot2 (5'-TCTCTGCGGCCGC-3', SEQ ID NO: 44), was ligated to the EcoRI site and digested with NotI, and then the 4.9 kb fragment was purified. The plasmid pARB1001 was digested with NotI and AscI and the 7.6 kb vector fragment was gel purified. The above cassette was ligated into these sites to generate pARB1005L (FIG. 19, SEQ ID NO: 27). The structure of the plasmid was verified with single-pass sequencing.

Example 19

Transformation of Early Flowering *Eucalyptus occidentalis*

This example details the infection and transformation of early flowering *Eucalyptus occidentalis*. In order to test flowering control constructs. *Eucalyptus occidentalis* seedlings were tested for early flowering in glasshouse growing conditions, and clones were selected on the basis of flowering within six months. These clones were introduced into sterile tissue culture for transformation with ablation constructs of the instant invention and control GUS constructs. Leaf explants were harvested and pre-cultured for 4 days and then separate explants were infected with *Agrobacterium* strain GV2260 harboring p35SGUSINT (35S:: GUSINT, NOS:: NPTII) or the constructs of the instant invention, as shown in the table below, according to the method of U.S. patent application Ser. No. 10/861,909, which is incorporated herein by reference. Following eradication of the *Agrobacterium*, explants were transplanted to selection medium, which consisted of regular regeneration medium as described in that same patent application, with 30 mg/l Geneticin. Regenerated shoots of the transformants and were rooted and grown in containers on soil in a glasshouse for testing the Eucalyptus transformed with ablation constructs for flowering time relative to controls.

Constructs of the instant invention were also transformed into clones of *Eucalyptus camaldulensis* and commercial clones of *Eucalyptus urophylla* and *Eucalyptus grandis* using the method of U.S. patent application Ser. No. 10/861,909. Regenerated shoots of the transformants were rooted, transferred to soil and acclimated in a glasshouse, then transferred to field planting sites in Florida and South Carolina under notifications to the US Agricultural Plant Health Inspection Service. Plants are monitored regularly for the development of floral buds. No flowering has been observed to date.

TABLE 8

| Name of Construct | Flowering Control Promoter | Attenuated Barnase Gene (for example, H102E) | Euc species and clone | Approx date into transformation (or planned to transform) | Any effects noted in tissue culture suggesting leakiness of the promoter driving the attenuated barnase gene |
|---|---|---|---|---|---|
| pARB598 | PrMC2 | H102E | E. occidentalis clones 129 and 208 | December 2003 | None |
| pAGF243 | PrMC2.400-3 | H102E | E. occidentalis clone 129 | March 2004 | |
| pARB598 | PrMC2 | H102E | E. urophylla clone IPB1 | June 2003 | None |
| pARB599 | PrMC2 | H102E | E. urophylla clone IPB1 | June 2003 | Reduced transformation efficiency relative to control |
| pARB675 | PrMC2 | H102E | E. urophylla clone IPB1 | April 2004 | |
| pARB639 | PrAG | E73G | E. urophylla clone IPB1 | June 2003 | Could not recover lines with all T-DNA components. |
| pWVCZ24 | PrAG | E73G | E. camaldulensis clone C9 | March 2003 | None |
| pWVCZ101 | PrAG | E73G | E. camaldulensis clone C10 | March 2003 | None |
| pWVCZ24 | PrAG | E73G | E. grandis clone IP1 | April 2003 | None |
| pWVCZ101 | PrAG | E73G | E. grandis clone IP1 | April 2003 | None |
| pWVR220 | PrMC2 | H102E | E. grandis clone IP1 | April 2003 | None |
| pAGF232 | PrMC2 | E73G | E. grandis clone IP1 | April 2003 | None |

Example 20

Hybrid Pine

Hybrid pine (*P. taeda×P. rigida*) and loblolly pine (*P. taeda*) embryogenic cell lines were initiated from zygotic embryos of individual immature megagametophytes using the procedures described in U.S. Pat. No. 5,856,191, and maintained using the procedures described in U.S. Pat. No. 5,506,136.

After one to three months of culture on maintenance medium, the tissue cultures were cryopreserved, stored for periods of up to several years, and then retrieved using the methods of U.S. Pat. No. 6,682,931. Those skilled in the art of plant tissue culture will recognize that other cryopreservation and recovery protocols would be applicable to the present method and that the detail in this example may not be construed to limit the application of the method.

Uniform suspension cultures from two genetically different hybrid pine tissue culture lines and multiple *P. taeda* lines were established by inoculating a 250 ml Nephelo sidearm flask (Kontes Chemistry and Life Sciences Products) with 1 g of tissue each according to the method of U.S. Pat. No. 5,491,090. The flasks containing the cells in liquid medium were placed on a gyrotory shaker at 100 rpm in a dark culture room at a temperature of 23° C.±2° C. One week later, the liquid in each flask was brought to 35 ml by pouring 15 ml fresh medium into the culture flask and swirling to evenly distribute the cells. Cell growth was measured in the sidearm by decanting cells and medium into the sidearm portion of the flasks, allowing the cells to settle for 30 minutes and then measuring the settled cell volume (SCV). When the SCV was greater than or equal to half the maximal SCV (50% of the volume of the flask was occupied by plant cells), each culture was transferred to a 500 ml sidearm flask containing a total of 80 ml cells and medium and the transferred culture was maintained under the same conditions.

To prepare for gene transfer, polyester membrane supports were sterilized by autoclaving and placed in separate sterile Buchner funnels, and for each of six replicate plates per cell line, one to three milliliters of pine embryogenic suspension was pipetted onto each support such that the embryogenic tissue was evenly distributed. The liquid medium was suctioned from the tissues and each support bearing the embryogenic tissue was placed on gelled preparation medium for *Agrobacterium* inoculation according to the methods described in U.S. Patent Publication No. 20020100083. Binary reporter gene constructs were introduced into different isolates *Agrobacterium tumefaciens* by techniques well known to those skilled in the art, and virulence was induced with administration of acetosyringone by commonly used techniques whereupon each of the induced *Agrobacterium* isolates was co-mingled with separate replicates of the plant material. The cells were co-cultivated in the dark at 22°±2° C. for approximately 72 hours.

Following co-cultivation, *Agrobacterium* was eradicated from the cultures according to the methods described in U.S. Patent Publication No. 20020100083. Cells borne on polyester membrane supports were then transferred onto fresh selection media at intervals of 2 weeks. Active growth on the selection medium occurred in a number of isolated sectors on many of the petri dishes. Such active growth in the presence of selection agent is normally an indication that the growing tissues have integrated the selection gene into their chromosomes and are stably transformed. These areas of active growth are treated as independent transformation events and are henceforth referred to as putative transgenic sublines. The putatively transgenic embryogenic tissue was multiplied by transferring growing transgenic sectors to fresh semi-solid maintenance medium supplemented with the respective selection agent.

Putatively transformed sublines, after reaching approximately 2 g, were chosen for polymerase chain reaction (PCR) amplification for verification of the presence of transgenes using standard techniques.

TABLE 9

Primer Pairs for PCR

| | | Product size |
|---|---|---|
| virD2 | GAA GAA AGC CGA AAT AAA GAG G (SEQ ID NO: 45) | 560 |
| virD2 | TTG AAC GTA TAG TCG CCG ATA G (SEQ ID NO: 46) These primers were used to check contamination by Agrobacterium | |
| NptII | AAG GAG ATA TAA CAA TGA TTG AAC AAG ATG GAT TGC (SEQ ID NO. 47) | 800 |
| NptII | TCA GAA GAA CTC GTC AAG AAG G (SEQ ID NO: 48) | 800 |
| uid(gus) | CGA AAA CGG CAA GAA AAA GCA G (SEQ ID NO: 49) | 450 |
| uid(gus) | ACG ACC AAA GCC AGT AAA GTA G (SEQ ID NO: 50) | |
| Pal | AAT GGG AAG CCT GAG TTT ACA (SEQ ID NO: 51) | 700 |
| Pal | GGC CAG CAT GTT TTC CTC CAG (SEQ ID NO: 52) These primers, for the PAL gene, were used as a positive control | |

Material from each subline also was sacrificed for GUS staining and microscopic examination. For GUS staining, an inserted uidA gene, encoding a β-glucuronidase enzyme expressing in tissue culture cells, was detected by deep blue staining of cells from each of the transgenic lines upon exposure to a colorigenic glucuronidase enzyme substrate, "X-gluc," commercially available from Inalco, according to techniques well known in the art of plant transformation. Microscopic examination demonstrates that cell division has resumed and that transient expression of the uidA transgene displays the normal frequency for these bombardments.

Germinable embryos were produced as follows. After the cell masses that had been cultured on selection medium proliferated to at least one gram, each was separately resuspended in liquid medium again. When the cell suspensions were brought to uniform (half-maximal) SCV, equivalent amounts of suspension culture cells were pipetted onto sterile membrane supports for placement on development/maturation medium as described in U.S. Pat. No. 5,506,136 to develop high quality harvestable stage 3 (cotyledonary) embryos. Dishes were incubated in a dark growth chamber at 23±2° C. The membrane supports were transferred to new petri dishes containing fresh medium every 3 weeks. At week 9, stage 3 (cotyledonary) embryos were visually analyzed for germination quality and harvested onto fabric supports on medium as described in U.S. Pat. No. 5,506,136, and incubated for about four weeks in the dark at a temperature of 4° C.±2° C. Next, embryos on their fabric supports were incubated above water in sealed containers for about three weeks in the dark at a temperature of 25° C.±2° C. Following the above two treatments, embryos on their fabric supports were transferred to medium germination medium and incubated for about three days in the dark at a temperature of 25° C.±2° C. Embryos were then removed from their fabric supports and placed onto the surface of fresh germination medium. Germination was conducted in the light at a temperature of 25° C.±2° C. Germination plates were examined weekly, over a period of about four weeks, and germinating embryos were transferred to MAGENTA® boxes containing 100 ml of germination medium for conversion to plantlets. MAGENTA® boxes containing developing plantlets were incubated in the light at 25° C.±2° C. for about eight to twelve weeks.

When the plantlets formed epicotyls (newly formed shoots of approximately two to four cm), they were transferred to containers filled with a potting mix [2:1:2 peat:perlite:vermiculite, containing 602 g/m³ OSMOCOTE fertilizer (18-6-12), 340 g/m³ dolomitic lime and 78 g/m³ MICRO-MAX micronutrient mixture (Sierra Chemical Co.)]. The plantlets were grown in a shaded greenhouse and misted infrequently for a period of about two weeks. They were removed from mist for acclimatization in the greenhouse for about four weeks. Plantlets were then transferred to outdoor shade for about six weeks for final acclimatization before moving to full-sun conditions. They were then grown in containers until conditions were ready for field planting.

Plants regenerated from loblolly pine (*P. taeda*) lines were also planted into the same field sites and no strobilus production has been observed in the field sites as long as six years after planting. However, unexpectedly, the transgenic hybrid pine lines produced strobili three years after planting. At that point the hybrid trees were approximately one meter in height, much smaller than the adjacent transgenic loblolly pine trees.

Table 10 below shows the results of a second planting that included the non-transgenic hybrid pine origin line as a control from somatic embryogenesis, a variety of seedling genotypes with the same parents that present a control that did not pass through tissue culture, and a total of 24 different transgenic lines generated from the 97LP0006 somatic embryogenic line using two different vectors, some transformed using biolistics and some using *Agrobacterium*, with multiple replicates of most lines for a total of over 250 plants, produced some strobili two years after planting and significant numbers of strobili within three years after planting. Tests were terminated following these observations.

The results shown in table 10 suggest that passage through tissue culture and transformation is necessary to achieving the inventive early strobili production result, as the SE control did not produce strobili, and few of the non tissue-cultured genotypes did. However, nearly all of the transgenics produced either male or female strobili or both at very high frequency. Only one of 18 transgenic lines did not produce strobili within three years. The result was independent of the transformation used and independent of the transformation vector used. This suggests that best mode is to use transgenic controls, e.g. transformed with reporter gene constructs, for comparisons intended to show the efficacy of reproduction control constructs such as the inventive ablation constructs.

The trees were, at the time the strobili were produced, approximately 1.2 meters average height, easily harvestable by a person of average height without specialised equipment.

This system was then used to test the reproduction control constructs of the instant application for their utility in gymnosperms, a test that would otherwise be impossible to carry out. The embryogenic callus provides an opportunity to test whether or not the promoters being tested are leaky in a gymnosperm and whether the attenuated barnase genes are detrimental when expressed in a leaky fashion (see column 4 in the table). Once the trees are regenerated and planted in the field, effects on date of strobilus formation relative to GUS-transformed controls can be measured within three years, upon which time the field test can be terminated. This will further allow for a faster rotation of expensive production forestry land for these field tests.

TABLE 10

| Reporter construct | Transformation method | Transgenic line number | #trees in planting from this line | No strobili | Female strobili | Male strobili | Both male and female | % trees showing no strobili | % trees showing female strobili | % trees showing male strobili | % trees showing both male and female strobili |
|---|---|---|---|---|---|---|---|---|---|---|---|
| Act2::GUS | *Agrobacterium* | 28 | 9 | 6 | 3 | 1 | 1 | 67% | 33% | 11% | 11% |
| Act2::GUS | *Agrobacterium* | 29 | 10 | 9 | 1 | 1 | 1 | 90% | 10% | 10% | 10% |
| Act2::GUS | *Agrobacterium* | 31 | 8 | 0 | 7 | 2 | 1 | 0% | 88% | 25% | 13% |
| Act2::GUS | *Agrobacterium* | 32 | 10 | 0 | 10 | 2 | 2 | 0% | 100% | 20% | 20% |
| Act2::GUS | *Agrobacterium* | 34 | 10 | 2 | 8 | 1 | 1 | 0% | 80% | 10% | 10% |
| Act2::GUS | *Agrobacterium* | 36 | 10 | 0 | 10 | 2 | 2 | 0% | 100% | 20% | 20% |
| Act2::GUS | *Agrobacterium* | 38 | 10 | 0 | 10 | 3 | 3 | 0% | 100% | 30% | 30% |
| Act2::GUS | *Agrobacterium* | 39 | 3 | 3 | 0 | 0 | 0 | 100% | 0% | 0% | 0% |
| Act2::GUS | *Agrobacterium* | 53 | 9 | 1 | 8 | 3 | 3 | 11% | 89% | 33% | 33% |
| Act2::GUS | Biolistics | 64 | 8 | 1 | 5 | 4 | 2 | 20% | 100% | 80% | 40% |
| UBQ3::GUS | *Agrobacterium* | 117 | 9 | 1 | 8 | 3 | 3 | 11% | 89% | 33% | 33% |
| UBQ3::GUS | *Agrobacterium* | 118 | 9 | 0 | 9 | 2 | 2 | 0% | 100% | 22% | 22% |
| UBQ3::GUS | *Agrobacterium* | 119 | 10 | 1 | 9 | 5 | 5 | 10% | 90% | 50% | 50% |
| UBQ3::GUS | *Agrobacterium* | 120 | 10 | 0 | 10 | 0 | 0 | 0% | 100% | 0% | 0% |
| UBQ3::GUS | *Agrobacterium* | 122 | 8 | 0 | 8 | 0 | 0 | 0% | 100% | 0% | 0% |
| UBQ3::GUS | *Agrobacterium* | 125 | 10 | 0 | 10 | 2 | 2 | 0% | 100% | 20% | 20% |
| UBQ3::GUS | *Agrobacterium* | 127 | 10 | 0 | 10 | 3 | 3 | 0% | 100% | 30% | 30% |
| UBQ3::GUS | *Agrobacterium* | 128 | 10 | 1 | 9 | 2 | 2 | 10% | 90% | 20% | 20% |
| n.a. | Non-transgenic somatic embryogenesis control | 97LP0006 | 7 | 2 | 5 | 0 | 0 | 29% | 71% | 0% | 0% |
| n.a. | Non-transgenic zygotic plant control | pitch x loblolly seedlings | 46 | 27 | 15 | 7 | 3 | 59% | 33% | 15% | 7% |

TABLE 11

| Name of Construct | Promoter | Gene | What effects noted in pine callus | Plants to field planting | Approx date into pine transformation | SE lines transformed |
|---|---|---|---|---|---|---|
| pWVR216 | PrMC2.400 | barnaseK27A | None | No | Jul. 1, 2002 | 92AA0033 |
| pWVR217 | PrMC2.400 | LPRNase1 | None | No | Jul. 1, 2002 | 92AA0033 |
| pAGF234 | PrMC2.400-1 | GUS | NA | Yes | Dec. 6, 2002 | 97LP0033 |
| pWVR220 | PrMC2.400-1 | barnaseH102E | None | Yes | Dec. 6, 2002 | 97LP0033 |
| pWVR216 | PrMC2.400-1 | barnaseK27A | detrimental | No | Dec. 6, 2002 | 97LP0033 |
| pAGF232 | PrMC2.400-1 | barnaseE73G | detrimental | No | Dec. 6, 2002 | 97LP0033 |
| pAGF245 | PrMC2.400-3 | GUS | NA | No | Dec. 2, 2003 | 97LP0033 |
| pAGF243 | PrMC2.400-3 | barnaseH102E | None | Yes | Dec. 2, 2003 | 97LP0033 |

Example 21

Method for Ablating Pine Male and Female Cones Using a Construct Having LPAG1 and LPAG1d4 Promoters Based on the results shown in Example 6, Table 4, the LPAG1 and LPAG1d4 promoters can be used for ablating male and female cones of pine trees. For example, an ablation construct could have the LPAG1 promoter operably linked to a gene encoding barnase, while the LPAG1d4 promoter is operably linked to a gene encoding barstar (barnase inhibitor). As shown above in Example 6, LPAG1 promoter is active in pine cones and embryos while the LPAG1d4 promoter is active only in pine embryos. This assumption is made based on the observation that LPAG1 has high activities in tobacco flowers while LPAG1d4 has little activities in tobacco flowers. By placing the gene encoding barstar under the control of LPAG1d4 promoter that may have little activity in a pine cone, barnase toxicity produced by the other promoter (LPAG1) can effectively ablate male and female cones. On the other hand, similar levels of activities of the two promoters in pine embryos produce similar amounts of barnase and barstar, and so the barnase toxicity in the embryos is effectively neutralized, leading to transformation and regeneration of pine embryogenic calli and embryos.

DESCRIPTION OF SEQUENCE IDENTIFIERS

SEQ ID NO. 1—LPAG1
SEQ ID NO. 2—LPAG2
SEQ ID NO. 3—PrAG-ATenh
SEQ ID NO. 4—PrMC2.400-1
SEQ ID NO. 5—barnase mutant E73G (DNA)
SEQ ID NO. 6—barnase mutant F106S (DNA)
SEQ ID NO. 7—barnase mutant H102E (DNA)
SEQ ID NO. 8—barnase mutant K27A (DNA)
SEQ ID NO. 9—barnase mutant E73G (AA)
SEQ ID NO. 10—barnase mutant F106S (AA)
SEQ ID NO. 11—barnase mutant H102E (AA)
SEQ ID NO. 12—barnase mutant K27A (AA)
SEQ ID NO. 13—PrMC2+barnase mutant H102E
SEQ ID NO. 14—PrMC2+barnase mutant K27A
SEQ ID NO. 15—PrMC2+barnase mutant E73G
SEQ ID NO. 16—PrMC2.400-3
SEQ ID NO. 17—LPAG1d4
SEQ ID NO. 18—pWVR220 [PrMC2.400::barnaseH102E] (FIG. 1)
SEQ ID NO. 19—pWVCZ20 [(AtAGenh)PrAG::GUS(intron)] (FIG. 2)
SEQ ID NO. 20—pWVCZ23 [PrAG::barnaseE73G] (FIG. 3)
SEQ ID NO. 21—pWVCZ24 [(AtAGenh)PrAG::barnaseE73G] (FIG. 4)
SEQ ID NO. 22—pARB599B [PrMC2::barnaseH102E] (FIG. 5)
SEQ ID NO. 23—pARB639B [(AtAGenh)PrAG::barnaseE73G] (FIG. 6)
SEQ ID NO. 24—pAGF243 [PrMC2.400-3::barnaseH102E] (FIG. 7)
SEQ ID NO. 25—pABDP010 [complementary copy of CZ28-bstar+UBQ10::NPTII::E9/LPAG1d4::bstar::NOST] (FIG. 8)
SEQ ID NO. 26—pABDP04 [complementary copy of CZ28-bstar+UBQ10::NPTII::E9/LPAG1d4::bstar::NOST] (FIG. 9)

Sequences follow below.

```
SEQ ID NO. 1 - LPAG1

CAGCAAATATGATTTAGATTATGACCTAGAAATAAGCATAGCATTA

AAGCATATACAAAACAAGCGGTGATATACTCTGACTGCCACTGTAC

TTGAGGAAAGGTAGTGGACTCTGCTCAGGTACATTAGTTTGGTAAG

GTTGGCTTGGCTTCTGGGTAATATGAGAAGTAAAGAAGTAAAAGGT

ATTTGACTCTAGTCAAGTACATTGGATTGCCTTCGTCGGGGCTTGG

ATGGCTTGGGTTCGTGTGAGAAGCCAACAATTTATAAAAAAATATA

TTGAAAAAAAAAAAAATCGTCTAAGTGTTGGAAGTGAAAACGGTGG

GACATAAATATACACAGAAGAGTACTTTAACAATGCGCAACCAAGG

CAGATTCACAACTTGATTTCTGGACCTCGAATACGAGATAATGGTG

GTAAGAAATAAAGGAAGAGTGGAGTGCATTTGAAAATGAATGGAGA

GCGCACAAAATGGAGGACGAATAAATGAAATATAATGCAAGAGTGC

ATTTCCCTATTATTTCCAGAAATGTATATGTGGGGTCGGCATTCAC

ATGGGCGTCGCATTCAGGGGGTGTCATAGCGGTCCTTTGATTGCAG

TGTGGGAGTTGCAACATGTACCAACAAATTCATTCATCCCAAAACC

TAAATTTATCCTCTCCATTACTATTACCTACACCTATACCTAGTAA

ATATGTCCTGCCTTGTAACTCCTCCACTGCCTGCACACGTCTTAGT

CAATCCATCTGCCTTCAAATAGGCATTATTTTGTTCTTTCCCCTCC

GACTGAAAGGCTATCGACCGACCGACCGCTCATCTTCTTCTTCTGC

GCAATTTTTTCTGCTGGATCATCATCATTACCATCATCGCCATCCC

CACCATCATCATCATGATGGTATCTCTATCTCTCCCTGGCAATCGA

TTGTAGAGGAAAGGAAGAGGGAAGGGGCATATGTATTGATCAACCT

ACCCGAAAAAACAATCTGATCAGCCCTGCTAATCTTGCTTATAAAT
```

CTCTTATCCACTGTTCAATCATTCAGGTTTCTTCCCACTTCCAAGC

AAAGGCGCCCGGATTGGCCGTGTTCTTAGATTTTCAGGTACTTAAA

TGGACAATATTCCCCACCTGAAGCCGTTCTGAAAAGATTTGTTTG

TAGAAACAAACGATTGTAATATTTGCTTAAGTTGAGCTTAAGGGGT

TTGGTACCTAACTTGCCTTGTGGTTATTTGTTTCTCAGAACTCGGG

CTGCGTCCAACTGTAGGAACGAACCAGCACAAGGGGTTGCAGCTTT

TGCTGTTGCTGTTGCGCCCATTGCTTTTGGACTGGTATTAGTAGTT

GCAGCTTTGTTTTGCATACGCTGTGAGGATCTGTGCGCGGAAATTT

TGTGTACAAATCATG

SEQ ID NO. 2 - LPAG2

CAGCAAATATGATTTAGATTATGACCTAGAAATAAGCATAGCATTA

AAGCATATACATAACAAGCGGTGATATACTCTGACTGCCACTGTAC

TTGATGAAGGTAGTGGACTCTGCTCAGGTACATTAGTTTGGTAAG

GTTGGCTTGGCTTCTGGGTAATATGAGAAGTAAAGAAGTAAAAGGT

ATTTGACTCTAGTCAAGTACATTGGATTGCCTTTGTCGGGGCTTGG

ATGGCTTGGGTTCGTGTGAGAAGCCAACAATTTATAATAAAAATAA

AATAAAAAATCGAAGTGTTGGAAGTGAAAACGGTGGGGCATAAATA

TACACAGAAGAGTACTTTAACAATGCGCAACCAAGGCAGATTCACA

ACTTGATTTCTGGACCTCGAATACGAGATAATGGTGGTAAGAAATA

AAGGAAGAGTGGAGTGCATTTGAAAATGAATGGAGAGCGCACAAAA

TGGAGGACGAATAAATGAAATATAATGCAAGAGTGCATTTCCCTAT

TATTTCCAGAAATGTATATGTGGGTCGGCATTCACATGGGCGTCG

CATTCAGGGGGTGTCATAGCGGTCCTTTGATTGCAGTGTGGGAGTT

GCAACATGTACCAACAAATTCATTCATCCCAAAACCTAAATTTATC

CTCTCCATTACTATTACCTACACCTATACCTAGTAAATATGTCCTG

CCTTGTAACTCCTCCACTGCCTGCACACGTCTTAGTCAATCCATCT

GCCTTCAAATAGGCATTATTTTGTTCTTTCCCCTCCGACTGAAAGG

CTATCGACCGACCGACCGCTCATCTTCTTCTTCTGCGCAATTTTTT

CTGCTGGATCATCATCATTACCATCATCGCCATCCCCACCATCATC

ATCATGATGGTATCTCTATCTCTCCCTGGCAATCGATTGTAGAGGA

AAGGAAGAGGGAAGGGGCATATGTATTGATCAACCTACCCGAAAAA

ACAATCTGATCAGCCCTGCTAATCTTGCTTATAAATCTCTTATCCA

CTGTTCAATCATTCAGGTTTCTTCCCACTTTCAAGCAAAGGCGCCC

GGATTGGCCGTGTTCTTAGATTTTCAGGTACTTAAATGGACAATAT

TCCCCACCTGAAGCCGTTCTGAAAAGATTTGTTTGTAGAAACAAA

CGATTGTAATATTTGCTTAAGTTGAGCTTAAGGGGTTTGGTACCTA

ACTTGCCTTGTGGTTATTTGTTTCTCAGAACTCGGGCTGCGTCCAA

CTGTAGGAACGAACCAGCACAAGGGGTTGCAGCTTTTGCTGTTGCT

GTTGCGCCCATTGCTTTTGGACTGGTATTAGTAGTTGCAGCTTTGT

TTTGCATACGCTGTGAGGATCTGTGCGCGGAAATTTTGTGTACAAA

TCATG

SEQ ID NO. 3 - PrAG-ATenh

GATAGGGTCAAATCGACCACTTGCACAGTTAAGTGATTCTAATACG

AAACCTTAAAAGCAAACATCGGTTCTTTTGAGTCAGAAGAAATGCA

ACTTAATGTGACACATGATGTGAAGAAAAACAAAAGTAATATAAG

AAAAGGGAACAATTAAATAGTTAATAAAAATATTTCCTTAAAGTTGT

AACAAATAAAGAATCATTTTATGAAACAATATGAACCCTAAATAAA

TTAAAATTCCTCTGAAACCTTAAATTTATCGAGCTAGTGATTGGCT

GCCAACTGCCATGCTGGCAAAATTAGAGTGACATGATTGGTCTGAA

CATGTCTAGGGTTTCAGACATGTGACATGTGTCAACAACCCATTAA

CACATTGGGTATAAATCCAATAGACATTTGATAGTATTAAAATTGT

AACCATTGGATTAAATTTAAACGTGATGGATGTAACTAAATGACTT

GTCCGAGTAACATCACAACGTTCCATACTTTCCTTATTTGGAATAT

AATTAAATTTACCATTTATTCTTTTTTCTTGAGTTTCCTGTATATG

TACTTGTACATAGATATATATGCACAAATACGTATTACAATGACAT

ATTATAGACTTTGATGTCTGAACTCTCAACCTTCTCGATGGAGAGA

TCATGACCGTAGATTTTTTTGGATCGTAGAAGGCAGACCAAACTCT

TAAACTATTGGATCCGGACTAAAAATCTCACTTTCCTCTCAGTACC

CATAATGAGAGAGAAAATGATAAAAATCCCTAACATTATTCTCTCT

CTAGAAAAAAAAGATACTTCAAAAGAAAGAGAAATTGCATAAAT

CTATCTACACCAAAGATGTTGAAGCAATTCCAATGCTATACTTCTA

TGCCAAATCTATTTATTCAGTGATCATTAATCTTTTTACTTCCAAG

AAATATGAACAATTTAGTATCCTTATAATTTTTGTCTCTATATATG

TAATATGAACATTGGGTATTGACCAAATGAGAAATCTAATATTAAA

TGGTCAAAAGTAGTAATATGATGACATTTTTGAATTTATAAATAGG

TTACAAATTAATTCATTATGACATAAAACCTTCTTGTCAGAAGTCA

AGAACTGAAACTAACAAAACTTTATAATAAATTAGTAAAATACAA

ATGAAAAATAAAAAGAAATAATATCTGAGTGATGACGTGATCAAAG

ATTCTTTAACAAAGACAACAAATCTTACAGACCCAAAACCTAATCT

TGCGCTCAATTCCAACCTCTGAAAAAACCTCAAAAATCTTATAAAA

GAAAATAAATAAAGAAACGAAACTCTGATTTCGTAGAGTACCCATC

GGATATATAAAAGAAATTAGTAGGTAAATGAAGACTAATTTTGAT

TGACTGATTTAATTTGAAGTCGTTGTTAGCTTTTCTTGTTTTGGAC

ATGAGAATTATATATTTCAGGACATGAGAGTTGACAACTGTAAACG

ATTAAGAAAATTGATCTTTTAATTTTCAAACACCATTTAATCTTGA

CATGTTTTATGTTTTGGTGGAAGAAAGTAATCACGTGGGACTCT

CTACTAATAAGTATTTGGAAATTGCGTGTCGAATTAGAGATTACTA

GTTTGAGTAATGTAGTTCGAAATGAGATTAGTTATTTTTAATTTTA

AAAAGAGTAATTTTAAGGAATAACAAAAAAGAGTCCCCATAAGCTA

ATTTGTCTTAATTACCTCCTTGTTTCATTGACTATTTGAAATCTTG
AAAATTCAGTTGAAATTTCAAATCTATGTTTCTTTTGACCACTTCT
AAACTAATCTTAGCTCATATATAATTTTCCAAAACTACAAAAATAA
CACTAACATTTAACATTCTCAAGAGAAAACAAAAACAAAAACTTAG
ATAACCATCTAAATTGTCCTACATGTACGTATAAGTTCCATTATTT
TCTATCACTCATATAAGTTAAAATTTCATGAAAACTCAAAAATCTA
GCTAGTTTCACCTTATTCACTCTCACTTACCATCACATGTGTTTGT
ATCAAATATATGATATGATATAATTCATGAGAGAGAAAGAGAGCTA
GAGATAAGAAAGGAAAGTAAGAGAAAGAAGAGAAGAAAAAGAGAGA
CACAGACATTAACAACAATGGAGGATGGATGATCACAAAACAGAAG
ATATGACCTCATAGTCCTTCCTTACTCTCTCCCCAATTTGTTTCCC
AAAACTTACTTTTATAGTCATAAAAATCAAGTTTTTTACCTATTACA
ACACCGATCTATAAATATATCTAAATCTTCAAGTACTTGTTAGTA
AGGAAAATAGAAAGATATAAGATTTTATTATTATTATAATAACAGA
AATGAGTGAAGAAGAACACCCAACAAAGTGAATCTTAGTTCTACA
AAACTGAATCTAAAACTCCACATTAGAAAAAACCCTGATGGTTTCT
TATTTCTTTTCATTTATTATCTAACTCTCACTCAGATCTCCTTTAA
CTTTGTACCATTTCCCTCACTTCATATATCTATATATAACAAACTC
TCTCTTTTTATTTAAGTCTTAAGGGAAAATTAATATACACATGAAG
AACAAGAAATTAGATCTACAAAATTGTTACAAAAACCCCCGAAGTA
AATAAAATAAACATATCAAACAAATATTCCCACTAATGTTAGTGTG
TTTATATATATATGTGTGTGGAATATGAAGGAAAAAAGTGAAAAAT
AATCCTACCCATAAGAGCATTCAAGAAGAAGCTCGAGGTCGACGGT
ATCGATAAGCTTAAACTCGACAGCAAATATGATTTAGATTATGACC
TAGAAATAAGCATAGCATTAAAGCATATACATAACAAGCGGTGATA
TACTCTGACTGCCACTGTACTTGAGGAAAGGTAGTGGACTCTGCTC
AGGTACATTAGTTTGGTAAGGTTGGCTTGGCTTCTGGGTAATATGA
GAAGTAAAGAAGTAAAAGGTATTTGACTCTAGTCAAGTACATTGGA
TTGCCTTTGTCGGGGCTTGGATGGCTTGGGTTCGTGTGAGAAGCCA
ACAATTTATAAGAAATATATAAATAAAAAATAAAAAATTTAAGT
GTTGGAAGTGAAAACGGTGGGGCAGAAATATACACAGAAGAGTACT
TTAACAATGCGCAACCAAGGCAGATTCACAACTTGATTTCTGGACC
TCGAATACGAGATAATGGTGGTAAGAAATAAAGGAAGAGTGGAGCG
CATTTGAAAATGAATGGAGAGCGCACAAAATGGAGGACGAATAAAT
GAAATATAATGCAAGGGTGCATTTCCCTATTATTTCCAGAAATGTA
TATGTGGGGTCGGCATTCTCATGGGCGTCGCATTCAGGGGGTGTCA
TAGCGGTCCTTTGATTGCAGTGTGGGAGTTGCAACATGTACCAACA
AATCCATTCATCCCAAAACCTAAATTTATCCTCTCCATTACTATTA
CCTACACCTATACCTAGTAAATATGTCCTGCCTTGTAACTCCTCCA
CTGCCTGCACACGTCTTAGTCAATCCATCTGCCTTCAAATAGGCAT
TATTTTGTTCTTTCCCCTCCGACTGAAAGGCTATCGACCGACCGAC
CGCTCATCTTCTTCTTCTGCGCAATTTTTTCTGCTGGATCATCATC
ATTACCATCATCGCCATCCCCACCATCATCATCATGATGGTATCTC
TATCTCTCCCTGGCAATCGATTGTAGAGGAAAGGAAGAGGGAAGGG
GCATATGTATTGATCAACCTACCCGAAAAAACAATCTGATCAGCCC
TGCTAATCTTGCTTATAAATCTCTTATCCACTGTTCAATCATTCAG
GTTTCTTCCCACTTTCAAGCAAAGGCGCCCGGATTGGCCGTGTTCT
TAGATTTTCAGGTACTTAAATGGACAATATTCCCCACCTGAAGCCG
TTCTGAAAAGATTTGTTTGTAGAAACAAACGATTGTAATATTTGC
TTAAGTTGAGCTTAAGGGGTTTGGTACCTAACTTGCCTTGTGGTTA
TTTGTTTCTCAGAACTCGGGCTGCGTCCAACTGTAGGAACGAACCA
GCACAAGGGGTTGCAGCTTTTGCTGTTGCTGTTGCGCCCATTGCTT
TTGGACTGGTATTAGTAGTTGCAGCTTTGTTTTGCATACGCTGTGA
GGATCTGTGCGCGGAAATTTTGTGTACAAATC

SEQ ID NO. 4 - PrMC2-400.1

CTCGAGTAAAACATAATTTTGGCAGTAAAAAGTGAATTCTATTGTT
TTGAAAACAAAACAAAATACAGGAAGCGTGATTGTGGGGTTGTTGT
TGAACTTGCCCGGGCAAAAGAAGAATGATTAGCGGTAGAGGAGTTA
GTAGTTACGTTCAACTAAATGCGTGACTAAATTATTTATCCTCCGC
CATGGAAGCAGGTGATTCACACACAACTTGCTGCACACATTGCTCT
CAAACCTTTCCTATAAATATCCGTAGCAGGGGCTGCGATGATACAC
AACGCATTTAATCAAACTACTTTGATTACTTTCTGTGGGTTCTACT
TTCTTTGAATAGTCAGTTCTGCTGTTTTTAGAAGATTATGAGAAT
GGCCAAAATTCAGGTATCAAACGGGAAC

SEQ ID NO. 5 - barnase mutant E73G (DNA)

ATGGCACAGGTTATCAACACGTTTGACGGGGTTGCGGATTATCTTC
AGACATATCATAAGCTACCTGATAATTACATTACAAAATCAGAAGC
ACAAGCCCTCGGCTGGGTGGCATCAAAAGGGAACCTTGCAGACGTC
GCTCCGGGGAAAAGCATCGGCGGAGACATCTTCTCAAACAGGGAAG
GCAAACTCCCGGGCAAAAGCGGACGAACATGGCGTGGAGCGGATAT
TAACTATACATCAGGCTTCAGAAATTCAGACCGGATTCTTTACTCA
AGCGACTGGCTGATTTACAAAACAACGGACCATTATCAGACCTTTA
CAAAAATCAGATAA

SEQ ID NO. 6 - barnase mutant F106S (DNA)

ATGGCACAGGTTATCAACACGTTTGACGGGGTTGCGGATTATCTTC
AGACATATCATAAGCTACCTGATAATTACATTACAAAATCAGAAGC
ACAAGCCCTCGGCTGGGTGGCATCAAAAGGGAACCTTGCAGACGTC
GCTCCGGGGAAAAGCATCGGCGGAGACATCTTCTCAAACAGGGAAG
GCAAACTCCCGGGCAAAAGCGGACGAACATGGCGTGAAGCGGATAT
TAACTATACATCAGGCTTCAGAAATTCAGACCGGATTCTTTACTCA

AGCGACTGGCTGATTTACAAAACAACGGACCATTATCAGACCTCTA

CAAAAATCAGATAA

SEQ ID NO. 7 - barnase mutant H102E (DNA)

ATGGCACAGGTTATCAACACGTTTGACGGGGTTGCGGATTATCTTC

AGACATATCATAAGCTACCTGATAATTACATTACAAAATCAGAAGC

ACAAGCCCTCGGCTGGGTGGCATCAAAAGGGAACCTTGCAGACGTC

GCTCCGGGGAAAAGCATCGGCGGAGACATCTTCTCAAACAGGGAAG

GCAAACTCCCGGGCAAAAGCGGACGAACATGGCGTGAAGCGGATAT

TAACTATACATCAGGCTTCAGAAATTCAGACCGGATTCTTTACTCA

AGCGACTGGCTGATTTACAAAACAACGGACGAGTATCAGACCTTTA

CAAAAATCAGATAA

SEQ ID NO. 8 - barnase mutant K27A (DNA)

ATGGCACAGGTTATCAACACGTTTGACGGGGTTGCGGATTATCTTC

AGACATATCATAAGCTACCTGATAATTACATTACAGCATCAGAAGC

ACAAGCCCTCGGCTGGGTGGCATCAAAAGGGAACCTTGCAGACGTC

GCTCCGGGGAAAAGCATCGGCGGAGACATCTTCTCAAACAGGGAAG

GCAAACTCCCGGGCAAAAGCGGACGAACATGGCGTGAAGCGGATAT

TAACTATACATCAGGCTTCAGAAATTCAGACCGGATTCTTTACTCA

AGCGACTGGCTGATTTACAAAACAACGGACCATTATCAGACCTTTA

CAAAAATCAGATAA

SEQ ID NO. 9 - barnase mutant E73G (AA)

MetAlaGlnValIleAsnThrPheAspGlyValAlaAspTyrLeuGln

ThrTyrHisLysLeuProAspAsnTyrIleThrLysSerGluAlaGln

AlaLeuGlyTrpValAlaSerLysGlyAsnLeuAlaAspValAlaPro

GlyLysSerIleGlyGlyAspIlePheSerAsnArgGluGlyLysLeu

ProGlyLysSerGlyArgThrTrpArgGlyAlaAspIleAsnTyrThr

SerGlyPheArgAsnSerAspArgIleLeuTyrSerSerAspTrpLeu

IleTyrLysThrThrAspHisTyrGlnThrPheThrLysIleArg

SEQ ID NO. 10 - barnase mutant F106S (AA)

MetAlaGlnValIleAsnThrPheAspGlyValAlaAspTyrLeuGln

ThrTyrHisLysLeuProAspAsnTyrIleThrLysSerGluAlaGln

AlaLeuGlyTrpValAlaSerLysGlyAsnLeuAlaAspValAlaPro

GlyLysSerIleGlyGlyAspIlePheSerAsnArgGluGlyLysLeu

ProGlyLysSerGlyArgThrTrpArgGluAlaAspIleAsnTyrThr

SerGlyPheArgAsnSerAspArgIleLeuTyrSerSerAspTrpLeu

IleTyrLysThrThrAspHisTyrGlnThrSerThrLysIleArg

SEQ ID NO. 11 - barnase mutant H102E (AA)

MetAlaGlnValIleAsnThrPheAspGlyValAlaAspTyrLeuGln

ThrTyrHisLysLeuProAspAsnTyrIleThrLysSerGluAlaGln

AlaLeuGlyTrpValAlaSerLysGlyAsnLeuAlaAspValAlaPro

GlyLysSerIleGlyGlyAspIlePheSerAsnArgGluGlyLysLeu

ProGlyLysSerGlyArgThrTrpArgGluAlaAspIleAsnTyrThr

SerGlyPheArgAsnSerAspArgIleLeuTyrSerSerAspTrpLeu

IleTyrLysThrThrAspGluTyrGlnThrPheThrLysIleArg

SEQ ID NO. 12 - barnase mutant K27A (AA)

MetAlaGlnValIleAsnThrPheAspGlyValAlaAspTyrLeuGln

ThrTyrHisLysLeuProAspAsnTyrIleThrAlaSerGluAlaGln

AlaLeuGlyTrpValAlaSerLysGlyAsnLeuAlaAspValAlaPro

GlyLysSerIleGlyGlyAspIlePheSerAsnArgGluGlyLysLeu

ProGlyLysSerGlyArgThrTrpArgGluAlaAspIleAsnTyrThr

SerGlyPheArgAsnSerAspArgIleLeuTyrSerSerAspTrpLeu

IleTyrLysThrThrAspHisTyrGlnThrPheThrLysIleArg

SEQ ID NO. 13 - PrMC2::Barnase H102E::RNS2TER cassette

TCTCGAGTAAAACATAATTTTGGCAGTAAAAAGTGAATTCTATTGT

TTTGAAAACAAAACAAAATACAGGAAGCGTGATTGTGGGGTTGTTG

TTGAACTTGCCCGGGCAAAAGAAGAATGATTAGCGGTAGAGGAGTT

AGTAGTTACGTTCAACTAAATGCGTGACTAAATTATTTATCCTCCG

CCATGGAAGCAGGTGATTCACACACAACTTGCTGCACACATTGCTC

TCAAACCTTTCCTATAAATATCCGTAGCAGGGGCTGCGATGATACA

CAACGCATTTAATCAAACTACTTTGATTACTTTCTGTGGGTTCTAC

TTTCTTTGAATAGTCAGTTCTGCTGTTTTTAGAAGATTTATGAGAA

TGGCCAAAATTCAGGTATCAAACGGGAACATGGCACAGGTTATCAA

CACGTTTGACGGGGTTGCGGATTATCTTCAGACATATCATAAGCTA

CCTGATAATTACATTACAAAATCAGAAGCACAAGCCCTCGGCTGGG

TGGCATCAAAAGGGAACCTTGCAGACGTCGCTCCGGGGAAAAGCAT

CGGCGGAGACATCTTCTCAAACAGGGAAGGCAAACTCCCGGGCAAA

AGCGGACGAACATGGCGTGAAGCGGATATTAACTATACATCAGGCT

TCAGAAATTCAGACCGGATTCTTTACTCAAGCGACTGGCTGATTTA

CAAAACAACGGACGAGTATCAGACCTTTACAAAAATCAGATAACGA

AAAAAACGGCTTCCCTGCGGGAGGCCGTTTTTTTCAGCTTTACATA

AAGTGTGTAATAAATTTTCTTCAAACTCTGATCGGTCAAGAGCTC

TTCTGAGAGACAATACATACATGTCTCTGATGTTGTAACTTTACTA

CCAAAACCTATAAAGATTGGCTTATTTCGTTCTATTGGATATGTAT

CATCATTACTGGTAAATCAAGTTTCTTTCTAATAATGTAGAAGATC

AGAAAATCCATAAGAAGATATCAACATTTGAGTTCTATGGTAAATT

GAATTATATCAACTTAGTTGCAATGATTCATTCTTGACTGATGCAT

TGATGGCTTATCAAACCAGTTTACAAAATTCGATTAGATAGGGCCC

A

SEQ ID NO. 14 - PrMC2::Barnase K27A::RNS2TER cassette

CTCGAGTAAAACATAATTTTGGCAGTAAAAAGTGAATTCTATTGTT
TTGAAAACAAAACAAAATACAGGAAGCGTGATTGTGGGGTTGTTGT
TGAACTTGCCCGGGCAAAAGAAGAATGATTAGCGGTAGAGGAGTTA
GTAGTTACGTTCAACTAAATGCGTGACTAAATTATTTATCCTCCGC
CATGGAAGCAGGTGATTCACACACAACTTGCTGCACACATTGCTCT
CAAACCTTTCCTATAAATATCCGTAGCAGGGGCTGCGATGATACAC
AACGCATTTAATCAAACTACTTTGATTACTTTCTGTGGGTTCTACT
TTCTTTGAATAGTCAGTTCTGCTGTTTTTAGAAGATTTATGAGAAT
GGCCAAAATTCAGGTATCAAACGGGAACATGGCACAGGTTATCAAC
ACGTTTGACGGGGTTGCGGATTATCTTCAGACATATCATAAGCTAC
CTGATAATTACATTACAGCATCAGAAGCACAAGCCCTCGGCTGGGT
GGCATCAAAAGGGAACCTTGCAGACGTCGCTCCGGGGAAAAGCATC
GGCGGAGACATCTTCTCAAACAGGGAAGGCAAACTCCCGGGCAAAA
GCGGACGAACATGGCGTGAAGCGGATATTAACTATACATCAGGCTT
CAGAAATTCAGACCGGATTCTTTACTCAAGCGACTGGCTGATTTAC
AAAACAACGGACGAGTATCAGACCTTTACAAAAATCAGATAACGAA
AAAAACGGCTTCCCTGCGGGAGGCCGTTTTTTTCAGCTTTACATAA
AGTGTGTAATAAATTTTTCTTCAAACTCTGATCGGTCAAGAGCTCT
TCTGAGAGACAATACATACATGTCTCTGATGTTGTAACTTTACTAC
CAAAACCTATAAAGATTGGCTTATTTCGTTCTATTGGATATGTATC
ATCATTACTGGTAAATCAAGTTTCTTTCTAATAATGTAGAAGATCA
GAAAATCCATAAGAAGATATCAACATTTGAGTTCTATGGTAAATTG
AATTATATCAACTTAGTTGCAATGATTCATTCTTGACTGATGCATT
GATGGCTTATCAAACCAGTTTACAAAATTCGATTAGATAGGGCCC

SEQ ID NO. 15 - PrMC2::Barnase E73G::RNS2TER cassette

CTCGAGTAAAACATAATTTTGGCAGTAAAAAGTGAATTCTATTGTT
TTGAAAACAAAACAAAATACAGGAAGCGTGATTGTGGGGTTGTTGT
TGAACTTGCCCGGGCAAAAGAAGAATGATTAGCGGTAGAGGAGTTA
GTAGTTACGTTCAACTAAATGCGTGACTAAATTATTTATCCTCCGC
CATGGAAGCAGGTGATTCACACACAACTTGCTGCACACATTGCTCT
CAAACCTTTCCTATAAATATCCGTAGCAGGGGCTGCGATGATACAC
AACGCATTTAATCAAACTACTTTGATTACTTTCTGTGGGTTCTACT
TTCTTTGAATAGTCAGTTCTGCTGTTTTTAGAAGATTTATGAGAAT
GGCCAAAATTCAGGTATCAAACGGGAACATGGCACAGGTTATCAAC
ACGTTTGACGGGGTTGCGGATTATCTTCAGACATATCATAAGCTAC
CTGATAATTACATTACAAAATCAGAAGCACAAGCCCTCGGCTGGGT
GGCATCAAAAGGGAACCTTGCAGACGTCGCTCCGGGGAAAAGCATC
GGCGGAGACATCTTCTCAAACAGGGAAGGCAAACTCCCGGGCAAAA
GCGGACGAACATGGCGTGGAGCGGATATTAACTATACATCAGGCTT
CAGAAATTCAGACCGGATTCTTTACTCAAGCGACTGGCTGATTTAC
AAAACAACGGACGAGTATCAGACCTTTACAAAAATCAGATAACGAA
AAAAACGGCTTCCCTGCGGGAGGCCGTTTTTTTCAGCTTTACATAA
AGTGTAATAAATTTTTCTTCAAACTCTGATCGGTCAAGAGCTCT
TCTGAGAGACAATACATACATGTCTCTGATGTTGTAACTTTACTAC
CAAAACCTATAAAGATTGGCTTATTTCGTTCTATTGGATATGTATC
ATCATTACTGGTAAATCAAGTTTCTTTCTAATAATGTAGAAGATCA
GAAAATCCATAAGAAGATATCAACATTTGAGTTCTATGGTAAATTG
AATTATATCAACTTAGTTGCAATGATTCATTCTTGACTGATGCATT
GATGGCTTATCAAACCAGTTTACAAAATTCGATTAGATAGGGCCC

SEQ ID NO. 16 - PrMC2.400-3 promoter

TAAAACATAATTTTGGCAGTAAAAAGTGAATTCTATTGTTTTGAAA
ACAAAACAAAATACAGGAAGCGTGATTGTGGGGTTGTTGTTGAACT
TGCCCGGGCAAAAGAAGAATGATTAGCGGTAGAGGAGTTAGTAGTT
ACGTTCAACTAAATGCGTGACTAAATTATTTATCCTCCGCCATGGA
AGCAGGTGATTCACACACAACTTGCTGCACACATTGCTCTCAAACC
TTTCCTATAAATATCCGTAGCAGGGGCTGCGATGATACACAACGCA
TTTAATCAAACTACTTTGATTACTTTCTGTGGGTTCTACTTTCTTT
GAATAGTCAGTTCTGCTGTTTTTAGAAGATTT

SEQ ID NO. 17 - LPAG1d4

TTCATTCATCCCAAAACCTAAATTTATCCTCTCCATTACTATTACC
TACACCTATACCTAGTAAATATGTCCTGCCTTGTAACTCCTCCACT
GCCTGCACACGTCTTAGTCAATCCATCTGCCTTCAAATAGGCATTA
TTTTGTTCTTTCCCCTCCGACTGAAAGGCTATCGACCGACCGACCG
CTCATCTTCTTCTTCTGCGCAATTTTTTCTGCTGGATCATCATCAT
TACCATCATCGCCATCCCCACCATCATCATCATGATGGTATCTCTA
TCTCTCCCTGGCAATCGATTGTAGAGGAAAGGAAGAGGGAAGGGGC
ATATGTATTGATCAACCTACCCGAAAAAACAATCTGATCAGCCCTG
CTAATCTTGCTTATAAATCTCTTATCCACTGTTCAATCATTCAGGT
TTCTTCCCACTTCCAAGCAAAGGCGCCCGGATTGGCCGTGTTCTTA
GATTTTCAGGTACTTAAATGGACAATATTCCCCACCTGAAGCCGTT
CTGAAAAGATTTGTTTGTAGAAACAAACGATTGTAATATTTGCTT
AAGTTGAGCTTAAGGGGTTTGGTACCTAACTTGCCTTGTGGTTATT
TGTTTCTCAGAACTCGGGCTGCGTCCAACTGTAGGAACGAACCAGC
ACAAGGGGTTGCAGCTTTTGCTGTTGCTGTTGCGCCCATTGCTTTT
GGACTGGTATTAGTAGTTGCAGCTTTGTTTTGCATACGCTGTGAGG
ATCTGTGCGCGGAAATTTTGTGTACAAATC

For the sequences denoted as SEQ ID NOs. 18-26 see FIGS. 1-9 and 13.

What is claimed is:

1. A method for obtaining wood pulp, comprising:
   (a) introducing into a plant cell of a woody plant a construct comprising (i) a *Pinus radiata* AGAMOUS promoter operably linked to
   (ii) a desired nucleic acid encoding an E73G barnase mutant that comprises the sequence of SEQ ID NO: 5 or which comprises a nucleotide sequence that encodes the amino acid sequence of SEQ ID NO: 9;
   (b) culturing said transformed plant cell under conditions that promote growth of a plant; and
   (c) obtaining wood pulp from said plant.

2. A construct, comprising (i) a *Pinus radiata* AGAMOUS promoter operably linked to the sequence of SEQ ID NO: 5, or (ii) the sequence depicted in SEQ ID NOS: 20 or 21.

3. The construct of claim 2, further comprising in part (i) an *Arabidopsis* AGAMOUS floral-specific enhancer (At-AGenh) fused to the 5' end of the promoter, wherein expression of the construct is capable of disrupting reproductive development of at least one reproductive structure in a plant.

4. A transgenic plant, comprising the construct of claim 2 or 3.

5. A transgenic plant, comprising a construct that comprises a *Pinus radiata* AGAMOUS promoter operably linked to a desired nucleic acid that comprises the sequence of SEQ ID NO: 5 or which encodes the amino acid sequence of SEQ ID NO: 9.

6. A method for producing a transgenic plant, comprising:
   (a) transforming a plant cell with a construct that comprises a *Pinus radiata* AGAMOUS promoter operably linked to a desired nucleic acid, wherein said desired nucleic acid has the sequence of SEQ ID NO:5 or encodes the amino acid of SEQ ID NO:9, wherein said promoter regulates the activity of said desired nucleic acid; and
   (b) culturing said transformed plant cell under conditions that promote growth of a plant, wherein said plant is a transgenic plant that exhibits a phenotype that is different from a plant of the same species that does not contain said construct.

7. A construct comprising a *Pinus radiata* AGAMOUS promoter operably linked to a desired nucleic acid that comprises the sequence of SEQ ID NO: 5 or which encodes SEQ ID NO: 9, wherein said promoter regulates the expression of said desired nucleic acid in a plant cell transformed with the construct.

8. A hybrid progeny plant transformed with the construct of claim 2 or 3.

9. The hybrid progeny plant of claim 8, wherein the hybrid progeny plant is obtained from the cross of pitch pine (*Pinus rigida*) with loblolly pine (*Pinus taeda*).

10. A method for producing a transgenic plant, comprising:
    (a) transforming a plant cell with a construct that comprises the sequence of SEQ ID NOS: 20 or 21; and
    (b) culturing the transformed plant cell under conditions that promote growth of a plant, wherein said plant is a transgenic plant that exhibits a phenotype that is different from a plant of the same species that has not been transformed with the construct.

11. The method of claim 1 or 6, wherein the construct further comprises an *Arabidopsis* AGAMOUS floral-specific enhancer (AtAGenh) fused to the 5' end of the promoter, wherein expression of the construct is capable of disrupting reproductive development of at least one reproductive structure in a plant.

12. A nucleic acid encoding an E73G barnase mutant that comprises the sequence of SEQ ID NO: 5 or which comprises a nucleotide sequence that encodes the amino acid sequence of SEQ ID NO: 9.

* * * * *

SEQUENCE LISTING

<160> NUMBER OF SEQ ID NOS: 52

<210> SEQ ID NO 1
<211> LENGTH: 1395
<212> TYPE: DNA
<213> ORGANISM: Pinus taeda

<400> SEQUENCE: 1

| | | | | | |
|---|---|---|---|---|---|
| cagcaaatat | gatttagatt | atgacctaga | aataagcata | gcattaaagc | atatacaaaa | 60 |
| caagcggtga | tatactctga | ctgccactgt | acttgaggaa | aggtagtgga | ctctgctcag | 120 |
| gtacattagt | ttggtaaggt | tggcttggct | tctgggtaat | atgagaagta | aagaagtaaa | 180 |
| aggtatttga | ctctagtcaa | gtacattgga | ttgccttcgt | cggggcttgg | atggcttggg | 240 |
| ttcgtgtgag | aagccaacaa | tttataaaaa | aatatattga | aaaaaaaaaa | aatcgtctaa | 300 |
| gtgttggaag | tgaaaacggt | gggacataaa | tatacacaga | agagtacttt | aacaatgcgc | 360 |
| aaccaaggca | gattcacaac | ttgatttctg | gacctcgaat | acgagataat | ggtggtaaga | 420 |
| aataaaggaa | gagtggagtg | catttgaaaa | tgaatggaga | gcgcacaaaa | tggaggacga | 480 |
| ataaatgaaa | tataatgcaa | gagtgcattt | ccctattatt | tccagaaatg | tatatgtggg | 540 |
| gtcggcattc | acatgggcgt | cgcattcagg | gggtgtcata | gcggtccttt | gattgcagtg | 600 |
| tgggagttgc | aacatgtacc | aacaaattca | ttcatcccaa | aacctaaatt | tatcctctcc | 660 |
| attactatta | cctacaccta | tacctagtaa | atatgtcctg | ccttgtaact | cctccactgc | 720 |
| ctgcacacgt | cttagtcaat | ccatctgcct | tcaaataggc | attattttgt | tctttcccct | 780 |
| ccgactgaaa | ggctatcgac | cgaccgaccg | ctcatcttct | tcttctgcgc | aattttttct | 840 |
| gctggatcat | catcattacc | atcatcgcca | tccccaccat | catcatcatg | atggtatctc | 900 |
| tatctctccc | tggcaatcga | ttgtagagga | aaggaagagg | gaaggggcat | atgtattgat | 960 |
| caacctaccc | gaaaaaacaa | tctgatcagc | cctgctaatc | ttgcttataa | atctcttatc | 1020 |
| cactgttcaa | tcattcaggt | ttcttcccac | ttccaagcaa | aggcgcccgg | attggccgtg | 1080 |
| ttcttagatt | ttcaggtact | taaatggaca | atattcccca | cctgaagccg | ttctgaaaaa | 1140 |
| gatttgtttg | tagaaacaaa | cgattgtaat | atttgcttaa | gttgagctta | aggggtttgg | 1200 |
| tacctaactt | gccttgtggt | tatttgtttc | tcagaactcg | ggctgcgtcc | aactgtagga | 1260 |
| acgaaccagc | acaaggggtt | gcagcttttg | ctgttgctgt | tgcgcccatt | gcttttggac | 1320 |
| tggtattagt | agttgcagct | ttgttttgca | tacgctgtga | ggatctgtgc | gcggaaattt | 1380 |
| tgtgtacaaa | tcatg | | | | | 1395 |

<210> SEQ ID NO 2
<211> LENGTH: 1385
<212> TYPE: DNA
<213> ORGANISM: Pinus taeda

<400> SEQUENCE: 2

| | | | | | |
|---|---|---|---|---|---|
| cagcaaatat | gatttagatt | atgacctaga | aataagcata | gcattaaagc | atatacataa | 60 |
| caagcggtga | tatactctga | ctgccactgt | acttgatgaa | aggtagtgga | ctctgctcag | 120 |
| gtacattagt | ttggtaaggt | tggcttggct | tctgggtaat | atgagaagta | aagaagtaaa | 180 |
| aggtatttga | ctctagtcaa | gtacattgga | ttgcctttgt | cggggcttgg | atggcttggg | 240 |
| ttcgtgtgag | aagccaacaa | tttataataa | aaataaaata | aaaatcgaa | gtgttggaag | 300 |
| tgaaaacggt | ggggcataaa | tatacacaga | agagtacttt | aacaatgcgc | aaccaaggca | 360 |

-continued

```
gattcacaac ttgatttctg gacctcgaat acgagataat ggtggtaaga aataaaggaa      420
gagtggagtg catttgaaaa tgaatggaga gcgcacaaaa tggaggacga ataaatgaaa      480
tataatgcaa gagtgcattt ccctattatt tccagaaatg tatatgtggg gtcggcattc      540
acatgggcgt cgcattcagg gggtgtcata gcggtccttt gattgcagtg tgggagttgc      600
aacatgtacc aacaaattca ttcatcccaa aacctaaatt tatcctctcc attactatta      660
cctacaccta tacctagtaa atatgtcctg ccttgtaact cctccactgc ctgcacacgt      720
cttagtcaat ccatctgcct tcaaataggc attattttgt tctttcccct ccgactgaaa      780
ggctatcgac cgaccgaccg ctcatcttct tcttctgcgc aattttttct gctggatcat      840
catcattacc atcatcgcca tccccaccat catcatcatg atggtatctc tatctctccc      900
tggcaatcga ttgtagagga aggaagagg gaagggcat atgtattgat caacctaccc       960
gaaaaaacaa tctgatcagc cctgctaatc ttgcttataa atctcttatc cactgttcaa     1020
tcattcaggt ttcttcccac tttcaagcaa aggcgcccgg attggccgtg ttcttagatt     1080
ttcaggtact aaatggaca atattcccca cctgaagccg ttctgaaaaa gatttgtttg      1140
tagaaacaaa cgattgtaat atttgcttaa gttgagctta aggggtttgg tacctaactt     1200
gccttgtggt tatttgtttc tcagaactcg ggctgcgtcc aactgtagga acgaaccagc     1260
acaaggggtt gcagcttttg ctgttgctgt tgcgcccatt gcttttggac tggtattagt     1320
agttgcagct ttgttttgca tacgctgtga ggatctgtgc gcggaaattt tgtgtacaaa     1380
tcatg                                                                 1385
```

<210> SEQ ID NO 3
<211> LENGTH: 4172
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 3

```
gatagggtca atcgaccac ttgcacagtt aagtgattct aatacgaaac cttaaaagca       60
aacatcggtt cttttgagtc agaagaaatg caacttaatg tgacacatga tgtgaagaaa      120
aaacaaaagt aatataagaa aagggaacaa ttaaatagtt aataaaatat ttccttaaag      180
ttgtaacaaa taagaatca ttttatgaaa caatatgaac cctaaataaa ttaaaattcc       240
tctgaaacct taaatttatc gagctagtga ttggctgcca actgccatgc tggcaaaatt      300
agagtgacat gattggtctg aacatgtcta gggtttcaga catgtgacat gtgtcaacaa      360
cccattaaca cattgggtat aaatccaata gacatttgat agtattaaaa ttgtaaccat      420
tggattaaat ttaaacgtga tggatgtaac taaatgactt gtccgagtaa catcacaacg      480
ttccatactt tccttatttg aatataatt aaatttacca tttattcttt ttcttgagt        540 ttcctgtata tgtacttgta catagatata tatgcacaaa tacgtattac aatgacatat      600
tatagacttt gatgtctgaa ctctcaacct tctcgatgga gagatcatga ccgtagattt      660
ttttggatcg tagaaggcag accaaactct taaactattg gatccggact aaaaatctca     720 cttcctctc agtacccata atgagagaga aatgataaa atccctaac attattctct         780 ctctagaaaa aaaaagatac ttcaaaaga agagaaatt gcataaatct atctacacca        840
aagatgttga agcaattcca atgctatact tctatgccaa atctatttat tcagtgatca     900
ttaatctttt tacttccaag aaatatgaac aatttagtat ccttataatt tttgtctcta     960
```

```
tatatgtaat atgaacattg ggtattgacc aaatgagaaa tctaatatta aatggtcaaa    1020
agtagtaata tgatgacatt tttgaattta aaataggtt acaaattaat tcattatgac     1080
ataaaacctt cttgtcagaa gtcaagaact gaaactaaca aaactttata ataaattagt    1140
aaaaatacaa atgaaaaata aaagaaata atatctgagt gatgacgtga tcaaagattc     1200
tttaacaaag acaacaaatc ttacagaccc aaaacctaat cttgcgctca attccaacct    1260
ctgaaaaaac ctcaaaaatc ttataaaaga aataaataa agaaacgaaa ctctgatttc     1320
gtagagtacc catcggatat ataaaaagaa attagtaggg aaatgaagac taattttgat    1380
tgactgattt aatttgaagt cgttgttagc ttttcttgtt ttggacatga gaattatata    1440
tttcaggaca tgagagttga caactgtaaa cgattaagaa aattgatctt ttaattttca    1500
aacaccattt aatcttgaca tgttttatgt tttggtggag aagaaagtaa tcacgtggga    1560
ctctctacta ataagtattt ggaaattgcg tgtcgaatta gagattacta gtttgagtaa    1620
tgtagttcga aatgagatta gttatttta attttaaaaa gagtaatttt aaggaataac    1680
aaaaaagagt ccccataagc taatttgtct taattacctc cttgtttcat tgactatttg    1740
aaatcttgaa aattcagttg aaatttcaaa tctatgtttc ttttgaccac ttctaaacta    1800
atcttagctc atatataatt ttccaaaact acaaaaataa cactaacatt taacattctc    1860
aagagaaaac aaaaacaaaa acttagataa ccatctaaat tgtcctacat gtacgtataa    1920
gttccattat tttctatcac tcatataagt taaaatttca tgaaaactca aaaatctagc    1980
tagtttcacc ttattcactc tcacttacca tcacatgtgt ttgtatcaaa tatatgatat    2040
gatataattc atgagagaga aagagagcta gagataagaa aggaaagtaa gagaaagaag    2100
agaagaaaaa gagagacaca gacattaaca acaatggagg atggatgatc acaaaacaga    2160
agatatgacc tcatagtcct tccttactct ctccccaatt tgtttcccaa aacttacttt    2220
tatagtcata aaaatcaagt tttacctat tacaacacca gatctataaa tatatctaaa    2280
tcttcaagta cttgttagta aggaaaatag aaagatataa gattttatta ttattataat    2340
aacagaaatg agtgaagaaa gaacacccaa caaagtgaat cttagttcta caaaactgaa    2400
tctaaaactc cacattagaa aaaaccctga tggtttctta tttctttca tttattatct    2460 aactctcact cagatctcct ttaactttgt accatttccc tcacttcata tatctatata    2520
taacaaactc tctctttta tttaagtctt aagggaaaat taatatacac atgaagaaca    2580
agaaattaga tctacaaaat tgttacaaaa accccgaag taaataaaat aaacatatca    2640
aacaaatatt cccactaatg ttagtgtgtt tatatatata tgtgtgtgga atatgaagga    2700
aaaaagtgaa aaataatcct acccataaga gcattcaaga agaagctcga ggtcgacggt    2760
atcgataagc ttaaactcga cagcaaatat gatttagatt atgacctaga aataagcata    2820
gcattaaagc atatacataa caagcggtga tatactctga ctgccactgt acttgaggaa    2880
aggtagtgga ctctgctcag gtacattagt ttggtaaggt tggcttggct tctgggtaat    2940
atgagaagta aagaagtaaa aggtatttga ctctagtcaa gtacattgga ttgcctttgt    3000
cggggcttgg atggcttggg ttcgtgtgag aagccaacaa tttataagaa atatataaaa    3060
taaaaaataa aaaatttaa gtgttggaag tgaaaacggt ggggcagaaa tatacacaga    3120
agagtacttt aacaatgcgc aaccaaggca gattcacaac ttgatttctg gacctcgaat    3180
acgagataat ggtggtaaga aataaaggaa gagtggagcg catttgaaaa tgaatggaga    3240
gcgcacaaaa tggaggacga ataaatgaaa tataatgcaa gggtgcattt ccctattatt    3300
```

```
tccagaaatg tatatgtggg gtcggcattc tcatgggcgt cgcattcagg gggtgtcata    3360
gcggtccttt gattgcagtg tgggagttgc aacatgtacc aacaaatcca ttcatcccaa    3420
aacctaaatt tatcctctcc attactatta cctacaccta tacctagtaa atatgtcctg    3480
ccttgtaact cctccactgc ctgcacacgt cttagtcaat ccatctgcct tcaaataggc    3540
attattttgt tctttcccct ccgactgaaa ggctatcgac cgaccgaccg ctcatcttct    3600
tcttctgcgc aattttttct gctggatcat catcattacc atcatcgcca tccccaccat    3660
catcatcatg atggtatctc tatctctccc tggcaatcga ttgtagagga aggaagagg     3720 gaaggggcat atgtattgat caacctaccc gaaaaaacaa tctgatcagc cctgctaatc    3780
ttgcttataa atctcttatc cactgttcaa tcattcaggt ttcttcccac tttcaagcaa    3840
aggcgcccgg attggccgtg ttcttagatt ttcaggtact taaatggaca atattcccca    3900
cctgaagccg ttctgaaaaa gatttgtttg tagaaacaaa cgattgtaat atttgcttaa    3960
gttgagctta aggggtttgg tacctaactt gccttgtggt tatttgtttc tcagaactcg    4020
ggctgcgtcc aactgtagga acgaaccagc acaaggggtt gcagcttttg ctgttgctgt    4080
tgcgcccatt gcttttggac tggtattagt agttgcagct ttgttttgca tacgctgtga    4140
ggatctgtgc gcggaaattt tgtgtacaaa tc                                  4172

<210> SEQ ID NO 4
<211> LENGTH: 396
<212> TYPE: DNA
<213> ORGANISM: Pinus radiata

<400> SEQUENCE: 4
ctcgagtaaa acataatttt ggcagtaaaa agtgaattct attgttttga aaacaaaaca     60
aaatacagga agcgtgattg tggggttgtt gttgaacttg cccgggcaaa agaagaatga    120
ttagcggtag aggagttagt agttacgttc aactaaatgc gtgactaaat tatttatcct    180
ccgccatgga agcaggtgat tcacacacaa cttgctgcac acattgctct caaacctttc    240
ctataaatat ccgtagcagg ggctgcgatg atacacaacg catttaatca aactactttg    300
attactttct gtgggttcta ctttctttga atagtcagtt ctgctgtttt tagaagattt    360
atgagaatgg ccaaaattca ggtatcaaac gggaac                              396

<210> SEQ ID NO 5
<211> LENGTH: 336
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 5
atggcacagg ttatcaacac gtttgacggg gttgcggatt atcttcagac atatcataag     60
ctacctgata attacattac aaaatcagaa gcacaagccc tcggctgggt ggcatcaaaa    120
gggaaccttg cagacgtcgc tccggggaaa agcatcggcg gagacatctt ctcaaacagg    180
gaaggcaaac tcccgggcaa aagcggacga acatggcgtg gagcggatat taactataca    240
tcaggcttca gaaattcaga ccggattctt tactcaagcg actggctgat ttacaaaaca    300
acggaccatt atcagacctt tacaaaaatc agataa                              336

<210> SEQ ID NO 6
<211> LENGTH: 336
<212> TYPE: DNA
```

<213> ORGANISM: Artificial Sequence
<220> FEATURE:
<223> OTHER INFORMATION: Description of Artificial Sequence: Synthetic
       construct

<400> SEQUENCE: 6
atggcacagg ttatcaacac gtttgacggg gttgcggatt atcttcagac atatcataag      60
ctacctgata attacattac aaaatcagaa gcacaagccc tcggctgggt ggcatcaaaa     120
gggaaccttg cagacgtcgc tccggggaaa agcatcggcg agacatctt ctcaaacagg      180 gaaggcaaac tcccgggcaa aagcggacga acatggcgtg aagcggatat taactataca     240
tcaggcttca gaaattcaga ccggattctt tactcaagcg actggctgat ttacaaaaca     300
acggaccatt atcagacctc tacaaaaatc agataa                              336

<210> SEQ ID NO 7
<211> LENGTH: 336
<212> TYPE: DNA
<213> ORGANISM: Artificial Sequence
<220> FEATURE:
<223> OTHER INFORMATION: Description of Artificial Sequence: Synthetic
       construct

<400> SEQUENCE: 7
atggcacagg ttatcaacac gtttgacggg gttgcggatt atcttcagac atatcataag      60
ctacctgata attacattac aaaatcagaa gcacaagccc tcggctgggt ggcatcaaaa     120
gggaaccttg cagacgtcgc tccggggaaa agcatcggcg agacatctt ctcaaacagg      180 gaaggcaaac tcccgggcaa aagcggacga acatggcgtg aagcggatat taactataca     240
tcaggcttca gaaattcaga ccggattctt tactcaagcg actggctgat ttacaaaaca     300
acggacgagt atcagacctt tacaaaaatc agataa                              336

<210> SEQ ID NO 8
<211> LENGTH: 336
<212> TYPE: DNA
<213> ORGANISM: Artificial Sequence
<220> FEATURE:
<223> OTHER INFORMATION: Description of Artificial Sequence: Synthetic
       construct

<400> SEQUENCE: 8
atggcacagg ttatcaacac gtttgacggg gttgcggatt atcttcagac atatcataag      60
ctacctgata attacattac agcatcagaa gcacaagccc tcggctgggt ggcatcaaaa     120
gggaaccttg cagacgtcgc tccggggaaa agcatcggcg agacatctt ctcaaacagg      180 gaaggcaaac tcccgggcaa aagcggacga acatggcgtg aagcggatat taactataca     240
tcaggcttca gaaattcaga ccggattctt tactcaagcg actggctgat ttacaaaaca     300
acggaccatt atcagacctt tacaaaaatc agataa                              336

<210> SEQ ID NO 9
<211> LENGTH: 111
<212> TYPE: PRT
<213> ORGANISM: Artificial Sequence
<220> FEATURE:
<223> OTHER INFORMATION: Description of Artificial Sequence: Synthetic
       construct

<400> SEQUENCE: 9

Met Ala Gln Val Ile Asn Thr Phe Asp Gly Val Ala Asp Tyr Leu Gln
 1               5                  10                  15

```
Thr Tyr His Lys Leu Pro Asp Asn Tyr Ile Thr Lys Ser Glu Ala Gln
            20                  25                  30

Ala Leu Gly Trp Val Ala Ser Lys Gly Asn Leu Ala Asp Val Ala Pro
        35                  40                  45

Gly Lys Ser Ile Gly Gly Asp Ile Phe Ser Asn Arg Glu Gly Lys Leu
    50                  55                  60

Pro Gly Lys Ser Gly Arg Thr Trp Arg Gly Ala Asp Ile Asn Tyr Thr
 65                 70                  75                  80

Ser Gly Phe Arg Asn Ser Asp Arg Ile Leu Tyr Ser Ser Asp Trp Leu
                85                  90                  95

Ile Tyr Lys Thr Thr Asp His Tyr Gln Thr Phe Thr Lys Ile Arg
            100                 105                 110

<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 10

Met Ala Gln Val Ile Asn Thr Phe Asp Gly Val Ala Asp Tyr Leu Gln
 1               5                  10                  15

Thr Tyr His Lys Leu Pro Asp Asn Tyr Ile Thr Lys Ser Glu Ala Gln
            20                  25                  30

Ala Leu Gly Trp Val Ala Ser Lys Gly Asn Leu Ala Asp Val Ala Pro
        35                  40                  45

Gly Lys Ser Ile Gly Gly Asp Ile Phe Ser Asn Arg Glu Gly Lys Leu
    50                  55                  60

Pro Gly Lys Ser Gly Arg Thr Trp Arg Glu Ala Asp Ile Asn Tyr Thr
 65                 70                  75                  80

Ser Gly Phe Arg Asn Ser Asp Arg Ile Leu Tyr Ser Ser Asp Trp Leu
                85                  90                  95

Ile Tyr Lys Thr Thr Asp His Tyr Gln Thr Ser Thr Lys Ile Arg
            100                 105                 110

<210> SEQ ID NO 11
<211> LENGTH: 111
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 11

Met Ala Gln Val Ile Asn Thr Phe Asp Gly Val Ala Asp Tyr Leu Gln
 1               5                  10                  15

Thr Tyr His Lys Leu Pro Asp Asn Tyr Ile Thr Lys Ser Glu Ala Gln
            20                  25                  30

Ala Leu Gly Trp Val Ala Ser Lys Gly Asn Leu Ala Asp Val Ala Pro
        35                  40                  45

Gly Lys Ser Ile Gly Gly Asp Ile Phe Ser Asn Arg Glu Gly Lys Leu
    50                  55                  60

Pro Gly Lys Ser Gly Arg Thr Trp Arg Glu Ala Asp Ile Asn Tyr Thr
 65                 70                  75                  80

Ser Gly Phe Arg Asn Ser Asp Arg Ile Leu Tyr Ser Ser Asp Trp Leu
                85                  90                  95
```

```
Ile Tyr Lys Thr Thr Asp Glu Tyr Gln Thr Phe Thr Lys Ile Arg
            100                 105                 110
```

<210> SEQ ID NO 12
<211> LENGTH: 111
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 12

```
Met Ala Gln Val Ile Asn Thr Phe Asp Gly Val Ala Asp Tyr Leu Gln
 1               5                  10                  15

Thr Tyr His Lys Leu Pro Asp Asn Tyr Ile Thr Ala Ser Glu Ala Gln
                20                  25                  30

Ala Leu Gly Trp Val Ala Ser Lys Gly Asn Leu Ala Asp Val Ala Pro
            35                  40                  45

Gly Lys Ser Ile Gly Gly Asp Ile Phe Ser Asn Arg Glu Gly Lys Leu
        50                  55                  60

Pro Gly Lys Ser Gly Arg Thr Trp Arg Glu Ala Asp Ile Asn Tyr Thr
 65                  70                  75                  80

Ser Gly Phe Arg Asn Ser Asp Arg Ile Leu Tyr Ser Ser Asp Trp Leu
                85                  90                  95

Ile Tyr Lys Thr Thr Asp His Tyr Gln Thr Phe Thr Lys Ile Arg
            100                 105                 110
```

<210> SEQ ID NO 13
<211> LENGTH: 1105
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 13

```
tctcgagtaa aacataatttt tggcagtaaa aagtgaattc tattgttttg aaaacaaaac    60
aaaatacagg aagcgtgatt gtggggttgt tgttgaactt gcccgggcaa aagaagaatg   120
attagcggta gaggagttag tagttacgtt caactaaatg cgtgactaaa ttatttatcc   180
tccgccatgg aagcaggtga ttcacacaca acttgctgca cacattgctc tcaaaccttt   240
cctataaata tccgtagcag gggctgcgat gatacacaac gcatttaatc aaactacttt   300
gattactttc tgtgggttct actttctttg aatagtcagt tctgctgttt ttagaagatt   360
tatgagaatg gccaaaattc aggtatcaaa cgggaacatg gcacaggtta tcaacacgtt   420
tgacggggtt gcggattatc ttcagacata tcataagcta cctgataatt acattacaaa   480
atcagaagca caagccctcg gctgggtggc atcaaaaggg aaccttgcag acgtcgctcc   540
ggggaaaagc atcggcggag acatcttctc aaacaggaa ggcaaactcc cgggcaaaag   600
cggacgaaca tggcgtgaag cggatattaa ctatacatca ggcttcagaa attcagaccg   660
gattctttac tcaagcgact ggctgattta caaacaacg gacgagtatc agacctttac   720
aaaaatcaga taacgaaaaa aacggcttcc ctgcgggagg ccgtttttt cagctttaca   780 taaagtgtgt aataaatttt tcttcaaact ctgatcggtc aagagctctt ctgagagaca   840
atacatacat gtctctgatg ttgtaacttt actaccaaaa cctataaaga ttggcttatt   900
tcgttctatt ggatatgtat catcattact ggtaaatcaa gtttctttct aataatgtag   960
aagatcagaa aatccataag aagatatcaa catttgagtt ctatggtaaa ttgaattata  1020
```

```
tcaacttagt tgcaatgatt cattcttgac tgatgcattg atggcttatc aaaccagttt    1080
acaaaattcg attagatagg gccca                                          1105

<210> SEQ ID NO 14
<211> LENGTH: 1103
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 14
ctcgagtaaa acataatttt ggcagtaaaa agtgaattct attgttttga aaacaaaaca     60
aaatacagga agcgtgattg tggggttgtt gttgaacttg cccgggcaaa agaagaatga    120
ttagcggtag aggagttagt agttacgttc aactaaatgc gtgactaaat tatttatcct    180
ccgccatgga agcaggtgat tcacacacaa cttgctgcac acattgctct caaacctttc    240
ctataaatat ccgtagcagg ggctgcgatg atacacaacg catttaatca aactactttg    300
attactttct gtgggttcta ctttctttga atagtcagtt ctgctgtttt tagaagattt    360
atgagaatgg ccaaaattca ggtatcaaac gggaacatgg cacaggttat caacacgttt    420
gacggggttg cggattatct tcagacatat cataagctac ctgataatta cattacagca    480
tcagaagcac aagccctcgg ctgggtggca tcaaaggga accttgcaga cgtcgctccg     540
gggaaaagca tcggcggaga catcttctca acaggaag gcaaactccc ggcaaaagc      600 ggacgaacat ggcgtgaagc ggatattaac tatacatcag gcttcagaaa ttcagaccgg    660
attctttact caagcgactg gctgattac aaaacaacgg acgagtatca gcctttaca     720 aaaatcagat aacgaaaaaa acggcttccc tgcgggaggc cgttttttc agctttacat     780 aaagtgtgta ataatttttt cttcaaactc tgatcggtca agagctcttc tgagagacaa    840
tacatacatg tctctgatgt tgtaacttta ctaccaaaac ctataaagat tggcttattt    900
cgttctattg gatatgtatc atcattactg gtaaatcaag tttctttcta ataatgtaga    960
agatcagaaa atccataaga agatatcaac atttgagttc tatggtaaat tgaattatat   1020
caacttagtt gcaatgattc attcttgact gatgcattga tggcttatca aaccagttta   1080
caaaattcga ttagatagg ccc                                            1103

<210> SEQ ID NO 15
<211> LENGTH: 1103
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 15
ctcgagtaaa acataatttt ggcagtaaaa agtgaattct attgttttga aaacaaaaca     60
aaatacagga agcgtgattg tggggttgtt gttgaacttg cccgggcaaa agaagaatga    120
ttagcggtag aggagttagt agttacgttc aactaaatgc gtgactaaat tatttatcct    180
ccgccatgga agcaggtgat tcacacacaa cttgctgcac acattgctct caaacctttc    240
ctataaatat ccgtagcagg ggctgcgatg atacacaacg catttaatca aactactttg    300
attactttct gtgggttcta ctttctttga atagtcagtt ctgctgtttt tagaagattt    360
atgagaatgg ccaaaattca ggtatcaaac gggaacatgg cacaggttat caacacgttt    420
```

-continued

| | |
|---|---|
| gacggggttg cggattatct tcagacatat cataagctac ctgataatta cattacaaaa | 480 |
| tcagaagcac aagccctcgg ctgggtggca tcaaaaggga accttgcaga cgtcgctccg | 540 |
| gggaaaagca tcgcggaga catcttctca acagggaag gcaaactccc gggcaaaagc | 600 |
| ggacgaacat ggcgtggagc ggatattaac tatacatcag gcttcagaaa ttcagaccgg | 660 |
| attcttact caagcgactg gctgattac aaaacaacgg acgagtatca gacctttaca | 720 |
| aaaatcagat aacgaaaaaa acggcttccc tgcgggaggc cgtttttttc agctttacat | 780 |
| aaagtgtgta ataaatttt cttcaaactc tgatcggtca agagctcttc tgagagacaa | 840 |
| tacatacatg tctctgatgt tgtaaccttta ctaccaaaac ctataaagat tggcttattt | 900 |
| cgttctattg gatatgtatc atcattactg gtaaatcaag tttctttcta ataatgtaga | 960 |
| agatcagaaa atccataaga agatatcaac atttgagttc tatggtaaat tgaattatat | 1020 |
| caacttagtt gcaatgattc attcttgact gatgcattga tggcttatca aaccagttta | 1080 |
| caaaattcga ttagatagg ccc | 1103 |

<210> SEQ ID NO 16
<211> LENGTH: 354
<212> TYPE: DNA
<213> ORGANISM: Pinus radiata

<400> SEQUENCE: 16

| | |
|---|---|
| taaaacataa ttttggcagt aaaaagtgaa ttctattgtt ttgaaaacaa acaaaatac | 60 |
| aggaagcgtg attgtggggt tgttgttgaa cttgcccggg caaagaaga atgattagcg | 120 |
| gtagaggagt tagtagttac gttcaactaa atgcgtgact aaattattta tcctccgcca | 180 |
| tggaagcagg tgattcacac acaacttgct gcacacattg ctctcaaacc tttcctataa | 240 |
| atatccgtag caggggctgc gatgatacac aacgcattta atcaaactac tttgattact | 300 |
| ttctgtgggt tctactttct ttgaatagtc agttctgctg tttttagaag attt | 354 |

<210> SEQ ID NO 17
<211> LENGTH: 766
<212> TYPE: DNA
<213> ORGANISM: Artificial Sequence
<220> FEATURE:
<223> OTHER INFORMATION: Description of Artificial Sequence: Synthetic construct

<400> SEQUENCE: 17

| | |
|---|---|
| ttcattcatc ccaaaaccta aatttatcct ctccattact attacctaca cctataccta | 60 |
| gtaaatatgt cctgccttgt aactcctcca ctgcctgcac acgtcttagt caatccatct | 120 |
| gccttcaaat aggcattatt tgttctttc ccctccgact gaaaggctat cgaccgaccg | 180 |
| accgctcatc ttcttcttct gcgcaatttt ttctgctgga tcatcatcat taccatcatc | 240 |
| gccatcccca ccatcatcat catgatggta tctctatctc tccctggcaa tcgattgtag | 300 |
| aggaaaggaa gagggaaggg gcatatgtat tgatcaacct acccgaaaaa acaatctgat | 360 |
| cagccctgct aatcttgctt ataaatctct tatccactgt tcaatcattc aggtttcttc | 420 |
| ccacttccaa gcaaaggcgc ccggattggc cgtgttctta gattttcagg tacttaaatg | 480 |
| gacaatattc cccacctgaa gccgttctga aaaagatttg tttgtagaaa caaacgattg | 540 |
| taatatttgc ttaagttgag cttaagggg ttggtaccta acttgccttg tggttatttg | 600 |
| tttctcagaa ctcgggctgc gtccaactgt aggaacgaac cagcacaagg ggttgcagct | 660 |
| tttgctgttg ctgttgcgcc cattgctttt ggactggtat tagtagttgc agctttgttt | 720 | tgcatacgct gtgaggatct gtgcgcggaa attttgtgta caaatc          766

<210> SEQ ID NO 18
<211> LENGTH: 8006
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 18
cgccggcgtt gtggatacct cgcggaaaac ttggccctca ctgacagatg aggggcggac    60
gttgacactt gaggggccga ctcacccggc gcggcgttga cagatgaggg gcaggctcga   120
tttcggccgg cgacgtggag ctggccagcc tcgcaaatcg gcgaaaacgc ctgattttac   180
gcgagtttcc cacagatgat gtggacaagc ctggggataa gtgccctgcg gtattgacac   240
ttgaggggcg cgactactga cagatgaggg gcgcgatcct tgacacttga ggggcagagt   300
gctgacagat gaggggcgca cctattgaca tttgaggggc tgtccacagg cagaaaatcc   360
agcatttgca agggtttccg cccgtttttc ggccaccgct aacctgtctt ttaacctgct   420
tttaaaccaa tatttataaa ccttgttttt aaccagggct gcgccctgtg cgcgtgaccg   480
cgcacgccga agggggtgc ccccccttct cgaaccctcc cggcccgcta acgcgggcct   540
cccatccccc caggggctgc gccctcggc cgcgaacggc ctcaccccaa aaatggcagc   600
gctggcagtc cataattgtg gtccaatttg cagccgtccg agacaggagg acatcgtcca   660
gctgaaaccg gggcagaatc cggccatttc tgaagagaaa aatggtaaac tgatagaata   720
aaatcataag aaaggagccg cacatgaaaa aagcagtcat taacggggaa caaatcagaa   780
gtatcagcga cctccaccag acattgaaaa aggagcttgc ccttccggaa tactacggtg   840
aaaacctgga cgctttatgg gattgtctga ccggatgggt ggagtacccg ctcgttttgg   900
aatggaggca gtttgaacaa gcaagcagc tgactgaaaa tggcgccgag agtgtgcttc   960
aggttttccg tgaagcgaaa gcggaaggct gcgacatcac catcatactt tcttaatacg  1020
atcaatggga gaggaacaat atggaaacac aaaccacaat tgtggtttca aaatcggctc  1080
cgtcgatact atgttatacg ccaactttga aaacaacttt gaaaagctg ttttctggta  1140 tttaaggttt tagaatgcaa ggaacagtga attggagttc gtcttgttat aattagcttc  1200
ttggggtatc tttaaatact gtagaaaaga ggaaggaaat aataaatggc taaaatgaga  1260
atatcaccgg aattgaaaaa actgatcgaa aaataccgct gcgtaaaaga tacggaagga  1320
atgtctcctg ctaaggtata aagctggtg ggagaaaatg aaaacctata tttaaaaatg  1380
acggacagcc ggtataaagg gaccacctat gatgtggaac gggaaaagga catgatgcta  1440
tggctggaag gaaagctgcc tgttccaaag gtcctgcact ttgaacggca tgatggctgg  1500
agcaatctgc tcatgagtga ggccgatggc gtcctttgct cggaagagta tgaagatgaa  1560
caaagccctg aaaagattat cgagctgtat gcggagtgca tcaggctctt tcactccatc  1620
gacatatcgg attgtcccta tacgaatagc ttagacagcc gcttagccga attggattac  1680
ttactgaata acgatctggc cgatgtggat tgcgaaaact gggaagaaga cactccattt  1740
aaagatccgc gcgagctgta tgatttttta aagacgaaa agcccgaaga ggaacttgtc  1800
ttttcccacg gcgacctggg agacagcaac atctttgtga agatggcaa agtaagtggc  1860 tttattgatc ttgggagaag cggcagggcg acaagtggt atgacattgc cttctgcgtc  1920
cggtcgatca gggaggatat cggggaagaa cagtatgtcg agctattttt tgacttactg  1980

```
gggatcaagc ctgattggga gaaaataaaa tattatattt tactggatga attgttttag    2040
tacctagatg tggcgcaacg atgccggcga caagcaggag cgcaccgact tcttccgcat    2100
caagtgtttt ggctctcagg ccgaggccca cggcaagtat ttgggcaagg ggtcgctggt    2160
attcgtgcag ggcaagattc ggaataccaa gtacgagaag gacggccaga cggtctacgg    2220
gaccgacttc attgccgata aggtggatta tctggacacc aaggcaccag gcgggtcaaa    2280
tcaggaataa gggcacattg cccccggcgtg agtcggggca atcccgcaag gagggtgaat    2340
gaatcggacg tttgaccgga aggcatacag gcaagaactg atcgacgcgg ggttttccgc    2400
cgaggatgcc gaaaccatcg caagccgcac cgtcatgcgt gcgccccgcg aaaccttcca    2460
gtccgtcggc tcgatggtcc agcaagctac ggccaagatc gagcgcgaca gcgtgcaact    2520
ggctcccccct gccctgcccg cgccatcggc cgccgtggac cgttcgcgtc gtctcgaaca    2580
ggaggcggca ggtttggcga agtcgatgac catcgacacg cgaggaacta tgacgaccaa    2640
gaagcgaaaa accgccggcg aggacctggc aaaacaggtc agcgaggcca agcaggccgc    2700
gttgctgaaa cacacgaagc agcagatcaa ggaaatgcag cttttccttgt tcgatattgc    2760
gccgtggccg gacacgatgc gagcgatgcc aaacgacacg gcccgctctg ccctgttcac    2820
cacgcgcaac aagaaaatcc cgcgcgaggc gctgcaaaac aaggtcattt tccacgtcaa    2880
caaggacgtg aagatcacct acaccggcgt cgagctgcgg gccgacgatg acgaactggt    2940
gtggcagcag gtgttggagt acgcgaagcg cacccctatc ggcgagccga tcaccttcac    3000
gttctacagag ctttgccagg acctgggctg gtcgatcaat ggccggtatt acacgaaggc    3060
cgaggaatgc ctgtcgcgcc tacaggcgac ggcgatgggc ttcacgtccg accgcgttgg    3120
gcacctggaa tcggtgtcgc tgctgcaccg cttccgcgtc ctggaccgtg caagaaaaac    3180
gtcccgttgc caggtcctga tcgacgagga aatcgtcgtg ctgtttgctg gcgaccacta    3240
cacgaaattc atatgggaga agtaccgcaa gctgtcgccg acggcccgac ggatgttcga    3300
ctatttcagc tcgcaccggg agccgtaccc gctcaagctg gaaaccttcc gcctcatgtg    3360
cggatcggat tccacccgcg tgaagaagtg gcgcgagcag gtcggcgaag cctgcgaaga    3420
gttgcgaggc agcggcctgg tggaacacgc ctgggtcaat gatgacctgg tgcattgcaa    3480
acgctagggc cttgtggggt cagttccggc tgggggttca gcagccagcg ctttactggc    3540
atttcaggaa caagcgggca ctgctcgacg cacttgcttc gctcagtatc gctcgggacg    3600
cacggcgcgc tctacgaact gccgatagac aactgtcacg gttaagcgag aaatgaataa    3660
gaaggctgat aattcggatc tctgcgaggg agatgatatt tgatcacagg cagcaacgct    3720
ctgtcatcgt tacaatcaac atgctacccct ccgcgagatc atccgtgttt caaacccggc    3780
agcttagttg ccgttcttcc gaatagcatc ggtaacatga gcaaagtctg ccgccttaca    3840
acggctctcc cgctgacgcc gtcccggact gatgggctgc ctgtatcgag tggtgatttt    3900
gtgccgagct gccggtcggg gagctgttgg ctggctggtg gcaggatata ttgtggtgta    3960
aacaaattga cgcttagaca acttaataac acattgcgga cgttttttaat gtactggggt    4020
ggtttttctt ttcaccagtg agacgggcaa cagctgattg cccttcaccg cctggccctg    4080
agagagttgc agcaagcggt ccacgctggt ttgccccagc aggcgaaaat cctgtttgat    4140
ggtggttccg aaatcggcaa aatcccttat aaatcaaaag aatagcccga gataggggttg    4200
agtgttgttc cagtttggaa caagagtcca ctattaaaga acgtggactc caacgtcaaa    4260
gggcgaaaaa ccgtctatca gggcgatggc ccacggccgc tctagaacta gtggatcccc    4320
cctacgtgcg atctagtaac atagatgaca ccgcgcgcga taattttatcc tagtttgcgc    4380
```

```
gctatatttt gttttctatc gcgtattaaa tgtataattg cgggactcta atcataaaaa    4440
cccatctcat aaataacgtc atgcattaca tgttaattat tacatgctta acgtaattca    4500
acagaaatta tatgataatc atcgcaagac cggcaacagg attcaatctt aagaaacttt    4560
attgccaaat gtttgaacga tccctcagaa gaactcgtca agaaggcgat agaaggcgat    4620
gcgctgcgaa tcgggagcgg cgataccgta aagcacgagg aagcggtcag cccattcgcc    4680
gccaagctct tcagcaatat cacgggtagc caacgctatg tcctgatagc ggtccgccac    4740
acccagccgg ccacagtcga tgaatccaga aaagcggcca ttttccacca tgatattcgg    4800
caagcaggca tcgccatggg tcacgacgag atcctcgccg tcgggcatgc gcgccttgag    4860
cctggcgaac agttcggctg gcgcgagccc ctgatgctct tcgtccagat catcctgatc    4920
gacaagaccg gcttccatcc gagtacgtgc tcgctcgatg cgatgtttcg cttggtggtc    4980
gaatgggcag gtagccggat caagcgtatg cagccgccgc attgcatcag ccatgatgga    5040
tactttctcg gcaggagcaa ggtgagatga caggagatcc tgccccggca cttcgcccaa    5100
tagcagccag tcccttcccg cttcagtgac aacgtcgagc acagctgcgc aaggaacgcc    5160
cgtcgtggcc agccacgata ccgcgctgc ctcgtcctgg agttcattca gggcaccgga    5220
caggtcggtc ttgacaaaaa gaaccgggcg cccctgcgct gacagccgga acacggcggc    5280
atcagagcag ccgattgtct gttgtgccca gtcatagccg aatagcctct ccacccaagc    5340
ggccggagaa cctgcgtgca atccatcttg ttcaatcatc tgttaatcag aaaaactcag    5400
attaatcgac aaattcgatc gcacaaacta gaaactaaca ccagatctag atagaaatca    5460
caaatcgaag agtaattatt cgacaaaact caaattattt gaacaaatcg atgatatt     5520
atgaaaccct aatcgagaat taagatgata tctaacgatc aaacccagaa aatcgtcttc    5580
gatctaagat taacagaatc taaaccaaag aacatatacg aaattgggat cgaacgaaaa    5640
caaaatcgaa gattttgaga gaataaggaa cacagaaatt taccttgatc acggtagaga    5700
gaattgagag aaagttttta agattttgag aaattgaaat ctgaattgtg aagaagaaga    5760
gctctttggg tattgtttta tagaagaaga agaagaaaag acgaggacga ctaggtcacg    5820
agaaagctaa ggcggtgaag caatagctaa taataaaatg acacgtgtat tgagcgttgt    5880
ttacacgcaa agttgttttt ggctaattgc cttattttta ggttgaggaa agtatttgt     5940
gctttgagtt gataaacacg actcgtgtgt gccggctgca accactttga cgccgtttat    6000
tactgactcg tcgacaacca caattctcaa cggtcgtcat aagatccagc cgttgagatt    6060
taacgatcgt tacgatttat atttttttag cattatcgtt ttattttta aatatacggt     6120
ggagctgaaa attggcaata attgaaccgt gggtcccact gcattgaagc gtatttcgta    6180
ttttctagaa ttcttcgtgc tttatttctt ttcctttttg tttttttttg ccatttatct    6240
aatgcaagtg ggcttataaa atcagtgaat ttcttggaaa agtaacttct ttatcgtata    6300
acatattgtg aaattatcca tttctttaa ttttttagtg ttattggata tttttgtatg     6360
attattgatt tgcataggat aatgactttt gtatcaagtt ggtgaacaag tctcgttaaa    6420
aaaggcaagt ggtttggtga ctcgatttat tcttgttatt taattcatat atcaatggat    6480
cttatttggg gcctggtcca tatttaacac tcgtgttcag tccaatgacc aataatatt     6540
tttcattaat aacaatgtaa caagaatgat acacaaaaca ttctttgaat aagttcgcta    6600
tgaagaaggg aacttatccg gtcctagatc atcagttcat acaaacctcc atagagttca    6660
acatcttaaa caaggatatc ctgatccgtt gacggcgcgc caagcggccg catttaaatg    6720
```

```
ggccctatct aatcgaattt tgtaaactgg tttgataagc catcaatgca tcagtcaaga    6780
atgaatcatt gcaactaagt tgatataatt caatttacca tagaactcaa atgttgatat    6840
cttcttatgg attttctgat cttctacatt attagaaaga aacttgattt accagtaatg    6900
atgatacata tccaatagaa cgaaataagc caatctttat aggttttggt agtaaagtta    6960
caacatcaga gacatgtatg tattgtctct cagaagagct cttgaccgat cagagtttga    7020
agaaaaattt attacacact ttatgtaaag ctgaaaaaaa cggcctcccg cagggaagcc    7080
gtttttttcg ttatctgatt tttgtaaagg tctgatactc gtccgttgtt ttgtaaatca    7140
gccagtcgct tgagtaaaga atccggtctg aatttctgaa gcctgatgta tagttaatat    7200
ccgcttcacg ccatgttcgt ccgcttttgc ccgggagttt gccttccctg tttgaagaa    7260 tgtctccgcc gatgcttttc cccggagcga cgtctgcaag gttccctttt gatgccaccc    7320
agccgagggc ttgtgcttct gattttgtaa tgtaattatc aggtagctta tgatatgtct    7380
gaagataatc cgcaaccccg tcaaacgtgt tgataacctg tgccatgttc ccgtttgata    7440
cctgaatttt ggccattctc ataaatcttc taaaaacagc agaactgact attcaaagaa    7500
agtagaaccc acagaaagta atcaaagtag tttgattaaa tgcgttgtgt atcatcgcag    7560
cccctgctac ggatatttat aggaaaggtt tgagagcaat gtgtgcagca agttgtgtgt    7620
gaatcacctg cttccatggc ggaggataaa taatttagtc acgcatttag ttgaacgtaa    7680
ctactaactc ctctaccgct aatcattctt cttttgcccg ggcaagttca acaacaaccc    7740
cacaatcacg cttcctgtat tttgttttgt tttcaaaaca atagaattca cttttttactg   7800 ccaaaattat gttttactcg agagcccggg ctcctgcagg taccttaatt aaaagtttaa    7860
actatcagtg tttgacagga tatattggcg ggtaaaccta agagaaaaga gcgtttatta    7920
gaataatcgg atatttaaaa gggcgtgaaa aggtttatcc gttcgtccat ttgtatgtgc    7980
atgccaacca cagggttccc cagatc                                         8006

<210> SEQ ID NO 19
<211> LENGTH: 13001
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 19 gtttaccccgc caatatatcc tgtcaaacac tgatagttta aacttttaat taaggtacct      60
gcaggagccc gggctgcagg aattcgatat caagcttgat agggtcaaat cgaccacttg     120
cacagttaag tgattctaat acgaaacctt aaaagcaaac atcggttctt ttgagtcaga     180
agaaatgcaa cttaatgtga cacatgatgt gaagaaaaaa caaaagtaat ataagaaaag     240
ggaacaatta aatagttaat aaaatatttc cttaaagttg taacaaataa agaatcattt     300
tatgaaacaa tatgaaccct aaataaatta aaattcctct gaaaccttaa atttatcgag     360
ctagtgattg gctgccaact gccatgctgg caaaattaga gtgacatgat tggtctgaac     420
atgtctaggg tttcagacat gtgacatgtg tcaacaaccc attaacacat tgggtataaa     480
tccaatagac atttgatagt attaaaattg taaccattgg attaaattta aacgtgatgg     540
atgtaactaa atgacttgtc cgagtaacat cacaacgttc catactttcc ttatttggaa     600
tataattaaa tttaccattt attcttttt cttgagtttc ctgtatatgt acttgtacat     660
agatatatat gcacaaatac gtattacaat gacatattat agactttgat gtctgaactc     720
```

```
tcaaccttct cgatggagag atcatgaccg tagattttt tggatcgtag aaggcagacc      780
aaactcttaa actattggat ccgtactaaa aatctcactt tcctctcagt acccataatg      840
agagagaaaa tgataaaaat ccctaacatt attctctctc tagaaaaaaa aagatacttc      900 aaaagaaag agaaattgca taaatctatc tacaccaaag atgttgaagc aattccaatg      960
ctatacttct atgccaaatc tatttattca gtgatcatta atcttttac ttccaagaaa     1020 tatgaacaat ttagtatcct tataatttt gtctctatat atgtaatatg aacattgggt     1080
attgaccaaa tgagaaatct aatattaaat ggtcaaaagt agtaatatga tgacattttt     1140
gaatttataa ataggttaca aattaattca ttatgacata aaaccttctt gtcagaagtc     1200
aagaactgaa actaacaaaa ctttataata aattagtaaa aatacaaatg aaaataaaa     1260 agaaataata tctgagtgat gacgtgatca aagattcttt aacaaagaca acaaatctta     1320
cagacccaaa acctaatctt gcgctcaatt ccaacctctg aaaaaacctc aaaaatctta     1380
taaaagaaaa taaataaaga aacgaaactc tgatttcgta gagtacccat cggatatata     1440
aaaagaaatt agtaggtaaa tgaagactaa ttttgattga ctgatttaat ttgaagtcgt     1500
tgttagcttt tcttgttttg gacatgagaa ttatatattt caggacatga gagttgacaa     1560
ctgtaaacga ttaagaaaat tgatctttta attttcaaac accatttaat cttgacatgt     1620
tttatgtttt ggtggagaag aaagtaatca cgtgggactc tctactaata agtatttgga     1680
aattgcgtgt cgaattagag attactagtt tgagtaatgt agttcgaaat gagattagtt     1740 attttttaatt ttaaaaagag taattttaag gaataacaaa aaagagtccc cataagctaa     1800
tttgtcttaa ttacctcctt gtttcattga ctatttgaaa tcttgaaaat tcagttgaaa     1860
tttcaaatct atgtttcttt tgaccacttc taaactaatc ttagctcata tataattttc     1920
caaaactaca aaaataacac taacatttaa cattctcaag agaaacaaa aacaaaaact     1980 tagataacca tctaaattgt cctacatgta cgtataagtt ccattatttt ctatcactca     2040
tataagttaa aatttcatga aaactcaaaa atctagctag tttcaccttta ttcactctca     2100 cttaccatca catgtgtttg tatcaaatat atgatatgat ataattcatg agagagaaag     2160
agagctagag ataagaaagg aaagtaagag aaagaagaga agaaaagag agacacagac     2220 attaacaaca atggaggatg gatgatcaca aaacagaaga tatgacctca tagtccttcc     2280
ttactctctc cccaatttgt ttcccaaaac ttacttttat agtcataaaa atcaagtttt     2340
tacctattac aacaccagat ctataaatat atctaaatct tcaagtactt gttagtaagg     2400
aaaatagaaa gatataagat tttattatta ttataataac agaaatgagt gaagaaagaa     2460
cacccaacaa agtgaatctt agttctacaa aactgaatct aaaactccac attagaaaaa     2520
accctgatgg tttcttattt cttttcattt attatctaac tctcactcag atctccttta     2580
actttgtacc atttccctca cttcatatat ctatatataa caactctct ctttttattt     2640 aagtcttaag ggaaaattaa tatacacatg aagacaagaa attagatcta caaaattgtt     2700
acaaaaaccc ccgaagtaaa taaaataaac atatcaaaca atattccca ctaatgttag     2760 tgtgtttata tatatatgtg tgtggaatat gaaggaaaaa agtgaaaaat aatcctaccc     2820
ataagagcat tcaagaagaa gctcgagggt atcgataagc ttaaactcga cagcaaatat     2880
gatttagatt atgacctaga aataagcata gcattaaagc atatacataa caagcggtga     2940
tatactctga ctgccactgt acttgaggaa aggtagtgga ctctgctcag gtacattagt     3000
ttggtaaggt tggcttggct tctgggtaat atgagaagta aagaagtaaa aggtatttga     3060
ctctagtcaa gtacattgga ttgcctttgt cggggcttgg atggcttggg ttcgtgtgag     3120
```

```
aagccaacaa tttataagaa atatataaaa taaaaaataa aaaaatttaa gtgttggaag   3180
tgaaaacggt ggggcagaaa tatacacaga agagtacttt aacaatgcgc aaccaaggca   3240
gattcacaac ttgatttctg gacctcgaat acgagataat ggtggtaaga aataaaggaa   3300
gagtggagcg catttgaaaa tgaatggaga gcgcacaaaa tggaggacga ataaatgaaa   3360
tataatgcaa gggtgcattt ccctattatt tccagaaatg tatatgtggg gtcggcattc   3420
tcatgggcgt cgcattcagg gggtgtcata gcggtccttt gattgcagtg tgggagttgc   3480
aacatgtacc aacaaatcca ttcatcccaa aacctaaatt tatcctctcc attactatta   3540
cctacaccta tacctagtaa atatgtcctg ccttgtaact cctccactgc ctgcacacgt   3600
cttagtcaat ccatctgcct tcaaataggc attattttgt tctttccccct ccgactgaaa   3660 ggctatcgac cgaccgaccg ctcatcttct tcttctgcgc aattttttct gctggatcat   3720
catcattacc atcatcgcca tccccaccat catcatcatg atggtatctc tatctctccc   3780
tggcaatcga ttgtagagga aaggaagagg gaagggggcat atgtattgat caacctaccc   3840
gaaaaaacaa tctgatcagc cctgctaatc ttgcttataa atctcttatc cactgttcaa   3900
tcattcaggt ttcttcccac tttcaagcaa aggcgcccgg attggccgtg ttcttagatt   3960
ttcaggtact taaatggaca atattcccca cctgaagccg ttctgaaaaa gatttgtttg   4020
tagaaacaaa cgattgtaat atttgcttaa gttgagctta aggggtttgg tacctaactt   4080
gccttgtggt tatttgtttc tcagaactcg ggctgcgtcc aactgtagga acgaaccagc   4140
acaaggggtt gcagcttttg ctgttgctgt tgcgcccatt gcttttggac tggtattagt   4200
agttgcagct ttgttttgca tacgctgtga ggatctgtgc gcggaaattt tgtgtacaaa   4260
tcatgttacg tcctgtagaa accccaaccc gtgaaatcaa aaaactcgac ggcctgtggg   4320
cattcagtct ggatcgcgaa aactgtggaa ttggtcagcg ttggtgggaa agcgcgttac   4380
aagaaagccg ggcaattgct gtgccaggca gttttaacga tcagttcgcc gatgcagata   4440
ttcgtaatta tgcgggcaac gtctggtatc agcgcgaagt ctttataccg aaaggttggg   4500
caggccagcg tatcgtgctg cgtttcgatg cggtcactca ttacggcaaa gtgtgggtca   4560
ataatcagga agtgatggag catcagggcg gctatacgcc atttgaagcc gatgtcacgc   4620
cgtatgttat tgccgggaaa agtgtacgta agtttctgct tctacctttg atatatatat   4680
aataattatc attaattagt agtaatataa tatttcaaat atttttttca aaataaaaga   4740
atgtagtata tagcaattgc ttttctgtag tttataagtg tgtatatttt aatttataac   4800 cttttctaata tatgaccaaa atttgttgat gtgcaggtat caccgtttgt gtgaacaacg   4860
aactgaactg gcagactatc ccgccgggaa tggtgattac cgacgaaaac ggcaagaaaa   4920
agcggtctta cttccatgat ttctttaact atgccggaat ccatcgcagc gtaatgctct   4980
acaccacgcc gaacacctgg gtggacgata tcaccgtggt gacgcatgtc gcgcaagact   5040
gtaaccacgc gtctgttgac tggcaggtgg tggccaatgg tgatgtcagc gttgaactgc   5100
gtgatgcgga tcaacaggtg gttgcaactg gacaaggcac tagcgggact ttgcaagtgg   5160
tgaatccgca cctctggcaa ccgggtgaag gttatctcta tgaactgtgc gtcacagcca   5220
aaagccagac agagtgtgat atctaccgcg ttcgcgtcgg catccggtca gtggcagtga   5280
agggcgaaca gttcctgatt aaccacaaac cgttctactt tactggcttt ggtcgtcatg   5340
aagatgcgga cttgcgtggc aaaggattcg ataacgtgct gatggtgcac gaccacgcat   5400
taatggactg gattggggcc aactcctacc gtaccctcgca ttacccttac gctgaagaga   5460
```

```
tgctcgactg ggcagatgaa catggcatcg tggtgattga tgaaactgct gctgtcggct    5520
ttaacctctc tttaggcatt ggtttcgaag cgggcaaca gccgaaagaa ctgtacagcg      5580
aagaggcagt caacggggaa actcagcaag cgcacttaca ggcgattaaa gagctgatag    5640
cgcgtgacaa aaaccaccca agcgtggtga tgtggagtat tgccaacgaa ccggataccc    5700
gtccgcaagg tgcacgggaa tatttcgcgc cactggcgga agcaacgcgt aaactcgacc    5760
cgacgcgtcc gatcacctgc gtcaatgtaa tgttctgcga cgctcacacc gataccatca    5820
gcgatctctt tgatgtgctg tgcctgaacc gttattacgg atggtatgtc caaagcggcg    5880
atttggaaac ggcagagaag gtactggaaa agaacttct ggcctggcag gagaaactgc    5940
atcagccgat tatcatcacc gaatacggcg tggatacgtt agccgggctg cactcaatgt    6000
acaccgacat gtggagtgaa gagtatcagt gtgcatggct ggatatgtat caccgcgtct    6060
ttgatcgcgt cagcgccgtc gtcggtgaac aggtatggaa tttcgccgat tttgcgacct    6120
cgcaaggcat attgcgcgtt ggcggtaaca agaaagggga cttcactcgc gaccgcaaac    6180
cgaagtcggc ggcttttcctg ctgcaaaaac gctggactgg catgaacttc ggtgaaaaac    6240
cgcagcaggg aggcaaacaa tgaatcaaca actctcctgg cgcaccatcg tcggctacag    6300
cctcgggaat tgctaccgga gagagagctc gaatttcccc gatcgttcaa acatttggca    6360
ataaagtttc ttaagattga atcctgttgc cggtcttgcg atgattatca tataatttct    6420
gttgaattac gttaagcatg taataattaa catgtaatgc atgacgttat ttatgagatg    6480 ggttttatg attagagtcc cgcaattata catttaatac gcgatagaaa acaaaatata    6540
gcgcgcaaac taggataaat tatcgcgcgc ggtgtcatct atgttactag atcgggaatt    6600
cctgcagccc gggggatcca ctagttctag agcggccgct tggcgcgccg tcaacggatc    6660
aggatatcct tgtttaagat gttgaactct atggaggttt gtatgaactg atgatctagg    6720
accggataag ttcccttctt catagcgaac ttattcaaag aatgttttgt gtatcattct    6780
tgttacattg ttattaatga aaaaatatta ttggtcattg gactgaacac gagtgttaaa    6840
tatggaccag gccccaaata agatccattg atatatgaat taaataacaa gaataaatcg    6900
agtcaccaaa ccacttgcct tttttaacga gacttgttca ccaacttgat acaaaagtca    6960
ttatcctatg caaatcaata atcatacaaa aatatccaat aacactaaaa aattaaaaga    7020
aatggataat ttcacaatat gttatacgat aaagaagtta cttttccaag aaattcactg    7080
attttataag cccacttgca ttagataaat ggcaaaaaaa aacaaaaagg aaaagaaata    7140
aagcacgaag aattctagaa aatacgaaat acgcttcaat gcagtgggac ccacggttca    7200
attattgcca attttcagct ccaccgtata tttaaaaaat aaaacgataa tgctaaaaaa    7260
atataaatcg taacgatcgt taaatctcaa cggctggatc ttatgacgac cgttagaaat    7320
tgtggttgag tcagtaataa acggcgtcaa agtggttgca gccggcacac acgagtcgtg    7380
tttatcaact caaagcacaa atactttttcc tcaacctaaa aataaggcaa ttagccaaaa    7440
acaactttgc gtgtaaacaa cgctcaatac acgtgtcatt ttattattag ctattgcttc    7500
accgccttag ctttctcgtg acctagtcgt cctcgtcttt tcttcttctt cttctataaa    7560 acaatacca aagagctctt cttcttcaca attcagattt caatttctca aaatcttaaa    7620
aactttctct caattctctc taccgtgatc aaggtaaatt tctgtgttcc ttattctctc    7680
aaaatcttcg attttgtttt cgttcgatcc caatttcgta tatgttcttt ggtttagatt    7740
ctgttaatct tagatcgaag acgattttct gggtttgatc gttagatatc atcttaattc    7800
tcgattaggg tttcataaat atcatccgat ttgttcaaat aatttgagtt ttgtcgaata    7860
```

```
attactcttc gatttgtgat ttctatctag atctggtgtt agtttctagt ttgtgcgatc   7920
gaatttgtcg attaatctga gtttttctga ttaacagatg attgaacaag atggattgca   7980
cgcaggttct ccggccgctt gggtggagag gctattcggc tatgactggg cacaacagac   8040
aatcggctgc tctgatgccg ccgtgttccg gctgtcagcg caggggcgcc cggttctttt   8100
tgtcaagacc gacctgtccg gtgccctgaa tgaactccag gacgaggcag cgcggctatc   8160
gtggctggcc acgacgggcg ttccttgcgc agctgtgctc gacgttgtca ctgaagcggg   8220
aagggactgg ctgctattgg gcgaagtgcc ggggcaggat ctcctgtcat ctcaccttgc   8280
tcctgccgag aaagtatcca tcatggctga tgcaatgcgg cggctgcata cgcttgatcc   8340
ggctacctgc ccattcgacc accaagcgaa acatcgcatc gagcgagcac gtactcggat   8400
ggaagccggt cttgtcgatc aggatgatct ggacgaagag catcaggggc tcgcgccagc   8460
cgaactgttc gccaggctca aggcgcgcat gcccgacggc gaggatctcg tcgtgaccca   8520
tggcgatgcc tgcttgccga atatcatggt ggaaaatggc cgcttttctg gattcatcga   8580
ctgtggccgg ctgggtgtgg cggaccgcta tcaggacata gcgttggcta cccgtgatat   8640
tgctgaagag cttggcggcg aatgggctga ccgcttcctc gtgctttacg gtatcgccgc   8700
tcccgattcg cagcgcatcg ccttctatcg ccttcttgac gagttcttct gagggatcgt   8760
tcaaacattt ggcaataaag tttcttaaga ttgaatcctg ttgccggtct tgcgatgatt   8820
atcatataat ttctgttgaa ttacgttaag catgtaataa ttaacatgta atgcatgacg   8880
ttatttatga gatgggtttt tatgattaga gtcccgcaat tatacattta atacgcgata   8940
gaaaacaaaa tatagcgcgc aaactaggat aaattatcgc gcgcggtgtc atctatgtta   9000
ctagatcgca cgtaggggggg atccactagt tctagagcgg ccgtgggcca tcgccctgat   9060
agacggtttt tcgccctttg acgttggagt ccacgttctt taatagtgga ctcttgttcc   9120
aaactggaac aacactcaac cctatctcgg gctattcttt tgatttataa gggattttgc   9180
cgatttcgga accaccatca aacaggattt tcgcctgctg gggcaaacca gcgtggaccg   9240
cttgctgcaa ctctctcagg gccaggcggt gaagggcaat cagctgttgc ccgtctcact   9300
ggtgaaaaga aaaaccaccc cagtacatta aaaacgtccg caatgtgtta ttaagttgtc   9360
taagcgtcaa tttgtttaca ccacaatata tcctgccacc agccagccaa cagctccccg   9420
accggcagct cggcacaaaa tcaccactcg atacaggcag cccatcagtc cgggacggcg   9480
tcagcgggag agccgttgta aggcggcaga cttttgctcat gttaccgatg ctattcggaa   9540
gaacggcaac taagctgccg ggtttgaaac acggatgatc tcgcggaggg tagcatgttg   9600
attgtaacga tgacagagcg ttgctgcctg tgatcaaata tcatctccct cgcagagatc   9660
cgaattatca gccttcttat tcatttctcg cttaaccgtg acagttgtct atcggcagtt   9720
cgtagagcgc gccgtgcgtc ccgagcgata ctgagcgaag caagtgcgtc gagcagtgcc   9780
cgcttgttcc tgaaatgcca gtaaagcgct ggctgctgaa ccccagccg gaactgaccc   9840 cacaaggccc tagcgtttgc aatgcaccag gtcatcattg acccaggcgt gttccaccag   9900
gccgctgcct cgcaactctt cgcaggcttc gccgacctgc tcgcgccact tcttcacgcg   9960
ggtggaatcc gatccgcaca tgaggcgaa ggtttccagc ttgagcgggt acggctcccg  10020
gtgcgagctg aaatagtcga acatccgtcg ggccgtcggc gacagcttgc ggtacttctc  10080
ccatatgaat ttcgtgtagt ggtcgccagc aaacagcacg acgatttcct cgtcgatcag  10140
gacctggcaa cgggacgttt tcttgccacg gtccaggacg cggaagcggt gcagcagcga  10200
```

```
caccgattcc aggtgcccaa cgcggtcgga cgtgaagccc atcgccgtcg cctgtaggcg    10260
cgacaggcat tcctcggcct tcgtgtaata ccggccattg atcgaccagc ccaggtcctg    10320
gcaaagctcg tagaacgtga aggtgatcgg ctcgccgata ggggtgcgct tcgcgtactc    10380
caacacctgc tgccacacca gttcgtcatc gtcgcccgc  agctcgacgc cggtgtaggt    10440
gatcttcacg tccttgttga cgtggaaaat gaccttgttt tgcagcgcct cgcgcgggat    10500
tttcttgttg cgcgtggtga acagggcaga gcgggccgtg tcgtttggca tcgctcgcat    10560
cgtgtccggc cacggcgcaa tatcgaacaa ggaaagctgc atttccttga tctgctgctt    10620
cgtgtgtttc agcaacgcgg cctgcttggc ctcgctgacc tgttttgcca ggtcctcgcc    10680
ggcggttttt cgcttcttgg tcgtcatagt tcctcgcgtg tcgatggtca tcgacttcgc    10740
caaacctgcc gcctcctgtt cgagacgacg cgaacgctcc acggcggccg atggcgcggg    10800
cagggcaggg ggagccagtt gcacgctgtc gcgctcgatc ttggccgtag cttgctggac    10860
catcgagccg acggactgga aggtttcgcg gggcgcacgc atgacggtgc ggcttgcgat    10920
ggtttcggca tcctcggcgg aaaaccccgc gtcgatcagt tcttgcctgt atgccttccg    10980
gtcaaacgtc cgattcattc accctccttg cgggattgcc ccgactcacg ccggggcaat    11040
gtgcccttat tcctgatttg acccgcctgg tgccttggtg tccagataat ccaccttatc    11100
ggcaatgaag tcgtcccgt  agaccgtctg gccgtccttc tcgtacttgg tattccgaat    11160
cttgccctgc acgaatacca gcgaccccct tgcccaaatac ttgccgtggg cctcggcctg    11220
agagccaaaa cacttgatgc ggaagaagtc ggtgcgctcc tgcttgtcgc cggcatcgtt    11280
gcgccacatc taggtactaa acaattcat  ccagtaaaat ataatatttt attttctccc    11340
aatcaggctt gatccccagt aagtcaaaaa atagctcgac atactgttct tccccgatat    11400
cctcctgat  cgaccggacg cagaaggcaa tgtcatacca cttgtccgcc ctgccgcttc    11460
tcccaagatc aataaagcca cttactttgc catctttcac aaagatgttg ctgtctccca    11520
ggtcgccgtg ggaaaagaca agttcctctt cgggcttttc cgtctttaaa aaatcataca    11580
gctcgcgcgg atctttaaat ggagtgtctt cttcccagtt ttcgcaatcc acatcggcca    11640
gatcgttatt cagtaagtaa tccaattcgg ctaagcggct gtctaagcta ttcgtatagg    11700
gacaatccga tatgtcgatg gagtgaaaga gcctgatgca ctccgcatac agctcgataa    11760
tcttttcagg gctttgttca tcttcatact cttccgagca aaggacgcca tcggcctcac    11820
tcatgagcag attgctccag ccatcatgcc gttcaaagtg caggacctt  ggaacaggca    11880
gctttccttc cagccatagc atcatgtcct ttttccgttc cacatcatag gtggtccctt    11940
tataccggct gtccgtcatt tttaaatata ggttttcatt ttctcccacc agcttatata    12000
ccttagcagg agacattcct tccgtatctt ttacgcagcg gtattttttcg atcagttttt    12060
tcaattccgg tgatattctc attttagcca tttattattt ccttcctctt ttctacagta    12120
tttaaagata ccccaagaag ctaattataa caagacgaac tccaattcac tgttccttgc    12180
attctaaaac cttaaatacc agaaaacagc ttttttcaaag ttgttttcaa agttggcgta    12240
taacatagta tcgacggagc cgattttgaa accacaatta tggactgcca gcgctgccat    12300
ttttggggtg aggccgttcg cggccgaggg gcgcagcccc tgggggatg  ggaggcccgc    12360
gttagcgggc cggagggtt  cgagaagggg gggcaccccc cttcggcgtg cgcggtcacg    12420
cgcacagggc gcagccctgg ttaaaaacaa ggtttataaa tattggttta aaagcaggtt    12480
aaaagacagg ttagcggtgg ccgaaaaacg ggcggaaacc cttgcaaatg ctggattttc    12540
tgcctgtgga cagcccctca aatgtcaata ggtgcgcccc tcatctgtca gcactctgcc    12600
```

```
cctcaagtgt caaggatcgc gccctcatc tgtcagtagt cgcgccctc aagtgtcaat    12660 accgcagggc acttatcccc aggcttgtcc acatcatctg tgggaaactc gcgtaaaatc    12720
aggcgttttc gccgatttgc gaggctggcc agctccacgt cgccggccga aatcgagcct    12780
gcccctcatc tgtcaacgcc gcgccgggtg agtcggcccc tcaagtgtca acgtccgccc    12840
ctcatctgtc agtgagggcc aagttttccg cgaggtatcc acaacgccgg cggatctggg    12900
gaaccctgtg gttggcatgc acatacaaat ggacgaacgg ataaaccttt tcacgccctt    12960
ttaaatatcc gattattcta ataaacgctc ttttctctta g                         13001

<210> SEQ ID NO 20
<211> LENGTH: 8534
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 20
gtttacccgc caatatatcc tgtcaaacac tgatagttta aacttttaat taaggtacct      60
gcaggagccc gggctctcga ggtcgacggt atcgataagc ttaaactcga cagcaaatat     120
gatttagatt atgacctaga aataagcata gcattaaagc atatacataa caagcggtga     180
tatactctga ctgccactgt acttgaggaa aggtagtgga ctctgctcag gtacattagt     240
ttggtaaggt tggcttggct tctgggtaat atgagaagta agaagtaaa aggtatttga     300 ctctagtcaa gtacattgga ttgcctttgt cggggcttgg atggcttggg ttcgtgtgag     360
aagccaacaa tttataagaa atatataaaa taaaaaataa aaaatttaa gtgttggaag     420 tgaaaacggt ggggcagaaa tatacacaga agagtacttt aacaatgcgc aaccaaggca     480
gattcacaac ttgatttctg gacctcgaat acgagataat ggtggtaaga aataaaggaa     540
gagtggagcg catttgaaaa tgaatggaga gcgcacaaaa tggaggacga taaatgaaa     600 tataatgcaa gggtgcattt ccctattatt tccagaaatg tatatgtggg gtcggcattc     660
tcatgggcgt cgcattcagg gggtgtcata gcggtccttt gattgcagtg tgggagttgc     720
aacatgtacc aacaaatcca ttcatcccaa aacctaaatt tatcctctcc attactatta     780
cctacaccta tacctagtaa atatgtcctg ccttgtaact cctccactgc ctgcacacgt     840
cttagtcaat ccatctgcct tcaaataggc attattttgt tctttcccct ccgactgaaa     900
ggctatcgac cgaccgaccg ctcatcttct tcttctgcgc aattttttct gctggatcat     960
catcattacc atcatcgcca tccccaccat catcatcatg atggtatctc tatctctccc    1020
tggcaatcga ttgtagagga aaggaagagg gaagggggcat atgtattgat caacctaccc    1080
gaaaaaacaa tctgatcagc cctgctaatc ttgcttataa atctcttatc cactgttcaa    1140
tcattcaggt ttcttcccac tttcaagcaa aggcgcccgg attggccgtg ttcttagatt    1200
ttcaggtact taaatggaca atattcccca cctgaagccg ttctgaaaaa gatttgtttg    1260
tagaaacaaa cgattgtaat atttgcttaa gttgagctta aggggtttgg tacctaactt    1320
gccttgtggt tatttgtttc tcagaactcg gctgcgtcc aactgtagga acgaaccagc    1380
acaaggggtt gcagcttttg ctgttgctgt tgcgcccatt gcttttggac tggtattagt    1440
agttgcagct ttgttttgca tacgctgtga ggatctgtgc gcggaaattt tgtgtacaaa    1500
tcatggcaca ggttatcaac acgtttgacg gggttgcgga ttatcttcag acatatcata    1560
agctacctga taattacatt acaaaatcag aagcacaagc cctcggctgg gtggcatcaa    1620
```

```
aagggaacct tgcagacgtc gctccgggga aaagcatcgg cggagacatc ttctcaaaca    1680
gggaaggcaa actcccgggc aaaagcggac gaacatggcg tgaagcggat attaactata    1740
catcaggctt cagaaattca gaccggattc tttactcaag cgactggctg atttacaaaa    1800
caacggacca ttatcagacc tctacaaaaa tcagataacg aaaaaaacgg cttccctgcg    1860
ggaggccgtt tttttcagct ttacataaag tgtgtaataa attttcttc aaactctgat     1920 cggtcaattg cactttgagc tcgaatttcc ccgatcgttc aaacatttgg caataaagtt    1980
tcttaagatt gaatcctgtt gccggtcttg cgatgattat catataattt ctgttgaatt    2040
acgttaagca tgtaataatt aacatgtaat gcatgacgtt atttatgaga tgggttttta    2100
tgattagagt cccgcaatta tacatttaat acgcgataga aaacaaaata tagcgcgcaa    2160
actaggataa attatcgcgc gcggtgtcat ctatgttact agatcgggaa ggcgcgccgc    2220
ggccgcaaca ctgatagttt aaactgaagg cgggaaacga caatctgatc atgagcggag    2280
aattaaggga gtcacgttat gacccccgcc gatgacgcgg gacaagccgt tttacgtttg    2340
gaactgacag aaccgcaacg ttgaaggagc cactcagccg cgggtttctg gagtttaatg    2400
agctaagcac atacgtcaga aaccattatt gcgcgttcaa aagtcgccta aggtcactat    2460
cagctagcaa atatttcttg tcaaaaatgc tccactgacg ttccataaat tcccctcggt    2520
atccaattag agtctcatat tcactctcaa tccaaataat ctgcaccgga tctggatcgt    2580
ttcgcatgat tgaacaagat ggattgcacg caggttctcc ggccgcttgg gtggagaggc    2640
tattcggcta tgactgggca caacagacaa tcggctgctc tgatgccgcc gtgttccggc    2700
tgtcagcgca ggggcgcccg gttcttttg tcaagaccga cctgtccggt gccctgaatg     2760
aactgcagga cgaggcagcg cggctatcgt ggctggccac gacgggcgtt ccttgcgcag    2820
ctgtgctcga cgttgtcact gaagcgggaa gggactggct gctattgggc gaagtgccgg    2880
ggcaggatct cctgtcatct caccttgctc ctgccgagaa agtatccatc atggctgatg    2940
caatgcggcg gctgcatacg cttgatccgg ctacctgccc attcgaccac caagcgaaac    3000
atcgcatcga gcgagcacgt actcggatgg aagccggtct tgtcgatcag gatgatctgg    3060
acgaagagca tcagggctc gcgccagccg aactgttcgc caggctcaag gcgcgcatgc     3120
ccgacggcga tgatctcgtc gtgacccatg gcgatgcctg cttgccgaat atcatggtgg    3180
aaaatggccg cttttctgga ttcatcgact gtggccggct gggtgtggcg gaccgctatc    3240
aggacatagc gttggctacc cgtgatattg ctgaagagct tggcggcgaa tgggctgacc    3300
gcttcctcgt gctttacggt atcgccgctc ccgattcgca gcgcatcgcc ttctatcgcc    3360
ttcttgacga gttcttctga gcgggactct ggggttcgaa atgaccgacc aagcgacgcc    3420
caacctgcca tcacgagatt tcgattccac cgccgccttc tatgaaaggt tgggcttcgg    3480
aatcgttttc cgggacgccg gctggatgat cctccagcgc ggggatctca tgctggagtt    3540
cttcgcccac gggatctctg cggaacaggc ggtcgaaggt gccgatatca ttacgacagc    3600
aacggccgac aagcacaacg ccacgatcct gagcgacaat atgatcgggc ccggcgtcca    3660
catcaacggc gtcggcggcg actgcccagg caagaccgag atgcaccgcg atatcttgct    3720
gcgttcggat attttcgtgg agttcccgcc acagacccgg atgatcccg atcgttcaaa     3780 catttggcaa taaagtttct taagattgaa tcctgttgcc ggtcttgcga tgattatcat    3840
ataatttctg ttgaattacg ttaagcatgt aataattaac atgtaatgca tgacgttatt    3900
tatgagatgg ttttttatga ttagagtccc gcaattatac atttaatacg cgatagaaaa    3960
```

```
caaaatatag cgcgcaaact aggataaatt atcgcgcgcg gtgtcatcta tgttactaga   4020
tcgggcctcc tgtcaatgct ggcggcggct ctggtggtgg ttctggtgga tccactagtt   4080
ctagagcggc cgtgggccat cgccctgata gacggttttt cgcccttga cgttggagtc   4140 cacgttcttt aatagtggac tcttgttcca aactggaaca acactcaacc ctatctcggg   4200
ctattctttt gatttataag ggattttgcc gatttcggaa ccaccatcaa acaggatttt   4260
cgcctgctgg ggcaaaccag cgtggaccgc ttgctgcaac tctctcaggg ccaggcggtg   4320
aagggcaatc agctgttgcc cgtctcactg gtgaaaagaa aaaccacccc agtacattaa   4380
aaacgtccgc aatgtgttat taagttgtct aagcgtcaat ttgtttacac cacaatatat   4440
cctgccacca gccagccaac agctccccga ccggcagctc ggcacaaaat caccactcga   4500
tacaggcagc ccatcagtcc gggacggcgt cagcgggaga gccgttgtaa ggcggcagac   4560
tttgctcatg ttaccgatgc tattcggaag aacggcaact aagctgccgg gtttgaaaca   4620
cggatgatct cgcggagggt agcatgttga ttgtaacgat gacagagcgt tgctgcctgt   4680
gatcaaatat catctcccctc gcagagatcc gaattatcag ccttcttatt catttctcgc   4740
ttaaccgtga cagttgtcta tcggcagttc gtagagcgcg ccgtgcgtcc cgagcgatac   4800
tgagcgaagc aagtgcgtcg agcagtgccc gcttgttcct gaaatgccag taaagcgctg   4860
gctgctgaac ccccagccgg aactgacccc acaaggccct agcgtttgca atgcaccagg   4920
tcatcattga cccaggcgtg ttccaccagg ccgctgcctc gcaactcttc gcaggcttcg   4980
ccgacctgct cgcgccactt cttcacgcgg gtggaatccg atccgcacat gaggcggaag   5040
gtttccagct tgagcgggta cggctcccgg tgcgagctga aatagtcgaa catccgtcgg   5100
gccgtcggcg acagcttgcg gtacttctcc catatgaatt tcgtgtagtg gtcgccagca   5160
aacagcacga cgatttcctc gtcgatcagg acctggcaac gggacgtttt cttgccacgg   5220
tccaggacgc ggaagcggtg cagcagcgac accgattcca ggtgcccaac gcggtcggac   5280
gtgaagccca tcgccgtcgc ctgtaggcgc gacaggcatt cctcggcctt cgtgtaatac   5340
cggccattga tcgaccagcc caggtcctgg caaagctcgt agaacgtgaa ggtgatcggc   5400
tcgccgatag gggtgcgctt cgcgtactcc aacacctgct gccacaccag ttcgtcatcg   5460
tcggcccgca gctcgacgcc ggtgtaggtg atcttcacgt ccttgttgac gtggaaaatg   5520
accttgtttt gcagcgcctc gcgcgggatt ttcttgttgc gcgtggtgaa cagggcagag   5580
cgggccgtgt cgtttggcat cgctcgcatc gtgtccggcc acggcgcaat atcgaacaag   5640
gaaagctgca tttccttgat ctgctgcttc gtgtgtttca gcaacgcggc ctgcttggcc   5700
tcgctgacct gttttgccag gtcctcgccg gcggttttc gcttcttggt cgtcatagtt   5760
cctcgcgtgt cgatggtcat cgacttcgcc aaacctgccg cctcctgttc gagacgacgc   5820
gaacgctcca cggcggccga tggcgcgggc agggcagggg gagccagttg cacgctgtcg   5880
cgctcgatct tggccgtagc ttgctggacc atcgagccga cggactggaa ggtttcgcgg   5940
ggcgcacgca tgacggtgcg gcttgcgatg gtttcggcat cctcggcgga aaaccccgcg   6000
tcgatcagtt cttgcctgta tgccttccgg tcaaacgtcc gattcattca ccctccttgc   6060
gggattgccc cgactcacgc cggggcaatg tgcccttatt cctgatttga cccgcctggt   6120
gccttggtgt ccagataatc caccttatcg gcaatgaagt cggtcccgta gaccgtctgg   6180
ccgtccttct cgtacttggt attccgaatc ttgccctgca cgaataccag cgacccttg   6240 cccaaatact tgccgtgggc ctcggcctga gagccaaaac acttgatgcg gaagaagtcg   6300
gtgcgctcct gcttgtcgcc ggcatcgttg cgccacatct aggtactaaa acaattcatc   6360
```

```
cagtaaaata taatatttta ttttctccca atcaggcttg atccccagta agtcaaaaaa    6420
tagctcgaca tactgttctt ccccgatatc ctccctgatc gaccggacgc agaaggcaat    6480
gtcataccac ttgtccgccc tgccgcttct cccaagatca ataaagccac ttactttgcc    6540
atctttcaca aagatgttgc tgtctcccag gtcgccgtgg gaaaagacaa gttcctcttc    6600
gggcttttcc gtctttaaaa aatcatacag ctcgcgcgga tctttaaatg gagtgtcttc    6660
ttcccagttt tcgcaatcca catcggccag atcgttattc agtaagtaat ccaattcggc    6720
taagcggctg tctaagctat tcgtataggg acaatccgat atgtcgatgg agtgaaagag    6780
cctgatgcac tccgcataca gctcgataat cttttcaggg ctttgttcat cttcatactc    6840
ttccgagcaa aggacgccat cggcctcact catgagcaga ttgctccagc catcatgccg    6900
ttcaaagtgc aggacctttg aacaggcag cttttccttcc agccatagca tcatgtcctt    6960
ttcccgttcc acatcatagg tggtccctttt ataccggctg tccgtcattt ttaaatatag    7020
gttttcattt tctcccacca gcttatatac cttagcagga gacattcctt ccgtatcttt    7080
tacgcagcgg tattttttcga tcagtttttt caattccggt gatattctca ttttagccat    7140
ttattatttc cttcctctttt tctacagtat ttaaagatac cccaagaagc taattataac    7200
aagacgaact ccaattcact gttccttgca ttctaaaacc ttaaatacca gaaacagct    7260
ttttcaaagt tgttttcaaa gttggcgtat aacatagtat cgacggagcc gattttgaaa    7320
ccacaattat gggagagacc ataatgtggt ccaatttgca gcagccgtcc gagacaggag    7380
gacatcgtcc agctgaaacc ggggcagaat ccggccattt ctgaagagaa aaatggtaaa    7440
ctgatagaat aaaatcataa gaaaggagcc gcacatgaaa aaagcagtca ttaacgggga    7500
acaaatcaga agtatcagcg acctccacca gacattgaaa aaggagcttg cccttccgga    7560
atactacggt gaaaacctgg acgctttatg ggattgtctg accggatggg tggagtaccc    7620
gctcgttttg gaatggaggc agtttgaaca aagcaagcag ctgactgaaa atggcgccga    7680
gagtgtgctt caggttttcc gtgaagcgaa agcggaaggc tgcgacatca ccatcatact    7740
ttcttaatac gatcaatggg agatgaacaa tatgaaaaca caaccacaa ttatgtctct    7800
cagcccacaa ttatggactg ccagcgctgc cattttggg gtgaggccgt tcgcggccga    7860
ggggcgcagc cctgggggg atgggaggcc cgcgttagcg ggccgggagg gttcgagaag    7920
ggggggcacc cccctttcggc gtgcgcggtc acgcgcacag ggcgcagccc tggttaaaaa    7980
caaggtttat aaatattggt ttaaaagcag gttaaaagac aggttagcgg tggccgaaaa    8040
acgggcggaa acccttgcaa atgctggatt ttctgcctgt ggacagcccc tcaaatgtca    8100
ataggtgcgc ccctcatctg tcagcactct gcccctcaag tgtcaaggat cgcgcccctc    8160
atctgtcagt agtcgcgccc ctcaagtgtc aataccgcag ggcacttatc cccaggcttg    8220
tccacatcat ctgtgggaaa ctcgcgtaaa atcaggcgtt ttcgccgatt tgcgaggctg    8280
gccagctcca cgtcgccggc cgaaatcgag cctgccctc atctgtcaac gccgcgccgg    8340
gtgagtcggc ccctcaagtg tcaacgtccg cccctcatct gtcagtgagg gccaagtttt    8400
ccgcgaggta tccacaacgc cggcggatct ggggaaccct gtggttggca tgcacataca    8460
aatggacgaa cggataaacc ttttcacgcc ctttttaaata tccgattatt ctaataaacg    8520
ctcttttctc ttag                                                     8534
```

```
<210>  SEQ ID NO 21
<211>  LENGTH: 11300
<212>  TYPE: DNA
```

<213> ORGANISM: Artificial Sequence
<220> FEATURE:
<223> OTHER INFORMATION: Description of Artificial Sequence: Synthetic vector sequence

<400> SEQUENCE: 21

```
gtttacccgc caatatatcc tgtcaaacac tgatagttta aacttttaat taaggtacct      60
gcaggagccc gggctgcagg aattcgatat caagcttgat agggtcaaat cgaccacttg     120
cacagttaag tgattctaat acgaaacctt aaaagcaaac atcggttctt ttgagtcaga     180
agaaatgcaa cttaatgtga cacatgatgt gaagaaaaaa caaagtaat ataagaaaag      240
ggaacaatta aatagttaat aaaatatttc cttaaagttg taacaaataa agaatcattt     300
tatgaaacaa tatgaaccct aaataaatta aaattcctct gaaaccttaa atttatcgag     360
ctagtgattg gctgccaact gccatgctgg caaaattaga gtgacatgat tggtctgaac     420
atgtctaggg tttcagacat gtgacatgtg tcaacaaccc attaacacat tgggtataaa     480
tccaatagac atttgatagt attaaaattg taaccattgg attaaattta aacgtgatgg     540
atgtaactaa atgacttgtc cgagtaacat cacaacgttc catactttcc ttatttggaa     600
tataattaaa tttaccattt attctttttt cttgagtttc ctgtatatgt acttgtacat     660
agatatatat gcacaaatac gtattacaat gacatattat agactttgat gtctgaactc     720
tcaaccttct cgatggagag atcatgaccg tagattttt tggatcgtag aaggcagacc      780
aaactcttaa actattggat ccgtactaaa aatctcactt tcctctcagt acccataatg     840
agagagaaaa tgataaaaat ccctaacatt attctctctc tagaaaaaaa aagatacttc     900
aaaaagaaag agaaattgca taaatctatc tacaccaaag atgttgaagc aattccaatg     960
ctatacttct atgccaaatc tatttattca gtgatcatta atcttttac ttccaagaaa     1020
tatgaacaat ttagtatcct tataatttt gtctctatat atgtaatatg aacattgggt     1080
attgaccaaa tgagaaatct aatattaaat ggtcaaaagt agtaatatga tgacatttt     1140
gaatttataa ataggttaca aattaattca ttatgacata aaaccttctt gtcagaagtc     1200
aagaactgaa actaacaaaa ctttataata aattagtaaa aatacaaatg aaaaataaaa     1260
agaaataata tctgagtgat gacgtgatca aagattcttt aacaaagaca acaaatctta     1320
cagacccaaa acctaatctt gcgctcaatt ccaacctctg aaaaaacctc aaaaatctta     1380
taaaagaaaa taaataaaga aacgaaactc tgatttcgta gagtacccat cggatatata     1440
aaaagaaatt agtaggtaaa tgaagactaa ttttgattga ctgatttaat ttgaagtcgt     1500
tgttagcttt tcttgttttg gacatgagaa ttatatattt caggacatga gagttgacaa     1560
ctgtaaacga ttaagaaaat tgatctttta atttcaaac accatttaat cttgacatgt     1620
tttatgtttt ggtggagaag aaagtaatca cgtgggactc tctactaata agtatttgga     1680
aattgcgtgt cgaattagag attactagtt tgagtaatgt agttcgaaat gagattagtt     1740
attttttaatt ttaaaagag taattttaag gaataacaaa aaagagtccc cataagctaa     1800
tttgtcttaa ttacctcctt gtttcattga ctatttgaaa tcttgaaaat tcagttgaaa     1860
tttcaaatct atgtttcttt tgaccacttc taaactaatc ttagctcata tataatttc     1920
caaaactaca aaataacac taacatttaa cattctcaag agaaaacaaa acaaaaaact     1980
tagataacca tctaaattgt cctacatgta cgtataagtt ccattattt ctatcactca     2040
tataagttaa aatttcatga aaactcaaaa atctagctag tttcaccttta ttcactctca    2100
cttaccatca catgtgtttg tatcaaatat atgatatgat ataattcatg agagagaaag     2160
```

```
agagctagag ataagaaagg aaagtaagag aaagaagaga agaaaaagag agacacagac    2220
attaacaaca atggaggatg gatgatcaca aaacagaaga tatgacctca tagtccttcc    2280
ttactctctc cccaatttgt ttcccaaaac ttacttttat agtcataaaa atcaagtttt    2340
tacctattac aacaccagat ctataaatat atctaaatct tcaagtactt gttagtaagg    2400
aaaatagaaa gatataagat tttattatta ttataataac agaaatgagt gaagaaagaa    2460
cacccaacaa agtgaatctt agttctacaa aactgaatct aaaactccac attagaaaaa    2520
accctgatgg tttcttattt cttttcattt attatctaac tctcactcag atctccttta    2580
actttgtacc atttccctca cttcatatat ctatatataa caaactctct cttttattt     2640 aagtcttaag ggaaaattaa tatacacatg aagacaagaa attagatcta caaaattgtt    2700 acaaaaccc ccgaagtaaa taaaataaac atatcaaaca aatattccca ctaatgttag     2760
tgtgtttata tatatatgtg tgtggaatat gaaggaaaaa agtgaaaaat aatcctaccc    2820
ataagagcat tcaagaagaa gctcgaggtc gacggtatcg ataagcttaa actcgacagc    2880
aaatatgatt tagattatga cctagaaata agcatagcat taaagcatat acataacaag    2940
cggtgatata ctctgactgc cactgtactt gaggaaaggt agtggactct gctcaggtac    3000
attagtttgg taaggttggc ttggcttctg ggtaatatga gaagtaaaga agtaaaaggt    3060
atttgactct agtcaagtac attggattgc ctttgtcggg gcttgatgg cttgggttcg     3120 tgtgagaagc caacaattta taagaaatat ataaaataaa aataaaaaa atttaagtgt     3180 tggaagtgaa aacggtgggg cagaaatata cacagaagag tactttaaca atgcgcaacc    3240
aaggcagatt cacaacttga tttctggacc tcgaatacga gataatggtg gtaagaaata    3300
aaggaagagt ggagcgcatt tgaaaatgaa tggagagcgc acaaaatgga ggacgaataa    3360
atgaaatata atgcaagggt gcatttccct attatttcca gaaatgtata tgtggggtcg    3420
gcattctcat gggcgtcgca ttcagggggt gtcatagcgg tcctttgatt gcagtgtggg    3480
agttgcaaca tgtaccaaca aatccattca tcccaaaacc taaatttatc ctctccatta    3540
ctattaccta cacctatacc tagtaaatat gtcctgcctt gtaactcctc cactgcctgc    3600
acacgtctta gtcaatccat ctgccttcaa ataggcatta ttttgttctt tcccctccga    3660
ctgaaaggct atcgaccgac cgaccgctca tcttcttctt ctgcgcaatt ttttctgctg    3720
gatcatcatc attaccatca tcgccatccc caccatcatc atcatgatgg tatctctatc    3780
tctccctggc aatcgattgt agaggaaagg aagagggaag gggcatatgt attgatcaac    3840
ctacccgaaa aaacaatctg atcagccctg ctaatcttgc ttataaatct cttatccact    3900
gttcaatcat tcaggtttct tcccactttc aagcaaaggc gcccggattg gccgtgttct    3960
tagattttca ggtacttaaa tggacaatat tccccacctg aagccgttct gaaaaagatt    4020
tgtttgtaga aacaaacgat tgtaatattt gcttaagttg agcttaaggg gtttggtacc    4080
taacttgcct tgtggttatt tgtttctcag aactcgggct cgtccaact gtaggaacga     4140 accagcacaa ggggttgcag cttttgctgt tgctgttgcg cccattgctt ttggactggt    4200
attagtagtt gcagctttgt tttgcatacg ctgtgaggat ctgtgcgcgg aaattttgtg    4260
tacaaatcat ggcacaggtt atcaacacgt ttgacggggt tgcggattat cttcagacat    4320
atcataagct acctgataat tacattacaa aatcagaagc acaagccctc ggctgggtgg    4380
catcaaaagg gaaccttgca gacgtcgctc cggggaaaag catcggcgga gacatcttct    4440
caaacaggga aggcaaactc ccgggcaaaa gcggacgaac atggcgtgaa gcggatatta    4500
actatacatc aggcttcaga aattcagacc ggattcttta ctcaagcgac tggctgattt    4560
```

```
acaaaacaac ggaccattat cagacctcta caaaaatcag ataacgaaaa aaacggcttc    4620
cctgcgggag gccgttttt  tcagctttac ataaagtgtg taataaattt ttcttcaaac    4680
tctgatcggt caattgcact ttgagctcga atttccccga tcgttcaaac atttggcaat    4740
aaagtttctt aagattgaat cctgttgccg gtcttgcgat gattatcata taatttctgt    4800
tgaattacgt taagcatgta ataattaaca tgtaatgcat gacgttattt atgagatggg    4860
tttttatgat tagagtcccg caattataca tttaatacgc gatagaaaac aaaatatagc    4920
gcgcaaacta ggataaatta tcgcgcgcgg tgtcatctat gttactagat cgggaaggcg    4980
cgccgcggcc gcaacactga tagtttaaac tgaaggcggg aaacgacaat ctgatcatga    5040
gcggagaatt aagggagtca cgttatgacc cccgccgatg acgcgggaca agccgtttta    5100
cgtttggaac tgacagaacc gcaacgttga aggagccact cagccgcggg tttctggagt    5160
ttaatgagct aagcacatac gtcagaaacc attattgcgc gttcaaaagt cgcctaaggt    5220
cactatcagc tagcaaatat tcttgtcaa aaatgctcca ctgacgttcc ataaattccc    5280
ctcggtatcc aattagagtc tcatattcac tctcaatcca aataatctgc accgatctg    5340 gatcgtttcg catgattgaa caagatggat tgcacgcagg ttctccggcc gcttgggtgg    5400
agaggctatt cggctatgac tgggcacaac agacaatcgg ctgctctgat gccgccgtgt    5460
tccggctgtc agcgcagggg cgcccggttc tttttgtcaa gaccgacctg tccggtgccc    5520
tgaatgaact gcaggacgag gcagcgcggc tatcgtggct ggccacgacg ggcgttcctt    5580
gcgcagctgt gctcgacgtt gtcactgaag cgggaaggga ctggctgcta ttgggcgaag    5640
tgccggggca ggatctcctg tcatctcacc ttgctcctgc cgagaaagta tccatcatgg    5700
ctgatgcaat gcggcggctg catacgcttg atccggctac ctgcccattc gaccaccaag    5760
cgaaacatcg catcgagcga gcacgtactc ggatggaagc cggtcttgtc gatcaggatg    5820
atctggacga agagcatcag gggctcgcgc cagccgaact gttcgccagg ctcaaggcgc    5880
gcatgcccga cggcgatgat ctcgtcgtga cccatggcga tgcctgcttg ccgaatatca    5940
tggtggaaaa tggccgcttt tctggattca tcgactgtgg ccggctgggt gtggcggacc    6000
gctatcagga catagcgttg gctacccgtg atattgctga agagcttggc ggcgaatggg    6060
ctgaccgctt cctcgtgctt tacggtatcg ccgctcccga ttcgcagcgc atcgccttct    6120
atcgccttct tgacgagttc ttctgagcgg gactctgggg ttcgaaatga ccgaccaagc    6180
gacgcccaac ctgccatcac gagatttcga ttccaccgcc gccttctatg aaaggttggg    6240
cttcggaatc gttttccggg acgccggctg gatgatcctc cagcgcgggg atctcatgct    6300
ggagttcttc gcccacggga tctctgcgga acaggcggtc gaaggtgccg atatcattac    6360
gacagcaacg gccgacaagc acaacgccac gatcctgagc gacaatatga tcgggcccgg    6420
cgtccacatc aacggcgtcg gcggcgactg cccaggcaag accgagatgc accgcgatat    6480
cttgctgcgt tcggatattt tcgtggagtt cccgccacag acccggatga tccccgatcg    6540
ttcaaacatt tggcaataaa gtttcttaag attgaatcct gttgccggtc ttgcgatgat    6600
tatcatataa tttctgttga attacgttaa gcatgtaata attaacatgt aatgcatgac    6660
gttatttatg agatgggttt ttatgattag agtcccgcaa ttatacattt aatacgcgat    6720
agaaaacaaa atatagcgcg caaactagga taaattatcg cgcggtgt catctatgtt    6780 actagatcgg gcctcctgtc aatgctggcg gcggctctgg tggtggttct ggtggatcca    6840
ctagttctag agcggccgtg ggccatcgcc ctgatagacg gttttcgcc ctttgacgtt    6900
```

```
ggagtccacg ttctttaata gtggactctt gttccaaact ggaacaacac tcaaccctat    6960
ctcgggctat tcttttgatt tataagggat tttgccgatt tcggaaccac catcaaacag    7020
gattttcgcc tgctggggca aaccagcgtg gaccgcttgc tgcaactctc tcagggccag    7080
gcggtgaagg gcaatcagct gttgcccgtc tcactggtga aaagaaaaac caccccagta    7140
cattaaaaac gtccgcaatg tgttattaag ttgtctaagc gtcaatttgt ttacaccaca    7200
atatatcctg ccaccagcca gccaacagct ccccgaccgg cagctcggca caaaatcacc    7260
actcgataca ggcagcccat cagtccggga cggcgtcagc gggagagccg ttgtaaggcg    7320
gcagactttg ctcatgttac cgatgctatt cggaagaacg gcaactaagc tgccgggttt    7380
gaaacacgga tgatctcgcg gagggtagca tgttgattgt aacgatgaca gagcgttgct    7440
gcctgtgatc aaatatcatc tccctcgcag agatccgaat tatcagcctt cttattcatt    7500
tctcgcttaa ccgtgacagt tgtctatcgg cagttcgtag agcgcgccgt gcgtcccgag    7560
cgatactgag cgaagcaagt gcgtcgagca gtgcccgctt gttcctgaaa tgccagtaaa    7620
gcgctggctg ctgaaccccc agccggaact gaccccacaa ggccctagcg tttgcaatgc    7680
accaggtcat cattgaccca ggcgtgttcc accaggccgc tgcctcgcaa ctcttcgcag    7740
gcttcgccga cctgctcgcg ccacttcttc acgcgggtgg aatccgatcc gcacatgagg    7800
cggaaggttt ccagcttgag cgggtacggc tcccggtgcg agctgaaata gtcgaacatc    7860
cgtcgggccg tcggcgacag cttgcggtac ttctcccata tgaatttcgt gtagtggtcg    7920
ccagcaaaca gcacgacgat ttcctcgtcg atcaggacct ggcaacggga cgttttcttg    7980
ccacggtcca ggacgcggaa gcggtgcagc agcgacaccg attccaggtg cccaacgcgg    8040
tcggacgtga agcccatcgc cgtcgcctgt aggcgcgaca ggcattcctc ggccttcgtg    8100
taataccggc cattgatcga ccagcccagg tcctggcaaa gctcgtagaa cgtgaaggtg    8160
atcggctcgc cgatagggt gcgcttgcg tactccaaca cctgctgcca caccagttcg    8220
tcatcgtcgg cccgcagctc gacgccggtg taggtgatct tcacgtcctt gttgacgtgg    8280
aaaatgacct tgttttgcag cgcctcgcgc gggattttct tgttgcgcgt ggtgaacagg    8340
gcagagcggg ccgtgtcgtt tggcatcgct cgcatcgtgt ccggccacgg cgcaatatcg    8400
aacaaggaaa gctgcatttc cttgatctgc tgcttcgtgt gtttcagcaa gcggcctgc    8460
ttggcctcgc tgacctgttt tgccaggtcc tcgccggcgg ttttttcgctt cttggtcgtc    8520
atagttcctc gcgtgtcgat ggtcatcgac ttcgccaaac ctgccgcctc ctgttcgaga    8580
cgacgcgaac gctccacggc ggccgatggc gcggcaggg caggggagc cagttgcacg    8640
ctgtcgcgct cgatcttggc cgtagcttgc tggaccatcg agccgacgga ctggaaggtt    8700
tcgcggggcg cacgcatgac ggtgcggctt gcgatggttt cggcatcctc ggcggaaaac    8760
cccgcgtcga tcagttcttg cctgtatgcc ttccggtcaa acgtccgatt cattcaccct    8820
ccttgcggga ttgccccgac tcacgccggg gcaatgtgcc cttattcctg atttgacccg    8880
cctggtgcct tggtgtccag ataatccacc ttatcggcaa tgaagtcggt cccgtagacc    8940
gtctggccgt ccttctcgta cttggtattc cgaatcttgc cctgcacgaa taccagcgac    9000
cccttgccca aatacttgcc gtgggcctcg gcctgagagc caaaacactt gatgcggaag    9060
aagtcggtgc gctcctgctt gtcgccggca tcgttgcgcc acatctaggt actaaaacaa    9120
ttcatccagt aaaatataat atttttatttt ctcccaatca ggcttgatcc ccagtaagtc    9180
aaaaaatagc tcgacatact gttcttcccc gatatcctcc ctgatcgacc ggacgcagaa    9240
ggcaatgtca taccacttgt ccgccctgcc gcttctccca agatcaataa agccacttac    9300
```

```
tttgccatct tcacaaaga tgttgctgtc tcccaggtcg ccgtgggaaa agacaagttc    9360
ctcttcgggc ttttccgtct ttaaaaaatc atacagctcg cgcggatctt taaatggagt    9420
gtcttcttcc cagttttcgc aatccacatc ggccagatcg ttattcagta agtaatccaa    9480
ttcggctaag cggctgtcta agctattcgt atagggacaa tccgatatgt cgatggagtg    9540
aaagagcctg atgcactccg catacagctc gataatcttt tcagggcttt gttcatcttc    9600
atactcttcc gagcaaagga cgccatcggc ctcactcatg agcagattgc tccagccatc    9660
atgccgttca agtgcagga cctttggaac aggcagcttt ccttccagcc atagcatcat    9720
gtccttttcc cgttccacat cataggtggt ccctttatac cggctgtccg tcatttttaa    9780
atataggttt tcattttctc ccaccagctt ataiaccttta gcaggagaca ttccttccgt    9840
atcttttacg cagcggtatt tttcgatcag ttttttcaat tccggtgata ttctcatttt    9900
agccatttat tatttccttc ctcttttcta cagtatttaa agatacccca agaagctaat    9960
tataacaaga cgaactccaa ttcactgttc cttgcattct aaaaccttaa ataccagaaa   10020
acagcttttt caaagttgtt tcaaagttg gcgtataaca tagtatcgac ggagccgatt   10080
ttgaaaccac aattatggga gagaccataa tgtggtccaa tttgcagcag ccgtccgaga   10140
caggaggaca tcgtccagct gaaaccgggg cagaatccgg ccatttctga agagaaaat    10200 ggtaaactga tagaataaaa tcataagaaa ggagccgcac atgaaaaaag cagtcattaa   10260
cggggaacaa atcagaagta tcagcgacct ccaccagaca ttgaaaaagg agcttgccct   10320
tccggaatac tacggtgaaa acctggacgc tttatggat tgtctgaccg gatgggtgga   10380
gtacccgctc gttttggaat ggaggcagtt tgaacaaagc aagcagctga ctgaaaatgg   10440
cgccgagagt gtgcttcagg ttttccgtga agcgaaagcg gaaggctgcg acatcaccat   10500
catactttct taatacgatc aatgggagat gaacaatatg gaaacacaaa ccacaattat   10560
gtctctcagc ccacaattat ggactgccag cgctgccatt tttggggtga ggccgttcgc   10620
ggccgagggg cgcagcccct gggggatgg gaggcccgcg ttagcgggcc gggagggttc   10680
gagaaggggg ggcacccccc ttcggcgtgc gcggtcacgc gcacagggcg cagccctggt   10740
taaaaacaag gtttataaat attggtttaa aagcaggtta aaagacaggt tagcggtggc   10800
cgaaaaacgg gcgaaaaccc ttgcaaatgc tggattttct gcctgtggac agcccctcaa   10860
atgtcaatag gtgcgcccct catctgtcag cactctgccc ctcaagtgtc aaggatcgcg   10920
cccctcatct gtcagtagtc gcgccccctca agtgtcaata ccgcagggca cttatcccca   10980
ggcttgtcca catcatctgt gggaaactcg cgtaaaatca ggcgttttcg ccgatttgcg   11040
aggctggcca gctccacgtc gccggccgaa atcgagcctg cccctcatct gtcaacgccg   11100
cgccgggtga gtcggcccct caagtgtcaa cgtccgcccc tcatctgtca gtgagggcca   11160
agttttccgc gaggtatcca caacgccggc ggatctgggg aaccctgtgg ttggcatgca   11220
catacaaatg gacgaacgga taacctttt cacgcccttt taaatatccg attattctaa   11280
taaacgctct tttctcttag                                              11300
```

<210> SEQ ID NO 22
<211> LENGTH: 12631
<212> TYPE: DNA
<213> ORGANISM: Artificial Sequence
<220> FEATURE:
<223> OTHER INFORMATION: Description of Artificial Sequence: Synthetic vector sequence

<400> SEQUENCE: 22

```
ggccgcattt gggctcctgc aggtacctta attaaaagtt taaactatca gtgtttgaca      60
ggatatattg gcgggtaaac ctaagagaaa agagcgttta ttagaataat cggatattta     120
aaagggcgtg aaaaggttta tccgttcgtc catttgtatg tgcatgccaa ccacagggtt     180
ccccagatcc gccggcgttg tggatacctc gcggaaaact tggccctcac tgacagatga     240
ggggcggacg ttgacacttg aggggccgac tcacccggcg cggcgttgac agatgagggg     300
caggctcgat ttcggccggc gacgtggagc tggccagcct cgcaaatcgg cgaaaacgcc     360
tgattttacg cgagtttccc acagatgatg tggacaagcc tggggataag tgccctgcgg     420
tattgacact tgagggcgc gactactgac agatgagggg cgcgatcctt gacacttgag      480
gggcagagtg ctgacagatg aggggcgcac ctattgacat ttgaggggct gtccacaggc     540
agaaaatcca gcatttgcaa gggtttccgc ccgttttcg gccaccgcta acctgtcttt      600
taacctgctt ttaaaccaat atttataaac cttgttttta accagggctg cgccctgtgc     660
gcgtgaccgc gcacgccgaa ggggggtgcc ccccttctc gaaccctccc ggcccgctaa      720
cgcgggcctc ccatccccc aggggctgcg cccctcggcc gcgaacggcc tcaccccaaa      780
aatggcagcg ctggcagtcc ataattgtgg tccaatttgc agccgtccga cacaggagga    840
catcgtccag ctgaaaccgg ggcagaatcc ggccatttct gaagagaaaa atggtaaact    900
gatagaataa aatcataaga aaggagccgc acatgaaaaa agcagtcatt aacggggaac    960
aaatcagaag tatcagcgac ctccaccaga cattgaaaaa ggagcttgcc cttccggaat   1020
actacggtga aaacctggac gctttatggg attgtctgac cggatgggtg gagtacccgc   1080
tcgttttgga atggaggcag tttgaacaaa gcaagcagct gactgaaaat ggcgccgaga   1140
gtgtgcttca ggttttccgt gaagcgaaag cggaaggctg cgacatcacc atcatacttt   1200
cttaatacga tcaatgggag atgaacaata tggaaacaca aaccacaatt gtggtttcaa   1260
aatcggctcc gtcgatacta tgttatacgc caactttgaa aacaactttg aaaaagctgt   1320
tttctggtat ttaaggtttt agaatgcaag gaacagtgaa ttggagttcg tcttgttata   1380
attagcttct tgggtatct ttaaatactg tagaaaagag gaaggaaata ataaatggct    1440
aaaatgagaa tatcaccgga attgaaaaaa ctgatcgaaa aataccgctg cgtaaaagat   1500
acggaaggaa tgtctcctgc taaggtatat aagctggtgg gagaaaatga aaacctatat   1560
ttaaaaatga cggacagccg gtataaaggg accacctatg atgtggaacg ggaaaaggac   1620
atgatgctat ggctggaagg aaagctgcct gttccaaagg tcctgcactt tgaacggcat   1680
gatggctgga gcaatctgct catgagtgag gccgatggcg tcctttgctc ggaagagtat   1740
gaagatgaac aaagccctga aaagattatc gagctgtatg cggagtgcat caggctcttt   1800
cactccatcg acatatcgga ttgtccctat acgaatagct tagacagccg cttagccgaa   1860
ttggattact tactgaataa cgatctggcc gatgtggatt cgaaaactg gaagaagac    1920
actccattta aagatccgcg cgagctgtat gatttttaa agacggaaaa gcccgaagag    1980
gaacttgtct tttcccacgg cgacctggga gacagcaaca tctttgtgaa agatggcaaa   2040
gtaagtggct ttattgatct tgggagaagc ggcagggcgg acaagtggta tgacattgcc   2100
ttctgcgtcc ggtcgatcag ggaggatatc ggggaagaac agtatgtcga gctatttttt   2160
gacttactgg ggatcaagcc tgattgggag aaaataaaat attatatttt actggatgaa   2220
ttgttttagt acctagatgt ggcgcaacga tgccggcgac aagcaggagc gcaccgactt   2280
cttccgcatc aagtgttttg gctctcaggc cgaggcccac ggcaagtatt tgggcaaggg   2340
```

```
gtcgctggta ttcgtgcagg gcaagattcg gaataccaag tacgagaagg acggccagac   2400
ggtctacggg accgacttca ttgccgataa ggtggattat ctggacacca aggcaccagg   2460
cgggtcaaat caggaataag ggcacattgc cccggcgtga gtcggggcaa tcccgcaagg   2520
agggtgaatg aatcggacgt ttgaccggaa ggcatacagg caagaactga tcgacgcggg   2580
gttttccgcc gaggatgccg aaaccatcgc aagccgcacc gtcatgcgtg cgccccgcga   2640
aaccttccag tccgtcggct cgatggtcca gcaagctacg gccaagatcg agcgcgacag   2700
cgtgcaactg gctcccctg ccctgcccgc gccatcggcc gccgtggagc gttcgcgtcg   2760
tctcgaacga gaggcggcag gtttggcgaa gtcgatgacc atcgacacgc gaggaactat   2820
gacgaccaag aagcgaaaaa ccgccggcga ggacctggca aaacaggtca gcgaggccaa   2880
gcaggccgcg ttgctgaaac acacgaagca gcagatcaag gaaatgcagc tttccttgtt   2940
cgatattgcg ccgtggccgg acacgatgcg agcgatgcca aacgacacgg cccgctctgc   3000
cctgttcacc acgcgcaaca agaaaatccc gcgcgaggcg ctgcaaaaca aggtcatttt   3060
ccacgtcaac aaggacgtga agatcaccta caccggcgtc gagctgcggg ccgacgatga   3120
cgaactggtg tggcagcagg tgttggagta cgcgaagcgc accctatcg gcgagccgat   3180 caccttcacg ttctacgagc tttgccagga cctgggctgg tcgatcaatg gccggtatta   3240
cacgaaggcc gaggaatgcc tgtcgcgcct acaggcgacg gcgatgggct tcacgtccga   3300
ccgcgttggg cacctggaat cggtgtcgct gctgcaccgc ttccgcgtcc tggaccgtgg   3360
caagaaaacg tcccgttgcc aggtcctgat cgacgaggaa atcgtcgtgc tgtttgctgg   3420
cgaccactac acgaaattca tatgggagaa gtaccgcaag ctgtcgccga cggcccgacg   3480
gatgttcgac tatttcagct cgcaccggga gccgtacccg ctcaagctgg aaaccttccg   3540
cctcatgtgc ggatcggatt ccacccgcgt gaagaagtgg cgcgagcagg tcggcgaagc   3600
ctgcgaagag ttgcgaggca gcggcctggt ggaacacgcc tgggtcaatg atgacctggt   3660
gcattgcaaa cgctagggcc ttgtggggtc agttccggct gggggttcag cagccagcgc   3720
tttactggca tttcaggaac aagcgggcac tgctcgacgc acttgcttcg ctcagtatcg   3780
ctcgggacgc acggcgcgct ctacgaactg ccgatagaca actgtcacgg ttaagcgaga   3840
aatgaataag aaggctgata attcggatct ctgcgaggga gatgatattt gatccggtgt   3900
gaaataccgc acagatgcgt aaggagaaaa taccgcatca ggcgctcttc cgcttcctcg   3960
ctcactgact cgctgcgctc ggtcgttcgg ctgcggcgag cggtatcagc tcactcaaag   4020
gcggtaatac ggttatccac agaatcaggg gataacgcag gaaagaacat gtgagcaaaa   4080
ggccagcaaa aggccaggaa ccgtaaaaag gccgcgttgc tggcgttttt ccataggctc   4140
cgcccccctg acgagcatca caaaaatcga cgctcaagtc agaggtggcg aaacccgaca   4200
ggactataaa gataccaggc gtttccccct ggaagctccc tcgtgcgctc tcctgttccg   4260
accctgccgc ttaccggata cctgtccgcc tttctccctt cgggaagcgt ggcgctttct   4320
catagctcac gctgtaggta tctcagttcg gtgtaggtcg ttcgctccaa gctgggctgt   4380
gtgcacgaac cccccgttca gcccgaccgc tgcgccttat ccggtaacta tcgtcttgag   4440
tccaacccgg taagacacga cttatcgcca ctggcagcag ccactggtaa caggattagc   4500
agagcgaggt atgtaggcgg tgctacagag ttcttgaagt ggtggcctaa ctacggctac   4560
actagaagga cagtatttgg tatctgcgct ctgctgaagc cagttacctt cggaaaaaga   4620
gttggtagct cttgatccgg caaacaaacc accgctggta gcggtggttt ttttgtttgc   4680
aagcagcaga ttacgcgcag aaaaaaagga tatcaagaag atcctttgat cttttctacg   4740
```

```
gggtctgacg ctcagtggaa cgaaaactca cgttaaggga ttttggtcat gagattatca    4800
aaaaggatct tcacctagat cctttaaat taaaaatgaa gttttaaatc aatctaaagt    4860
atatatgagt aaacttggtc tgacagttac caatgcttca tcagtgaggc tgatcacagg    4920
cagcaacgct ctgtcatcgt tacaatcaac atgctaccct ccgcgagatc atccgtgttt    4980
caaacccggc agcttagttg ccgttcttcc gaatagcatc ggtaacatga gcaaagtctg    5040
ccgccttaca acggctctcc cgctgacgcc gtcccggact gatgggctgc ctgtatcgag    5100
tggtgatttt gtgccgagct gccggtcggg gagctgttgg ctggctggtg caggatata    5160 ttgtggtgta acaaattga cgcttagaca acttaataac acaccgcggt ctagaactag    5220
tggatccccc ctacgtgcga tctagtaaca tagatgacac cgcgcgcgat aatttatcct    5280
agtttgcgcg ctatattttg ttttctatcg cgtattaaat gtataattgc gggactctaa    5340
tcataaaaac ccatctcata ataacgtca tgcattacat gttaattatt acatgcttaa    5400
cgtaattcaa cagaaattat atgataatca tcgcaagacc ggcaacagga ttcaatctta    5460 agaaactta ttgccaaatg tttgaacgat ccctcagaag aactcgtcaa gaaggcgata    5520
gaaggcgatg cgctgcgaat cgggagcggc gataccgtaa agcacgagga agcggtcagc    5580
ccattcgccg ccaagctctt cagcaatatc acgggtagcc aacgctatgt cctgatagcg    5640
gtccgccaca cccagccggc cacagtcgat gaatccagaa aagcggccat tttccaccat    5700
gatattcggc aagcaggcat cgccatgggt cacgacgaga tcctcgccgt cgggcatgcg    5760
cgccttgagc ctggcgaaca gttcggctgg cgcgagcccc tgatgctctt cgtccagatc    5820
atcctgatcg acaagaccgg cttccatccg agtacgtgct cgctcgatgc gatgtttcgc    5880
ttggtggtcg aatgggcagg tagccggatc aagcgtatgc agccgccgca ttgcatcagc    5940
catgatggat actttctcgg caggagcaag gtgagatgac aggagatcct gccccggcac    6000
ttcgcccaat agcagccagt cccttcccgc ttcagtgaca acgtcgagca cagctgcgca    6060
aggaacgccc gtcgtggcca gccacgatag ccgcgctgcc tcgtcctgga gttcattcag    6120
ggcaccggac aggtcggtct tgacaaaaag aaccgggcgc ccctgcgctg acagccggaa    6180
cacggcggca tcagagcagc cgattgtctg ttgtgcccag tcatagccga atagcctctc    6240
cacccaagcg gccggagaac ctgcgtgcaa tccatcttgt tcaatcatct gttaatcaga    6300
aaaactcaga ttaatcgaca aattcgatcg cacaaactag aaactaacac cagatctaga    6360
tagaaatcac aaatcgaaga gtaattattc gacaaaactc aaattatttg aacaaatcgg    6420
atgatattta tgaaacccta atcgagaatt aagatgatat ctaacgatca aacccagaaa    6480
atcgtcttcg atctaagatt aacagaatct aaaccaaaga acatatacga aattgggatc    6540
gaacgaaaac aaaatcgaag attttgagag aataaggaac acagaaattt accttgatca    6600
cggtagagag aattgagaga agtttttaa gattttgaga aattgaaatc tgaattgtga    6660
agaagaagag ctctttgggt attgttttat agaagaagaa gaagaaaaga cgaggacgac    6720
taggtcacga gaaagctaag gcggtgaagc aatagctaat aataaaatga cacgtgtatt    6780
gagcgttgtt tacacgcaaa gttgttttg gctaattgcc ttattttag gttgaggaaa    6840 agtatttgtg ctttgagttg ataaacacga ctcgtgtgtg ccggctgcaa ccactttgac    6900
gccgtttatt actgactcgt cgacaaccac aatttctaac ggtcgtcata agatccagcc    6960
gttgagattt aacgatcgtt acgatttata ttttttagc attatcgttt tatttttaa    7020 atatacggtg gagctgaaaa ttggcaataa ttgaaccgtg ggtcccactg cattgaagcg    7080
```

```
tatttcgtat tttctagaat tcttcgtgct ttatttcttt tccttttttgt ttttttttgc    7140 catttatcta atgcaagtgg gcttataaaa tcagtgaatt tcttggaaaa gtaacttctt    7200
tatcgtataa catattgtga aattatccat ttcttttaat ttttttagtgt tattggatat    7260 ttttgtatga ttattgattt gcataggata atgactttg tatcaagttg gtgaacaagt     7320
ctcgttaaaa aaggcaagtg gtttggtgac tcgatttatt cttgttattt aattcatata    7380
tcaatggatc ttatttgggg cctggtccat atttaacact cgtgttcagt ccaatgacca    7440
ataatatttt ttcattaata acaatgtaac aagaatgata cacaaaacat tctttgaata    7500
agttcgctat gaagaaggga acttatccgg tcctagatca tcagttcata caaacctcca    7560
tagagttcaa catcttaaac aaggatatcc tgatccgttg acggcgcgcc aagcggggcc    7620
gcatttaaat gggccctatc taatcgaatt ttgtaaactg gtttgataag ccatcaatgc    7680
atcagtcaag aatgaatcat tgcaactaag ttgatataat tcaatttacc atagaactca    7740
aatgttgata tcttcttatg gattttctga tcttctacat tattagaaag aaacttgatt    7800
taccagtaat gatgatacat atccaataga acgaaataag ccaatcttta taggttttgg    7860
tagtaaagtt acaacatcag agacatgtat gtattgtctc tcagaagagc tcttgaccga    7920
tcagagtttg aagaaaaatt tattacacac tttatgtaaa gctgaaaaaa acggcctccc    7980
gcagggaagc cgttttttc gttatctgat ttttgtaaag gtctgatact cgtccgttgt     8040
tttgtaaatc agccagtcgc ttgagtaaag aatccggtct gaatttctga agcctgatgt    8100
atagttaata tccgcttcac gccatgttcg tccgcttttg cccgggagtt tgccttccct    8160
gtttgagaag atgtctccgc cgatgctttt ccccggagcg acgtctgcaa ggttcccttt    8220
tgatgccacc cagccgaggg cttgtgcttc tgattttgta atgtaattat caggtagctt    8280
atgatatgtc tgaagataat ccgcaacccc gtcaaacgtg ttgataacct gtgccatgtt    8340
cccgtttgat acctgaattt tggccattct cataaatctt ctaaaaacag cagaactgac    8400
tattcaaaga aagtagaacc cacagaaagt aatcaaagta gtttgattaa atgcgttgtg    8460
tatcatcgca gccctgcta cggatatta taggaaaggt ttgagagcaa tgtgtgcagc      8520
aagttgtgtg tgaatcacct gcttccatgg cggaggataa ataatttagt cacgcattta    8580
gttgaacgta actactaact cctctaccgc taatcattct tcttttgccc gggcaagttc    8640
aacaacaacc ccacaatcac gcttcctgta ttttgttttg ttttcaaaac aatagaattc    8700
actttttact gccaaaatta tgttttactc gagagcccaa atgcggccgc ggccgggtgg    8760
tgacatttat tcataaattc atctcaaaac aagaaggatt tacaaaaata aaagaaaaca    8820 aaatttttcat ctttaacata attataattg tgttcacaaa attcaaactt aaacccttaa   8880
tataaagaat ttctttcaac aatacacttt aatcacaact tcttcaatca caacctcctc    8940
caacaaaatt aaaatagatt aataaataaa taaacttaac tatttaaaaa aaatatattat   9000 acaaaattta ttaaaacttc aaaataaaca aacttttat acaaaattca tcaaaacttt     9060
aaaataaagc taaacactga aaatgtgagt acatttaaaa ggacgctgat cacaaaaatt    9120
ttgaaaacat aaacaaactt gaaactctac cttttaagaa tgagtttgtc gtctcattaa    9180
ctcattagtt ttatagttcg aatccaatta acgtatcttt tattttatgg aataagggtg    9240
ttttaataag tgattttggg attttttttag taatttattt gtgatatgtt atggagtttt   9300
taaaaatata tatatatata tatattttg ggttgagttt acttaaaatt tggaaaaggt     9360
tggtaagaac tataaattga gttgtgaatg agtgttttat ggattttta agatgttaaa    9420 tttatatatg taattaaaat tttattttga ataacaaaaa ttataattgg ataaaaaatt    9480
```

```
gttttgttaa atttagagta aaaatttcaa aatctaaaat aattaaacac tattattttt    9540
aaaaaatttg ttggtaaatt ttatcttata tttagttaaa atttagaaaa aattaatttt    9600
aaattaataa acttttgaag tcaaatattc caaatatttt ccaaaatatt aaatctattt    9660
tgcattcaaa atacaattta aataataaaa cttcatggaa tagattaacc aatttgtata    9720
aaaaccaaaa atctcaaata aaatttaaat tacaaaacat tatcaacatt atgatttcaa    9780
gaaagacaat aaccagtttc aataaaaata aaaaacctca tggcccgtaa ttaagatctc    9840
attaattaat tcttattttt taatttttt acatagaaaa tatctttata tcgtatccaa    9900
gaaatataga atgttctcgt ccagggacta ttaatctcca aacaagtttc aaaatcatta    9960
cattaaagct catcatgtca tttgtggatt ggaaattata ttgtataaga gaaatataga   10020
atgttctcgt ctagggacta ttaatttcca aacaaatttc aaaatcatta cattaaagct   10080
catcatgtca tttgtggatt ggaaattaga caaaaaaaat cccaaatatt tctctcaatc   10140
tcccaaaata tagttcgaac tccatatttt tggaaattga gaattttttt acccaataat   10200
atatttttt atacatttta gagattttcc agacatattt gctctgggat ttattggaat   10260
gaaggtttga gttataaact ttcagtaatc caagtatctt cggttttga agatactaaa   10320
tccattatat aataaaaaca catttttaaac accaatttaa tgggatttca gatttgtatc   10380
ccatgctatt ggctaaggca ttttttcttat tgtaatctaa ccaattctaa tttccaccct   10440
ggtgtgaact gactgacaaa tgcggtccga aaacagcgaa tgaaatgtct gggtgatcgg   10500
tcaaacaagc ggtgggcgag agagcgcggg tgttggccta gccgggatgg gggtaggtag   10560
acggcgtatt accggcgagt tgtccgaatg gagttttcgg ggtaggtagt aacgtagacg   10620
tcaatggaaa aagtcataat ctccgtcaaa aatccaaccg ctccttcaca tcgcagagtt   10680
ggtggccacg ggaccctcca cccactcact cgatcgcctg ccgtggttgc ccattattca   10740
accatacgcc acttgactct tcaccaacaa ttccaggccg gctttctata caatgtactg   10800
cacaggaaaa tccaatataa aaagccggcc tctgcttcct tctcagtagc ccccagctca   10860
ttcaattctt cccactgcag gctacatttg tcagacacgt tttccgccat ttttcgcctg   10920
tttctgcgga gaatttgatc aggttcggat tgggattgaa tcaattgaaa ggttttatt   10980
ttcagtattt cgatcgccgg atcccccggg ctgcaggaat tgggctgcag atcgatattt   11040
gatttcacat gctattgtaa tgtatttatt gtttcaattc cgaattagac aaagtgctta   11100
aagctctctt ttcggatttt ttttttcatt aatgtataat aattgcggac attacaatat   11160
actgtacaac gtgatttgag cttgatgaat tacaagattg gaagaacttc gaagacaaaa   11220
aaaaaatcga tctgcaggaa ttcgtccagc agtaattcgg taccctgat cagcactgct   11280
gccaagaatg taagttttta tttctttat atgttcaaac agttttataa agtactataa   11340
gcttttttta gccaaaagaa atatcttaag ttttagtaac caataaagaa ttattgcggc   11400
ctccttattt aattatagta catatgtcat agtagatgtt ttttttatta ttattatttt   11460
ttatttttt atagtttttt acaaattcga cttggagacc ttatgatttg gaagatactc   11520
catttaattt tatgagttgt gtttgaaaac atatttaag actaaacacg tagagaacat   11580
tcttaacaaa tttgtaaata aataaatta actctattct ctaggattta aatattatag   11640
gtatatatat aattttctaa taagtttata tcgagtcact catacgagtt gtgtagaaag   11700
ttaatcacgg gtaccaattt taaattaaaa ataagaataa ttatatgatc ttaaattttat   11760
acaactctga taaagattg ggctttgaca tctttgaaga aaactagatt tagtaatatt   11820
```

```
ctgattaaat tgggttcaca ctttgtagtg ggcacacttt ccgggttcga aatcgaaatc    11880
tggaagctta tcgatctcga ggggcccact agtatcgatc tcgagggggcc cactagtatc   11940 gatcgatttt ttttttgtct tcgaagttct tccaatcttg taattcatca agctcaaatc   12000
acgttgtaca gtatattgta atgtccgcaa ttattataca ttaatgaaaa aaaaaatccg   12060
aaaagagagc tttaagcact ttgtctaatt cggaattgaa acaataaata cattacaata   12120
gcatgtgaaa tcaaatatcg atccgatggg tgttatttgt ggataataaa ttcgggtgat   12180
gttcagtgtt tgtcgtattt ctcacgaata aattgtgttt atgtatgtgt tagtgttgtt   12240
tgtctgtttc agaccctctt atgttatatt tttcttttcg tcggtcagtt gaagccaata   12300
ctggtgtcct ggccggcact gcaataccat ttcgtttaat ataaagactc tgttatccgt   12360
gagctcgaat tccccgatc gttcaaacat ttggcaataa agtttcttaa gattgaatcc   12420
tgttgccggt cttgcgatga ttatcatata atttctgttg aattacgtta agcatgtaat   12480
aattaacatg taatgcatga cgttatttat gagatgggtt tttatgatta gagtcccgca   12540
attatacatt taatacgcga tagaaaacaa aatatagcgc gcaaactagg ataaattatc   12600
gcgcgcggtg tcatctatgt tactagatcg c                                   12631

<210> SEQ ID NO 23
<211> LENGTH: 16396
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 23
ggccgcattt gggctcctgc aggtaccttaa attaaaagtt taaactatca gtgtttgaca     60
ggatatattg gcgggtaaac ctaagagaaa agagcgttta ttagaataat cggatattta    120
aaagggcgtg aaaaggttta tccgttcgtc catttgtatg tgcatgccaa ccacagggtt    180
ccccagatcc gccggcgttg tggatacctc gcggaaaact tggccctcac tgacagatga    240
ggggcggacg ttgacacttg aggggccgac tcacccggcg cggcgttgac agatgagggg    300
caggctcgat ttcggccggc gacgtggagc tggccagcct cgcaaatcgg cgaaaacgcc    360 tgatttttacg cgagtttccc acagatgatg tggacaagcc tggggataag tgccctgcgg    420
tattgacact tgaggggcgc gactactgac agatgagggg cgcgatcctt gacacttgag    480
gggcagagtg ctgacagatg aggggcgcac ctattgacat tgagggggct gtccacaggc    540
agaaaatcca gcatttgcaa gggtttccgc ccgttttttcg gccaccgcta acctgtcttt    600
taacctgctt ttaaaccaat atttataaac cttgttttta accagggctg cgccctgtgc    660
gcgtgaccgc gcacgccgaa ggggggtgcc ccccttctc gaaccctccc ggcccgctaa    720
cgcgggcctc ccatccccccc aggggctgcg cccctcggcc gcgaacggcc tcaccccaaa    780
aatggcagcg ctggcagtcc ataattgtgg tccaatttgc agccgtccga cacaggagga    840
catcgtccag ctgaaaccgg ggcagaatcc ggccatttct gaagagaaaa atggtaaact    900
gatagaataa aatcataaga aaggagccgc acatgaaaaa agcagtcatt aacggggaac    960
aaatcagaag tatcagcgac ctccaccaga cattgaaaaa ggagcttgcc cttccggaat   1020
actacggtga aaacctggac gctttatggg attgtctgac cggatgggtg gagtaccgc    1080 tcgttttgga atggaggcag tttgaacaaa gcaagcagct gactgaaaat ggcgccgaga   1140
gtgtgcttca ggttttccgt gaagcgaaag cggaaggctg cgacatcacc atcatactttt   1200
```

```
cttaatacga tcaatgggag atgaacaata tggaaacaca aaccacaatt gtggtttcaa    1260
aatcggctcc gtcgatacta tgttatacgc caactttgaa aacaactttg aaaaagctgt    1320
tttctggtat ttaaggtttt agaatgcaag gaacagtgaa ttggagttcg tcttgttata    1380
attagcttct tggggtatct ttaaatactg tagaaaagag gaaggaaata ataaatggct    1440
aaaatgagaa tatcaccgga attgaaaaaa ctgatcgaaa aataccgctg cgtaaaagat    1500
acggaaggaa tgtctcctgc taaggtatat aagctggtgg gagaaaatga aaacctatat    1560
ttaaaaatga cggacagccg gtataaaggg accacctatg atgtggaacg ggaaaaggac    1620
atgatgctat ggctggaagg aaagctgcct gttccaaagg tcctgcactt tgaacggcat    1680
gatggctgga gcaatctgct catgagtgag gccgatggcg tcctttgctc ggaagagtat    1740
gaagatgaac aaagccctga aaagattatc gagctgtatg cggagtgcat caggctcttt    1800
cactccatcg acatatcgga ttgtccctat acgaatagct tagacagccg cttagccgaa    1860
ttggattact tactgaataa cgatctggcc gatgtggatt gcgaaaactg gaagaagac     1920 actccattta aagatccgcg cgagctgtat gattttttaa agacggaaaa gcccgaagag    1980
gaacttgtct tttcccacgg cgacctggga gacagcaaca tctttgtgaa agatggcaaa    2040
gtaagtggct ttattgatct tgggagaagc ggcagggcgg acaagtggta tgacattgcc    2100
ttctgcgtcc ggtcgatcag ggaggatatc ggggaagaac agtatgtcga gctattttt    2160 gacttactgg ggatcaagcc tgattgggag aaaataaaat attatatttt actggatgaa    2220 ttgtttagt acctagatgt ggcgcaacga tgccggcgac aagcaggagc gcaccgactt     2280
cttccgcatc aagtgttttg gctctcaggc cgaggcccac ggcaagtatt tgggcaaggg    2340
gtcgctggta ttcgtgcagg gcaagattcg gaataccaag tacgaaagg acggccagac    2400 ggtctacggg accgacttca ttgccgataa ggtggattat ctggacacca aggcaccagg    2460
cgggtcaaat caggaataag gcacattgc cccggcgtga gtcggggcaa tcccgcaagg     2520
agggtgaatg aatcggacgt tgaccggaa ggcatacagg caagaactga tcgacgcggg     2580
gttttccgcc gaggatgccg aaaccatcgc aagccgcacc gtcatgcgtg cgccccgcga    2640
aaccttccag tccgtcggct cgatggtcca gcaagctacg gccaagatcg agcgcgacag    2700
cgtgcaactg gctcccctg cctgcccgc gccatcggcc gccgtggagc gttcgcgtcg      2760
tctcgaacag gaggcggcag gtttggcgaa gtcgatgacc atcgacacgc gaggaactat    2820
gacgaccaag aagcgaaaaa ccgccggcga ggacctggca aaacaggtca gcgaggccaa    2880
gcaggccgcg ttgctgaaac acacgaagca gcagatcaag gaaatgcagc tttccttgtt    2940
cgatattgcg ccgtggccgg acacgatgcg agcgatgcca aacgacacgg cccgctctgc    3000
cctgttcacc acgcgcaaca agaaaatccc gcgcgaggcg ctgcaaaaca aggtcatttt    3060
ccacgtcaac aaggacgtga agatcaccta caccggcgtc gagctgcggg ccgacgatga    3120
cgaactggtg tggcagcagg tgttggagta cgcgaagcgc acccctatcg gcgagccgat    3180
caccttcacg ttctacgagc tttgccagga cctgggctgg tcgatcaatg gccggtatta    3240
cacgaaggcc gaggaatgcc tgtcgcgcct acaggcgacg gcgatgggct tcacgtccga    3300
ccgcgttggg cacctggaat cggtgtcgct gctgcaccgc ttccgcgtcc tggaccgtgg    3360
caagaaaacg tcccgttgcc aggtcctgat cgacgaggaa atcgtcgtgc tgtttgctgg    3420
cgaccactac acgaaattca tatgggagaa gtaccgcaag ctgtcgccga cggcccgacg    3480
gatgttcgac tatttcagct cgcaccggga gccgtaccgg ctcaagctgg aaaccttccg    3540
cctcatgtgc ggatcggatt ccacccgcgt gaagaagtgg cgcgagcagg tcggcgaagc    3600
```

```
ctgcgaagag ttgcgaggca gcggcctggt ggaacacgcc tgggtcaatg atgacctggt    3660
gcattgcaaa cgctagggcc ttgtggggtc agttccggct gggggttcag cagccagcgc    3720
tttactggca tttcaggaac aagcgggcac tgctcgacgc acttgcttcg ctcagtatcg    3780
ctcgggacgc acggcgcgct ctacgaactg ccgatagaca actgtcacgg ttaagcgaga    3840
aatgaataag aaggctgata attcggatct ctgcgaggga gatgatattt gatccggtgt    3900
gaaataccgc acagatgcgt aaggagaaaa taccgcatca ggcgctcttc cgcttcctcg    3960
ctcactgact cgctgcgctc ggtcgttcgg ctgcggcgag cggtatcagc tcactcaaag    4020
gcggtaatac ggttatccac agaatcaggg gataacgcag gaaagaacat gtgagcaaaa    4080
ggccagcaaa aggccaggaa ccgtaaaaag gccgcgttgc tggcgttttt ccataggctc    4140
cgcccccctg acgagcatca caaaaatcga cgctcaagtc agaggtggcg aaacccgaca    4200
ggactataaa gataccaggc gtttccccct ggaagctccc tcgtgcgctc tcctgttccg    4260
accctgccgc ttaccggata cctgtccgcc tttctccctt cgggaagcgt ggcgctttct    4320
catagctcac gctgtaggta tctcagttcg gtgtaggtcg ttcgctccaa gctgggctgt    4380
gtgcacgaac cccccgttca gcccgaccgc tgcgccttat ccggtaacta tcgtcttgag    4440
tccaacccgg taagacacga cttatcgcca ctggcagcag ccactggtaa caggattagc    4500
agagcgaggt atgtaggcgg tgctacagag ttcttgaagt ggtggcctaa ctacggctac    4560
actagaagga cagtatttgg tatctgcgct ctgctgaagc cagttacctt cggaaaaaga    4620
gttggtagct cttgatccgg caaacaaacc accgctggta gcggtggttt ttttgtttgc    4680
aagcagcaga ttacgcgcag aaaaaaagga tatcaagaag atcctttgat cttttctacg    4740
gggtctgacg ctcagtggaa cgaaaactca cgttaaggga ttttggtcat gagattatca    4800
aaaaggatct tcacctagat ccttttaaat taaaaatgaa gttttaaatc aatctaaagt    4860
atatatgagt aaacttggtc tgacagttac caatgcttca tcagtgaggc tgatcacagg    4920
cagcaacgct ctgtcatcgt tacaatcaac atgctaccct ccgcgagatc atccgtgttt    4980
caaacccggc agcttagttg ccgttcttcc gaatagcatc ggtaacatga gcaaagtctg    5040
ccgccttaca acggctctcc cgctgacgcc gtcccggact gatgggctgc ctgtatcgag    5100
tggtgatttt gtgccgagct gccggtcggg gagctgttgg ctggctggtg gcaggatata    5160
ttgtggtgta aacaaattga cgcttagaca acttaataac acaccgcggt ctagaactag    5220
tggatccccc ctacgtgcga tctagtaaca tagatgacac cgcgcgcgat aatttatcct    5280
agtttgcgcg ctatattttg ttttctatcg cgtattaaat gtataattgc gggactctaa    5340
tcataaaaac ccatctcata ataacgtca tgcattacat gttaattatt acatgcttaa    5400
cgtaattcaa cagaaattat atgataatca tcgcaagacc ggcaacagga ttcaatctta    5460
agaaacttta ttgccaaatg tttgaacgat ccctcagaag aactcgtcaa gaaggcgata    5520
gaaggcgatg cgctgcgaat cgggagcggc gataccgtaa agcacgagga agcggtcagc    5580
ccattcgccg ccaagctctt cagcaatatc acgggtagcc aacgctatgt cctgatagcg    5640
gtccgccaca cccagccggc cacagtcgat gaatccagaa agcggccat tttccaccat    5700 gatattcggc aagcaggcat cgccatgggt cacgacgaga tcctcgccgt cgggcatgcg    5760
cgccttgagc ctggcgaaca gttcggctgg cgcgagcccc tgatgctctt cgtccagatc    5820
atcctgatcg acaagaccgg cttccatccg agtacgtgct cgctcgatgc gatgtttcgc    5880
ttggtggtcg aatgggcagg tagccggatc aagcgtatgc agccgccgca ttgcatcagc    5940
```

```
catgatggat actttctcgg caggagcaag gtgagatgac aggagatcct gccccggcac    6000
ttcgcccaat agcagccagt cccttcccgc ttcagtgaca acgtcgagca cagctgcgca    6060
aggaacgccc gtcgtggcca gccacgatag ccgcgctgcc tcgtcctgga gttcattcag    6120
ggcaccggac aggtcggtct tgacaaaaag aaccgggcgc ccctgcgctg acagccggaa    6180
cacggcggca tcagagcagc cgattgtctg ttgtgcccag tcatagccga atagcctctc    6240
cacccaagcg gccggagaac ctgcgtgcaa tccatcttgt tcaatcatct gttaatcaga    6300
aaaactcaga ttaatcgaca aattcgatcg cacaaactag aaactaacac cagatctaga    6360
tagaaatcac aaatcgaaga gtaattattc gacaaaactc aaattatttg aacaaatcgg    6420
atgatattta tgaaaccta atcgagaatt aagatgatat ctaacgatca aacccagaaa    6480
atcgtcttcg atctaagatt aacagaatct aaaccaaaga acatatacga aattgggatc    6540
gaacgaaaac aaaatcgaag attttgagag aataaggaac acagaaattt accttgatca    6600
cggtagagag aattgagaga aagtttttaa gattttgaga aattgaaatc tgaattgtga    6660
agaagaagag ctctttgggt attgttttat agaagaagaa gaagaaaaga cgaggacgac    6720
taggtcacga gaaagctaag gcggtgaagc aatagctaat aataaaatga cacgtgtatt    6780
gagcgttgtt tacacgcaaa gttgtttttg gctaattgcc ttatttttag gttgaggaaa    6840
agtatttgtg ctttgagttg ataaacacga ctcgtgtgtg ccggctgcaa ccactttgac    6900
gccgtttatt actgactcgt cgacaaccac aatttctaac ggtcgtcata agatccagcc    6960
gttgagattt aacgatcgtt acgatttata tttttttagc attatcgttt tattttttaa    7020
atatacggtg gagctgaaaa ttggcaataa ttgaaccgtg ggtcccactg cattgaagcg    7080
tatttcgtat tttctagaat tcttcgtgct ttatttcttt tccttttgt ttttttttgc     7140
catttatcta atgcaagtgg gcttataaaa tcagtgaatt tcttggaaaa gtaacttctt    7200
tatcgtataa catattgtga aattatccat ttcttttaat ttttagtgt tattggatat      7260
ttttgtatga ttattgattt gcataggata atgacttttg tatcaagttg gtgaacaagt    7320
ctcgttaaaa aaggcaagtg gtttggtgac tcgattattt cttgttattt aattcatata    7380
tcaatggatc ttatttgggg cctggtccat atttaacact cgtgttcagt ccaatgacca    7440
ataatatttt ttcattaata acaatgtaac aagaatgata cacaaaacat tctttgaata    7500
agttcgctat gaagaaggga acttatccgg tcctagatca tcagttcata caaacctcca    7560
tagagttcaa catcttaaac aaggatatcc tgatccgttg acggcgcgcc ttcccgatct    7620
agtaacatag atgacaccgc gcgcgataat ttatcctagt ttgcgcgcta tattttgttt    7680
tctatcgcgt attaaatgta taattgcggg actctaatca taaaaaccca tctcataaat    7740
aacgtcatgc attacatgtt aattattaca tgcttaacgt aattcaacag aaattatatg    7800
ataatcatcg caagaccggc aacaggattc aatcttaaga aactttattg ccaaatgttt    7860
gaacgatcgg ggaaattcga gctcaaagtg caattgaccg atcagagttt gaagaaaaat    7920
ttattacaca ctttatgtaa agctgaaaaa aacggcctcc cgcagggaag ccgtttttt      7980
cgttatctga tttttgtaaa ggtctgataa tggtccgttg ttttgtaaat cagccagtcg    8040
cttgagtaaa gaatccggtc tgaatttctg aagcctgatg tatagttaat atccgctcca    8100
cgccatgttc gtccgctttt gcccgggagt ttgccttccc tgtttgagaa gatgtctccg    8160
ccgatgcttt tccccggagc gacgtctgca aggttccctt tgatgccac ccagccgagg    8220
gcttgtgctt ctgattttgt aatgtaatta tcaggtagct tatgatatgt ctgaagataa    8280
tccgcaaccc cgtcaaacgt gttgataacc tgtgccatga tttgtacaca aaatttccgc    8340
```

```
gcacagatcc tcacagcgta tgcaaaacaa agctgcaact actaatacca gtccaaaagc    8400
aatgggcgca acagcaacag caaaagctgc aaccccttgt gctggttcgt tcctacagtt    8460
ggacgcagcc cgagttctga gaaacaaata accacaaggc aagttaggta ccaaacccct    8520
taagctcaac ttaagcaaat attacaatcg tttgtttcta caaacaaatc ttttttcagaa   8580 cggcttcagg tggggaatat tgtccattta agtacctgaa atctaagaa cacggccaat     8640 ccgggcgcct ttgcttgaaa gtgggaagaa acctgaatga ttgaacagtg gataagagat    8700
ttataagcaa gattagcagg gctgatcaga ttgttttttc gggtaggttg atcaatacat    8760
atgccccttc cctcttcctt tcctctacaa tcgattgcca gggagagata gagataccat    8820
catgatgatg atggtgggga tggcgatgat ggtaatgatg atgatccagc agaaaaaatt    8880
gcgcagaaga agaagatgag cggtcggtcg gtcgatagcc tttcagtcgg aggggaaaga    8940
acaaaataat gcctatttga aggcagatgg attgactaag acgtgtgcag gcagtggagg    9000
agttacaagg caggacatat ttactaggta taggtgtagg taatagtaat ggagaggata    9060
aatttaggtt ttgggatgaa tggatttgtt ggtacatgtt gcaactccca cactgcaatc    9120
aaaggaccgc tatgacaccc cctgaatgcg acgcccatga gaatgccgac cccacatata    9180
catttctgga aataatagggaaatgcaccc ttgcattata tttcatttat tcgtcctcca     9240
ttttgtgcgc tctccattca ttttcaaatg cgctccactc ttcctttatt tcttaccacc    9300
attatctcgt attcgaggtc cagaaatcaa gttgtgaatc tgccttggtt gcgcattgtt    9360
aaagtactct tctgtgtata tttctgcccc accgttttca cttccaacac ttaaattttt    9420
ttatttttta ttttatatat ttcttataaa ttgttggctt ctcacacgaa cccaagccat    9480
ccaagccccg acaaaggcaa tccaatgtac ttgactagag tcaaatacct tttacttctt    9540
tacttctcat attacccaga agccaagcca accttaccaa actaatgtac ctgagcagag    9600
tccactacct ttcctcaagt acagtggcag tcagagtata tcaccgcttg ttatgtatat    9660
gctttaatgc tatgcttatt tctaggtcat aatctaaatc atatttgctg tcgagtttaa    9720
gcttatcgat accgtcgacc tcgagcttct tcttgaatgc tcttatgggt aggattattt    9780 ttcactttt tccttcatat tccacacaca tatatatata aacacactaa cattagtggg    9840
aatatttgtt tgatatgttt atttttattta cttcggggt ttttgtaaca attttgtaga    9900
tctaatttct tgttcttcat gtgtatatta attttcccct aagacttaaa taaaaagaga    9960
gagtttgtta tatatagata tatgaagtga gggaaatggt acaaagttaa aggagatctg    10020
agtgagagtt agataataaa tgaaaagaaa taagaaacca tcagggtttt ttctaatgtg    10080
gagttttaga ttcagttttg tagaactaag attcactttg ttgggtgttc tttcttcact    10140
catttctgtt attataataa taataaaatc ttatatcttt ctatttcct tactaacaag     10200 tacttgaaga tttagatata tttatagatc tggtgttgta ataggtaaaa acttgatttt    10260
tatgactata aaagtaagtt ttgggaaaca aattggggag agagtaagga aggactatga    10320
ggtcatatct tctgtttgt gatcatccat cctccattgt tgttaatgtc tgtgtctctc     10380 ttttctcct cttctttctc ttacttcct ttcttatctc tagctctctt tctctctcat     10440
gaattatatc atatcatata tttgatacaa acacatgtga tggtaagtga gagtgaataa    10500
ggtgaaacta gctagatttt tgagttttca tgaaattta acttatatga gtgatagaaa    10560
ataatggaac ttatacgtac atgtaggaca atttagatgg ttatctaagt ttttgttttt    10620
gttttctctt gagaatgtta aatgttagtg ttattttgt agttttggaa aattatatat    10680
```

-continued

```
gagctaagat tagtttagaa gtggtcaaaa gaaacataga tttgaaattt caactgaatt     10740
ttcaagattt caaatagtca atgaaacaag gaggtaatta agacaaatta gcttatgggg     10800 actcttttt gttattcctt aaaattactc tttttaaaat taaaaataac taatctcatt     10860
tcgaactaca ttactcaaac tagtaatctc taattcgaca cgcaatttcc aaatacttat     10920
tagtagagag tcccacgtga ttactttctt ctccaccaaa acataaaaca tgtcaagatt     10980
aaatggtgtt tgaaaattaa aagatcaatt ttcttaatcg tttacagttg tcaactctca     11040
tgtcctgaaa tatataattc tcatgtccaa aacaagaaaa gctaacaacg acttcaaatt     11100
aaatcagtca atcaaaatta gtcttcattt acctactaat ttcttttat atatccgatg      11160 ggtactctac gaaatcagag tttcgtttct ttatttattt tcttttataa gattttgag      11220 gttttttcag aggttggaat tgagcgcaag attaggtttt gggtctgtaa gatttgttgt     11280
ctttgttaaa gaatctttga tcacgtcatc actcagatat tatttctttt tattttcat     11340 ttgtatttt actaatttat tataaagttt tgttagtttc agttcttgac ttctgacaag      11400
aaggttttat gtcataatga attaatttgt aacctattta taaattcaaa aatgtcatca     11460
tattactact tttgaccatt taatattaga tttctcattt ggtcaatacc caatgttcat     11520
attacatata tagagacaaa aattataagg atactaaatt gttcatattt cttggaagta     11580
aaaagattaa tgatcactga ataaatagat ttggcataga agtatagcat tggaattgct     11640
tcaacatctt tggtgtagat agattatgc aatttctctt tcttttgaa gtatcttttt      11700 ttttctagag agagaataat gttagggatt tttatcattt tctctctcat tatgggtact     11760
gagaggaaag tgagattttt agtacggatc caatagttta agagtttggt ctgccttcta     11820
cgatccaaaa aaatctacgg tcatgatctc tccatcgaga aggttgagag ttcagacatc     11880
aaagtctata atatgtcatt gtaatacgta tttgtgcata tatatctatg tacaagtaca     11940
tatacaggaa actcaagaaa aaagaataaa tggtaaattt aattatattc caaataagga     12000
aagtatggaa cgttgtgatg ttactcggac aagtcattta gttacatcca tcacgtttaa     12060
atttaatcca atggttacaa ttttaatact atcaaatgtc tattggattt atacccaatg     12120
tgttaatggg ttgttgacac atgtcacatg tctgaaaccc tagacatgtt cagaccaatc     12180
atgtcactct aattttgcca gcatggcagt tggcagccaa tcactagctc gataaattta     12240
aggtttcaga ggaattttaa tttatttagg gttcatattg tttcataaaa tgattcttta     12300
tttgttacaa ctttaaggaa atatttatt aactatttaa ttgttccctt ttcttatatt      12360
acttttgttt tttcttcaca tcatgtgtca cattaagttg catttcttct gactcaaaag     12420
aaccgatgtt tgcttttaag gtttcgtatt agaatcactt aactgtgcaa gtggtcgatt     12480
tgaccctatc aagcttgata tcgaattgcg gccgcggccg ggtggtgaca tttattcata     12540
aattcatctc aaaacaagaa ggatttacaa aaataaaaga aaacaaaatt ttcatcttta     12600
acataattat aattgtgttc acaaaattca aacttaaacc cttaatataa agaatttctt     12660
tcaacaatac actttaatca caacttcttc aatcacaacc tcctccaaca aaattaaaat     12720
agattaataa ataaataaac ttaactattt aaaaaaaaat attatacaaa atttattaaa     12780
acttcaaaat aaacaaactt tttatacaaa attcatcaaa actttaaaat aaagctaaac     12840
actgaaaatg tgagtacatt taaaaggacg ctgatcacaa aaattttgaa aacataaaca     12900
aacttgaaac tctaccttt aagaatgagt ttgtcgtctc attaactcat tagttttata      12960
gttcgaatcc aattaacgta tcttttattt tatggaataa gggtgttta  ataagtgatt     13020 ttgggatttt tttagtaatt tatttgtgat atgttatgga gtttttaaaa atatatatat     13080
```

```
atatatatat tttttgggttg agtttactta aaatttggaa aaggttggta agaactataa    13140
attgagttgt gaatgagtgt tttatggatt ttttaagatg ttaaatttat atatgtaatt    13200
aaaattttat tttgaataac aaaaattata attggataaa aaattgtttt gttaaattta    13260
gagtaaaaat ttcaaaatct aaaataatta aacactatta ttttttaaaaa atttgttggt    13320 aaattttatc ttatatttag ttaaaattta gaaaaaatta attttaaatt aataaacttt    13380
tgaagtcaaa tattccaaat attttccaaa atattaaatc tattttgcat tcaaaataca    13440
atttaaataa taaaacttca tggaatagat taaccaattt gtataaaaac caaaaatctc    13500
aaataaaatt taaattacaa aacattatca acattatgat ttcaagaaag acaataacca    13560
gtttccaata aaataaaaaa cctcatggcc cgtaattaag atctcattaa ttaattctta    13620
ttttttaatt tttttacata gaaaatatct ttatatcgta tccaagaaat atagaatgtt    13680
ctcgtccagg gactattaat ctccaaacaa gtttcaaaat cattacatta aagctcatca    13740
tgtcatttgt ggattggaaa ttatattgta taagagaaat atagaatgtt ctcgtctagg    13800
gactattaat ttccaaacaa atttcaaaat cattacatta aagctcatca tgtcatttgt    13860
ggattggaaa ttagacaaaa aaaatcccaa atatttctct caatctccca aaatatagtt    13920
cgaactccat atttttggaa attgagaatt ttttaccca ataatatatt tttttataca     13980
ttttagagat tttccagaca tatttgctct gggatttatt ggaatgaagg tttgagttat    14040
aaactttcag taatccaagt atcttcggtt tttgaagata ctaaatccat tatataataa    14100
aaacacattt taaacaccaa tttaatggga tttcagattt gtatcccatg ctattggcta    14160
aggcattttt cttattgtaa tctaaccaat tctaatttcc accctggtgt gaactgactg    14220
acaaatgcgg tccgaaaaca gcgaatgaaa tgtctgggtg atcggtcaaa caagcggtgg    14280
gcgagagagc gcgggtgttg gcctagccgg gatgggggta ggtagacggc gtattaccgg    14340
cgagttgtcc gaatggagtt ttcggggtag gtagtaacgt agacgtcaat ggaaaaagtc    14400
ataatctccg tcaaaaatcc aaccgctcct tcacatcgca gagttggtgg ccacgggacc    14460 ctccaccccac tcactcgatc gcctgccgtg gttgcccatt attcaaccat acgccacttg    14520
actcttcacc aacaattcca ggccggcttt ctatacaatg tactgcacag gaaaatccaa    14580
tataaaaagc cggcctctgc ttccttctca gtagccccca gctcattcaa ttcttcccac    14640
tgcaggctac atttgtcaga cacgttttcc gccattttt gcctgtttct gcggagaatt     14700
tgatcaggtt cggattggga ttgaatcaat tgaaaggttt ttattttcag tatttcgatc    14760
gccggatccc ccgggctgca ggaattgggc tgcagatcga tatttgattt cacatgctat    14820
tgtaatgtat ttattgtttc aattccgaat tagacaaagt gcttaaagct ctcttttcgg    14880 atttttttt tcattaatgt ataataattg cggacattac aatatactgt acaacgtgat     14940
ttgagcttga tgaattacaa gattggaaga acttcgaaga caaaaaaaaa atcgatctgc    15000
aggaattcgt ccagcagtaa ttcggtaccc ctgatcagca ctgctgccaa gaatgtaagt    15060 tttttatttct tttatatgtt caaacagttt tataaagtac tataagcttt ttttagccaa    15120
aagaaatatc ttaagtttta gtaaccaata aagaattatt gcggcctcct tatttaatta    15180
tagtacatat gtcatagtag atgttttttt tattattatt attttttatt tttttatagt    15240
tttttacaaa ttcgacttgg agaccttatg atttggaaga tactccattt aattttatga    15300
gttgtgtttg aaaacatatt ttaagactaa acacgtagag aacattctta acaaatttgt    15360 aaataaaataa atttaactct attctctagg atttaaatat tataggtata tatataattt    15420
```

```
tctaataagt ttatatcgag tcactcatac gagttgtgta gaaagttaat cacgggtacc    15480
aattttaaat taaaaataag aataattata tgatcttaaa tttatacaac tctgataaaa    15540
gattgggctt tgacatcttt gaagaaaact agatttagta atattctgat taaattgggt    15600
tcacactttg tagtgggcac actttccggg ttcgaaatcg aaatctggaa gcttatcgat    15660
ctcgaggggc ccactagtat cgatctcgag gggcccacta gtatcgatcg atttttttt    15720 tgtcttcgaa gttcttccaa tcttgtaatt catcaagctc aaatcacgtt gtacagtata    15780
ttgtaatgtc cgcaattatt atacattaat gaaaaaaaaa atccgaaaag agagctttaa    15840
gcactttgtc taattcggaa ttgaaacaat aaatacatta caatagcatg tgaaatcaaa    15900
tatcgatccg atgggtgtta tttgtggata ataaattcgg gtgatgttca gtgtttgtcg    15960
tatttctcac gaataaattg tgtttatgta tgtgttagtg ttgtttgtct gtttcagacc    16020
ctcttatgtt atatttttct tttcgtcggt cagttgaagc caatactggt gtcctggccg    16080
gcactgcaat accatttcgt ttaatataaa gactctgtta tccgtgagct cgaatttccc    16140
cgatcgttca aacatttggc aataaagttt cttaagattg aatcctgttg ccggtcttgc    16200
gatgattatc atataatttc tgttgaatta cgttaagcat gtaataatta acatgtaatg    16260
catgacgtta tttatgagat gggtttttat gattagagtc ccgcaattat acatttaata    16320
cgcgatagaa aacaaaatat agcgcgcaaa ctaggataaa ttatcgcgcg cggtgtcatc    16380
tatgttacta gatcgc                                                   16396

<210> SEQ ID NO 24
<211> LENGTH: 7970
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 24
cgccggcgtt gtggatacct cgcggaaaac ttggcccctca ctgacagatg aggggcggac      60
gttgacactt gaggggccga ctcacccggc gcggcgttga cagatgaggg gcaggctcga     120
tttcggccgg cgacgtggag ctggccagcc tcgcaaatcg gcgaaaacgc ctgatttac     180 gcgagtttcc cacagatgat gtggacaagc ctggggataa gtgccctgcg gtattgacac     240
ttgaggggcg cgactactga cagatgaggg gcgcgatcct tgacacttga ggggcagagt     300
gctgacagat gaggggcgca cctattgaca tttgaggggc tgtccacagg cagaaaatcc     360
agcatttgca agggttttccg cccgtttttc ggccaccgct aacctgtctt ttaacctgct     420
tttaaaccaa tatttataaa ccttgttttt aaccagggct gcgccctgtg cgcgtgaccg     480
cgcacgccga aggggggtgc ccccccttct cgaaccctcc cggcccgcta acgcgggcct     540
cccatccccc caggggctgc gcccctcggc cgcgaacggc ctcacccaa aaatggcagc     600 gctggcagtc cataattgtg gtccaatttg cagccgtccg agacaggagg acatcgtcca     660
gctgaaaccg gggcagaatc cggccatttc tgaagagaaa aatggtaaac tgatagaata     720
aaatcataag aaaggagccg cacatgaaaa aagcagtcat taacggggaa caaatcagaa     780
gtatcagcga cctccaccag acattgaaaa aggagcttgc ccttccggaa tactacggtg     840
aaaacctgga cgctttatgg gattgtctga ccggatgggg gagtacccg ctcgttttgg     900 aatgggaggca gtttgaacaa agcaagcagc tgactgaaaa tggcgccgag agtgtgcttc     960
aggttttccg tgaagcgaaa gcggaaggct gcgacatcac catcatactt tcttaatacg    1020
```

```
atcaatggga gaggaacaat atggaaacac aaaccacaat tgtggtttca aaatcggctc   1080
cgtcgatact atgttatacg ccaactttga aaacaacttt gaaaaagctg ttttctggta   1140
tttaaggttt tagaatgcaa ggaacagtga attggagttc gtcttgttat aattagcttc   1200
ttggggtatc tttaaatact gtagaaaaga ggaaggaaat aataaatggc taaaatgaga   1260
atatcaccgg aattgaaaaa actgatcgaa aaataccgct gcgtaaaaga tacggaagga   1320
atgtctcctg ctaaggtata taagctggtg ggagaaaatg aaaacctata tttaaaaatg   1380
acggacagcc ggtataaagg gaccacctat gatgtggaac gggaaaagga catgatgcta   1440
tggctggaag gaaagctgcc tgttccaaag gtcctgcact ttgaacggca tgatggctgg   1500
agcaatctgc tcatgagtga ggccgatggc gtcctttgct cggaagagta tgaagatgaa   1560
caaagccctg aaaagattat cgagctgtat gcggagtgca tcaggctctt tcactccatc   1620
gacatatcgg attgtcccta tacgaatagc ttagacagcc gcttagccga attggattac   1680
ttactgaata cgatctggc cgatgtggat tgcgaaaact gggaagaaga cactccattt   1740
aaagatccgc gcgagctgta tgattttta aagacggaaa agcccgaaga ggaacttgtc   1800
ttttcccacg gcgacctggg agacagcaac atctttgtga agatggcaa agtaagtggc   1860
tttattgatc ttgggagaag cggcagggcg acaagtggt atgacattgc cttctgcgtc   1920
cggtcgatca ggggaggatat cggggaagaa cagtatgtcg agctattttt tgacttactg   1980
gggatcaagc ctgattggga gaaaataaaa tattatattt tactggatga attgttttag   2040
tacctagatg tggcgcaacg atgccggcga caagcaggag cgcaccgact tcttccgcat   2100
caagtgtttt ggctctcagg ccgaggccca cggcaagtat ttgggcaagg ggtcgctggt   2160
attcgtgcag ggcaagattc ggaataccaa gtacgagaag gacggccaga cggtctacgg   2220
gaccgacttc attgccgata aggtggatta tctggacacc aaggcaccag gcgggtcaaa   2280
tcaggaataa gggcacattg ccccggcgtg agtcggggca atcccgcaag gagggtgaat   2340
gaatcggacg tttgaccgga aggcatacag gcaagaactg atcgacgcgg ggttttccgc   2400
cgaggatgcc gaaaccatcg caagccgcac cgtcatgcgt gcgccccgcg aaaccttcca   2460
gtccgtcggc tcgatggtcc agcaagctac ggccaagatc gagcgcgaca gcgtgcaact   2520
ggctcccct gccctgcccg cgccatcggc cgccgtggag cgttcgcgtc gtctcgaaca   2580
ggaggcggca ggtttggcga agtcgatgac catcgacacg cgaggaacta tgacgaccaa   2640
gaagcgaaaa accgccggcg aggacctggc aaaacaggtc agcgaggcca agcaggccgc   2700
gttgctgaaa cacacgaagc agcagatcaa ggaaatgcag ctttccttgt tcgatattgc   2760
gccgtggccg acacgatgc gagcgatgcc aaacgacacg gcccgctctg ccctgttcac   2820
cacgcgcaac aagaaaatcc cgcgcgaggc gctgcaaaac aaggtcattt tccacgtcaa   2880
caaggacgtg aagatcacct acaccggcgt cgagctgcgg gccgacgatg acgaactggt   2940
gtggcagcag gtgttggagt acgcgaagcg caccctatc ggcgagccga tcaccttcac   3000
gttctacgag ctttgccagg acctgggctg gtcgatcaat ggccggtatt acacgaaggc   3060
cgaggaatgc ctgtcgcgcc tacaggcgac ggcgatgggc ttcacgtccg accgcgttgg   3120
gcacctggaa tcggtgtcgc tgctgcaccg cttccgcgtc ctggaccgtg caagaaaac   3180
gtcccgttgc caggtcctga tcgacgagga aatcgtcgtg ctgtttgctg gcgaccacta   3240
cacgaaattc atatgggaga agtaccgcaa gctgtcgccg acggcccgac ggatgttcga   3300
ctatttcagc tcgcacgggg agccgtaccc gctcaagctg gaaaacttcc gcctcatgtg   3360
cggatcggat tccacccgcg tgaagaagtg gcgcgagcag gtcggcgaag cctgcgaaga   3420
```

```
gttgcgaggc agcggcctgg tggaacacgc ctgggtcaat gatgacctgg tgcattgcaa   3480
acgctagggc cttgtggggt cagttccggc tgggggttca gcagccagcg ctttactggc   3540
atttcaggaa caagcgggca ctgctcgacg cacttgcttc gctcagtatc gctcggacg    3600 cacggcgcgc tctacgaact gccgatagac aactgtcacg gttaagcgag aaatgaataa   3660
gaaggctgat aattcggatc tctgcgaggg agatgatatt tgatcacagg cagcaacgct   3720
ctgtcatcgt tacaatcaac atgctaccct ccgcgagatc atccgtgttt caaacccggc   3780
agcttagttg ccgttcttcc gaatagcatc ggtaacatga gcaaagtctg ccgccttaca   3840
acggctctcc cgctgacgcc gtcccggact gatgggctgc ctgtatcgag tggtgatttt   3900
gtgccgagct gccggtcggg gagctgttgg ctggctggtg gcaggatata ttgtggtgta   3960
aacaaattga cgcttagaca acttaataac acattgcgga cgttttttaat gtactggggt   4020 ggttttctt ttcaccagtg agacgggcaa cagctgattg cccttccg cctggccctg     4080 agagagttgc agcaagcggt ccacgctggt ttgccccagc aggcgaaaat cctgtttgat   4140
ggtggttccg aaatcggcaa aatcccttat aaatcaaaag aatagcccga gatagggttg   4200
agtgttgttc cagtttggaa caagagtcca ctattaaaga acgtggactc caacgtcaaa   4260
gggcgaaaaa ccgtctatca gggcgatggc ccacggccgc tctagaacta gtggatcccc   4320
cctacgtgcg atctagtaac atagatgaca ccgcgcgcga taatttatcc tagtttgcgc   4380
gctatatttt gttttctatc gcgtattaaa tgtataattg cgggactcta atcataaaaa   4440
cccatctcat aaataacgtc atgcattaca tgttaattat tacatgctta acgtaattca   4500
acagaaatta tatgataatc atcgcaagac cggcaacagg attcaatctt aagaaacttt   4560
attgccaaat gtttgaacga tccctcagaa gaactcgtca agaaggcgat agaaggcgat   4620
gcgctgcgaa tcgggagcgg cgataccgta agcacgagg aagcggtcag cccattcgcc   4680
gccaagctct tcagcaatat cacgggtagc caacgctatg tcctgatagc ggtccgccac   4740
acccagccgg ccacagtcga tgaatccaga aaagcggcca ttttccacca tgatattcgg   4800
caagcaggca tcgccatggg tcacgacgag atcctcgccg tcgggcatgc gcgccttgag   4860
cctggcgaac agttcggctg gcgcgagccc ctgatgctct tcgtccagat catcctgatc   4920
gacaagaccg gcttccatcc gagtacgtgc tcgctcgatg cgatgtttcg cttggtggtc   4980
gaatgggcag gtagccggat caagcgtatg cagccgccgc attgcatcag ccatgatgga   5040
tactttctcg gcaggagcaa ggtgagatga caggagatcc tgccccggca cttcgcccaa   5100
tagcagccag tcccttcccg cttcagtgac aacgtcgagc acagctgcgc aaggaacgcc   5160
cgtcgtggcc agccacgata ccgcgctgc tcgtcctgg agttcattca gggcaccgga   5220
caggtcggtc ttgacaaaaa gaaccgggcg cccctgcgct gacagccgga acacggcggc   5280
atcagagcag ccgattgtct gttgtgccca gtcatagccg aatagcctct cacccaagc    5340 ggccggagaa cctgcgtgca atccatcttg ttcaatcatc tgttaatcag aaaaactcag   5400
attaatcgac aaattcgatc gcacaaacta gaaactaaca ccagatctag atagaaatca   5460
caaatcgaag agtaattatt cgacaaaact caaattattt gaacaaatcg gatgatattt   5520
atgaaaccct aatcgagaat taagatgata tctaacgatc aaaccagaa aatcgtcttc    5580 gatctaagat taacagaatc taaaccaaag aacatatacg aaattgggat cgaacgaaaa   5640
caaaatcgaa gattttgaga gaataaggaa cacagaaatt taccttgatc acggtagaga   5700
gaattgagag aaagttttta agattttgag aaattgaaat ctgaattgtg aagaagaaga   5760
```

```
gctctttggg tattgtttta tagaagaaga agaagaaaag acgaggacga ctaggtcacg    5820
agaaagctaa ggcggtgaag caatagctaa taataaaatg acacgtgtat tgagcgttgt    5880
ttacacgcaa agttgttttt ggctaattgc cttatttta ggttgaggaa agtatttgt     5940 gctttgagtt gataaacacg actcgtgtgt gccggctgca accactttga cgccgtttat    6000
tactgactcg tcgacaacca caatttctaa cggtcgtcat aagatccagc cgttgagatt    6060
taacgatcgt tacgatttat attttttag cattatcgtt ttatttttta aatatacggt    6120
ggagctgaaa attggcaata attgaaccgt gggtcccact gcattgaagc gtatttcgta    6180
ttttctagaa ttcttcgtgc tttatttctt ttcctttttg ttttttttg ccatttatct     6240 aatgcaagtg ggcttataaa atcagtgaat ttcttggaaa agtaacttct ttatcgtata    6300
acatattgtg aaattatcca tttctttaa ttttttagtg ttattggata ttttgtatg      6360 attattgatt tgcataggat aatgactttt gtatcaagtt ggtgaacaag tctcgttaaa    6420
aaaggcaagt ggtttggtga ctcgatttat tcttgttatt taattcatat atcaatggat    6480
cttatttggg gcctggtcca tatttaacac tcgtgttcag tccaatgacc aataatattt    6540
tttcattaat aacaatgtaa caagaatgat acacaaaaca ttctttgaat aagttcgcta    6600
tgaagaaggg aacttatccg gtcctagatc atcagttcat acaaacctcc atagagttca    6660
acatcttaaa caaggatatc ctgatccgtt gacggcgcgc caagcggccg catttaaatg    6720
ggccctatct aatcgaattt tgtaaactgg tttgataagc catcaatgca tcagtcaaga    6780
atgaatcatt gcaactaagt tgatataatt caatttacca tagaactcaa atgttgatat    6840
cttcttatgg attttctgat cttctacatt attagaaaga aacttgattt accagtaatg    6900
atgatacata tccaatagaa cgaaataagc caatctttat aggttttggt agtaaagtta    6960
caacatcaga gacatgtatg tattgtctct cagaagagct cttgaccgat cagagtttga    7020
agaaaaattt attacacact ttatgtaaag ctgaaaaaaa cggcctcccg cagggaagcc    7080 gttttttcg ttatctgatt tttgtaaagg tctgatactc gtccgttgtt ttgtaaatca     7140
gccagtcgct tgagtaaaga atccggtctg aatttctgaa gcctgatgta tagttaatat    7200
ccgcttcacg ccatgttcgt ccgcttttgc ccgggagttt gccttccctg tttgagaaga    7260
tgtctccgcc gatgcttttc cccggagcga cgtctgcaag gttccctttt gatgccaccc    7320
agccgagggc ttgtgcttct gattttgtaa tgtaattatc aggtagctta tgatatgtct    7380
gaagataatc cgcaaccccg tcaaacgtgt tgataacctg tgccataaat cttctaaaaa    7440
cagcagaact gactattcaa agaaagtaga acccacagaa agtaatcaaa gtagtttgat    7500
taaatgcgtt gtgtatcatc gcagcccctg ctacggatat ttataggaaa ggtttgagag    7560
caatgtgtgc agcaagttgt gtgtgaatca cctgcttcca tggcggagga taataatttt    7620
agtcacgcat ttagttgaac gtaactacta actcctctac cgctaatcat tcttcttttg    7680
cccgggcaag ttcaacaaca accccacaat cacgcttcct gtattttgtt ttgttttcaa    7740
aacaatagaa ttcactttt actgccaaaa ttatgtttta ctcgagagcc cgggctcctg    7800
caggtacctt aattaaaagt ttaaactatc agtgtttgac aggatatatt ggcgggtaaa    7860
cctaagagaa aagagcgttt attagaataa tcggatattt aaagggcgt gaaaaggttt      7920 atccgttcgt ccatttgtat gtgcatgcca accacagggt tccccagatc              7970
```

<210> SEQ ID NO 25
<211> LENGTH: 10312
<212> TYPE: DNA
<213> ORGANISM: Artificial Sequence
<220> FEATURE:
<223> OTHER INFORMATION: Description of Artificial Sequence: Synthetic vector sequence

<400> SEQUENCE: 25

| | | | | | |
|---|---|---|---|---|---|
| gtttacccgc | caatatatcc | tgtcaaacac | tgatagttta | aacttttaat | taaggtacct | 60 |
| gcaggagccc | gggctctcga | gcagcaaata | tgatttagat | tatgacctag | aaataagcat | 120 |
| agcattaaag | catatacaaa | acaagcggtg | atatactctg | actgccactg | tacttgagga | 180 |
| aaggtagtgg | actctgctca | ggtacattag | tttggtaagg | ttggcttggc | ttctgggtaa | 240 |
| tatgagaagt | aaagaagtaa | aaggtatttg | actctagtca | agtacattgg | attgccttcg | 300 |
| tcggggcttg | gatggcttgg | gttcgtgtga | gaagccaaca | atttataaaa | aaatatattg | 360 |
| aaaaaaaaaa | aaatcgtcta | agtgttggaa | gtgaaaacgg | tgggacataa | atatacacag | 420 |
| aagagtactt | taacaatgcg | caaccaaggc | agattcacaa | cttgatttct | ggacctcgaa | 480 |
| tacgagataa | tggtggtaag | aaataaagga | agagtggagt | gcatttgaaa | atgaatggag | 540 |
| agcgcacaaa | atggaggacg | aataaatgaa | atataatgca | agagtgcatt | tccctattat | 600 |
| ttccagaaat | gtatatgtgg | ggtcggcatt | cacatgggcg | tcgcattcag | ggggtgtcat | 660 |
| agcggtcctt | tgattgcagt | gtgggagttg | caacatgtac | caacaaattc | attcatccca | 720 |
| aaacctaaat | ttatcctctc | cattactatt | acctacacct | atacctagta | aatatgtcct | 780 |
| gccttgtaac | tcctccactg | cctgcacacg | tcttagtcaa | tccatctgcc | ttcaaatagg | 840 |
| cattattttg | ttctttcccc | tccgactgaa | aggctatcga | ccgaccgacc | gctcatcttc | 900 |
| ttcttctgcg | caattttttc | tgctggatca | tcatcattac | catcatcgcc | atccccacca | 960 |
| tcatcatcat | gatggtatct | ctatctctcc | ctggcaatcg | attgtagagg | aaaggaagag | 1020 |
| ggaaggggca | tatgtattga | tcaacctacc | cgaaaaaaca | atctgatcag | ccctgctaat | 1080 |
| cttgcttata | aatctcttat | ccactgttca | atcattcagg | tttcttccca | cttccaagca | 1140 |
| aaggcgcccg | gattggccgt | gttcttagat | tttcaggtac | ttaaatggac | aatattcccc | 1200 |
| acctgaagcc | gttctgaaaa | agatttgttt | gtagaaacaa | acgattgtaa | tatttgctta | 1260 |
| agttgagctt | aagggggtttg | gtacctaact | tgccttgtgg | ttatttgttt | ctcagaactc | 1320 |
| gggctgcgtc | caactgtagg | aacgaaccag | cacaaggggt | tgcagctttt | gctgttgctg | 1380 |
| ttgcgcccat | tgcttttgga | ctggtattag | tagttgcagc | tttgtttttgc | atacgctgtg | 1440 |
| aggatctgtg | cgcggaaatt | ttgtgtacaa | atcatggcac | aggttatcaa | cacgtttgac | 1500 |
| ggggttgcgg | attatcttca | gacatatcat | aagctacctg | ataattacat | tacaaaatca | 1560 |
| gaagcacaag | ccctcggctg | ggtggcatca | aaagggaacc | ttgcagacgt | cgctccgggg | 1620 |
| aaaagcatcg | gcggagacat | cttctcaaac | agggaaggca | aactcccggg | caaaagcgga | 1680 |
| cgaacatggc | gtggagcgga | tattaactat | acatcaggct | tcagaaattc | agaccggatt | 1740 |
| ctttactcaa | gcgactggct | gatttacaaa | acaacgacc | attatcagac | ctttacaaaa | 1800 |
| atcagataac | gaaaaaaacg | gcttccctgc | gggaggccgt | ttttttcagc | tttacataaa | 1860 |
| gtgtgtaata | aattttttctt | caaactctga | tcggtcaatt | gcactttgag | ctcgaatttc | 1920 |
| cccgatcgtt | caaacatttg | gcaataaagt | ttcttaagat | tgaatcctgt | tgccggtctt | 1980 |
| gcgatgatta | tcatataatt | tctgttgaat | tacgttaagc | atgtaataat | taacatgtaa | 2040 |
| tgcatgacgt | tatttatgag | atgggttttt | atgattagag | tcccgcaatt | atacatttaa | 2100 |
| tacgcgatag | aaaacaaaat | atagcgcgca | aactaggata | aattatcgcg | cgcggtgtca | 2160 |
| tctatgttac | tagatcggga | aggcgcgccg | cggccgcttg | gcgcgccgtc | aacggatcag | 2220 |

```
gatatccttg tttaagatgt tgaactctat ggaggtttgt atgaactgat gatctaggac    2280
cggataagtt cccttcttca tagcgaactt attcaaagaa tgttttgtgt atcattcttg    2340
ttacattgtt attaatgaaa aatatattt ggtcattgga ctgaacacga gtgttaaata     2400
tggaccaggc cccaaataag atccattgat atatgaatta aataacaaga ataaatcgag    2460
tcaccaaacc acttgccttt tttaacgaga cttgttcacc aacttgatac aaaagtcatt    2520
atcctatgca aatcaataat catacaaaaa tatccaataa cactaaaaaa ttaaaagaaa    2580
tggataattt cacaatatgt tatacgataa agaagttact tttccaagaa attcactgat    2640
tttataagcc cacttgcatt agataaatgg caaaaaaaaa caaaaggaa aagaaataaa     2700
gcacgaagaa ttctagaaaa tacgaaatac gcttcaatgc agtgggaccc acggttcaat    2760
tattgccaat tttcagctcc accgtatatt taaaaaataa aacgataatg ctaaaaaaat    2820
ataaatcgta acgatcgtta aatctcaacg gctggatctt atgacgaccg ttagaaattg    2880
tggttgtcga cgagtcagta ataaacggcg tcaaagtggt tgcagccggc acacgagt     2940
cgtgtttatc aactcaaagc acaaatactt ttcctcaacc taaaaataag gcaattagcc    3000
aaaaacaact ttgcgtgtaa acaacgctca atacacgtgt catttatta ttagctattg     3060
cttcaccgcc ttagctttct cgtgacctag tcgtcctcgt cttttcttct tcttcttcta    3120
taaaacaata cccaaagagc tcttcttctt cacaattcag atttcaattt ctcaaaatct    3180
taaaaacttt ctctcaattc tctctaccgt gatcaaggta aatttctgtg ttccttattc    3240
tctcaaaatc ttcgattttg ttttcgttcg atcccaattt cgtatatgtt ctttggttta    3300
gattctgtta atcttagatc gaagacgatt ttctgggttt gatcgttaga tatcatctta    3360
attctcgatt agggtttcat aaatatcatc cgatttgttc aaataatttg agttttgtcg    3420
aataattact cttcgatttg tgatttctat ctagatctgg tgttagtttc tagtttgtgc    3480
gatcgaattt gtcgattaat ctgagttttt ctgattaaca gatgattgaa caagatggat    3540
tgcacgcagg ttctccggcc gcttgggtgg agaggctatt cggctatgac tgggcacaac    3600
agacaatcgg ctgctctgat gccgccgtgt tccggctgtc agcgcagggg cgcccggttc    3660
ttttttgtcaa gaccgacctg tccggtgccc tgaatgaact ccaggacgag gcagcgcggc    3720
tatcgtggct ggccacgacg ggcgttcctt gcgcagctgt gctcgacgtt gtcactgaag    3780
cgggaaggga ctggctgcta ttgggcgaag tgccggggca ggatctcctg tcatctcacc    3840
ttgctcctgc cgagaaagta tccatcatgg ctgatgcaat gcggcggctg catacgcttg    3900
atccggctac ctgcccattc gaccaccaag cgaaacatcg catcgagcga gcacgtactc    3960
ggatggaagc cggtcttgtc gatcaggatg atctggacga agagcatcag gggctcgcgc    4020
cagccgaact gttcgccagg ctcaaggcgc gcatgcccga cggcgaggat ctcgtcgtga    4080
cccatggcga tgcctgcttg ccgaatatca tggtggaaaa tggccgcttt tctggattca    4140
tcgactgtgg ccggctgggt gtggcggacc gctatcagga catagcgttg gctacccgtg    4200
atattgctga agagcttggc ggcgaatggg ctgaccgctt cctcgtgctt tacggtatcg    4260
ccgctcccga ttcgcagcgc atcgccttct atcgccttct tgacgagttc ttctgagaat    4320
tcagcttcg ttcgtatcat cggtttcgac aacgttcgtc aagttcaatg catcagtttc     4380
attgcgcaca caccagaatc ctactgagtt cgagtattat ggcattggga aaactgtttt    4440
tcttgtacca tttgttgtgc ttgtaattta ctgtgttttt tattcggttt tcgctatcga    4500
actgtgaaat ggaaatggat ggagaagagt taatgaatga tatggtcctt ttgttcattc    4560
```

```
tcaaattaat attatttgtt ttttctctta tttgttgtgt gttgaatttg aaattataag    4620
agatatgcaa acattttgtt ttgagtaaaa atgtgtcaaa tcgtggcctc taatgaccga    4680
agttaatatg aggagtaaaa cacttgtagt tgtaccatta tgcttattca ctaggcaaca    4740
aatatatttt cagacctaga aaagctgcaa atgttactga atacaagtat gtcctcttgt    4800
gttttagaca tttatgaact ttcctttatg taattttcca gaatccttgt cagattctaa    4860
tcattgcttt ataattatag ttatactcat ggatttgtag ttgagtatga aaatatttt    4920 taatgcattt tatgacttgc caattgattg acaacgcaag cttttcattc atcccaaaac    4980
ctaaatttat cctctccatt actattacct acacctatac ctagtaaata tgtcctgcct    5040
tgtaactcct ccactgcctg cacacgtctt agtcaatcca tctgccttca aataggcatt    5100
attttgttct ttcccctccg actgaaaggc tatcgaccga ccgaccgctc atcttcttct    5160
tctgcgcaat ttttctgct ggatcatcat cattaccatc atcgccatcc ccaccatcat    5220
catcatgatg gtatctctat ctctccctgg caatcgattg tagaggaaag gaagagggaa    5280
ggggcatatg tattgatcaa cctacccgaa aaacaatct gatcagccct gctaatcttg    5340
cttataaatc tcttatccac tgttcaatca ttcaggtttc ttcccacttc caagcaaagg    5400
cgcccggatt ggccgtgttc ttagattttc aggtacttaa atggacaata ttccccacct    5460
gaagccgttc tgaaaagat ttgtttgtag aaacaaacga ttgtaatatt tgcttaagtt    5520
gagcttaagg ggtttggtac ctaacttgcc ttgtggttat ttgtttctca gaactcgggc    5580
tgcgtccaac tgtaggaacg aaccagcaca aggggttgca gcttttgctg ttgctgttgc    5640
gcccattgct tttggactgg tattagtagt tgcagctttg ttttgcatac gctgtgagga    5700
tctgtgcgcg gaattttgt gtacaaatca tgaaaaaagc agtcattaac ggggaacaaa    5760
tcagaagtat cagcgacctc caccagacat tgaaaaagga gcttgccctt ccggaatact    5820
acggtgaaaa cctggacgct ttatgggatt gtctgaccgg atgggtggag tacccgctcg    5880
ttttggaatg gaggcagttt gaacaaagca agcagctgac tgaaaatggc gccgagagtg    5940
tgcttcaggt tttccgtgaa gcgaaagcgg aaggctgcga catcaccatc atactttctt    6000
aatacgatca atgggagatg aacaatatgg aaacacaaac cacaattatg tctctcagcg    6060
agctcgaatt tccccgatcg ttcaaacatt tggcaataaa gtttcttaag attgaatcct    6120
gttgccggtc ttgcgatgat tatcatataa tttctgttga attacgttaa gcatgtaata    6180
attaacatgt aatgcatgac gttatttatg agatgggttt ttatgattag agtcccgcaa    6240
ttatacattt aatacgcgat agaaaacaaa atatagcgcg caaactagga taaattatcg    6300
cgcgcggtgt catctatgtt actagatcgg ggatccacta gttctagagc ggcgtgggcc    6360
atcgccctga tagacggttt ttcgcccttt gacgttggag tccacgttct ttaatagtgg    6420
actcttgttc caaactggaa caacactcaa ccctatctcg ggctattctt tgatttata    6480 agggattttg ccgatttcgg aaccaccatc aaacaggatt ttcgcctgct ggggcaaacc    6540
agcgtggacc gcttgctgca actctctcag ggccaggcgg tgaagggcaa tcagctgttg    6600
cccgtctcac tggtgaaaag aaaaaccacc ccagtacatt aaaaacgtcc gcaatgtgtt    6660
attaagttgt ctaagcgtca atttgtttac accacaatat atcctgccac cagccagcca    6720
acagctcccc gaccggcagc tcggcacaaa atcaccactc gatacaggca gcccatcagt    6780
ccgggacggc gtcagcggga gagccgttgt aaggcggcag actttgctca tgttaccgat    6840
gctattcgga agaacggcaa ctaagctgcc gggtttgaaa cacggatgat ctcgcggagg    6900
gtagcatgtt gattgtaacg atgacagagc gttgctgcct gtgatcaaat atcatctccc    6960
```

```
tcgcagagat ccgaattatc agccttctta ttcatttctc gcttaaccgt gacagttgtc    7020
tatcggcagt tcgtagagcg cgccgtgcgt cccgagcgat actgagcgaa gcaagtgcgt    7080
cgagcagtgc ccgcttgttc ctgaaatgcc agtaaagcgc tggctgctga accccagcc    7140
ggaactgacc ccacaaggcc ctagcgtttg caatgcacca ggtcatcatt gacccaggcg    7200
tgttccacca ggccgctgcc tcgcaactct tcgcaggctt cgccgacctg ctcgcgccac    7260
ttcttcacgc gggtggaatc cgatccgcac atgaggcgga aggtttccag cttgagcggg    7320
tacggctccc ggtgcgagct gaaatagtcg aacatccgtc gggccgtcgg cgacagcttg    7380
cggtacttct cccatatgaa tttcgtgtag tggtcgccag caaacagcac gacgatttcc    7440
tcgtcgatca ggacctggca acgggacgtt ttcttgccac ggtccaggac gcggaagcgg    7500
tgcagcagcg acaccgattc caggtgccca acgcggtcgg acgtgaagcc catcgccgtc    7560
gcctgtaggc gcgacaggca ttcctcggcc ttcgtgtaat accggccatt gatcgaccag    7620
cccaggtcct ggcaaagctc gtagaacgtg aaggtgatcg gctcgccgat aggggtgcgc    7680
ttcgcgtact ccaacacctg ctgccacacc agttcgtcat cgtcggcccg cagctcgacg    7740
ccggtgtagg tgatcttcac gtccttgttg acgtggaaaa tgaccttgtt ttgcagcgcc    7800
tcgcgcggga ttttcttgtt gcgcgtggtg aacagggcag agcgggccgt gtcgtttggc    7860
atcgctcgca tcgtgtccgg ccacggcgca atatcgaaca aggaaagctg catttccttg    7920
atctgctgct tcgtgtgttt cagcaacgcg gcctgcttgg cctcgctgac ctgttttgcc    7980
aggtcctcgc cggcggtttt tcgcttcttg gtcgtcatag ttcctcgcgt gtcgatggtc    8040
atcgacttcg ccaaacctgc cgcctcctgt tcgagacgac gcgaacgctc cacggcggcc    8100
gatgcgcgg gcagggcagg gggagccagt tgcacgctgt cgcgctcgat cttggccgta    8160
gcttgctgga ccatcgagcc gacggactgg aaggtttcgc ggggcgcacg catgacggtg    8220
cggcttgcga tggtttcggc atcctcggcg gaaaaccccg cgtcgatcag ttcttgcctg    8280
tatgccttcc ggtcaaacgt ccgattcatt caccctcctt gcgggattgc cccgactcac    8340
gccggggcaa tgtgccctta ttcctgattt gacccgcctg gtgccttggt gtccagataa    8400
tccaccttat cggcaatgaa gtcggtcccg tagaccgtct ggccgtcctt ctcgtacttg    8460
gtattccgaa tcttgccctg cacgaatacc agcgacccct tgcccaaata cttgccgtgg    8520
gcctcggcct gagagccaaa acacttgatg cggaagaagt cggtgcgctc ctgcttgtcg    8580
ccggcatcgt tgcgccacat ctaggtacta aaacaattca tccagtaaaa tataatattt    8640
tattttctcc caatcaggct tgatccccag taagtcaaaa aatagctcga catactgttc    8700
ttccccgata tcctccctga tcgaccggac gcagaaggca atgtcatacc acttgtccgc    8760
cctgccgctt ctcccaagat caataaagcc acttactttg ccatctttca caaagatgtt    8820
gctgtctccc aggtcgccgt gggaaaagac aagttcctct tcgggctttt ccgtctttaa    8880
aaaatcatac agctcgcgcg gatctttaaa tggagtgtct tcttcccagt tttcgcaatc    8940
cacatcggcc agatcgttat tcagtaagta atccaattcg gctaagcggc tgtctaagct    9000
attcgtatag ggacaatccg atatgtcgat ggagtgaaag agcctgatgc actccgcata    9060
cagctcgata atcttttcag ggctttgttc atcttcatac tcttccgagc aaaggacgcc    9120
atcggcctca ctcatgagca gattgctcca gccatcatgc cgttcaaagt gcaggacctt    9180
tggaacaggc agctttcctt ccagccatag catcatgtcc ttttcccgtt ccacatcata    9240
ggtggtccct ttataccggc tgtccgtcat ttttaaatat aggttttcat tttctcccac    9300
```

```
cagcttatat accttagcag gagacattcc ttccgtatct tttacgcagc ggtattttc        9360 gatcagtttt ttcaattccg gtgatattct cattttagcc atttattatt tccttcctct      9420
tttctacagt atttaaagat accccaagaa gctaattata acaagacgaa ctccaattca      9480
ctgttccttg cattctaaaa ccttaaatac cagaaaacag cttttcaaa gttgttttca       9540 aagttggcgt ataacatagt atcgacggag ccgattttga aaccacaatt atggactgcc     9600
agcgctgcca ttttggggt gaggccgttc gcggccgagg ggcgcagccc ctgggggat       9660 gggaggcccg cgttagcggg ccgggagggt tcgagaaggg ggggcacccc ccttcggcgt    9720
gcgcggtcac gcgcacaggg cgcagccctg gttaaaaaca aggtttataa atattggttt    9780
aaaagcaggt taaagacag gttagcggtg gccgaaaaac gggcggaaac ccttgcaaat   9840
gctggatttt ctgcctgtgg acagcccctc aaatgtcaat aggtgcgccc ctcatctgtc     9900
agcactctgc ccctcaagtg tcaaggatcg cgcccctcat ctgtcagtag tcgcgcccct    9960
caagtgtcaa taccgcaggg cacttatccc caggcttgtc cacatcatct gtgggaaact   10020
cgcgtaaaat caggcgtttt cgccgatttg cgaggctggc cagctccacg tcgccggccg  10080
aaatcgagcc tgcccctcat ctgtcaacgc cgcgccgggt gagtcggccc ctcaagtgtc   10140
aacgtccgcc cctcatctgt cagtgagggc caagttttcc gcgaggtatc cacaacgccg 10200
gcggatctgg ggaaccctgt ggttggcatg cacatacaaa tggacgaacg gataaaccctt 10260 ttcacgccct tttaaatatc cgattattct aataaacgct cttttctctt ag            10312

<210> SEQ ID NO 26
<211> LENGTH: 10312
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 26
gtttacccgc caatatatcc tgtcaaacac tgatagttta aacttttaat taaggtacct       60
gcaggagccc gggctctcga gcagcaaata tgatttagat tatgacctag aaataagcat    120
agcattaaag catatacaaa acaagcggtg atatactctg actgccactg tacttgagga   180
aaggtagtgg actctgctca ggtacattag tttggtaagg ttggcttggc ttctgggtaa    240
tatgagaagt aaagaagtaa aaggtatttg actctagtca agtacattgg attgccttcg  300
tcggggcttg gatggcttgg gttcgtgtga gaagccaaca atttataaaa aaatatattg 360
aaaaaaaaaa aaatcgtcta agtgttggaa gtgaaaacgg tgggacataa atatacacag 420
aagagtactt taacaatgcg caaccaaggc agattcacaa cttgatttct ggacctcgaa 480
tacgagataa tggtggtaag aaataaagga agagtggagt gcatttgaaa atgaatggag  540
agcgcacaaa atgaggacg aataaatgaa atataatgca agagtgcatt tccctattat   600
ttccagaaat gtatatgtgg ggtcggcatt cacatgggcg tcgcattcag ggggtgtcat   660
agcggtcctt tgattgcagt gtgggagttg caacatgtac caacaaattc attcatccca   720
aaacctaaat ttatcctctc cattactatt acctacacct atacctagta aatatgtcct    780
gccttgtaac tcctccactg cctgcacacg tcttagtcaa tccatctgcc ttcaaatagg   840
cattattttg ttctttcccc tccgactgaa aggctatcga ccgaccgacc gctcatcttc    900
ttcttctgcg caattttttc tgctggatca tcatcattac catcatcgcc atccccacca   960
tcatcatcat gatggtatct ctatctctcc ctggcaatcg attgtagagg aaaggaagag 1020
```

```
ggaagggca tatgtattga tcaacctacc cgaaaaaaca atctgatcag ccctgctaat    1080
cttgcttata aatctcttat ccactgttca atcattcagg tttcttccca cttccaagca    1140
aaggcgcccg gattggccgt gttcttagat tttcaggtac ttaaatggac aatattcccc    1200
acctgaagcc gttctgaaaa agatttgttt gtagaaacaa acgattgtaa tatttgctta    1260
agttgagctt aagggtttg gtacctaact tgccttgtgg ttatttgttt ctcagaactc    1320
gggctgcgtc caactgtagg aacgaaccag cacaagggt tgcagcttt gctgttgctg    1380 ttgcgcccat tgcttttgga ctggtattag tagttgcagc tttgttttgc atacgctgtg    1440
aggatctgtg cgcggaaatt tgtgtacaa atcatggcac aggttatcaa cacgtttgac    1500
ggggttgcgg attatcttca gacatatcat aagctacctg ataattacat tacaaaatca    1560
gaagcacaag ccctcggctg ggtggcatca aagggaacc ttgcagacgt cgctccgggg    1620
aaaagcatcg gcggagacat cttctcaaac agggaaggca aactcccggg caaaagcgga    1680
cgaacatggc gtgaagcgga tattaactat acatcaggct tcagaaattc agaccggatt    1740 cttactcaa gcgactggct gatttacaaa acaacggacc attatcagac ctctacaaaa    1800
atcagataac gaaaaaacg gcttccctgc gggaggccgt ttttttcagc tttacataaa    1860
gtgtgtaata aattttcctt caaactctga tcggtcaatt gcactttgag ctcgaatttc    1920
cccgatcgtt caaacattg gcaataaagt ttcttaagat tgaatcctgt tgccggtctt    1980
gcgatgatta tcatataatt tctgttgaat tacgttaagc atgtaataat taacatgtaa    2040
tgcatgacgt tatttatgag atgggtttt atgattagag tcccgcaatt atacatttaa    2100
tacgcgatag aaaacaaaat atagcgcgca aactaggata aattatcgcg cgcggtgtca    2160
tctatgttac tagatcggga aggcgcgccg cggccgcttg gcgcgccgtc aacggatcag    2220
gatatccttg tttaagatgt tgaactctat ggaggtttgt atgaactgat gatctaggac    2280
cggataagtt cccttcttca tagcgaactt attcaaagaa tgttttgtgt atcattcttg    2340
ttacattgtt attaatgaaa aaatattatt ggtcattgga ctgaacacga gtgttaaata    2400
tggaccaggc cccaaataag atccattgat atatgaatta ataacaaga ataaatcgag    2460 tcaccaaacc acttgccttt tttaacgaga cttgttcacc aacttgatac aaaagtcatt    2520
atcctatgca aatcaataat catacaaaaa tatccaataa cactaaaaaa ttaaaagaaa    2580
tggataattt cacaatatgt tatacgataa agaagttact tttccaagaa attcactgat    2640
tttataagcc cacttgcatt agataaatgg caaaaaaaaa caaaaaggaa aagaaataaa    2700
gcacgaagaa ttctagaaaa tacgaaatac gcttcaatgc agtgggaccc acggttcaat    2760
tattgccaat tttcagctcc accgtatatt taaaaaataa aacgataatg ctaaaaaat    2820 ataaatcgta acgatcgtta aatctcaacg gctggatctt atgacgaccg ttagaaattg    2880
tggttgtcga cgagtcagta ataaacggcg tcaaagtggt tgcagccggc acacacgagt    2940
cgtgtttatc aactcaaagc acaaatactt ttcctcaacc taaaaataag gcaattagcc    3000
aaaaacaact ttgcgtgtaa acaacgctca atacacgtgt cattttatta ttagctattg    3060
cttcaccgcc ttagctttct cgtgacctag tcgtcctcgt cttttcttct tcttcttcta    3120
taaaacaata cccaaagagc tcttcttctt cacaattcag atttcaattt ctcaaaatct    3180
taaaaacttt ctctcaattc tctctaccgt gatcaaggta aatttctgtg ttccttattc    3240
tctcaaaatc ttcgattttg ttttcgttcg atcccaattt cgtatatgtt ctttggttta    3300
gattctgtta atcttagatc gaagacgatt ttctgggttt gatcgttaga tatcatctta    3360
attctcgatt agggtttcat aaatatcatc cgatttgttc aaataatttg agttttgtcg    3420
```

```
aataattact cttcgatttg tgatttctat ctagatctgg tgttagtttc tagtttgtgc  3480
gatcgaattt gtcgattaat ctgagttttt ctgattaaca gatgattgaa caagatggat  3540
tgcacgcagg ttctccggcc gcttgggtgg agaggctatt cggctatgac tgggcacaac  3600
agacaatcgg ctgctctgat gccgccgtgt tccggctgtc agcgcagggg cgcccggttc  3660
tttttgtcaa gaccgacctg tccggtgccc tgaatgaact ccaggacgag gcagcgcggc  3720
tatcgtggct ggccacgacg gcgttcctt gcgcagctgt gctcgacgtt gtcactgaag  3780
cgggaaggga ctggctgcta ttgggcgaag tgccggggca ggatctcctg tcatctcacc  3840
ttgctcctgc cgagaaagta tccatcatgg ctgatgcaat gcggcggctg catacgcttg  3900
atccggctac ctgcccattc gaccaccaag cgaaacatcg catcgagcga gcacgtactc  3960
ggatggaagc cggtcttgtc gatcaggatg atctggacga agagcatcag gggctcgcgc  4020
cagccgaact gttcgccagg ctcaaggcgc gcatgcccga cggcgaggat ctcgtcgtga  4080
cccatggcga tgcctgcttg ccgaatatca tggtggaaaa tggccgcttt tctggattca  4140
tcgactgtgg ccggctgggt gtggcggacc gctatcagga catagcgttg gctacccgtg  4200
atattgctga agagcttggc ggcgaatggg ctgaccgctt cctcgtgctt tacggtatcg  4260
ccgctcccga ttcgcagcgc atcgccttct atcgccttct tgacgagttc ttctgagaat  4320
tcagctttcg ttcgtatcat cggtttcgac aacgttcgtc aagttcaatg catcagtttc  4380
attgcgcaca caccagaatc ctactgagtt cgagtattat ggcattggga aaactgtttt  4440
tcttgtacca tttgttgtgc ttgtaattta ctgtgttttt tattcggttt tcgctatcga  4500
actgtgaaat ggaaatggat ggagaagagt taatgaatga tatggtcctt ttgttcattc  4560
tcaaattaat attatttgtt ttttctctta tttgttgtgt gttgaatttg aaattataag  4620
agatatgcaa acatttgtt ttgagtaaaa atgtgtcaaa tcgtggcctc taatgaccga  4680
agttaatatg aggagtaaaa cacttgtagt tgtaccatta tgcttattca ctaggcaaca  4740
aatatatttt cagacctaga aaagctgcaa atgttactga atacaagtat gtcctcttgt  4800
gttttagaca tttatgaact ttcctttatg taattttcca gaatccttgt cagattctaa  4860
tcattgcttt ataattatag ttatactcat ggatttgtag ttgagtatga aaatattttt  4920
taatgcattt tatgacttgc caattgattg acaacgcaag cttttcattc atcccaaaac  4980
ctaaatttat cctctccatt actattacct acacctatac ctagtaaata tgtcctgcct  5040
tgtaactcct ccactgcctg cacacgtctt agtcaatcca tctgccttca aataggcatt  5100
attttgttct ttcccctccg actgaaaggc tatcgaccga ccgaccgctc atcttcttct  5160
tctgcgcaat ttttctgct ggatcatcat cattaccatc atcgccatcc ccaccatcat  5220
catcatgatg gtatctctat ctctccctgg caatcgattg tagaggaaag gaagagggaa  5280
ggggcatatg tattgatcaa cctacccgaa aaacaatct gatcagccct gctaatcttg  5340
cttataaatc tcttatccac tgttcaatca ttcaggtttc ttcccacttc caagcaaagg  5400
cgcccggatt ggccgtgttc ttagatttc aggtacttaa atggacaata ttccccacct  5460
gaagccgttc tgaaaaagat tgtttgtag aaacaaacga ttgtaatatt tgcttaagtt  5520
gagcttaagg ggtttggtac ctaacttgcc ttgtggttat ttgttttctca gaactcgggc  5580 tgcgtccaac tgtaggaacg aaccagcaca aggggttgca gcttttgctg ttgctgttgc  5640
gcccattgct tttggactgg tattagtagt tgcagctttg ttttgcatac gctgtgagga  5700
tctgtgcgcg gaaatttttgt gtacaaatca tgaaaaaagc agtcattaac ggggaacaaa  5760
```

```
tcagaagtat cagcgacctc caccagacat tgaaaaagga gcttgcccttccggaatact   5820
acggtgaaaa cctggacgct ttatgggatt gtctgaccgg atgggtggagtacccgctcg   5880
ttttggaatg gaggcagttt gaacaaagca agcagctgac tgaaaatggcgccgagagtg   5940
tgcttcaggt tttccgtgaa gcgaaagcgg aaggctgcga catcaccatcatactttctt   6000
aatacgatca atgggagatg aacaatatgg aaacacaaac cacaattatgtctctcagcg   6060
agctcgaatt tccccgatcg ttcaaacatt tggcaataaa gtttcttaagattgaatcct   6120
gttgccggtc ttgcgatgat tatcatataa tttctgttga attacgttaagcatgtaata   6180
attaacatgt aatgcatgac gttatttatg agatgggttt ttatgattagagtcccgcaa   6240
ttatacattt aatacgcgat agaaaacaaa atatagcgcg caaactaggataaattatcg   6300
cgcgcggtgt catctatgtt actagatcgg ggatccactagttctagagcggcgtgggcc   6360
atcgccctga tagacggttt ttcgcccttt gacgttggagtccacgttctttaatagtgg   6420
actcttgttc caaactggaa caacactcaa ccctatctcg ggctattctt ttgatttata   6480
agggattttg ccgatttcgg aaccaccatc aaacaggatt ttcgcctgctggggcaaacc   6540
agcgtggacc gcttgctgca actctctcag ggccaggcgg tgaagggcaa tcagctgttg   6600
cccgtctcac tggtgaaaag aaaaaccacc ccagtacatt aaaaacgtccgcaatgtgtt   6660
attaagttgt ctaagcgtca atttgtttac accacaatat atcctgccaccagccagcca   6720
acagctcccc gaccggcagc tcggcacaaa atcaccactc gatacaggcagcccatcagt   6780
ccgggacggc gtcagcggga gagccgttgt aaggcggcag actttgctcatgttaccgat   6840
gctattcgga agaacggcaa ctaagctgcc gggtttgaaa cacggatgatctcgcggagg   6900
gtagcatgtt gattgtaacg atgacagagc gttgctgcct gtgatcaaatatcatctccc   6960
tcgcagagat ccgaattatc agccttctta ttcatttctc gcttaaccgtgacagttgtc   7020
tatcggcagt tcgtagagcg cgccgtgcgt cccgagcgat actgagcgaagcaagtgcgt   7080
cgagcagtgc ccgcttgttc ctgaaatgcc agtaaagcgc tggctgctgaaccccccagcc   7140
ggaactgacc ccacaaggcc ctagcgtttg caatgcacca ggtcatcattgacccaggcg   7200
tgttccacca ggccgctgcc tcgcaactct tcgcaggctt cgccgacctgctcgcgccac   7260
ttcttcacgc gggtggaatc cgatccgcac atgaggcgga aggtttccagcttgagcggg   7320
tacggctccc ggtgcgagct gaaatagtcg aacatccgtc gggccgtcggcgacagcttg   7380
cggtacttct cccatatgaa tttcgtgtag tggtcgccag caaacagcacgacgatttcc   7440
tcgtcgatca ggacctggca acgggacgtt ttcttgccac ggtccaggacgcggaagcgg   7500
tgcagcagcg acaccgattc caggtgccca acgcggtcgg acgtgaagcccatcgccgtc   7560
gcctgtaggc gcgacaggca ttcctcggcc ttcgtgtaat accggccattgatcgaccag   7620
cccaggtcct ggcaaagctc gtagaacgtg aaggtgatcg gctcgccgatagggtgcgc    7680
ttcgcgtact ccaacacctg ctgccacacc agttcgtcat cgtcggcccgcagctcgacg   7740
ccggtgtagg tgatcttcac gtccttgttg acgtggaaaa tgaccttgttttgcagcgcc   7800
tcgcgcggga ttttcttgtt gcgcgtggtg aacaggcag agcgggccgtgtcgtttggc    7860
atcgctcgca tcgtgtccgg ccacggcgca atatcgaaca aggaaagctgcatttccttg   7920
atctgctgct tcgtgtgttt cagcaacgcg gcctgcttgg cctcgctgacctgttttgcc   7980
aggtcctcgc cggcggtttt tcgcttcttg gtcgtcatag ttcctcgcgtgtcgatggtc   8040
atcgacttcg ccaaacctgc cgcctcctgt tcgagacgac gcgaacgctccacggcggcc   8100
gatggcgcgg gcagggcagg gggagccagt tgcacgctgt cgcgctcgatcttggccgta   8160
```

```
gcttgctgga ccatcgagcc gacggactgg aaggtttcgc ggggcgcacg catgacggtg    8220
cggcttgcga tggtttcggc atcctcggcg gaaaaccccg cgtcgatcag ttcttgcctg    8280
tatgccttcc ggtcaaacgt ccgattcatt caccctcctt gcgggattgc cccgactcac    8340
gccggggcaa tgtgccctta ttcctgattt gacccgcctg gtgccttggt gtccagataa    8400
tccaccttat cggcaatgaa gtcggtcccg tagaccgtct ggccgtcctt ctcgtacttg    8460
gtattccgaa tcttgccctg cacgaatacc agcgacccct gcccaaaata cttgccgtgg    8520
gcctcggcct gagagccaaa acacttgatg cggaagaagt cggtgcgctc ctgcttgtcg    8580
ccggcatcgt tgcgccacat ctaggtacta aacaattca tccagtaaaa tataatattt    8640
tattttctcc caatcaggct tgatccccag taagtcaaaa aatagctcga catactgttc    8700
ttccccgata tcctccctga tcgaccggac gcagaaggca atgtcatacc acttgtccgc    8760
cctgccgctt ctcccaagat caataaagcc acttactttg ccatctttca caaagatgtt    8820
gctgtctccc aggtcgccgt gggaaaagac aagttcctct tcgggctttt ccgtctttaa    8880
aaaatcatac agctcgcgcg gatctttaaa tggagtgtct tcttcccagt tttcgcaatc    8940
cacatcggcc agatcgttat tcagtaagta atccaattcg gctaagcggc tgtctaagct    9000
attcgtatag ggacaatccg atatgtcgat ggagtgaaag agcctgatgc actccgcata    9060
cagctcgata atcttttcag ggctttgttc atcttcatac tcttccgagc aaaggacgcc    9120
atcggcctca ctcatgagca gattgctcca gccatcatgc cgttcaaagt gcaggacctt    9180
tggaacaggc agctttcctt ccagccatag catcatgtcc ttttcccgtt ccacatcata    9240
ggtggtccct ttataccggc tgtccgtcat ttttaaatat aggttttcat tttctcccac    9300
cagcttatat accttagcag gagacattcc ttccgtatct tttacgcagc ggtattttc    9360 gatcagtttt ttcaattccg gtgatattct cattttagcc atttattatt tccttcctct    9420
tttctacagt atttaaagat accccaagaa gctaattata acaagacgaa ctccaattca    9480
ctgttccttg cattctaaaa ccttaaatac cagaaaacag cttttttcaaa gttgttttca    9540 aagttggcgt ataacatagt atcgacggag ccgattttga aaccacaatt atggactgcc    9600
agcgctgcca tttttggggt gaggccgttc gcggccgagg ggcgcagccc ctgggggat    9660 gggaggcccg cgttagcggg ccgggagggt tcgagaaggg ggggcacccc ccttcggcgt    9720
gcgcggtcac gcgcacaggg cgcagccctg gttaaaaaca aggtttataa atattggttt    9780
aaaagcaggt taaagacag gttagcgtg gccgaaaaac gggcggaaac ccttgcaaat    9840
gctggatttt ctgcctgtgg acagcccctc aaatgtcaat aggtgcgccc ctcatctgtc    9900
agcactctgc ccctcaagtg tcaaggatcg cgccctcat ctgtcagtag tcgcgcccct    9960
caagtgtcaa taccgcaggg cacttatccc caggcttgtc cacatcatct gtgggaaact   10020
cgcgtaaaat caggcgtttt cgccgatttg cgaggctggc cagctccacg tcgcggccg    10080 aaatcgagcc tgcccctcat ctgtcaacgc cgcgcgggt gagtcggccc ctcaagtgtc   10140
aacgtccgcc cctcatctgt cagtgagggc caagttttcc gcgaggtatc cacaacgccg   10200
gcggatctgg ggaaccctgt ggttggcatg cacatacaaa tggacgaacg gataaacctt   10260
ttcacgccct tttaaatatc cgattattct aataaacgct ctttttctctt ag         10312
```

<210> SEQ ID NO 27
<211> LENGTH: 20
<212> TYPE: DNA
<213> ORGANISM: Artificial Sequence
<220> FEATURE:

-continued

<223> OTHER INFORMATION: Description of Artificial Sequence: Synthetic
      primer

<400> SEQUENCE: 27
ggtttggtac ctaacttgcc                                                  20

<210> SEQ ID NO 28
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgtgttgata acctgtgcca tgatttgtac acaaaatttc cg                          42

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cggaaatttt gtgtacaaat catggcacag gttatcaaca cg                          42

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggttctcgag tttcacgtta actggctag                                        29

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgacaaccat ggcacaggtt atcaacacgt ttgac                                 35

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aaagtgcaat tgaccgatca gagtttgaag                                       30

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
tttcacaacc tccacacact t                                              21

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtaaaggtct gatactcgtc cgttg                                          25

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gaagaagagc tcttgaccga tcagagtttg aag                                 33

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tgcttctgat gctgtaatgt aattatcag                                      29

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aattacatta cagcatcaga agcacaag                                       28

<210> SEQ ID NO 38
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gaagaactcg agtaaaacat aattttggca gtaaaaagtg a                        41

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 39
catgttcccg tttgatacct gaattttg                                          28

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cataaatctt ctaaaaacag cagaactgac                                        30

<210> SEQ ID NO 41
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gagagaggat ccggtgtgaa ataccgcaca g                                      31

<210> SEQ ID NO 42
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gagagatgat cagcctcact gattaagcat tggtaactg                              39

<210> SEQ ID NO 43
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
aatgcggccg cagaga                                                       16

<210> SEQ ID NO 44
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tctctgcggc cgc                                                          13

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 45
gaagaaagcc gaaataaaga gg                                               22

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ttgaacgtat agtcgccgat ag                                               22

<210> SEQ ID NO 47
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aaggagatat aacaatgatt gaacaagatg gattgc                                36

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tcagaagaac tcgtcaagaa gg                                               22

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cgaaaacggc aagaaaaagc ag                                               22

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
acgaccaaag ccagtaaagt ag                                               22

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
```

```
aatgggaagc ctgagtttac a                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggccagcatg ttttcctcca g                                              21
```